United States Patent
Jonjic

(10) Patent No.: US 10,537,621 B2
(45) Date of Patent: Jan. 21, 2020

(54) VACCINE COMPRISING BETA-HERPESVIRUS

(71) Applicant: University of Rijeka Faculty of Medicine, Rijeka (HR)

(72) Inventor: Stipan Jonjic, Viskovo (HR)

(73) Assignee: UNIVERSITY OF RIJEKA FACULTY OF MEDICINE, Rijeka (HR)

( * ) Notice: Subject to any disclaimer, the term of this patent is extended or adjusted under 35 U.S.C. 154(b) by 0 days.

(21) Appl. No.: 15/011,601

(22) Filed: Jan. 31, 2016

(65) Prior Publication Data

US 2017/0274057 A1  Sep. 28, 2017

Related U.S. Application Data

(63) Continuation of application No. 13/684,241, filed on Nov. 22, 2012, now abandoned.

(60) Provisional application No. 61/562,738, filed on Nov. 22, 2011.

(51) Int. Cl.
| | |
|---|---|
| A61K 39/00 | (2006.01) |
| C12N 7/04 | (2006.01) |
| A61K 39/02 | (2006.01) |
| A61K 39/04 | (2006.01) |
| A61K 39/12 | (2006.01) |
| C12N 7/00 | (2006.01) |

(52) U.S. Cl.
CPC .......... *A61K 39/00* (2013.01); *A61K 39/0208* (2013.01); *A61K 39/04* (2013.01); *A61K 39/12* (2013.01); *C12N 7/00* (2013.01); *C12N 7/045* (2013.01); *A61K 2039/5254* (2013.01); *A61K 2039/5256* (2013.01); *C12N 2710/16121* (2013.01); *C12N 2710/16134* (2013.01); *C12N 2710/16143* (2013.01); *C12N 2710/16162* (2013.01); *C12N 2740/16234* (2013.01); *C12N 2760/16134* (2013.01); *C12N 2760/18534* (2013.01)

(58) Field of Classification Search
CPC ................ A61K 45/00; A61K 2039/53; A61K 2039/545; A61K 2039/5256; A61K 2039/55; A61K 2039/572; A61K 39/12; A61K 39/0011; A61K 2039/5254; A61K 35/17; A61P 31/14; C07K 14/005; Y02A 50/412; C12N 2740/15034; C12N 2310/141; C12N 2710/16134; C12N 15/86; C12N 15/113; C12N 7/045; C12N 2710/16171; C12N 2710/16143; C12N 2710/16121; C12N 2710/16162; C12N 7/00
See application file for complete search history.

(56) References Cited

U.S. PATENT DOCUMENTS

| | | | |
|---|---|---|---|
| 8,129,167 B2 | 3/2012 | Cosman | |
| 8,207,316 B1 | 6/2012 | Bentwich | |
| 2003/0195337 A1 | 10/2003 | Cosman | |
| 2007/0077241 A1* | 4/2007 | Spies | C07K 16/2851 424/133.1 |
| 2008/0038248 A1 | 2/2008 | Trowsdale et al. | |
| 2008/0044384 A1* | 2/2008 | Kemble | A61K 39/245 424/93.2 |
| 2008/0242610 A1* | 10/2008 | Wagner | C07K 14/70539 514/1.1 |
| 2009/0274699 A1 | 11/2009 | Cosman | |
| 2009/0324597 A1* | 12/2009 | Cosman | C07K 14/705 424/139.1 |

FOREIGN PATENT DOCUMENTS

WO  2011138040 A2  11/2011

OTHER PUBLICATIONS

Farrell, H. & Shellam, G., Characterization of neutralizing monoclonal antibodies to murine cytomegalovirus, J. Gen. Virol., 71:655-64, 1990.
Farrell, H. & Shellam, G., Protection against murine cytomegalovirus infection by passive transfer of neutralizing and non-neutralizing monoclonal antibodies, J. Gen. Virol., 72:149-56, 1991.
Fossum, E. et al., Evolutionarily conserved herpesviral protein interaction networks, PLoS Pathog., 5:e1000570, 2009.
Fowler, K. et al., Maternal immunity and prevention of congenital cytomegalovirus infection, JAMA, 289:1008-11, 2003.
French, A. et al., Escape of mutant double-stranded DNA virus from innate immune control, Immunity, 20:747-56, 2004.
Gazit, R. et al., Lethal influenza infection in the absence of the natural killer cell receptor gene Ncr1, Nat. Immunol., 7:517-23, 2006.
Gerna, G. et al., Early identification of human cytomegalovirus strains by the shell vial assay is prevented by a novel amino acid substitution in UL123 IE1 gene product, J. Clin. Microbiol., 41:4494-5, 2003.
Gerna, G. et al., Human cytomegalovirus serum neutralizing antibodies block virus infection of endothelial/epithelial cells, but not fibroblasts, early during primary infection, J. Gen. Virol., 89:853-65, 2008.
Gerna, G. et al., The attenuated Towne strain of human cytomegalovirus may revert to both endothelial cell tropism and leuko- (neutrophil- and monocyte-) tropism in vitro, J. Gen. Virol., 83:1993-2000, 2002.
Gilfillan, S. et al., NKG2D recruits two distinct adapters to trigger NK cell activation and costimulation, Nat. Immunol., 3:1150-5, 2002.

(Continued)

*Primary Examiner* — Rachel B Gill
(74) *Attorney, Agent, or Firm* — Rothwell, Figg, Ernst & Manbeck, P.C.

(57) ABSTRACT

The present invention relates to a beta-herpesvirus, preferably a recombinant beta-herpesvirus, wherein the beta-herpesvirus comprises at least one heterologous nucleic acid, wherein the at least one heterologous nucleic acid comprises a gene encoding a cellular ligand.

15 Claims, 78 Drawing Sheets

Specification includes a Sequence Listing.

(56) References Cited

OTHER PUBLICATIONS

Girardi, M. et al., Regulation of cutaneous malignancy by gammadelta T cells, Science, 294:605-9, 2001.
Slavuljica I, et. al. Recombinant mouse cytomegalovirus expressing a ligand for the NKG2D receptor is attenuated and has improved vaccine properties. J Clin Invest. Dec. 2010;120(12):4532-45. Epub Nov. 22, 2010.
Rizvanov AA, van Geelen AG, Morzunov S, Otteson EW, Bohlman C, Pad GS, St Jeor SC. Generation of a recombinant cytomegalovirus for expression of a hantavirus glycoprotein. J Virol. Nov. 2003;77(22):12203-10.
Miller-Kittrell M, Sparer TE. Feeling manipulated: cytomegalovirus immune manipulation. Virol J. Jan. 9, 2009;6:4.
Casarosa P, Gruijthuijsen YK, Michel D, Beisser PS, Holl J, Fitzsimons CP, Verzijl D, Bruggeman CA, Mertens T, Leurs R, Vink C, Smit MJ. Constitutive signaling of the human cytomegalovirus-encoded receptor UL33 differs from that of its rat cytomegalovirus homolog R33 by promiscuous activation of G proteins of the Gq, Gi, and Gs classes. J Biol Chem.
Kielczewska A, Pyzik M, Sun T, Krmpotic A, Lodoen MB, Munks MW, Babic M, Hill AB, Koszinowski UH, Jonjic S, Lanier LL, Vidal SM. Ly49P recognition of cytomegalovirus-infected cells expressing H2-Dk and CMV-encoded m04 correlates with the NK cell antiviral response. J Exp Med. Mar. 16, 2009;206(3):515-23. Epub Mar. 2, 2009.
Malouli et al, Reevaluation of the Coding Potential and Proteomic Analysis of the BAC-Derived Rhesus Cytomegalovirus Strain 68-1. Journal of Virology, Sep. 2012, vol. 86, No. 17; pp. 8959-8973.
Gonczol, E. & Plotkin, S., Development of a cytomegalovirus vaccine: lessons from recent clinical trials, Expert Opin. Biol. Ther., 1:401-12, 2001.
Griffiths, P., The beginning of the end of a long wait for a vaccine against cytomegalovirus, Rev. Med. Virol., 19:117-9, 2009.
Groh, V. et al., Cell stress-regulated human major histocompatibility complex class I gene expressed in gastrointestinal epithelium, Proc. Natl. Acad. Sci. USA, 93:12445-50, 1996.
Groh, V. et al., Costimulation of CD8alphabeta T cells by NKG2D via engagement by MIC induced on virus-infected cells, Nat Immunol., 2:255-60, 2001.
Hahn, G. et al., Cloning of the genomes of human cytomegalovirus strains Toledo, TownevarRIT3, and Towne long as BACs and site-directed mutagenesis using a PCR-based technique, Virology, 307:164-77, 2003.
Hahn, G. et al., The human cytomegalovirus ribonucleotide reductase homolog UL45 is dispensable for growth in endothelial cells, as determined by a BAC-cloned clinical isolate of human cytomegalovirus with preserved wild-type characteristics, J. Virol., 76:9551-9555, 2002.
Hamprecht, K. et al., Epidemiology of transmission of cytomegalovirus from mother to preterm infant by breastfeeding, Lancet, 357:513-8, 2001.
Hasan, M. et al., Selective down-regulation of the NKG2D ligand H60 by mouse cytomegalovirus m155 glycoprotein, J. Virol., 79:2920-30, 2005.
Ho, E. et al., Murine Nkg2d and Cd94 are clustered within the natural killer complex and are expressed independently in natural killer cells, Proc. Natl. Acad. Sci. USA, 95:6320-5, 1998.
Hobom, U. et al., Fast screening procedures for random transposon libraries of cloned herpesvirus genomes: mutational analysis of human cytomegalovirus envelope glycoprotein genes, J. Virol., 74:7720-9, 2000.
Holtappels, R. et al., Adoptive CD8 T cell control of pathogens cannot be improved by combining protective epitope specificities, J. Infect. Dis., 197:622-9, 2008.
Holtappels, R. et al., CD8 T-cell-based immunotherapy of cytomegalovirus infection: "proof of concept" provided by the murine model, Med. Microbiol. Immunol., 197:125-34, 2008.
Holtappels, R. et al., Enrichment of immediate-early 1 (m123/pp89) peptide-specific CD8 T cells in a pulmonary CD62L(lo) memory-effector cell pool during latent murine cytomegalovirus infection of the lungs, J. Virol., 74:11495-11503, 2000.
Holtappels, R. et al., Experimental preemptive immunotherapy of murine cytomegalovirus disease with CD8 T-cell lines specific for ppM83 and pM84, the two homologs of human cytomegalovirus tegument protein ppUL83 (pp65), J. Virol., 75:6584-600, 2001.
Holtappels, R. et al., Two antigenic peptides from genes m123 and m164 of murine cytomegalovirus quantitatively dominate CD8 T-cell memory in the H-2d haplotype, J. Virol., 76:151-64, 2002.
Houchins, J. et al., DNA sequence analysis of NKG2, a family of related cDNA clones encoding type II integral membrane proteins on human natural killer cells, J. Exp. Med., 173:1017-20, 1991.
Humann, J. & Lenz, L., Activation of naive NK cells in response to Listeria monocytogenes requires IL-18 and contact with infected dendritic cells, J. Immunol., 184:5172-8, 2010.
Jackson, S. et al., Human cytomegalovirus immunity and immune evasion, Virus Res., 157:151-60, 2011.
Jamieson, A. et al., The role of the NKG2D immunoreceptor in immune cell activation and natural killing, Immunity, 17:19-29, 2002.
Jonjić, S. et al., Antibodies are not essential for the resolution of primary cytomegalovirus infection but limit dissemination of recurrent virus, J. Exp. Med., 179:1713-7, 1994.
Jonjić, S. et al., Dissection of the antiviral NK cell response by MCMV mutants, Methods Mol. Biol., 415:127-49, 2008.
Jonjić, S. et al., Efficacious control of cytomegalovirus infection after long-term depletion of CD8+ T lymphocytes, J. Virol., 64:5457-64, 1990.
Jonjić, S. et al., Site-restricted persistent cytomegalovirus infection after selective long-term depletion of CD4+ T lymphocytes, J. Exp. Med., 169:1199-212, 1989.
Kapp, M. et al., Adoptive immunotherapy of HCMV infection, Cytotherapy, 9:699-711, 2007.
Karrer, U. et al., Expansion of protective CD8+ T-cell responses driven by recombinant cytomegaloviruses, J. Virol., 78:2255-64, 2004.
Karrer, U. et al., Memory inflation: continuous accumulation of antiviral CD8+ T cells over time, J. Immunol., 170:2022-9, 2003.
Kimmel, B. et al., Identification of immunodominant antigens from Helicobacter pylori and evaluation of their reactivities with sera from patients with different gastroduodenal pathologies, Infect. Immun., 68:915-20, 2000.
Klenerman, P. & Dunbar, P., CMV and the art of memory maintenance, Immunity, 29:520-2, 2008.
Koffron, A. et al., Cellular localization of latent murine cytomegalovirus , J. Virol., 72:95-103, 1998.
Komatsu, H. et al., Population analysis of antiviral T cell responses using MHC class I-peptide tetramers, Clin. Exp. Immunol., 134:9-12, 2003.
Koontz, T. et al., Altered development of the brain after focal herpesvirus infection of the central nervous system, J. Exp. Med., 205:423-35, 2008.
Koszinowski, U. et al., The role of CD4 and CD8 T cells in viral infections, Curr. Opin. Immunol., 3:471-5, 1991.
Krmpotić, A. et al., MCMV glycoprotein gp40 confers virus resistance to CD8+ T cells and NK cells in vivo, Nat. Immunol., 3:529-35, 2002.
Krmpotić, A. et al., NK cell activation through the NKG2D ligand MULT-1 is selectively prevented by the glycoprotein encoded by mouse cytomegalovirus gene m145, J. Exp. Med., 201, 211-20, 2005.
Krmpotić, A. et al., Pathogenesis of murine cytomegalovirus infection, Microbes Infect., 5:1263-77, 2003.
Krmpotić, A. et al., The immunoevasive function encoded by the mouse cytomegalovirus gene m152 protects the virus against T cell control in vivo, J. Exp. Med., 190:1285-96, 1999.
Lanier, L. et al., On guard—activating NK cell receptors, Nat. Immunol., 2:23-7, 2001.
Lemmermann, N. et al., Immune evasion proteins of murine cytomegalovirus preferentially affect cell surface display of recently generated peptide presentation complexes, J. Virol., 84:1221-36, 2010.

(56) References Cited

OTHER PUBLICATIONS

Lenac, T. et al., Murine cytomegalovirus regulation of NKG2D ligands, Med. Microbiol. Immunol., 197:159-66, 2008.
Andrews, D. et al., Innate immunity defines the capacity of antiviral T cells to limit persistent infection, J. Exp. Med., 207:1333-43, 2010.
Arapovic, J. et al., Differential susceptibility of RAE-1 isoforms to mouse cytomegalovirus, J. Virol., 83:8198-207, 2009.
Arase, H. et al., Direct recognition of cytomegalovirus by activating and inhibitory NK cell receptors, Science, 296:1323-6, 2002.
Arvin, A. et al., Vaccine development to prevent cytomegalovirus disease: report from the National Vaccine Advisory Committee, Clin. Infect. Dis., 39:233-9, 2004.
Ashiru, O. et al., NKG2D ligand MICA is retained in the cis-Golgi apparatus by human cytomegalovirus protein UL142, J. Virol., 83:12345-54, 2009.
Babić, M. et al., All is fair in virus-host interactions: NK cells and cytomegalovirus, Trends Mol. Med., 17:677-85, 2011.
Bacon, L. et al., Two human ULBP/RAET1 molecules with transmembrane regions are ligands for NKG2D, J. Immunol., 173:1078-84, 2004.
Balthesen, M. et al., Lungs are a major organ site of cytomegalovirus latency and recurrence, J. Virol., 67:5360-6, 1993.
Barton, E. et al., Herpesvirus latency confers symbiotic protection from bacterial infection, Nature, 447:326-9, 2007.
Bauer, S. et al., Activation of NK cells and T cells by NKG2D, a receptor for stress-inducible MICA, Science, 285:727-9, 1999.
Berg, S. et al., Molecular characterization of rat NKR-P2, a lectin-like receptor expressed by NK cells and resting T cells, Int. Immunol., 10:379-85, 1998.
Boppana, S. & Britt, W., Antiviral antibody responses and intra-uterine transmission after primary maternal cytomegalovirus infection, J. Infect. Dis., 171:1115-21, 1995.
Boppana, S. et al., Intrauterine transmission of cytomegalovirus to infants of women with preconceptional immunity, N. Engl. J. Med., 344:1366-71, 2001.
Boppana, S. et al., Neuroradiographic findings in the newborn period and long-term outcome in children with symptomatic congenital cytomegalovirus infection, Pediatrics, 99:409-14, 1997.
Boppana, S. et al., Symptomatic Congenital Cytomegalovirus Infection in Infants Born to Mothers With Preexisting Immunity to Cytomegalovirus, Pediatrics, 104:55-60, 1999.
Boppana, S. et al., Symptomatic congenital cytomegalovirus infection: neonatal morbidity and mortality, Pediatr. Infect. Dis. J., 11:93-9, 1992.
Borst, E. et al., Cloning of the human cytomegalovirus (HCMV) genome as an infectious bacterial artificial chromosome in *Escherichia coli*: a new approach for construction of HCMV mutants, J. Virol., 73:8320-9, 1999.
Borst, E. et al., Use of bacterial artificial chromosomes in generating targeted mutations in human and mouse cytomegaloviruses, Curr. Protoc. Immunol., 77:10.32.1-10.32.30, 2007.
Brandt, L. et al., ESAT-6 subunit vaccination against *Mycobacterium tuberculosis*, Infect. Immun., 68:791-5, 2000.
Bratcher, D. et al., Effect of passive antibody on congenital cytomegalovirus infection in guinea pigs, J. Infect. Dis., 172:944-50, 1995.
Braud, V. et al., Viral evasion of natural killer cells during human cytomegalovirus infection, Curr. Top. Microbiol. Immunol., 269:117-29, 2002.
Brestrich, G. et al., Generation of HCMV-specific T-cell lines from seropositive solid-organ-transplant recipients for adoptive T-cell therapy, J. Immunother., 32:932-40, 2009.
Brune, W. et al., A mouse model for cytomegalovirus infection, Curr. Protoc. Immunol., Chapter 19:Unit 19.7, 2001.
Bubić, I. et al., Gain of virulence caused by loss of a gene in murine cytomegalovirus, J. Virol., 78:7536-44, 2004.
Campbell, A. et al., The salivary glands as a privileged site of cytomegalovirus immune evasion and persistence, Med. Microbiol. Immunol., 197:205-13, 2008.

Carayannopoulos, L. et al., Cutting edge: murine UL16-binding protein-like transcript 1: a newly described transcript encoding a high-affinity ligand for murine NKG2D, J. Immunol., 169:4079-83, 2002.
Carlyle, J. et al., Evolution of the Ly49 and Nkrp1 recognition systems, Semin. Immunol., 20:321-30, 2008.
Cekinović, D. et al., Passive immunization reduces murine cytomegalovirus-induced brain pathology in newborn mice, J. Virol., 82:12172-80, 2008.
Cerwenka, A. et al., Ectopic expression of retinoic acid early inducible-1 gene (RAE-1) permits natural killer cell-mediated rejection of a MHC class I-bearing tumor in vivo, Proc. Natl. Acad. Sci. USA, 98:11521-6, 2001.
Cerwenka, A. et al., Retinoic acid early inducible genes define a ligand family for the activating NKG2D receptor in mice, Immunity, 12:721-7, 2000.
Chalupny, N. et al., Down-regulation of the NKG2D ligand MICA by the human cytomegalovirus glycoprotein UL142, Biochem. Biophys. Res. Commun., 346:175-81, 2006.
Chatterjee, A. et al., Modification of maternal and congenital cytomegalovirus infection by anti-glycoprotein b antibody transfer in guinea pigs, J. Infect. Dis., 183:1547-53, 2001.
Čičin-Šain, L. et al., Frequent coinfection of cells explains functional in vivo complementation between cytomegalovirus variants in the multiply infected host, J. Virol., 79:9492-502, 2005.
Čičin-Šain, L. et al., Targeted deletion of regions rich in immune-evasive genes from the cytomegalovirus genome as a novel vaccine strategy, J. Virol., 81:13825-34, 2007.
Cosman, D. et al., ULBPs, novel MHC class I-related molecules, bind to CMV glycoprotein UL16 and stimulate NK cytotoxicity through the NKG2D receptor, Immunity, 14:123-33, 2001.
Crumpler, M. et al., A live guinea pig cytomegalovirus vaccine deleted of three putative immune evasion genes is highly attenuated but remains immunogenic in a vaccine/challenge model of congenital cytomegalovirus infection, Vaccine, 27:4209-18, 2009.
Davison, A., Herpesvirus systematics, Vet. Microbiol., 143:52-69, 2010.
Del Val, M. et al., Efficient processing of an antigenic sequence for presentation by MHC class I molecules depends on its neighboring residues in the protein, Cell, 66:1145-53, 1991.
Diefenbach, A. et al., A novel ligand for the NKG2D receptor activates NK cells and macrophages and induces tumor immunity, Eur. J. Immunol., 33:381-91, 2003.
Diefenbach, A. et al., Ligands for the murine NKG2D receptor: expression by tumor cells and activation of NK cells and macrophages, Nat. Immunol., 1:119-26, 2000.
Diefenbach, A. et al., Rae1 and H60 ligands of the NKG2D receptor stimulate tumour immunity, Nature, 413:165-71, 2001.
Diefenbach, A. et al., Selective associations with signaling proteins determine stimulatory versus costimulatory activity of NKG2D, Nat. Immunol., 3:1142-9, 2002.
Dietrich, J. et al., Exchanging ESAT6 with TB10.4 in an Ag85B fusion molecule-based tuberculosis subunit vaccine: efficient protection and ESAT6-based sensitive monitoring of vaccine efficacy, J. Immunol., 174:6332-9, 2005.
Dölken, L. et al., Mouse cytomegalovirus microRNAs dominate the cellular small RNA profile during lytic infection and show features of posttranscriptional regulation, J. Virol., 81:13771-82, 2007.
Dunn, C. et al., Human cytomegalovirus glycoprotein UL16 causes intracellular sequestration of NKG2D ligands, protecting against natural killer cell cytotoxicity, J. Exp. Med., 197:1427-39, 2003.
Ehrlich, L. et al., Engagement of NKG2D by cognate ligand or antibody alone is insufficient to mediate costimulation of human and mouse CD8+ T cells, J. Immunol., 174:1922-31, 2005.
Einsele, H., Immunotherapy for CMV infection, Cytotherapy, 4:435-6, 2002.
Eleme, K. et al., Cell surface organization of stress-inducible proteins ULBP and MICA that stimulate human NK cells and T cells via NKG2D, J. Exp. Med., 199:1005-10, 2004.
Elliott, J. & Yokoyama, W., Unifying concepts of MHC-dependent natural killer cell education, Trends Immunol., 32:364-72, 2011.

(56) References Cited

OTHER PUBLICATIONS

Erlach, K. et al., Activation of hepatic natural killer cells and control of liver-adapted lymphoma in the murine model of cytomegalovirus infection, Med. Microbiol. Immunol., 197:167-78, 2008.
Schleiss, M., Cytomegalovirus vaccine development, Curr. Top. Microbiol. Immunol., 325:361-382, 2008.
Schnee, M. et al., Common and specific properties of herpesvirus UL34/UL31 protein family members revealed by protein complementation assay, J. Virol., 80:11658-66, 2006.
Sinzger, C. & Jahn, G., Human cytomegalovirus cell tropism and pathogenesis, Intervirology, 39:302-19, 1996.
Sinzger, C. et al., Cloning and sequencing of a highly productive, endotheliotropic virus strain derived from human cytomegalovirus TB40/E, J. Gen. Virol., 89:359-68, 2008.
Sinzger, C. et al., Cytomegalovirus cell tropism, Curr. Top. Microbiol. Immunol., 325:63-83, 2008.
Sinzger, C. et al., Modification of human cytomegalovirus tropism through propagation in vitro is associated with changes in the viral genome, J. Gen. Virol., 80:2867-77, 1999.
Smith, H. et al., Recognition of a virus-encoded ligand by a natural killer cell activation receptor,Proc. Natl. Acad. Sci. USA, 99:8826-31, 2002.
Snyder, C. et al., Memory inflation during chronic viral infection is maintained by continuous production of short-lived, functional T cells, Immunity, 29:650-9, 2008.
Snyder, C. et al., Sustained CD8+ T cell memory inflation after infection with a single-cycle cytomegalovirus, PLoS Pathog., 7:e1002295, 2011.
Snydman, D. et al., Use of cytomegalovirus immune globulin to prevent cytomegalovirus disease in renal-transplant recipients, N. Engl. J. Med., 317:1049-54, 1987.
Stanton, R. et al., Reconstruction of the complete human cytomegalovirus genome in a BAC reveals RL13 to be a potent inhibitor of replication, J. Clin. Invest., 120:3191-208, 2010.
Steel, J. et al., Influenza virus vaccine based on the conserved hemagglutinin stalk domain, mBio, 1(1):e00018-10, 2010.
Steininger, C. et al., Cytomegalovirus disease in the era of highly active antiretroviral therapy (HAART), J. Clin. Virol., 37:1-9, 2006.
Stern-Ginossar, N. et al., Host immune system gene targeting by a viral miRNA, Science, 317:376-81, 2007.
Stern-Ginossar, N. et al., Human microRNAs regulate stress-induced immune responses mediated by the receptor NKG2D, Nat. Immunol., 9:1065-73, 2008.
Streblow, D. et al., Acceleration of allograft failure by cytomegalovirus, Curr. Opin. Immunol., 19:577-82, 2007.
Sutherland, C. et al., ULBPs, human ligands of the NKG2D receptor, stimulate tumor immunity with enhancement by IL-15, Blood, 108:1313-9, 2006.
Takada, A. et al., Two novel NKG2D ligands of the mouse H60 family with differential expression patterns and binding affinities to NKG2D, J. Immunol., 180:1678-85, 2008.
Tischer, B. et al., En passant mutagenesis: a two step markerless red recombination system, Methods Mol. Biol., 634:421-30, 2010.
Tischer, B. et al., Two-step red-mediated recombination for versatile high-efficiency markerless DNA manipulation in *Escherichia coli*, Biotechniques, 40:191-7, 2006.
Tomasec, P. et al., Downregulation of natural killer cell-activating ligand CD155 by human cytomegalovirus UL141, Nat Immunol., 6:181-8, 2005.
Trgovcich, J. et al., Immune responses and cytokine induction in the development of severe hepatitis during acute infections with murine cytomegalovirus, Arch. Virol., 145:2601-18, 2000.
Unanue, E., Studies in listeriosis show the strong symbiosis between the innate cellular system and the T-cell response, Immunol. Rev., 158:11-25, 1997.
Valés-Gómez, M. et al., Expression of the UL16 glycoprotein of Human Cytomegalovirus protects the virus-infected cell from attack by natural killer cells, BMC Immunol., 4:4, 2003.
Vance, R. et al., Cloning of a mouse homolog of CD94 extends the family of C-type lectins on murine natural killer cells, Eur. J. Immunol., 27:3236-41, 1997.
Vilches, C. & Parham, P., KIR: diverse, rapidly evolving receptors of innate and adaptive immunity, Annu. Rev. Immunol., 20:217-51, 2002.
Vivier, E. et al., Innate or adaptive immunity? The example of natural killer cells, Science, 331:44-9, 2011.
Voigt, V. et al., Murine cytomegalovirus m157 mutation and variation leads to immune evasion of natural killer cells, Proc. Natl. Acad. Sci. USA, 100:13483-8, 2003.
Wagner, M. et al., Major histocompatibility complex class I allele-specific cooperative and competitive interactions between immune evasion proteins of cytomegalovirus, J. Exp. Med., 196:805-16, 2002.
Wagner, M. et al., Systematic excision of vector sequences from the BAC-cloned herpesvirus genome during virus reconstitution, J. Virol., 73:7056-60, 1999.
Welte, S. et al., Selective intracellular retention of virally induced NKG2D ligands by the human cytomegalovirus UL16 glycoprotein, Eur. J. Immunol., 33:194-203, 2003.
Whang, M. et al., Costimulation of dendritic epidermal gammadelta T cells by a new NKG2D ligand expressed specifically in the skin, J. Immunol., 182:4557-64, 2009.
Wheat, R. et al., Quantitative measurement of infectious murine cytomegalovirus genomes in real-time PCR, J. Virol. Methods, 112:107-13, 2003.
Wherry, E. & Ahmed, R., Memory CDB T-cell differentiation during viral infection, J. Virol., 78:5535-45, 2004.
Whitley, R., Congenital cytomegalovirus infection: epidemiology and treatment, Adv. Exp. Med. Biol., 549:155-60, 2004.
Wilkinson, G. et al., Modulation of natural killer cells by human cytomegalovirus, J. Clin. Virol., 41:206-12, 2008.
Wu, J. et al., An activating immunoreceptor complex formed by NKG2D and DAP10, Science, 285:730-2, 1999.
Wu, J. et al., Intracellular retention of the MHC class I-related chain B ligand of NKG2D by the human cytomegalovirus UL16 glycoprotein, J. Immunol., 170:4196-200, 2003.
Yamaoka, Y. et al., Roles of Helicobacter pylori BabA in gastroduodenal pathogenesis, World J. Gastroenterol., 14:4265-72, 2008.
Yim, D. et al., Molecular cloning and characterization of pig immunoreceptor DAP10 and NKG2D, Immunogenetics, 53:243-9, 2001.
Yu, D. et al., Construction of a self-excisable bacterial artificial chromosome containing the human cytomegalovirus genome and mutagenesis of the diploid TRL/IRL13 gene, J. Virol., 76:2316-28, 2002.
Zhong, J. & Khanna, R., Vaccine strategies against human cytomegalovirus infection, Expert Rev. Anti. Infect. Ther., 5:449-59, 2007.
Ziegler, H. et al., A mouse cytomegalovirus glycoprotein retains MHC class I complexes in the ERGIC/cis-Golgi compartments, Immunity, 6:57-66, 1997.
Radosavljevic, M. et al., A cluster of ten novel MHC class I related genes on human chromosome 6q24.2-q25.3, Genomics, 79:114-23, 2002.
Lenac, T. et al., The herpesviral Fc receptor fcr-1 down-regulates the NKG2D ligands MULT-1 and H60, J. Exp. Med., 203:1843-50, 2006.
Lilleri, D. et al., Human cytomegalovirus-specific T cell reconstitution in young patients receiving T cell-depleted, allogeneic hematopoietic stem cell transplantation, J. Infect. Dis., 199:829-36, 2009.
Lisnić, V. et al., Modulation of natural killer cell activity by viruses, Curr. Opin. Microbiol., 13:530-9, 2010.
Ljungman, P., CMV infections after hematopoietic stem cell transplantation, Bone Marrow Transplant., 42 Suppl 1: S70-S72, 2008.
Lodoen, M. et al., NKG2D-mediated natural killer cell protection against cytomegalovirus is impaired by viral gp40 modulation of retinoic acid early inducible 1 gene molecules, J. Exp. Med., 197:1245-53, 2003.

(56) References Cited

OTHER PUBLICATIONS

Lodoen, M. et al., The cytomegalovirus m155 gene product subverts natural killer cell antiviral protection by disruption of H60-NKG2D interactions, J. Exp. Med., 200:1075-81, 2004.
Lopez-Botet, M. et al., Paired inhibitory and triggering NK cell receptors for HLA class I molecules, Hum. Immunol., 61:7-17, 2000.
Maasho, K. et al., NKG2D is a costimulatory receptor for human naive CD8+ T cells, J. Immunol., 174:4480-4, 2005.
Malarkannan, S. et al., The molecular and functional characterization of a dominant minor H antigen, H60, J. Immunol., 161:3501-9, 1998.
Marchini, A. et al., Human cytomegalovirus with IE-2 (UL22) deleted fails to express early lytic genes, J. Virol., 75:1870-8, 2001.
Markiewicz, M. et al., Costimulation through NKG2D enhances murine CD8+ CTL function: similarities and differences between NKG2D and CD28 costimulation, J. Immunol., 175:2825-33, 2005.
Messerle, M. et al., Cloning and mutagenesis of a herpesvirus genome as an infectious bacterial artificial chromosome, Proc. Natl. Acad. Sci. USA, 94:14759-63, 1997.
Mitrović, M. et al., The NK cell response to mouse cytomegalovirus infection affects the level and kinetics of the early CD8(+) T-cell response, J. Virol., 86:2165-75, 2012.
Mohr, C. et al., A spread-deficient cytomegalovirus for assessment of first-target cells in vaccination, J. Virol., 84:7730-42, 2010.
Moretta, A. et al., Activating receptors and coreceptors involved in human natural killer cell-mediated cytolysis, Annu. Rev. Immunol., 19:197-223, 2001.
Moretta, L & Moretta, A., Unravelling natural killer cell function: triggering and inhibitory human NK receptors, EMBO J., 23:255-9, 2004.
Müller, S. et al., Structure of the HCMV UL16-MICB complex elucidates select binding of a viral immunoevasin to diverse NKG2D ligands, PLoS Pathog., 6(1):e1000723, 2010.
Murphy, E. et al., Coding potential of laboratory and clinical strains of human cytomegalovirus, Proc. Natl. Acad. Sci. USA, 100:14976-81, 2003.
Mwintshi, K. & Brennan, D., Prevention and management of cytomegalovirus infection in solid-organ transplantation, Expert Rev. Anti. Infect. Ther., 5:295-304, 2007.
Nakagawa, M. et al., HLA class I binding promiscuity of the CD8 T-cell epitopes of human papillomavirus type 16 E6 protein, J. Virol., 81:1412-23, 2007.
Nigro, G. et al., Passive immunization during pregnancy for congenital cytomegalovirus infection, N. Engl. J. Med., 353:1350-62, 2005.
Nigro, G. et al., Regression of fetal cerebral abnormalities by primary cytomegalovirus infection following hyperimmunoglobulin therapy, Prenat. Diagn., 28:512-7, 2008.
Nomura, M. et al., Isolation and characterization of retinoic acid-inducible cDNA clones in F9 cells: one of the early inducible clones encodes a novel protein sharing several highly homologous regions with a *Drosophila* polyhomeotic protein, Differentiation, 57:39-50, 1994.
Ogasawara, K. et al., Function of NKG2D in natural killer cell-mediated rejection of mouse bone marrow grafts, Nat. Immunol., 6:938-45, 2005.
Pass, R. et al., Vaccine prevention of maternal cytomegalovirus infection, N. Engl. J. Med., 360:1191-9, 2009.
Peggs, K. et al., Adoptive cellular therapy for early cytomegalovirus infection after allogeneic stem-cell transplantation with virus-specific T-cell lines, Lancet, 362:1375-7, 2003.
Polić, B. et al., Hierarchical and redundant lymphocyte subset control precludes cytomegalovirus replication during latent infection, J. Exp. Med., 188:1047-54, 1998.
Pollock, J &Virgin, H., Latency, without persistence, of murine cytomegalovirus in the spleen and kidney, J. Virol.,69:1762-8, 1995.
Prod'Homme, V. et al., Human cytomegalovirus UL141 promotes efficient downregulation of the natural killer cell activating ligand CD112, J. Gen. Virol., 91:2034-9, 2010.

Raulet, D. & Guerra, N., Oncogenic stress sensed by the immune system: role of NK cell receptors, Nat. Rev. Immunol., 9:568-80, 2009.
Raulet, D., Roles of the NKG2D immunoreceptor and its ligands, Nat. Rev. Immunol., 3:781-90, 2003.
Ravetch, J. & Lanier, L., Immune inhibitory receptors, Science, 290:84-9, 2000.
Rawlinson, W. et al., Analysis of the complete DNA sequence of murine cytomegalovirus, J. Virol., 70:8833-49, 1996.
Reddehase, M. et al., Interstitial murine cytomegalovirus pneumonia after irradiation: characterization of cells that limit viral replication during established infection of the lungs, J. Virol., Aug;55(2):264-73, 1985.
Reddehase, M. et al., Mouse models of cytomegalovirus latency: overview, J. Clin. Virol., 25 Suppl 2:S23-36, 2002.
Reddehase, M. et al., The conditions of primary infection define the load of latent viral genome in organs and the risk of recurrent cytomegalovirus disease, J. Exp. Med., 179:185-93, 1994.
Reddehase, M., Antigens and immunoevasins: opponents in cytomegalovirus immune surveillance, Nat. Rev. Immunol., 2:831-44, 2002.
Reusser, P. et al., Cytotoxic T-lymphocyte response to cytomegalovirus after human allogeneic bone marrow transplantation: pattern of recovery and correlation with cytomegalovirus infection and disease, Blood, 78:1373-80, 1991.
Revello, M. M & Gerna, G., Human cytomegalovirus tropism for endothelial/epithelial cells: scientific background and clinical implications, Rev. Med. Virol., 20:136-55, 2010.
Riddell, S. & Greenberg, P., Principles for adoptive T cell therapy of human viral diseases, Annu. Rev. Immunol., 13:545-86, 1995.
Riddell, S. & Greenberg, P., T cell therapy of human CMV and EBV infection in immunocompromised hosts, Rev. Med. Virol., 7:181-92, 1997.
Riddell, S. et al., CD8+ cytotoxic T cell therapy of cytomegalovirus and HIV infection, Curr. Opin. Immunol., 5:484-91, 1993.
Riddell, S. et al., Restoration of viral immunity in immunodeficient humans by the adoptive transfer of T cell clones, Science, 257:238-41, 1992.
Robbins, S. et al., Natural killer cells promote early CD8 T cell responses against cytomegalovirus, PLoS Pathog., 3:e123, 2007.
Rölle, A. & Olweus, J., Dendritic cells in cytomegalovirus infection: viral evasion and host countermeasures, APMIS, 117:413-26, 2009.
Rölle, A. et al., Effects of human cytomegalovirus infection on ligands for the activating NKG2D receptor of NK cells: up-regulation of UL16-binding protein (ULBP)1 and ULBP2 is counteracted by the viral UL16 protein, J. Immunol., 171:902-8, 2003.
Rosen, D. et al., A Structural basis for the association of DAP12 with mouse, but not human, NKG2D, J. Immunol., 173:2470-8, 2004.
Sander, C. et al., Safety and immunogenicity of a new tuberculosis vaccine, MVA85A, in *Mycobacterium tuberculosis*-infected individuals, Am. J. Respir. Crit. Care Med., 179:724-733, 2009.
Schleiss, M., Comparison of vaccine strategies against congenital CMV infection in the guinea pig model, J. Clin. Virol., 41:224-230, 2008.
Arens et al., (2011) B7-mediated costimulation of CD4 T cells constrains cytomegalovirus persistence. J Virol 85(1): 390-396.
Barber and Sentman (2011) NKG2D receptor regulates human effector T-cell cytokine production. Blood 117(24): 6571-6581.
Dunn et al., (2003) Functional profiling of a human cytomegalovirus genome. Proc Natl Acad Sci U S A 100(24): 14223-14228.
Lemmermann et al., (2011) In vivo impact of cytomegalovirus evasion of CD8 T-cell immunity: facts and thoughts based on murine models. Virus Res 157(2): 161-174.
Loewendorf et al., (2004) Identification of a mouse cytomegalovirus gene selectively targeting CD86 expression on antigen-presenting cells. J Virol 78(23): 13062-13071.
Mintern et al., (2006) Viral interference with B7-1 costimulation: a new role for murine cytomegalovirus fc receptor—1. J Immunol 177(12): 8422-8431.
Rötzschke et al., (1991) Exact prediction of a natural T cell epitope. Eur J Immunol 21(11): 2891-2894.

(56) References Cited

OTHER PUBLICATIONS

Snyder et al., (2009) CD4+ T cell help has an epitope-dependent impact on CD8+ T cell memory inflation during murine cytomegalovirus infection. J Immunol 183(6): 3932-3941.
Soderquest et al., (2011) Monocytes control natural killer cell differentiation to effector phenotypes. Blood 117(17): 4511-4518 with erratum.

* cited by examiner

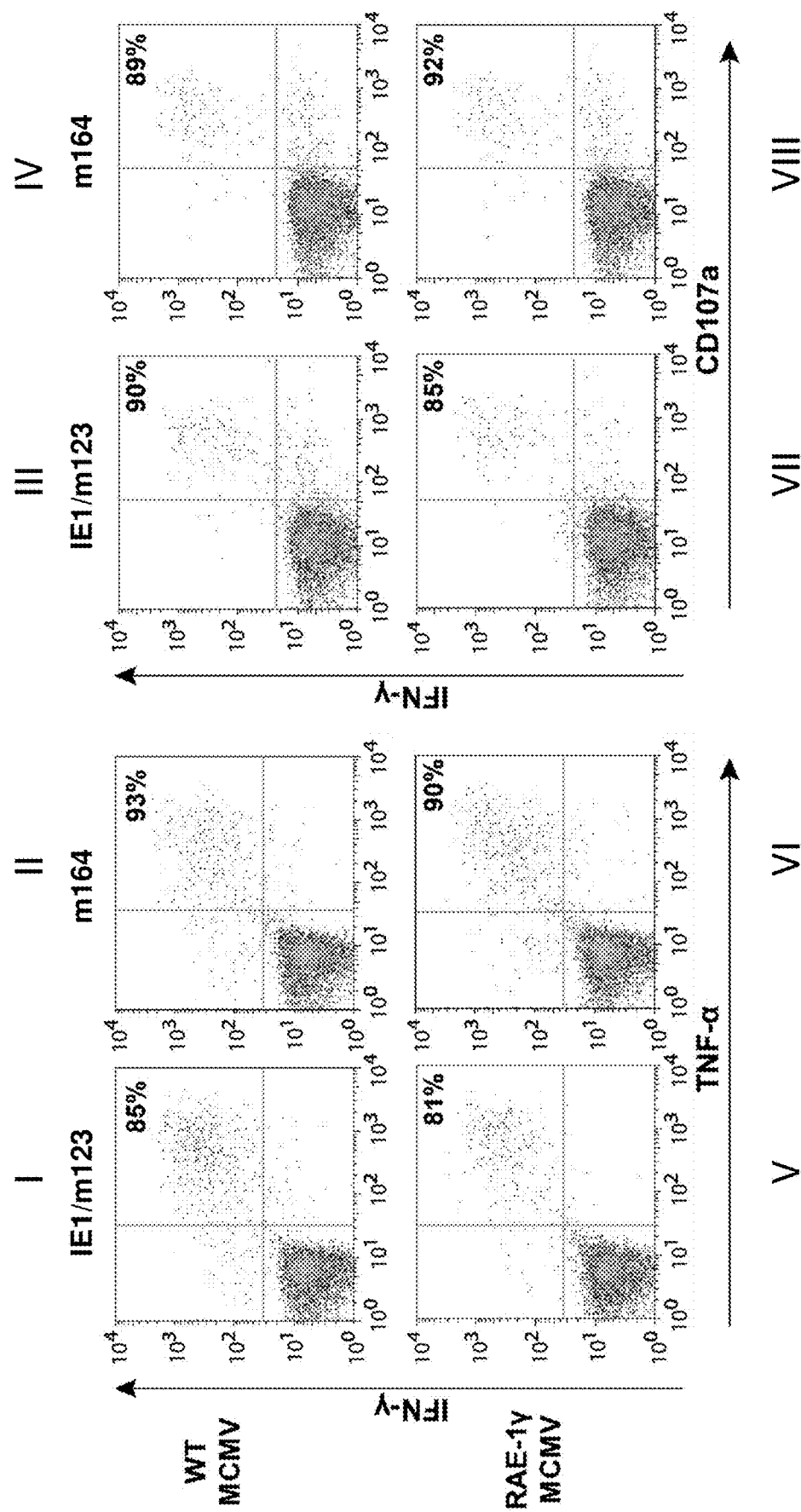

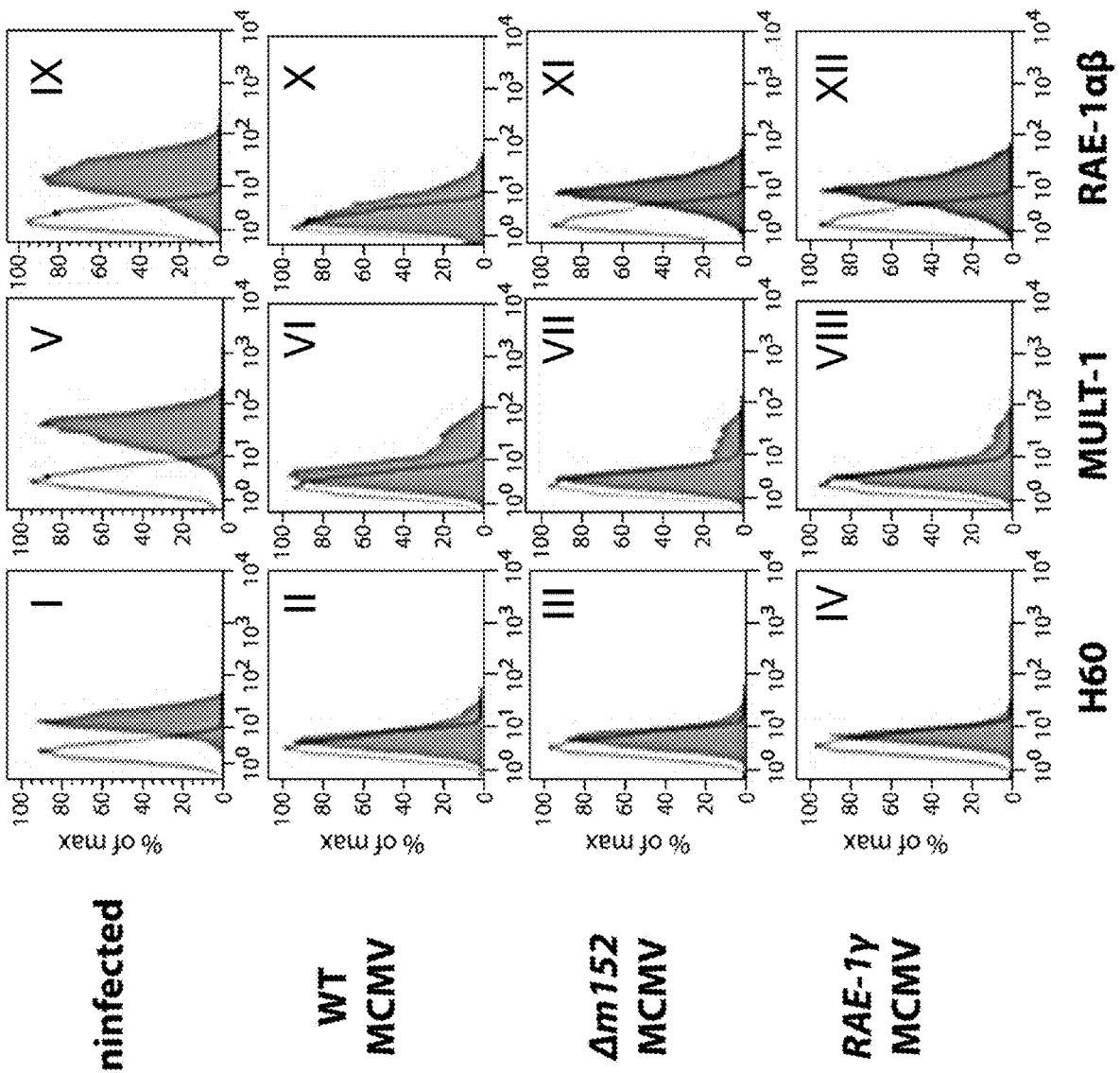

Fig. 12A-I
Fig. 12A-II
Fig. 12A-III
Fig. 12A-IV
Fig. 12A-V
Fig. 12A-VI
Fig. 12A-VII

A
control

B
unvaccinated

C
wt MCMV

D
MCMVList

E
Rae-1γMCMVList

F
Rae-1γMCMVList
CD8+ T cell depleted

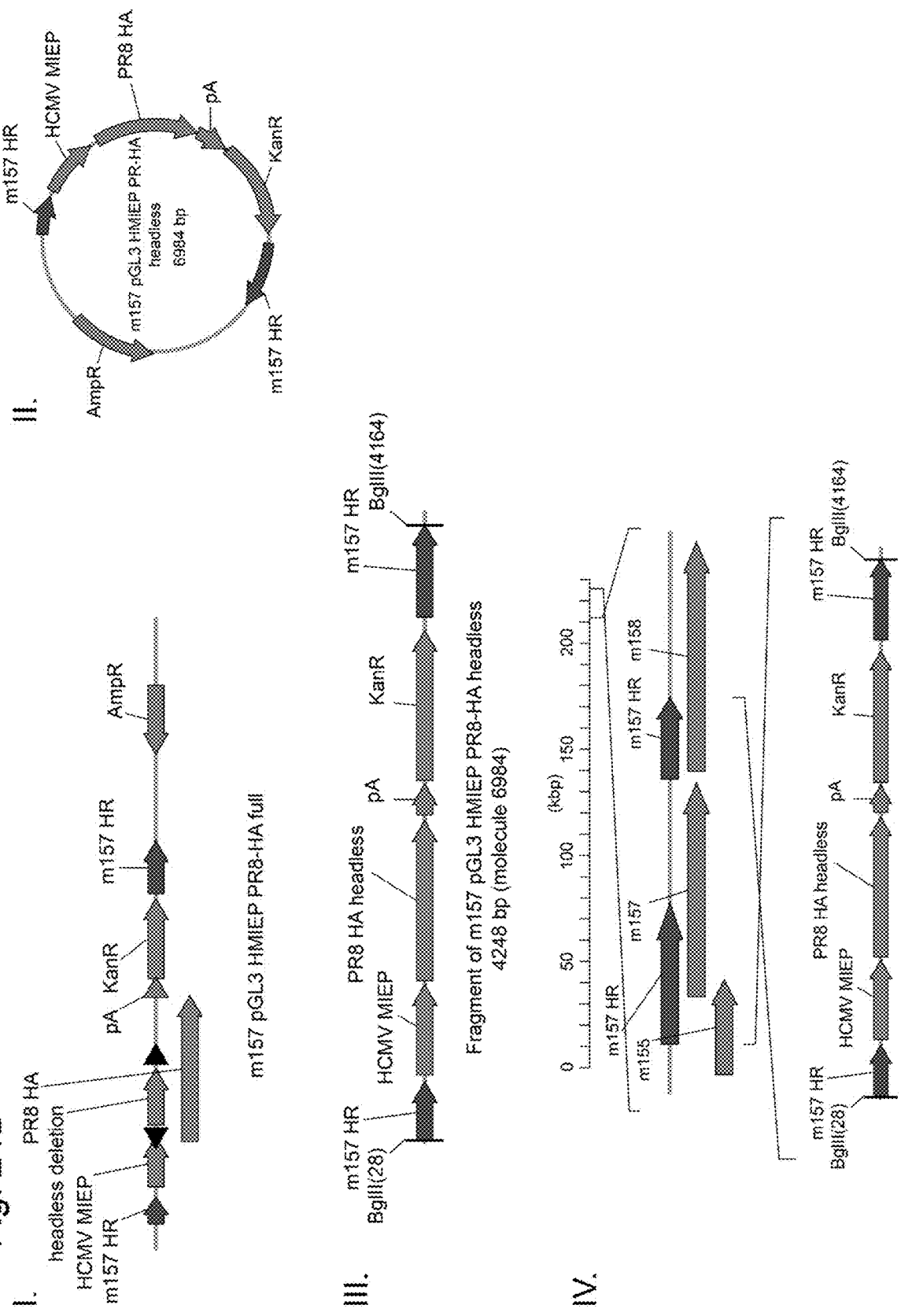

PR8-HA construct

PR8-HA headless

Fig.35C

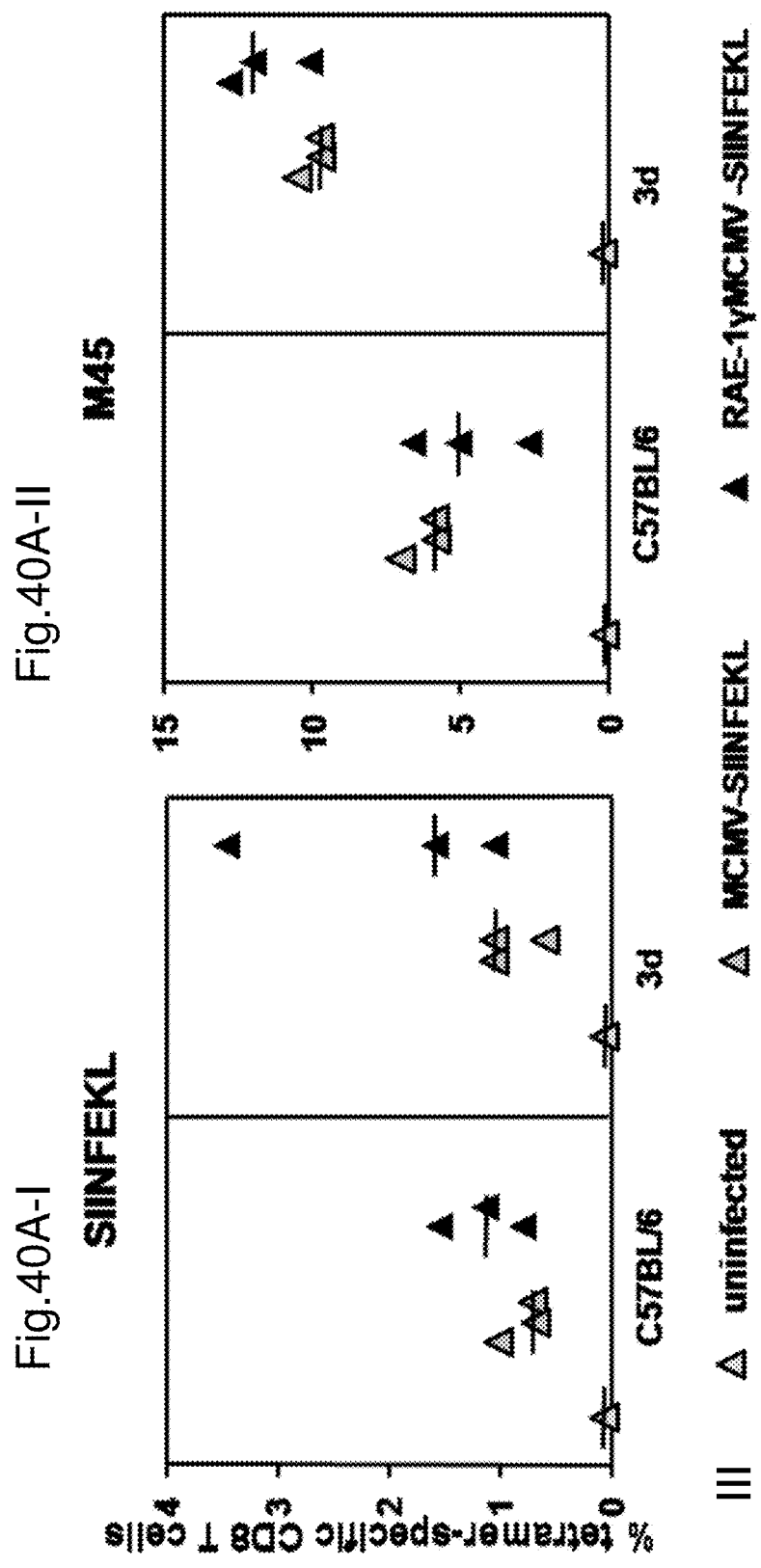

SEQUENCE LISTING

<160> NUMBER OF SEQ ID NOS: 51

<210> SEQ ID NO 1
<211> LENGTH: 9
<212> TYPE: PRT
<213> ORGANISM: Murine cytomegalovirus

<400> SEQUENCE: 1

Tyr Pro His Phe Met Pro Thr Asn Leu
1               5

<210> SEQ ID NO 2
<211> LENGTH: 9
<212> TYPE: PRT
<213> ORGANISM: Murine cytomegalovirus

<400> SEQUENCE: 2

Ala Gly Pro Pro Arg Tyr Ser Arg Ile

```
<210> SEQ ID NO 3
<211> LENGTH: 9
<212> TYPE: PRT
<213> ORGANISM: Listeria monocytogenes

<400> SEQUENCE: 3

Gly Tyr Lys Asp Gly Asn Glu Tyr Ile
1               5

<210> SEQ ID NO 4
<211> LENGTH: 67
<212> TYPE: DNA
<213> ORGANISM: artificial
<220> FEATURE:
<223> OTHER INFORMATION: synthetic

<400> SEQUENCE: 4
gcacccgacg atctgacatt gtccagtgtg ccggtcgcac gaacatccct agttattaat    60
agtaatc                                                              67

<210> SEQ ID NO 5
<211> LENGTH: 70
<212> TYPE: DNA
<213> ORGANISM: artificial
<220> FEATURE:
<223> OTHER INFORMATION: synthetic

<400> SEQUENCE: 5
tgtcaccgct ccacgtttca ccgtcggtct cccgatcgct agcctgtaca caggaacact    60
taacggctga                                                           70

<210> SEQ ID NO 6
<211> LENGTH: 76
<212> TYPE: DNA
<213> ORGANISM: artificial
<220> FEATURE:
<223> OTHER INFORMATION: synthetic

<400> SEQUENCE: 6
gactactgtc ggacgtgggg cgctgacaat atattcattt ccatctttgt aaccaggatg    60
acgacgataa gtaggg                                                    76

<210> SEQ ID NO 7
<211> LENGTH: 70
<212> TYPE: DNA
<213> ORGANISM: artificial
<220> FEATURE:
<223> OTHER INFORMATION: synthetic

<400> SEQUENCE: 7
gatcgagccg gtggtaccgg acgcggcgga gccgttcgga aaggactact gtcggacgtg    60
gggcgctgac                                                           70

<210> SEQ ID NO 8
<211> LENGTH: 79
<212> TYPE: DNA
<213> ORGANISM: artificial
<220> FEATURE:
<223> OTHER INFORMATION: synthetic

<400> SEQUENCE: 8
```

```
ggttacaaag atggaaatga atatattgtc agcgccccac gtccgacagt agtccaacca    60
attaaccaat tctgattag                                                 79

<210> SEQ ID NO 9
<211> LENGTH: 80
<212> TYPE: DNA
<213> ORGANISM: artificial
<220> FEATURE:
<223> OTHER INFORMATION: synthetic

<400> SEQUENCE: 9
atggcctggt tgttgacggc ccagaagatg cgcgagtacc gaggagggcc cgcggttaca    60
aagatggaaa tgaatatatt                                                80

<210> SEQ ID NO 10
<211> LENGTH: 8
<212> TYPE: PRT
<213> ORGANISM: Gallus gallus

<400> SEQUENCE: 10

Ser Ile Ile Asn Phe Glu Lys Leu
1               5

<210> SEQ ID NO 11
<211> LENGTH: 25
<212> TYPE: DNA
<213> ORGANISM: artificial
<220> FEATURE:
<223> OTHER INFORMATION: synthetic

<400> SEQUENCE: 11
gccgccatga aggcaaacct actgg                                          25

<210> SEQ ID NO 12
<211> LENGTH: 69
<212> TYPE: DNA
<213> ORGANISM: artificial
<220> FEATURE:
<223> OTHER INFORMATION: synthetic

<400> SEQUENCE: 12
cgtagaatcg agaccgagga gagggttagg gataggctta ccgatgcata ttctgcactg    60
caaagatcc                                                            69

<210> SEQ ID NO 13
<211> LENGTH: 57
<212> TYPE: DNA
<213> ORGANISM: artificial
<220> FEATURE:
<223> OTHER INFORMATION: synthetic

<400> SEQUENCE: 13
tcacagtttt tcaaagttga ttatactcgt agaatcgaga ccgaggagag ggttagg       57

<210> SEQ ID NO 14
<211> LENGTH: 26
<212> TYPE: DNA
<213> ORGANISM: artificial
<220> FEATURE:
<223> OTHER INFORMATION: synthetic

<400> SEQUENCE: 14
ggaggcaaca cgaagtgtca aacacc                                         26
```

<210> SEQ ID NO 15
<211> LENGTH: 26
<212> TYPE: DNA
<213> ORGANISM: artificial
<220> FEATURE:
<223> OTHER INFORMATION: synthetic

<400> SEQUENCE: 15
gccaccacat agttttccgt tgtggc                                      26

<210> SEQ ID NO 16
<211> LENGTH: 10
<212> TYPE: PRT
<213> ORGANISM: Mycobacterium tuberculosis

<400> SEQUENCE: 16

Gly Ala Pro Ile Asn Ser Ala Thr Ala Met
1               5                   10

<210> SEQ ID NO 17
<211> LENGTH: 105
<212> TYPE: DNA
<213> ORGANISM: artificial
<220> FEATURE:
<223> OTHER INFORMATION: synthetic

<400> SEQUENCE: 17
cgcccgctgc cacgatggcc tggttgttga cggcccagaa catggcggtg gccgagttga    60
tcggggcgcc gtcagcgccc agccagtgt tacaaccaat taacc                    105

<210> SEQ ID NO 18
<211> LENGTH: 92
<212> TYPE: DNA
<213> ORGANISM: artificial
<220> FEATURE:
<223> OTHER INFORMATION: synthetic

<400> SEQUENCE: 18
gccgttcgga aaggactact gtcggacgtg gggcgctgac ggcgccccga tcaactcggc    60
caccgccatg tagggataac agggtaatcg at                                 92

<210> SEQ ID NO 19
<211> LENGTH: 74
<212> TYPE: DNA
<213> ORGANISM: artificial
<220> FEATURE:
<223> OTHER INFORMATION: synthetic

<400> SEQUENCE: 19
gtcggtaccg tcgcagtctt cggtctgacc accgtagaac gcagagctcc accatggcag    60
cagccgccgc tacc                                                     74

<210> SEQ ID NO 20
<211> LENGTH: 37
<212> TYPE: DNA
<213> ORGANISM: artificial
<220> FEATURE:
<223> OTHER INFORMATION: synthetic

<400> SEQUENCE: 20
cccggatccc tctcctcaga tgccagggag gatgaag                            37

<210> SEQ ID NO 21

```
<211> LENGTH: 70
<212> TYPE: DNA
<213> ORGANISM: artificial
<220> FEATURE:
<223> OTHER INFORMATION: synthetic

<400> SEQUENCE: 21
gacaccgggc tccatgctga cgtaggtacc gactggggtc aaaagccttt aaacggtact      60
ttcccatagc                                                             70

<210> SEQ ID NO 22
<211> LENGTH: 66
<212> TYPE: DNA
<213> ORGANISM: artificial
<220> FEATURE:
<223> OTHER INFORMATION: synthetic

<400> SEQUENCE: 22
cttatagcag cgtgaacgtt gcacgtggcc tttgcggtta tccgttcagg aacacttaac      60
ggctga                                                                 66

<210> SEQ ID NO 23
<211> LENGTH: 21
<212> TYPE: DNA
<213> ORGANISM: artificial
<220> FEATURE:
<223> OTHER INFORMATION: synthetic

<400> SEQUENCE: 23
ggcgatgcgg tatcgcgcac a                                                21

<210> SEQ ID NO 24
<211> LENGTH: 21
<212> TYPE: DNA
<213> ORGANISM: artificial
<220> FEATURE:
<223> OTHER INFORMATION: synthetic

<400> SEQUENCE: 24
gacacctgtt cgtccagaat c                                                21

<210> SEQ ID NO 25
<211> LENGTH: 21
<212> TYPE: DNA
<213> ORGANISM: artificial
<220> FEATURE:
<223> OTHER INFORMATION: synthetic

<400> SEQUENCE: 25
tgacttaaac tccccaggca a                                                21

<210> SEQ ID NO 26
<211> LENGTH: 21
<212> TYPE: DNA
<213> ORGANISM: artificial
<220> FEATURE:
<223> OTHER INFORMATION: synthetic

<400> SEQUENCE: 26
taggtgaggc catagtggca g                                                21

<210> SEQ ID NO 27
<211> LENGTH: 21
<212> TYPE: DNA
<213> ORGANISM: artificial
```

```
<220> FEATURE:
<223> OTHER INFORMATION: synthetic

<400> SEQUENCE: 27
tgcctgttct ttgcagtctg t                                              21

<210> SEQ ID NO 28
<211> LENGTH: 22
<212> TYPE: DNA
<213> ORGANISM: artificial
<220> FEATURE:
<223> OTHER INFORMATION: synthetic

<400> SEQUENCE: 28
agtcgagtga agggtaacga gc                                             22

<210> SEQ ID NO 29
<211> LENGTH: 8
<212> TYPE: PRT
<213> ORGANISM: murine cytomegalovirus

<400> SEQUENCE: 29

Arg Ala Leu Glu Tyr Lys Asn Leu
1               5

<210> SEQ ID NO 30
<211> LENGTH: 8
<212> TYPE: PRT
<213> ORGANISM: murine cytomegalovirus

<400> SEQUENCE: 30

Thr Val Tyr Gly Phe Cys Leu Leu
1               5

<210> SEQ ID NO 31
<211> LENGTH: 9
<212> TYPE: PRT
<213> ORGANISM: murine cytomegalovirus

<400> SEQUENCE: 31

His Gly Ile Arg Asn Ala Ser Phe Ile
1               5

<210> SEQ ID NO 32
<211> LENGTH: 8
<212> TYPE: PRT
<213> ORGANISM: murine cytomegalovirus

<400> SEQUENCE: 32

Ser Ser Pro Pro Met Phe Arg Val
1               5

<210> SEQ ID NO 33
<211> LENGTH: 22
<212> TYPE: DNA
<213> ORGANISM: artificial
<220> FEATURE:
<223> OTHER INFORMATION: synthetic

<400> SEQUENCE: 33
gtgtatgtgg cccgacgggc gg                                             22

<210> SEQ ID NO 34
<211> LENGTH: 28
<212> TYPE: DNA
```

-continued

```
<213> ORGANISM: artificial
<220> FEATURE:
<223> OTHER INFORMATION: synthetic

<400> SEQUENCE: 34
cgcgggctac tcccgaaaga gtaacatc                                        28

<210> SEQ ID NO 35
<211> LENGTH: 20
<212> TYPE: DNA
<213> ORGANISM: artificial
<220> FEATURE:
<223> OTHER INFORMATION: syntehtic

<400> SEQUENCE: 35
atggccaagg cagcagtgac                                                 20

<210> SEQ ID NO 36
<211> LENGTH: 26
<212> TYPE: DNA
<213> ORGANISM: artificial
<220> FEATURE:
<223> OTHER INFORMATION: synthetic

<400> SEQUENCE: 36
tgctcgacct gaggtaatta taaccc                                          26

<210> SEQ ID NO 37
<211> LENGTH: 9
<212> TYPE: PRT
<213> ORGANISM: Influenza virus

<400> SEQUENCE: 37

Ile Tyr Ser Thr Val Ala Ser Ser Leu
1               5

<210> SEQ ID NO 38
<211> LENGTH: 9
<212> TYPE: PRT
<213> ORGANISM: artificial
<220> FEATURE:
<223> OTHER INFORMATION: synthetic

<400> SEQUENCE: 38

Tyr Pro Tyr Asp Val Pro Asp Tyr Ala
1               5

<210> SEQ ID NO 39
<211> LENGTH: 20
<212> TYPE: DNA
<213> ORGANISM: artificial
<220> FEATURE:
<223> OTHER INFORMATION: synthetic

<400> SEQUENCE: 39
tatatagact gaagcggagt                                                 20

<210> SEQ ID NO 40
<211> LENGTH: 69
<212> TYPE: DNA
<213> ORGANISM: artificial
<220> FEATURE:
<223> OTHER INFORMATION: synthetic

<400> SEQUENCE: 40
cagcttttga gtctagacag gggaacagcc ttcccttgta agacagaatg aaggcaaacc     60
```

-continued

```
tactggtcc                                                           69

<210> SEQ ID NO 41
<211> LENGTH: 50
<212> TYPE: DNA
<213> ORGANISM: artificial
<220> FEATURE:
<223> OTHER INFORMATION: synthetic

<400> SEQUENCE: 41
gagtcgtttc cgagcgactc gagatgcact ccgcttcagt ctatatatca              50

<210> SEQ ID NO 42
<211> LENGTH: 22
<212> TYPE: RNA
<213> ORGANISM: human cytomegalovirus

<400> SEQUENCE: 42
aagugacggu gagauccagg cu                                            22

<210> SEQ ID NO 43
<211> LENGTH: 10
<212> TYPE: PRT
<213> ORGANISM: HPV

<400> SEQUENCE: 43

Thr Ile His Asp Ile Ile Leu Glu Cys Val
1               5                   10

<210> SEQ ID NO 44
<211> LENGTH: 9
<212> TYPE: PRT
<213> ORGANISM: HPV

<400> SEQUENCE: 44

Thr Ile His Asp Ile Ile Leu Glu Cys
1               5

<210> SEQ ID NO 45
<211> LENGTH: 8
<212> TYPE: PRT
<213> ORGANISM: HPV

<400> SEQUENCE: 45

His Asp Ile Ile Leu Glu Cys Val
1               5

<210> SEQ ID NO 46
<211> LENGTH: 10
<212> TYPE: PRT
<213> ORGANISM: HPV

<400> SEQUENCE: 46

Phe Ala Phe Arg Asp Leu Cys Ile Val Tyr
1               5                   10

<210> SEQ ID NO 47
<211> LENGTH: 11
<212> TYPE: PRT
<213> ORGANISM: Artificial
<220> FEATURE:
<223> OTHER INFORMATION: Synthetic

<400> SEQUENCE: 47
```

```
Asp Ala Gly Pro Pro Arg Tyr Ser Arg Ile Phe
1               5                   10

<210> SEQ ID NO 48
<211> LENGTH: 33
<212> TYPE: DNA
<213> ORGANISM: Artificial
<220> FEATURE:
<223> OTHER INFORMATION: Synthetic

<400> SEQUENCE: 48
gacgcgggcc ctcctcggta ctcgcgcatc ttc                                33

<210> SEQ ID NO 49
<211> LENGTH: 11
<212> TYPE: PRT
<213> ORGANISM: Artificial
<220> FEATURE:
<223> OTHER INFORMATION: Synthetic

<400> SEQUENCE: 49

Asp Gly Tyr Lys Asp Gly Asn Glu Tyr Ile Phe
1               5                   10

<210> SEQ ID NO 50
<211> LENGTH: 33
<212> TYPE: DNA
<213> ORGANISM: Artificial
<220> FEATURE:
<223> OTHER INFORMATION: Synthetic

<400> SEQUENCE: 50
gacggttaca aagatggaaa tgaatatatt ttc                                33

<210> SEQ ID NO 51
<211> LENGTH: 18
<212> TYPE: PRT
<213> ORGANISM: Artificial
<220> FEATURE:
<223> OTHER INFORMATION: Synthetic

<400> SEQUENCE: 51

Trp Gly Ala Asp Gly Ala Pro Ile Asn Ser Ala Thr Ala Met Phe Trp
1               5                   10                  15

Ala Asn
```

VACCINE COMPRISING BETA-HERPESVIRUS

The present invention is related to a beta-herpesvirus comprising at least one heterologous nucleic acid, the beta-herpesvirus for use in a method for the treatment and/or prevention of a disease such as HIV infection, influenza virus infection, HPV infection, *Helicobacter pylori* infection, *Mycobacterium tuberculosis* infection and/or *Plasmodium falciparum* infection, the use of the beta-herpesvirus, a nucleic acid coding for the beta-herpesvirus, a vector comprising the nucleic acid, a host cell comprising the nucleic acid and a pharmaceutical composition comprising the beta-herpesvirus, the nucleic acid and/or the and a pharmaceutically acceptable carrier.

Human cytomegalovirus, also referred to herein as HCMV or human CMV, is an important human pathogen causing morbidity and mortality in congenitally infected and immunosuppressed individuals. Cytomegaloviruses, also referred to herein as CMV(s), are highly adapted to their mammalian hosts and are host-species specific in their replication which precludes the study of HCMV in animal models. Research on murine cytomegalovirus, also referred to herein as MCMV. Mouse CMV or murine CMV is the most advanced model in regard to the principles that govern the immune surveillance of CMVs. After primary infection the host immune response effectively terminates virus replication; however, clearance of the viral genome is not achieved and CMV is able to establish lifelong latency with periodic reactivation and shedding of virus (Pass, R. F. et al. 2001, in Fields Virology. D. M. Knipe and P. M. Howley, editors. Philadelphia: Lippincott Williams and Wilkins. 2675-2706, Stratton K R et al., in Vaccines for the 21st Century: A Tool for Decision Making: Report of the Committee to Study Priorities for Vaccine Development, Washington, D.C., USA: Institute of Medicine; 1999).

While HCMV infection is readily controlled by the immune competent host, the virus displays its pathogenic potential when host immunity is impaired. HCMV infection is the most common viral congenital infection which may result in live-long neurological sequelae, including brain damage, sensorineural hearing loss and mental retardation (Boppana, S. B. et al., 1997, Pediatrics 99:409-414; Boppana, S. B. et al., 1992, Pediatr Infect Dis J 11:93-99; Hamprecht, K. et al., 2001, Lancet 357:513-518; Whitley, R. J, 2004, Adv Exp Med Biol 549:155-160). Solid organ transplant recipients and hematopoietic stem cell transplant recipients are the second group of patients at risk for severe CMV infections (Mwintshi, K., and Brennan, D. C., 2007, Expert Rev Anti Infect Ther 5:295-304; Ljungman, P., 2008, Bone Marrow Transplant 42 Suppl 1:S70-S72; Streblow, D. N. et al., 2007, Curr Opin Immunol 19:577-582). In HIV-infected patients CMV continues to be the most frequent viral opportunistic pathogen although severe infections have become less common following the introduction of highly active antiretroviral therapy (Steininger, C. et al., 2006, J Clin Virol 37:1-9). Due to this immense public health importance, the development of a HCMV vaccine has been ranked as a top priority for the 21st century by the US Institute of Medicine (Arvin, A. M. et al., 2004, Clin Infect Dis 39:233-239).

Both innate and adaptive immune responses are important for the control of CMV infection (Krmpotic, A. et al., 2003 Microbes Infect 5:1263-1277; Koszinowski, U. H. et al., 1991, Curr Opin Immunol 3:471-475; Reusser, P. et al., 1991, Blood 78:1373-1380; Einsele, H., 2002, Cytotherapy 4:435-436; Peggs, K. S. et al., 2003, Lancet 362:1375-1377). Innate immunity, in particular NK cells, plays a key role in limiting CMV infection at an early stage and in priming of the adoptive immune response (Robbins, S. H. et al., 2007, PLoS Pathog 3:e123; Rolle, A., and Olweus, J., 2009, APMIS 117:413-426).

NK cells play a crucial role in fighting many pathogens. As part of the innate immune system they represent the first line of a host defense. Their activation is a result of signal balance from their inhibitory and activating receptors. Healthy and untransformed cells express MHC class I molecules which bind to NK cell inhibitory receptors providing inhibition of their activity. When MHC class I molecules are lacking from the cell surface, or cells express ligands for activating receptors on NK cells, NK cells are activated to kill infected or transformed cell.

One very potent activating receptor, whose engagement can override inhibitory signals, is NKG2D. In addition to NK cells, NKG2D is also expressed on γδ T cells and activated $CD8^+$ T cells, where it has co-stimulatory function. Ligands for the NKG2D receptor in mice are the members of the RAE-1 family of proteins (RAE-1α, β, γ, δ, ε) as well as MULT-1 and H60 proteins. NKG2D plays a major role in fighting MCMV. The best evidence for the importance of NKG2D is given by the fact that MCMV evolved numerous mechanisms against NKG2D (Lisnic, V. J. et al., 2010, Curr Opin Microbiol 13(4):530-9).

$CD8^+$ T cells are the principal effectors required for resolution of productive infection and establishment of latency (Reddehase, M. J., 2002, Nat Rev Immunol 2:831-844). Although $CD8^+$ T cells play a dominant role, $CD4^+$ T cells and NK cells contribute to the maintenance of latent CMV infection (Polic, B. et al., 1998, J Exp Med 188:1047-1054).

Antiviral antibodies, although not essential for the control of primary CMV infection and the establishment of latency, play a critical role in limiting the dissemination of recurrent virus (Jonjic, S. et al., 1994, J Exp Med 179:1713-1717). Antibodies can modify the disease associated with HCMV infection in transplant recipients as well as congenital CMV infection in humans and experimental animal models (Nigro, G. et al., 2005, N Engl J Med 353:1350-1362; Nigro, G. et al., 2008, Prenat Diagn 28:512-517; Bratcher, D. F. et al., 1995, J Infect Dis 172:944-950; Cekinovic, D. et al., 2008, J Virol 82:12172-12180; Chatterjee, A. et al., 2001, J Infect Dis 183:1547-1553; Snydman, D. R. et al., 1987, N Engl J Med 317:1049-1054). Consequently, a CMV vaccine should ideally aim to elicit an effective cellular and humoral immune response and at the same time the CMV vaccine should be safe for the vaccinated patient.

A number of subunit vaccine strategies and live, attenuated CMV vaccines have been developed (Schleiss, M. R., 2008, Curr Top Microbiol Immunol 325:361-382; Zhong, J., and Khanna, R., 2007, Expert Rev Anti Infect Ther 5:449-459; Gonczol, E., and Plotkin, S., 2001, Expert Opin Biol Ther 1:401-412; Griffiths, P., 2009, Rev Med Virol 19:117-119; Mohr, C. A. et al., 2010, J Virol 84(15):7730-42). Recently, a phase 2 clinical trial was described that suggested a protective capacity against maternal infection by use of recombinant monovalent glycoprotein B HCMV vaccine (Pass, R. F. et al., 2009, N Engl J Med 360:1191-1199). Glycoprotein B is also referred to herein as gB. While subunit vaccines induce an immune response to selected viral proteins, the advantage of live vaccines is that they elicit an immune response that mimics natural immunity and provides a broader protection. Their use, however, carries the risk of CMV disease caused by the vaccine strain or reactivation in the immunocompromised state, unless residual immunity would efficiently control the vaccine virus.

One approach to generate such an immunogenic, yet safe live vaccine is by deleting viral genes that subvert the host immune response (Cicin-Sain, L. et al., 2007, J Virol 81:13825-13834; Crumpler, M. M. et al., 2009, Vaccine 27:4209-4218) or essential genes resulting in spread-deficient virus (Mohr, C. A. et al. 2010, supra).

Nevertheless, until today there is no approved HCMV vaccine available and such HCMV vaccine has been recently ranked as a top priority for the 21st century by the US Institute of Medicine (Arvin, A. M. et al., 2004, supra; Stratton, K. R. et al., 1999, supra).

Thus a problem underlying the present invention is to provide an effective HCMV vaccine and a beta-herpesvirus contained in such vaccine, respectively.

It is also a problem underlying the present invention to provide a beta-herpesvirus being an effective vaccine against infection with a pathogen in addition to or other than HCMV, wherein the pathogen is selected from the group comprising viruses other than HCMV, bacteria and parasites.

It is a still further problem underlying the present invention to provide a nucleic acid coding for a beta-herpesvirus, wherein the beta-herpesvirus is suitable for use as an effective HCMV vaccine.

These and other problems underlying the instant invention are solved by the subject matter of the independent claims. Preferred embodiments may be taken from the dependent claims. Furthermore, these and other problems underlying the instant invention are solved by the subject matter of the aspects and embodiments of the invention outlined in the following in more detail.

EMBODIMENTS

Embodiment 1

A beta-herpesvirus, preferably a recombinant beta-herpesvirus, wherein the beta-herpesvirus comprises at least one heterologous nucleic acid, wherein the at least one heterologous nucleic acid comprises a gene encoding a cellular ligand.

Embodiment 2

The beta-herpesvirus according to embodiment 1, wherein the beta-herpesvirus is not a murine cytomegalovirus comprising at least one heterologous nucleic acid, wherein the at least one heterologous nucleic acid comprises a gene encoding a cellular ligand, wherein the cellular ligand is RAE1γ, and wherein the beta-herpesvirus is NOT a murine cytomegalovirus deficient in at least one gene product encoded by an immune modulatory gene, wherein the immune modulatory gene is m152.

Embodiment 3

The beta-herpesvirus according to embodiments 1 and 2, wherein the cellular ligand is capable of binding a receptor for the cellular ligand.

Embodiment 4

The beta-herpesvirus according to embodiment 3, wherein the receptor for the cellular ligand is present on the surface of at least one immune cell.

Embodiment 5

The beta-herpesvirus according to any one of embodiments 3 to 4, wherein the receptor for the cellular ligand is an activating receptor.

Embodiment 6

The beta-herpesvirus according to any one of embodiments 4 to 5, wherein the at least one immune cell is selected from the group comprising NK cells, γδ T cells and activated $CD8^+$ T cells.

Embodiment 7

The beta-herpesvirus according to any one of embodiments 4 to 6, wherein the at least one immune cell is selected from the group consisting of NK cells, γδ T cells and activated $CD8^+$ T cells.

Embodiment 8

The beta-herpesvirus according to any one of embodiments 4 to 7, wherein the receptor for the cellular ligand is present on the surface of NK cells.

Embodiment 9

The beta-herpesvirus according to any one of embodiments 4 to 8, wherein the receptor for the cellular ligand is present on the surface of NK cells, γδ T cells and activated $CD8^+$ T cells.

Embodiment 10

The beta-herpesvirus according to any one of embodiments 1 to 9, wherein the cellular ligand is a protein anchored to or in a membrane of a cell, preferably a cell infected by the beta-herpesvirus, via glycosylphosphatidylinositol (GPI).

Embodiment 11

The beta-herpesvirus according to any one of embodiments 1 to 9, wherein the cellular ligand is a transmembrane protein.

Embodiment 12

The beta-herpesvirus according to any one of embodiments 1 to 9, wherein the cellular ligand comprises at least one immunoglobulin-like domain.

Embodiment 13

The beta-herpesvirus according to any one of embodiments 1 to 9, wherein the at least one immunoglobulin-like domain is selected from the group comprising an α1 domain, an α2 domain and an α3 domain.

Embodiment 14

The beta-herpesvirus according to embodiment 13, wherein the cellular ligand comprises an α1 domain and an α2 domain.

Embodiment 15

The beta-herpesvirus according to embodiment 13, wherein the cellular ligand comprises an α1 domain, an α2 domain and an α3 domain.

Embodiment 16

The beta-herpesvirus according to any one of embodiments 1 to 15, wherein the cellular ligand is an NKG2D ligand.

Embodiment 17

The beta-herpesvirus according to embodiment 16, wherein the NKG2D ligand is a mammalian NKG2D ligand or a homolog thereof.

Embodiment 18

The beta-herpesvirus according to embodiment 17, wherein the NKG2D ligand is selected from the group comprising murine NKG2D ligand and human NKG2D ligand.

Embodiment 19

The beta-herpesvirus according to embodiment 18, wherein the NKG2D ligand is a human NKG2D ligand.

Embodiment 20

The beta-herpesvirus according to embodiment 18, wherein the NKG2D ligand is a murine NKG2D ligand.

Embodiment 21

The beta-herpesvirus according to any one of embodiments 18 and 19, wherein the human NKG2D ligand is selected from the group comprising UL16 binding proteins and MHC class-I-related protein.

Embodiment 22

The beta-herpesvirus according to embodiment 21, wherein the UL16 binding protein is selected from the group comprising ULBP2, ULPB1, ULBP3, ULBP4, ULBP5 and ULBP6.

Embodiment 23

The beta-herpesvirus according to embodiment 22, wherein the UL16 binding protein is ULBP2.

Embodiment 24

The beta-herpesvirus according to embodiment 22, wherein the UL16 binding protein is ULPB1.

Embodiment 25

The beta-herpesvirus according to embodiment 22, wherein the UL16 binding protein is ULBP3.

Embodiment 26

The beta-herpesvirus according to embodiment 22, wherein the UL16 binding protein is ULBP4.

Embodiment 27

The beta-herpesvirus according to embodiment 22, wherein the UL16 binding protein is ULBP5.

Embodiment 28

The beta-herpesvirus according to embodiment 22, wherein the UL16 binding protein is ULBP6.

Embodiment 29

The beta-herpesvirus according to embodiment 21, wherein the MHC class-I-related protein is selected from the group comprising MICA and MICB.

Embodiment 30

The beta-herpesvirus according to embodiment 29, wherein the MHC class-I-related protein is MICA.

Embodiment 31

The beta-herpesvirus according to embodiment 29, wherein the MHC class-I-related protein is MICB

Embodiment 32

The beta-herpesvirus according to any one of embodiments 18 and 20, wherein the murine NKG2D ligand is selected from the group comprising RAE-1 protein, H60 protein and murine UL16 protein-like transcript protein.

Embodiment 33

The beta-herpesvirus according to embodiment 32, wherein the RAE-1 protein is selected from the group comprising RAE-1α, RAE-1β, RAE-1γ, RAE-1δ, and RAE-1-ε.

Embodiment 34

The beta-herpesvirus according to embodiment 33, wherein the RAE-1 protein is RAE-1γ.

Embodiment 35

The beta-herpesvirus according to embodiment 33, wherein the RAE-1 protein is RAE-1α.

Embodiment 36

The beta-herpesvirus according to embodiment 33, wherein the RAE-1 protein is RAE-1β.

Embodiment 37

The beta-herpesvirus according to embodiment 33, wherein the RAE-1 protein is RAE-1δ.

Embodiment 38

The beta-herpesvirus according to embodiment 33, wherein the RAE-1 protein is RAE-1ε.

Embodiment 39

The beta-herpesvirus according to embodiment 33, wherein the murine UL16 protein-like transcript protein is MULT-1.

Embodiment 40

The beta-herpesvirus according to embodiment 33, wherein the H60 protein is selected from the group comprising H60a, H60b and H60c.

Embodiment 41

The beta-herpesvirus according to embodiment 40, wherein the H60 protein is H60a.

Embodiment 42

The beta-herpesvirus according to embodiment 40, wherein the H60 protein is H60b.

Embodiment 43

The beta-herpesvirus according to embodiment 40, wherein the H60 protein is H60c.

Embodiment 44

The beta-herpesvirus according to any one of embodiments 3 to 43, wherein the binding of the cellular ligand and the receptor for the cellular ligand is capable of activating NK cells.

Embodiment 45

The beta-herpesvirus according to any one of embodiments 1 to 44, wherein the beta-herpesvirus is suitable for inducing an immune response against a beta-herpesvirus.

Embodiment 46

The beta-herpesvirus according to embodiment 45, wherein the immune response comprises neutralizing antibodies against beta-herpesvirus and/or CD4$^+$ T-cells directed against epitopes of beta-herpesvirus and/or CD8$^+$ T-cells directed against epitopes of beta-herpesvirus.

Embodiment 47

The beta-herpesvirus according to any one of embodiments 1 to 46, wherein the beta-herpesvirus has a tropism like a wild type beta-herpesvirus.

Embodiment 48

The beta-herpesvirus according to any one of embodiments 1 to 47, wherein the beta-herpesvirus is capable of infecting professional antigen presenting cells.

Embodiment 49

The beta-herpesvirus according to any one of embodiments 1 to 48, wherein the beta-herpesvirus is capable of infecting dendritic cells and macrophages.

Embodiment 50

The beta-herpesvirus according to any one of embodiments 1 to 49, wherein the beta-herpesvirus is capable of infecting professional antigen presenting cells only.

Embodiment 51

The beta-herpesvirus according to any one of embodiments 1 to 50, wherein the beta-herpesvirus is capable of infecting fibroblasts.

Embodiment 52

The beta-herpesvirus according to any one of embodiments 1 to 51, wherein the beta-herpesvirus is a human beta-herpesvirus.

Embodiment 53

The beta-herpesvirus according to any one of embodiments 1 to 52, wherein the beta-herpesvirus is a cytomegalovirus.

Embodiment 54

The beta-herpesvirus according to embodiment 53, wherein the beta-herpesvirus is a cytomegalovirus is selected from the group comprising human cytomegalovirus, rhesus cytomegalovirus and mouse cytomegalovirus.

Embodiment 55

The beta-herpesvirus according to embodiment 54, wherein the beta-herpesvirus is human cytomegalovirus.

Embodiment 56

The beta-herpesvirus according to embodiment 55, wherein the human cytomegalovirus is a human cytomegalovirus derived from a Bacterial Artificial Chromosome.

Embodiment 57

The beta-herpesvirus according to embodiment 56, wherein the Bacterial Artificial Chromosome is selected from the group comprising AD169-BAC, modified AD169-BAC, TB40E-BAC, VHLE, Toledo-BAC, Toledo-BAC, TR-BAC, FIX-BAC and transgenic Merlin-BAC.

Embodiment 58

The beta-herpesvirus according to any one of embodiments 1 to 57, wherein the beta-herpesvirus is deficient in at least one gene product encoded by an immune modulatory gene.

Embodiment 59

The beta-herpesvirus according to embodiment 58, wherein the beta-herpesvirus comprises a deletion of the coding sequence of the at least one immune modulatory gene.

Embodiment 60

The beta-herpesvirus according to any one of embodiments 58 to 59; wherein the at least one gene product encoded by an immune modulatory gene is a gene product regulating NK cell response.

Embodiment 61

The beta-herpesvirus according to embodiment 60; wherein the gene product regulating NK cell response is capable of binding the cellular ligand.

Embodiment 62

The beta-herpesvirus according to embodiment 61, wherein the binding of the gene product regulating NK cell response and the cellular ligand results in reduction of expression of the cellular ligand.

Embodiment 63

The beta-herpesvirus according to embodiment 62, wherein the expression of the cellular ligand is an expression on the surface of a cell infected with the beta-herpesvirus.

Embodiment 64

The beta-herpesvirus according to any one of embodiments 58 to 63, wherein the at least one immune modulatory gene is selected from the group comprising UL16, UL142, m152, m155, m145 and m138.

Embodiment 65

The beta-herpesvirus according to embodiment 64, wherein the immune modulatory gene is UL16.

Embodiment 66

The beta-herpesvirus according to embodiment 64, wherein the immune modulatory gene is UL142.

Embodiment 67

The beta-herpesvirus according to embodiment 64, wherein the immune modulatory gene is m152.

Embodiment 68

The beta-herpesvirus according to embodiment 64, wherein the immune modulatory gene is m155.

Embodiment 69

The beta-herpesvirus according to embodiment 64, wherein the immune modulatory gene is m145.

Embodiment 70

The beta-herpesvirus according to embodiment 64, wherein the immune modulatory gene is m138.

Embodiment 71

The beta-herpesvirus according to any one of embodiments 58 to 65, wherein the at least one immune modulatory gene is UL16 and wherein the cellular ligand is ULBP2.

Embodiment 72

The beta-herpesvirus according to any one of embodiments 58 to 65, wherein the at least one immune modulatory gene is UL16 and wherein the cellular ligand is MICB.

Embodiment 73

The beta-herpesvirus according to any one of embodiments 58 to 65, wherein the at least one immune modulatory gene is UL16 and wherein the cellular ligand is ULBP1.

Embodiment 74

The beta-herpesvirus according to any one of embodiments 58 to 65, wherein the at least one immune modulatory gene is UL16 and wherein the cellular ligand is ULBP6.

Embodiment 75

The beta-herpesvirus according to any one of embodiments 58 to 64 and 65, wherein the at least one immune modulatory gene is UL142 and wherein the cellular ligand is MICA.

Embodiment 76

The beta-herpesvirus according to any one of embodiments 58 to 64 and 67, wherein the at least one immune modulatory gene is m152 and wherein the cellular ligand is selected from the group comprising RAE-1α, RAE-1β, RAE-1γ, RAE-1δ, and RAE-1-E.

Embodiment 77

The beta-herpesvirus according to any one of embodiments 58 to 64 and 68, wherein the at least one immune modulatory gene is m155 and wherein the cellular ligand is selected from the group comprising H60a, H60b and H60c.

Embodiment 78

The beta-herpesvirus according to any one of embodiments 58 to 64 and 69, wherein the at least one immune modulatory gene is m145 and wherein the cellular ligand is MULT-1.

Embodiment 79

The beta-herpesvirus according to any one of embodiments 58 to 64 and 70, wherein the at least one immune modulatory gene is m138 and wherein the cellular ligand is MULT-1.

Embodiment 80

The beta-herpesvirus according to any one of embodiments 58 to 64 and 70, wherein the at least one immune modulatory gene is m138 and wherein the cellular ligand is selected from the group comprising H60a, H60b and H60c.

Embodiment 81

The beta-herpesvirus according to any one of embodiments 58 to 64 and 70, wherein the at least one immune modulatory gene is m138 and wherein the cellular ligand is selected from the group comprising RAE-1α, RAE-1β, RAE-1γ, RAE-1δ, and RAE-1-E.

Embodiment 82

The beta-herpesvirus according to any one of embodiments 58 to 81, wherein the beta-herpesvirus is deficient in one or more additional gene product(s) each encoded by an additional immune modulatory gene.

Embodiment 83

The beta-herpesvirus according to any one of embodiments 58 to 82, preferably embodiment 82, wherein the beta-herpesvirus comprises a deletion of the coding sequence of the additional immune modulatory gene.

Embodiment 84

The beta-herpesvirus according to any one of embodiments 81 to 82; wherein the at least one additional gene product encoded by the additional immune modulatory gene is a gene product regulating NK cell response encoded by an immune modulatory gene selected from the group comprising UL16, UL18, UL40, UL142, m152, m155, m145 and m138.

Embodiment 85

The beta-herpesvirus according to any one of embodiments 81 to 83 wherein the at least one additional gene product encoded by the the additional immune modulatory gene is a gene product regulating MHC class I presentation.

Embodiment 86

The beta-herpesvirus according to embodiment 85, wherein the gene product regulating MHC class I presentation is a gene product encoded by an immune modulatory gene selected from the group comprising US6, US3, US2 and US11.

Embodiment 87

The beta-herpesvirus according to any one of embodiments 1 to 86, wherein the beta-herpesvirus comprises the deletion of at least one miRNA.

Embodiment 88

The beta-herpesvirus according to embodiment 87, wherein the miRNA is capable of binding a transcript of the cellular ligand.

Embodiment 89

The beta-herpesvirus according to any one of embodiments 87 to 88, preferably embodiment 88, wherein the miRNA is capable of repressing the translation of the gene coding for the cellular ligand.

Embodiment 90

The beta-herpesvirus according to any one of embodiments 87 to 89, preferably embodiment 89, wherein the miRNA is miRNA-UL112.

Embodiment 91

The beta-herpesvirus according to any one of embodiments 1 to 90, wherein the beta-herpesvirus is deficient in at least one gene product encoded by a gene regulating viral replication.

Embodiment 92

The beta-herpesvirus according to any one of embodiments 1 to 91, wherein the gene regulating viral replication is selected from the group comprising IE1, pp71 and pp65.

Embodiment 93

The beta-herpesvirus according to any one of embodiments 1 to 92, wherein the beta-herpesvirus is deficient in at least one gene product encoded by an essential gene.

Embodiment 94

The beta-herpesvirus according to embodiment 93, wherein the essential gene is selected from the group comprising UL32, UL34, UL37.1, UL44, UL46, UL48, UL48, UL49, UL50, UL51, UL52, UL53, UL54, UL55, UL56, UL57, UL60, UL70, UL71, UL73, UL75, UL76, UL77, UL79, UL80, UL84, UL85, UL86, UL87, UL89.1, UL90, UL91, UL92, UL93, UL94, UL95, UL96, UL98, UL99, UL100, UL102, UL104, UL105, UL115 and UL122.

Embodiment 95

The beta-herpesvirus according to any one of embodiments 1 to 93, wherein the beta-herpesvirus is deficient in at least one glycoprotein.

Embodiment 96

The beta-herpesvirus according to embodiment 95, wherein the glycoprotein is selected from the group comprising gB.

Embodiment 97

The beta-herpesvirus according to any one of embodiments 1 to 96, wherein the beta-herpesvirus encodes at least one additional heterologous nucleic acid.

Embodiment 98

The beta-herpesvirus according to embodiment 97, wherein the at least one additional heterologous nucleic acid is a functional nucleic acid, preferably the functional nucleic acid is selected from the group comprising antisense molecules, ribozymes and RNA interference mediating nucleic acids.

Embodiment 99

The beta-herpesvirus according to embodiment 97, wherein the at least one additional heterologous nucleic acid is a heterologous nucleic acid coding for a peptide, oligopeptide, polypeptide or protein.

Embodiment 100

The beta-herpesvirus according to embodiment 99, wherein the peptide, oligopeptide, polypeptide or protein constitutes or comprises at least one antigen.

Embodiment 101

The beta-herpesvirus according to embodiment 100, wherein the antigen is an antigen selected from the group comprising tumor antigens, tumor associated antigens, viral antigens, bacterial antigens and parasite antigens.

Embodiment 102

The beta-herpesvirus according to embodiment 101, wherein the viral antigen is an antigen derived from a virus, wherein the virus is selected from the group comprising HIV, Influenza, HPV and RSV.

Embodiment 103

The beta-herpesvirus according to embodiment 102, wherein the viral antigen from Influenza is selected from the group comprising haemaglutinin.

Embodiment 104

The beta-herpesvirus according to embodiment 103, wherein the haemaglutinin is selected from the group comprising haemaglutinin full-length form and haemaglutinin headless form.

Embodiment 105

The beta-herpesvirus according to embodiment 102, wherein the viral antigen from RSV is selected from the group comprising glycoprotein F and glycoprotein G.

Embodiment 106

The beta-herpesvirus according to embodiment 102, wherein the viral antigen from HIV is selected from the group comprising HIV-1 gag.

Embodiment 107

The beta-herpesvirus according to embodiment 102, wherein the viral antigen from HPV is selected from the group comprising E6 29-38, E6 29-37, E6 31-38, E6 52-61, E6 and E7.

Embodiment 108

The beta-herpesvirus according to embodiment 101, wherein the bacterial antigen is an antigen derived from a bacterium, wherein the bacterium is selected from the group comprising *mycobacterium, Helicobacter pylori* and *Listeria*.

Embodiment 109

The beta-herpesvirus according to embodiment 108, wherein the bacterial antigen from *Helicobacter pylori* is selected from the group comprising urease, VacA, CagA, heat shock protein, neutrophil-activating protein outer membrane lipoprotein and babA2.

Embodiment 110

The beta-herpesvirus according to embodiment 108, wherein *mycobacterium* is selected from the group comprising *Mycobacterium tuberculosis*.

Embodiment 111

The beta-herpesvirus according to embodiment 110, wherein the bacterial antigen from *Mycobacterium tuberculosis* is selected from the group comprising Antigen 85 A, Antigen 85B and Antigen 85B-TB10.4.

Embodiment 112

The beta-herpesvirus according to embodiment 108, wherein *Listeria* is selected from the group comprising *Listeria monocytogenes*.

Embodiment 113

The beta-herpesvirus according to embodiment 108, wherein the bacterial antigen from *Listeria* is selected from the group comprising listeriolysin O (LLO).

Embodiment 114

The beta-herpesvirus according to embodiment 101, wherein the parasite antigen is an antigen derived from a parasite, wherein the parasite is selected from the group comprising *Plasmodium*.

Embodiment 115

The beta-herpesvirus according to embodiment 114, wherein *Plasmodium* is selected from the group comprising *Plasmodium falciparum, Plasmodium vivax, Plasmodium ovale, Plasmodium malariae* and *Plasmodium knowlesi*.

Embodiment 116

The beta-herpesvirus according to embodiment 115, wherein *Plasmodium* is *Plasmodium falciparum*.

Embodiment 117

The beta-herpesvirus according to embodiment 116, wherein the parasite antigen from *Plasmodium falciparum* is selected from the group circumsporozoite protein.

Embodiment 118

The beta-herpesvirus according to any one of embodiments 1 to 117 for or suitable for use in a method for the treatment of a subject and/or for use in a method for the vaccination of a subject.

Embodiment 119

The beta-herpesvirus according to embodiment 118, wherein the subject is a mammal, preferably a human being.

Embodiment 120

The beta-herpesvirus according to any one of embodiments 118 to 119, wherein the subject is suffering from a disease or is at risk of suffering from a disease.

Embodiment 121

The beta-herpesvirus according to any one of embodiments 118 to 120, wherein the vaccination is a vaccination against a disease.

Embodiment 122

The beta-herpesvirus according to any one of embodiments 120 to 121, wherein the disease is a disease or condition which is associated with beta-herpesvirus infection, preferably human cytomegalovirus infection.

Embodiment 123

The beta-herpesvirus according to any one of embodiments 120 to 122, wherein the disease or condition is selected from the group comprising congenital inclusion disease.

Embodiment 124

The beta-herpesvirus according to any one of embodiments 118 to 123, wherein the subject is a pregnant female or female of reproductive age, preferably a pregnant human or a human of reproductive age.

Embodiment 125

The beta-herpesvirus according to any one of embodiments 118 to 124, wherein the treatment is or is suitable for or capable of preventing the transfer of a beta-herpesvirus, preferably human cytomegalovirus, from the female to a fetus and/or to an embryo carried by the female or to be carried in the future by the female.

Embodiment 126

The beta-herpesvirus according to any one of embodiments 118 to 125, wherein the treatment is for or is suitable for the generation of or capable of generating an immune response in the female body, whereby preferably such immune response confers protection to a fetus and/or to an embryo carried or to be carried in the future by the female against beta-herpesvirus and/or a disease or condition associated with beta-herpesvirus infection,

Embodiment 127

The beta-herpesvirus according to embodiment 126, wherein the beta-herpesvirus is a cytomegalovirus, preferably human cytomegalovirus.

Embodiment 128

The beta-herpesvirus according to any one of embodiments 1 to 127, wherein the beta-herpesvirus is suitable of inducing an immune response against a beta-herpesvirus.

Embodiment 129

The beta-herpesvirus according to embodiment 128, wherein the immune response comprises neutralizing antibodies against beta-herpesvirus and/or CD4$^+$ T-cells directed against epitopes of beta-herpesvirus and/or CD8$^+$ T-cells directed against epitopes of beta-herpesvirus.

Embodiment 130

The beta-herpesvirus according to any one of embodiments 120 to 121, wherein the disease is a disease selected from the group comprising bacterial disease, viral disease, parasite disease and tumors.

Embodiment 131

The beta-herpesvirus according to embodiment 130, wherein the viral disease is selected from the group comprising AIDS, Influenza and RSV infection

Embodiment 132

The beta-herpesvirus according to embodiment 130, wherein the bacterial disease is selected from the group comprising Tuberculosis and listeriosis.

Embodiment 133

The beta-herpesvirus according to embodiment 130, wherein the parasite disease is selected from the group comprising Malaria.

Embodiment 134

A beta-herpesvirus for use in a method for the treatment and/or prevention of HIV infection, wherein the beta-herpesvirus expresses a cellular ligand and an antigen, wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c, wherein the antigen is selected from the group comprising HIV-1 gag, and wherein the beta-herpesvirus preferably is a beta-herpesvirus according to any one of embodiments 1 to 133.

Embodiment 135

A beta-herpesvirus for use in a method for the treatment and/or prevention of influenza virus infection, wherein the beta-herpesvirus expresses a cellular ligand and an antigen, wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c, wherein the antigen is selected from the group comprising haemaglutinin full-length form and haemaglutinin headless form, and wherein the beta-herpesvirus preferably is a beta-herpesvirus according to any one of embodiments 1 to 133.

Embodiment 136

A beta-herpesvirus for use in a method for the treatment and/or prevention of HPV infection,
wherein the beta-herpesvirus expresses a cellular ligand and an antigen,
wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c, wherein the antigen is selected from the group comprising E6 29-38, E6 29-37, E6 31-38, E6 52-61, E6 and E7, and
wherein the beta-herpesvirus preferably is a beta-herpesvirus according to any one of embodiments 1 to 133.

Embodiment 137

A beta-herpesvirus for use in a method for the treatment and/or prevention of RSV infection,
wherein the beta-herpesvirus expresses a cellular ligand and an antigen,
wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c,
wherein the antigen is selected from the group comprising glycoprotein F and glycoprotein G, and
wherein the beta-herpesvirus preferably is a beta-herpesvirus according to any one of embodiments 1 to 133.

Embodiment 138

A beta-herpesvirus for use in a method for the treatment and/or prevention of *Helicobacter pylori* infection,
wherein the beta-herpesvirus expresses a cellular ligand and an antigen,
wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c,
wherein the antigen is selected from the group comprising urease, VacA, CagA, heat shock protein, neutrophil-activating protein outer membrane lipoprotein and babA2, and
wherein the beta-herpesvirus preferably is a beta-herpesvirus according to any one of embodiments 1 to 133.

Embodiment 139

A beta-herpesvirus for use in a method for the treatment and/or prevention of *Mycobacterium tuberculosis* infection,
wherein the beta-herpesvirus expresses a cellular ligand and an antigen,
wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c,
wherein the antigen is selected from the group comprising Antigen 85 A, Antigen 85B and Antigen 85B-TB10.4, and
wherein the beta-herpesvirus preferably is a beta-herpesvirus according to any one of embodiments 1 to 133.

Embodiment 140

A beta-herpesvirus for use in a method for the treatment and/or prevention of *Listeria* infection, preferably *Listeria monocytogenes* infection,
wherein the beta-herpesvirus expresses a cellular ligand and an antigen,
wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c,
wherein the antigen is selected from the group comprising listeriolysin O (LLO), and
wherein the beta-herpesvirus preferably is a beta-herpesvirus according to any one of embodiments 1 to 133.

Embodiment 141

A beta-herpesvirus for use in a method for the treatment and/or prevention of *Plasmodium falciparum* infection,
wherein the beta-herpesvirus expresses a cellular ligand and an antigen,
wherein the cellular ligand is selected from the group comprising ULBP2, ULPB1, ULBP3, ULBP4, ULBP5, ULBP6, MICA, MICB, RAE-1α, RAE-1β, RAE-1γ, RAE-1δ, RAE-1-ε, MULT-1, H60a, H60b and H60c,
wherein the antigen is selected from the group comprising circumsporozoite protein, and
wherein the beta-herpesvirus preferably is a beta-herpesvirus according to any one of embodiments 1 to 133.

Embodiment 142

Use of a beta-herpesvirus as defined in any one of embodiments 1 to 141 for the manufacture of a medicament.

Embodiment 143

Use of a beta-herpesvirus according to embodiment 142, wherein the medicament is for the treatment and/or prevention of beta-herpesvirus infection.

Embodiment 144

Use of a beta-herpesvirus according to any one of embodiment 142 to 143, wherein the medicament is for the treatment and/or prevention of a disease or condition associated with beta-herpesvirus infection, preferably human cytomegalovirus infection.

Embodiment 145

Use of a beta-herpesvirus according to any one of embodiment 1 to 141, for the manufacture of a vaccine.

Embodiment 146

Use of a beta-herpesvirus according to embodiment 145, wherein the vaccine is for the treatment and/or prevention of a disease.

Embodiment 147

Use of a beta-herpesvirus according to embodiment 146, wherein the disease is beta-herpesvirus infection.

Embodiment 148

Use of a beta-herpesvirus according to any one of embodiments 146 and 147, wherein the disease is a disease as defined in any one of embodiments 130 to 133.

Embodiment 149

Use of a beta-herpesvirus according to embodiment 145, wherein the vaccine is for the treatment and/or prevention of a disease or condition associated with beta-herpesvirus infection, preferably human cytomegalovirus infection.

Embodiment 150

Use of a beta-herpesvirus according to embodiment 149, wherein the vaccine is or is suitable for the administration to a subject, whereby the subject is selected form the group comprising a pregnant female, a female of reproductive age, a donor of a transplant, a recipient of a transplant and a subject being infected with HIV or being at risk of being infected with HIV.

Embodiment 151

Use of a beta-herpesvirus according to embodiment 150, wherein the donor is a potential donor and/or the recipient is a potential recipient.

Embodiment 152

A nucleic acid coding for a beta-herpesvirus as defined in any of the preceding embodiments.

Embodiment 153

A vector, preferably an expression vector, comprising the nucleic acid according to embodiment 152.

Embodiment 154

A host cell comprising a nucleic acid according to embodiment 152 or a vector according to embodiment 153.

Embodiment 155

A pharmaceutical composition comprising a beta-herpesvirus according to any one of the preceding embodiments, a nucleic acid of embodiment 152 and/or a vector of embodiment 153, and a pharmaceutically acceptable carrier.

The present inventor has surprisingly found that the infection of a subject by a beta-herpesvirus, preferably a recombinant beta-herpesvirus, wherein a cellular ligand, preferably recognized by an activating receptor on immune cells, is inserted into the genome of the beta-herpesvirus, results in eliciting an immune response against the beta-herpesvirus sufficient to protect against infection with wild type beta-herpesvirus, although said beta-herpesvirus is severely attenuated compared to a respective wild type beta-herpesvirus. Accordingly, said beta-herpesvirus was found to provide a safe and protective beta-herpesvirus vaccine, suitable for vaccination against beta-herpesvirus infection. More specifically, the present inventor has surprisingly found that the infection of a subject by a CMV, preferably a recombinant CMV, wherein a cellular ligand, preferably recognized by an activating receptor on immune cells, is inserted into the genome of the CMV, results in eliciting an immune response against the CMV sufficient to protect against infection with wild type CMV, although said CMV is severely attenuated compared to a respective wild type CMV. Accordingly, said CMV was found to provide a safe and protective CMV vaccine, suitable for vaccination against CMV infection.

The present inventor surprisingly found that a CMV encoding a ligand for NKG2D provides a safe and protective CMV vaccine, suitable for vaccination against CMV infection.

Furthermore, the present inventor has found that a beta-herpesvirus according to the present invention, wherein a nucleic acid coding for a cellular ligand and a nucleic acid coding for an antigen and epitope, respectively, of a pathogen, preferably an immunodominant antigen, is inserted into the genome of the beta-herpesvirus, may serve as a vaccine or be used as a vaccine or vaccination vector for vaccination against infection with the pathogen. The pathogen is preferably a virus, a bacterium or a parasite.

In connection therewith a person skilled in the art will immediately acknowledge that immune cells, such as natural killer cells, also referred to herein as NK cells, $CD8^+$ T cells and dendritic cells, also referred to herein as DCs, have basically the same function in different mammalian species, such as mouse and man, as may be taken from immunology text books such as "Janeway's Immunobiology", 8th addition, by Kenneth Murphy.

Furthermore, it has to be acknowledged by a person skilled in the art that any characteristic feature, embodiment of and any statement made herein in relation to beta-herpesviruses such as MCMV equally applies to HCMV. Furthermore, it will be acknowledged by a person skilled in the art that the beta-herpesvirus according to the present invention will, in a preferred embodiment, exhibit the following characteristics as observed for HCMV and MCMV, respectively: multiple infections occur with MCMV in mouse and HCMV in human, respectively, (Boppana, S. B. et al., 2001, N Engl J Med 344:1366-1371; Cicin-Sain, L. et al., 2005, J Virol 79:9492-9502); a response of neutralizing antibodies against CMV is caused by infection with MCMV in mouse and HCMV in human, respectively (Farrell, H. E. and Shellam, G. R. 1990, J Gen Virol 71 (Pt 3):655-664; Farrell, H. E. and Shellam, G. R. 1991, J Gen Virol 72 (Pt 1):149-156; Gerna, G. A. et al., 2008, J Gen Virol 89:853-865); memory inflation, which represents a very characteristic CD8+ T cell response, is caused by infection with MCMV in mouse and HCMV in human, respectively, and has almost identical kinetics in both human and mouse (Karrer, U. et al., 2003, J Immunol 170:2022-2029; Karrer, U. et al., 2004, J Virol 78:2255-2264; Klenerman, P. and Dunbar, P. R. 2008, Immunity. 29:520-522; Komatsu, H. et al., 2003, ClinExp Immunol 134:9-12; Holtappels R. et al., 2002, J Virol 76:151-164; Holtappels R. et al., 2001, J Virol 75:6584-6600; Snyder, C. M. et al., 2008, Immunity; 29(4):650-9).

It can thus be immediately taken from the above that infection of a host with its corresponding CMV species such as infection of human with HCMV and infection of mouse with MCMV, as well as immune responses to said infections in human and mouse, respectively, are comparable. More particularly, numerous publications of the prior art acknowledge the usefulness and appropriateness of the mouse model for studying CMV infection and immune response to said infection. For example, evidence for the above is found, among others, in the publications of Reddehase et al. (Reddehase, M. J. et al., 1985, J Virol 55(2):264-73; Reddehase, M. J., 2002, Nat Rev Immunol 2:831-844), Pollock and Virgin (Pollock, J. L. and Virgin, H. W. $4^{th}$, J Virol. 1995, 69(3):1762-8), Koffron et al. (Koffron, A. J. et al., 1998, J Virol 72(1):95-103), Brune et al. (Brune, W. et al., 2001, Curr Protoc Immunol., Chapter 19:Unit 19.7) and Bahíc et al. (Bahić, M. et al., 2011, Trends Mol Med. 17(11):677-85).

Furthermore there is increasing evidence that in connection with infection of a host with a corresponding CMV species, such as infection of human with HCMV and infection of mouse with MCMV, basically the same organs and tissues are infected, disease preferably occurs in immunocompromised subjects and the overall immune response caused by said infections is similar. Additionally, the value of $CD8^+$ T cells in CMV infection, particularly in HCMV infection has been shown. Evidence therefore may for example be taken from Riddell et al. (Riddell, S. R. et al., 1997, Rev Med Virol 7(3):181-192; Riddell, S. R. et al., 1993, Curr Opin Immunol 5(4):484-91; Riddell, S. R. et al., 1992, Science 257(5067):238-41), Riddell and Greenberg (Riddell, S. R. and Greenberg, P. D., 1995, Annu Rev Immunol 13:545-86), Brestrich et al. (Brestrich, G. et al., 2009, J Immunother, 32(9):932-40), Lilleri et al. (Lilleri, D. et al., 2009, J Infect Dis, 199(6):829-36), Kapp et al. (Kapp, M. et al., 2007, Cytotherapy, 9(8):699-711) Wilkinson et al., (Wilkinson, G. W. et al., 2008, J Clin Virol 41(3):206-12), Braud et al. (Braud, V. M. et al., 2002, Curr Top Microbiol Immunol 269:117-29) and Jackson et al. (Jackson, S. E. et al., 2011, Virus Res, 157(2):151-60).

In an embodiment of the beta-herpesvirus according to the present invention, wherein the beta-herpesvirus comprises at least one heterologous nucleic acid and wherein the at least one heterologous nucleic acid comprises a gene encoding a cellular ligand, the at least one heterologous nucleic acid is a nucleic acid which according to its nucleotide sequence preferably is not comprised in or part of the genome of the wild type beta-herpesvirus. In connection therewith it will be understood that a beta-herpesvirus according to the present invention in an embodiment comprises the heterologous nucleic acid comprising the gene encoding the cellular ligand as well as a heterologous nucleic acid comprising one or more than one gene encoding one or more cellular ligand(s). In connection therewith, the nucleic acid coding for the cellular ligand is also referred to herein as heterologous nucleic acid.

In an alternative embodiment the beta-herpesvirus according to the present invention comprises more than one heterologous nucleic acids. Accordingly, a beta-herpesvirus of the present invention comprises in an embodiment the at least one additional heterologous nucleic acid. In an embodiment said at least one additional heterologous nucleic acid is a heterologous nucleic acid which according to its sequence preferably is not comprised in or part of the genome of the wild type beta-herpesvirus and more preferably is a functional nucleic acid. Preferably, the functional nucleic acid is selected from the group comprising antisense molecules, ribozymes and RNA interference mediating nucleic acids. Alternatively, at least one additional heterologous nucleic acid is a nucleic acid coding for a peptide, oligopeptide, polypeptide or protein, wherein in a more preferred embodiment the peptide, oligopeptide, polypeptide or protein constitutes or comprises at least one antigen and epitope, respectively. Preferably said antigen is an antigen selected from the group comprising tumor antigens, tumor associated antigens, viral antigens, bacterial antigens and parasite antigens.

The term "antigen" as used herein preferably means a foreign molecule or part of a foreign molecule, such as a protein derived from a bacterium, or a peptide derived from said protein. Said foreign molecule when introduced into a body such as a human or mammalian body, is recognized by the receptor of an immune cell, such as the receptor of an NK cell, and preferably triggers an immune response against said antigen, such as the production of an antibody directed against said antigen or triggers an effector function of an immune cell.

The term "epitope" as used herein preferably means the distinct molecular feature of an antigen, preferably a feature on the surface of an antigen, that is recognized by the immune system, preferably by antibodies, B cells and/or T cells.

The term "homolog" or "homologue" as used herein in connection with herpesvirus proteins preferably means that a CMV gene of one CMV species, such as MCMV, can replace a homolog of said MCMV gene in another CMV species, such as HCMV. (Schnee, M. et al., 2006, J Virol 80:11658-11666). In other words homolog proteins preferably exhibit at least one common protein function. Accordingly, it will be acknowledged by a person skilled in the art that, for example, the homolog of UL50 of HCMV is M50 of MCMV and vice versa. A person skilled in the art will acknowledge that two proteins which exhibit at least one common protein function do not necessarily share the same amino acid sequence. For example, the gene product of m152 of MCMV and the gene product of US3 of HCMV are also understood to be homologs as both retain MHC I molecules in the ER.

Homologs or homologue proteins that display some degree of sequence homology in MCMV and HCMV are listed in Rawlinson et al. (Rawlinson, W. D. et al., 1996, J Virol 70(12):8833-49). Further examples are the viral immunevasins targeting the ligands for NK cell receptors in human and murine cells. In connection therewith it will be acknowledged that not all NKG2D ligands are homologs by sequence but by function. It will be acknowledged by a person skilled in the art that preferred human NKG2D ligands are MHC class-I-related protein A (MICA), MICB and UL16-binding proteins (ULPB1-6). In connection therewith it is important to note that ULBP1 and ULBP2 also bind to mouse NKG2D (Sutherland, C. L. et al., 2006, Blood 108 (4): 1313-1319).

Alternatively and/or additionaly, the term "homolog" or "homologue" as used herein in connection with herpesvirus proteins, preferably means a peptide, polypeptide or protein, wherein the gene encoding said peptide, polypeptide or protein is the gene of one herpesvirus species, such as HCMV, indicated to be a homolog of the gene of another species, such as another herpesvirus species according to Fossum et al. (Fossum, E. et al. 2009, PLoS Pathog 5(9):) or Davison et al. (Davison, A. J. et al., 2010, Vet Microbiol. 143(1):52-69 and Davison, A. J. et al., 2004, Compendium of Human Herpesvirus gene names, Reno).

Alternatively and/or additionaly, the term "homolog" or "homologue" as used herein in connection with cellular proteins, such as a cellular ligand as encoded by the beta-herpesvirus according to the present invention, preferably means that a protein and its homolog, i.e. its homolog protein exhibit a common biological function. Preferably, two proteins are homologs of each other if said two proteins show an amino acid (aa) sequence identity and/or an identity of the nucleotide sequence of the genes encoding the proteins. More preferably said sequence identity is of at least 50%, more preferably at least 75%, and most preferably at least 80%, 90% or 95%. Nevertheless it is important to note that as homolog proteins evolve, their 3D structure often remains more conserved than their sequence. Consequently, similarities in protein structure can be more reliable than sequence similarities for grouping together distant homologs, which often retain some aspect of such common biological function.

The term "receptor" as used herein preferably means a molecule expressed on the surface of a cell, whereby said molecule is capable of binding a cellular ligand. A receptor-ligand binding as used herein is preferably capable of initializing or inhibiting biochemical pathways and/or signal cascades when the proper ligand is binding to the receptor. It will be understood by a person skilled in the art that the cellular ligand(s) encoded by the beta-herpesvirus of the present invention is preferably one which is, as such and when naturally occurring, expressed by a cell from a subject, such as a neighboring cell of the receptor expressing cell or a cell of the wider environment within an organism. In an embodiment of the beta-herpesvirus according to the present invention the gene encoding such cellular ligand is inserted into the genome of the beta-herpesvirus, the beta-herpesvirus is capable of expressing said cellular ligand, preferably upon infection of a cell, irrespective of whether expression of said ligand is naturally occurring in said infected cell, i.e. without infection of the cell by said beta-herpesvirus. In a further embodiment the cellular ligand is a cellular ligand which, when naturally occurring, is expressed upon infection of the cell by the beta-herpesvirus according to the present invention expressing said ligand. In a still further embodiment the cellular ligand is a cellular ligand which, when naturally occurring, is expressed in the absence of infection of the cell by the beta-herpesvirus according to the present invention expressing said ligand. In connection therewith it is thus to be understood that a beta-herpesvirus of the present invention comprising a gene encoding a cellular ligand may mediate expression of a cellular ligand which when naturally occurring, is not expressed in the infected cell or is not expressed upon infection of the cell infected by the betaherpesvirus according to the present invention.

The binding of a cellular ligand a with its respective receptor preferably mediates a signal to the cell bearing said receptor to initialize or inhibit a biochemical pathway and/or signal cascade. This may, for example, result in the cell's activation or de-activation, cell division or cell death, or in certain molecules entering and/or exiting the cell.

Receptors as used herein preferably are protein molecules, embedded in either the plasma membrane of a cell in case of cell surface receptors or the cytoplasm of a cell in case of nuclear receptors, to which one or more specific types of signaling molecules, such as a cellular ligand as disclosed herein, may bind.

A molecule which binds to a receptor is preferably called a ligand, and is, in an embodiment of the beta-herpesvirus according to the present invention, a peptide, a polypeptide, a protein or a small molecule, such as a neurotransmitter, a hormone, a pharmaceutical drug, or a toxin. Each kind of receptor can bind only certain types or forms of ligands. Each cell typically has many receptors of many different types.

In an embodiment of the beta-herpesvirus of the present invention a ligand, including a cellular ligand, is also understood to be a substance that forms a complex with a biomolecule to serve a biological purpose. In a narrower sense of said embodiment, a ligand is a signal triggering molecule which binds to a site on a target molecule which is preferably a receptor for said ligand.

The binding of a ligand with a target molecule, such as a receptor molecule preferably occurs by intermolecular forces, such as ionic bonds, hydrogen bonds and van der Waals forces. The docking, i.e. the association, of ligand to target molecule, is usually reversible, i.e. dissociation of the ligand from the receptor may occur under specific reaction conditions. In an embodiment of the present invention irreversible covalent binding between a ligand and its target molecule, such as the respective receptor, occurs.

The binding of a ligand to a receptor usually alters the conformation of the receptor particularly in case the receptor is a peptide, polypeptide or protein. The conformation of a receptor determines the function of a receptor. Ligand as referred to herein preferably comprise substrates, inhibitors, activators, and neurotransmitters.

Immune cells such as NK cells, express a variety of receptors that serve either to activate or to suppress the immunologic activity of said immune cells, including the cytolytic activity thereof.

Natural killer cells, also referred to herein as NK cells, are a type of cytotoxic lymphocyte that constitutes a major component of the innate immune system. NK cells play a major role in the rejection of tumors, bacteria, parasites and cells infected by viruses. One particular immunological activity mediated by NK cells is the release of small cytoplasmic granules of proteins called perforin and granzyme that cause the target cell to die by apoptosis, i.e. programmed cell death and IFNγ and TNFα release.

NK cells are defined as large granular lymphocytes, also referred to herein as LGL, and constitute the third type of cells differentiated from the common lymphoid progenitor generating B and T lymphocytes. NK cells preferably do not express T-cell antigen receptors, also referred to herein as TCR, or Pan T marker CD3 or surface immunoglobulins (Ig) B cell receptors. More preferably, NK cells preferably and herein express surface markers such as CD16 (FcγRIII) and CD56 in humans and NK1.1 or NK1.2 in C57BL/6 mice. Up to 80% of human NK cells also express CD8.

Given their strong cytolytic activity and the potential for auto-reactivity, the activity of NK cells is tightly regulated. NK cells must receive an activating signal which can come in a variety of forms comprising cytokines, Fc receptor, activating and inhibitory receptors.

As known to a person skilled in the art NK cells were found to not require activation in order to kill cells that are missing "self" markers of major histocompatibility complex, also referred to herein as MHC class I.

In order for NK cells to defend the body against viruses and other pathogens, NK cells require mechanisms that enable the determination of whether a cell is infected or not. The exact mechanism has not yet been finally elucidated, but recognition of an "altered self" state is thought to be involved. To control their cytotoxic activity, NK cells possess two types of surface receptors: activating receptors and inhibitory receptors. Most of these receptors are not unique to NK cells and can be present in some T cell subsets as well.

The relative balance of signals from these receptors regulates NK cell activity (Lanier, L. L. et al., 2001, Nature Immunol 2:23-27; Moretta, A. et al., 2001, Annu Rev Immunol 19:197-223; Ravetch, J. V. and Lanier, L. L. 2000, Science 290:84-89 and Lopez-Botet, M. et al., 2000, Hum Immunol 61:7-17).

NK cell receptors, also referred to herein as NKR, can be subdivided into activating or inhibitory receptors. Although the extracellular domains of the various NKRs are extremely diverse, their intracellular domains are mostly conserved so that inhibitory or activating receptors share common inhibitory or activating signaling pathways. Inhibitory receptors contain a tyrosine-based inhibitory motif (ITIM) in their intracellular domain. Receptor ligation triggers tyrosine phosphorylation by a Src family kinase. This recruits SHIP-1 to the membrane, which then degrades phosphatidylinositol-3,4,5-trisphosphate to phosphatidylinositol-3,4-bisphosphate; SHP-1 or SHP-2 can also be recruited to the membrane at this time.

Activating NK cell receptors, such as NKG2D, lack ITIMs, but posses a positively charged arginine residue in their transmembrane domain which allows them to interact with adaptor proteins such as DAP10, DAP12, FcεRI-γ or CD3-ξ (Lanier, L. L. 2008, Nat Immunol 9(5):495-502). These adaptors bear tyrosine-based activation motifs (ITAMs), which are phosphorylated upon receptor engagement, also by a Src family kinase. Syk, ZAP-70, and PI₃K or Grb2 are then recruited to the membrane, where they mediate actin cytoskeleton reorganization, cell polarization, release of cytolytic granules, and the transcription of many cytokine and chemokine genes. The engagement of NKG2D leads to NK cell cytotoxicity and cytokine secretion or to a co-stimulation of CD8 T cells.

In connection therewith a person skilled in the art will acknowledge that the maturation of NK cells is characterized by a high frequency of NK cells expressing the most mature phenotype $CD27^{low}CD11b^{high}$. For example a high frequency of NK cells expressing the most mature phenotype $CD27^{low}CD11b^{high}$ is observed in in WT-MCMV infected mice. Additionally and alternatively, NK-cell expression of IFN-γ and CD69, but also several other markers, can be used to assess the activation of NK cells. In connection therewith a person skilled in the art knows assays for assassing wheter NK cell is activated or not. For example, NK cells can be analysed by flow cytometry after surface staining with anti-CD69 (H1.2F3) and for the detection of IFN-γ expression by NK cells, incubation in medium supplemented with 10% of FCS (Gibco), IL-2 and Brefeldin A (eBioscience) is needed.

Natural killer cells express inhibitory receptors specific for polymorphic MHC molecules, which enables them to mediate "missing self-recognition", which provides the capacity to attack cells of the body that extinguish expression of MHC class I molecules. These inhibitory receptors recognize MHC class I alleles, which is regarded as an explanation why NK cells kill cells possessing low levels of MHC class I molecules. This inhibition is crucial to the role played by NK cells. MHC class I molecules mediate a main mechanism by which cells display viral or tumor antigens to cytotoxic T-cells. A common evolutionary adaption to this is seen in both intracellular microbes and tumours is a chronic down-regulation of these MHC I molecules, rendering the cell impervious to T-cell mediated immunity. It is believed that NK cells, in turn, evolved as an evolutionary response to this adaption, as the loss of the MHC would deprive these cells of the inhibitory effect of MHC and would render these cells vulnerable to NK cell mediated apoptosis.

More specifically, inhibitory NK cell receptors comprise an ITIM motif in the intracellular domain of said NK cell receptors. Ligation of inhibitory receptors via their ligand, such as MHC-I, leads to phosphorylation of motifs and initiates the signaling cascade involving tyrosine phosphatase such as SHP-1 and SHP-2 and results in dephosphorilation of activating signaling motif and NK cell inhibition. (Lanier, L. L. 2003, Curr Opin Immunol 15(3):308-14). The inhibitory NK cell receptors include killer immunoglobulin-like receptors (KIR) and immunoglobulin-like receptors (LIR) in humans and the Ly49 family of receptors in the mouse, as well as CD94-NKG2A receptor in humans and mice (Vilches, C. and Parham, P. 2002, Annu Rev Immunol 20:217-51; Moretta, L. A. 2004, Embo J 23(2):255-259). Ligands for the inhibitory KIR receptor family, such as LIR and Ly49 receptors are classical MHC-I molecules, while CD94-NKG2A receptor binds to non-classical MHC-I molecule, HLA-E in humans and Qa-1 in mice (Raulet, D. H. 2003, Nat Rev Immunol 3(10):781-90). Recognition of MHC-I molecules is also required during the development of NK cells and for reaching their functional competence (reviewed in: Elliott, J. M. and Yokoyama, W. M. 2011, Trends Immunol 32(8):364-72; Vivier, E. et al., 2011, Science 7; 331(6013):44-49).

Furthermore, the family of natural cytotoxicity receptors, also referred to herein as NCR receptors, which comprises NKp30, NKp44, NKp80 and NKp46, is almost exclusively expressed by NK cells. All four receptors have been extensively studied in human NK cells, whereas NKp46 has been characterized in mice as well. In contrast to NKp30, NKp80 and NKp46, only NKp44 is not expressed on all NK cells, but is only found on activated NK cells. NCRs ligands are diverse and include viral haemagglutinins (NKp46 and NKp44), heparan sulphate proteoglycans (NKp30 and NKp46) and the nuclear factor HLA-B-associated transcript 3 (BATS) (NKp30) 47 and the activation-induced C-type lectin (AICL) (NKp80). However, no endogenous cellular NCR ligands have been identified as yet. (Raulet, D. H. and Guerra, N. 2009, Nat Rev Immunol. 9(8):568-80)

Preferably, NK cells as used herein are different from Natural Killer T cells.

Furthermore, NK cell receptor types, both with inhibitory as well as activating function, can be differentiated by structure.

Based on their chemical structure NK cell receptors are classified into two families:
a) receptors containing Ig-like ectodomains and
b) receptors containing C-type lectin-like domains (Raulet, D. H. 2003, supra).

The latter group include Ly49, NKG2 and NKRp1 receptors.

The following is a compilation of the most important NK cell receptor types.

CD94 also referred to as NKG2, which are C-type lectin family receptors, comprising NKG2D, are conserved in both rodents and primates and identifies non-classical (also non-polymorphic) MHC I molecules like HLA-E. Expression of HLA-E at the cell surface is dependent on the presence of a nonamer peptide epitope derived from the signal sequence of classical MHC class I molecules, which is generated by the sequential action of signal peptide peptidase and the proteasome.

Ly49 represents C-type lectin family receptors which are of multigenic presence in mice, while humans have only one pseudogenic Ly49. Ly49 is the receptor for classical (polymorphic) MHC I molecules. It will be immediately understood by a person skilled in the art that multigenic as used herein preferably refers to a receptor which is encoded by multiple genes. For example, C-type lectin family receptors are encoded by multiple genes in the NK gene complex (NKC) on mouse chromosome 6.

More particularly, Ly49 receptors are type II transmembrane proteins encoded by polymorphic and polygenic gene complex on chromosome 6 (reviewed in Ravetch, J. V. and Lanier, L. L., 2000, Science, 290(5489):84-9). The number of Ly49 genes varies among different mouse strains. Although many inhibitory receptors are shared among different haplotypes (e.g. Ly49A, Ly49C, Ly49G2, and Ly49I), their contribution in inhibitory signalling is different with regards to MHC-I haplotype-restricted education imposed during NK cell development. The number of activating genes varies a great deal among strains, from one (Ly49l) in BALB/c to seven (Ly49d, u, p3, p1, w, m, h) in NOD mice (Carlyle, J. R. et al., 2008, Semin Immunol 20(6):321-30).

KIR, also referred to herein as Killer-cell immunoglobulin-like receptors, belong to a multigene family of more recently-evolved Ig-like extracellular domain receptors. KIR are present in non-human primates and are the main receptors for both classical MHC I (HLA-A, HLA-B, HLA-C) and also non-classical HLA-G in primates. Some KIRs are specific for certain HLA subtypes.

ILT or LIR, also referred to herein as leukocyte inhibitory receptors, are recently-discovered members of the Ig receptor family.

NKG2D is an activating receptor for the NKG2 receptor family expressed on NK cells, NKT cells, γδ T cells and $CD8^+$ T cells. NKG2D recognizes cell surface molecules structurally related to MHC class I proteins induced by infection or any other type of cellular stress. The involvement of NKG2D leads to NK cell cytotoxicity and cytokine secretion or to a co-stimulation of CD8$^+$ T cells.

NKG2D is a type-2 trans-membrane glycoprotein expressed as a disulfide linked homodimer on the cell surface (Diefenbach, A. et al., 2002, Nat Immunol, 3:1142-9; Jamieson, A. M. et al., 2002, Immunity, 17:19-29). It is encoded by the KLRK1 (killer cell lecitin-like receptor subfamily member 1) gene located on a mouse chromosome 6 and in the syntenic position on human chromosome 12 (Houchins, J. P. et al., 1991, J Exp Med, 173:1017-20). NKG2D has no signaling motif and therefore associates with signal-transducing proteins through charged residues in the trans-membrane region. In mice, alternative RNA splicing results in two NKG2D isoforms, the long (NKG2D-L) and short (NKG2D-S) isoform which differ in 13 amino acids (Diefenbach, A. et al., 2002, supra; Gilfillan, S. et al., 2002, Nat Immunol, 3:1150-5). The NKG2D-L isoform pairs with the DAP10 signaling molecule, while NKG2D-S associates either with DAP10 or DAP12. Resting mouse NK cells express very little NKG2D-S, but the expression is induced after NK cell activation. Neither isoform can be detected in resting CD8$^+$ T cells but after T-cell receptor (TCR) stimulation the expression of both isoforms is upregulated. Because CD8$^+$ T cells do not express DAP12, the two NKG2D isoforms that are expressed by activated T cells can interact only with DAP10, whereas activated NK cells can transmit signals through DAP10 and DAP12. In humans there is only one isoform which corresponds to the long form in mouse and it only interacts with DAP10 (Bauer, S. et al., 1999, Science, 285:727-9; Wu, J. et al., 1999, Science, 285:730-2; Rosen, D. B. et al., 2004, J Immunol, 173:2470-8). NKG2D is expressed by all NK cells, most NKT cells, a subset of γδ T cells, all human CD8$^+$ T cells, activated mouse CD8$^+$ T cells and a subset of CD4 T cells (Diefenbach, A. et al., 2002, supra; Jamieson, A. M. et al., 2002, Immunity, 17:19-29; Bauer, S. et al., 1999, supra; Diefenbach, A. et al., 2000, Nat Immunol, 1:119-26; Girardi, M. et al., 2001, Science, 294:605-9; Ehrlich, L. I. et al., 2005, J Immunol, 174:1922-31). On NK cells NKG2D serves as a primary activating receptor meaning that the engagement of NKG2D can override inhibitory signals (Cerwenka, A. et al., 2001, Proc Natl Acad Sci USA, 98:11521-6). NKG2D receptor on CD8$^+$ T cells acts as a co-stimulatory receptor which augments TCR-induced responses (Groh, V. et al., 2001, Nat Immunol, 2:255-60; Maasho, K. et al., 2005, J Immunol, 174:4480-4; Markiewicz, M. A. et al., 2005, J Immunol, 175:2825-33).

Human NKG2D was originally identified in 1991 as an orphan receptor that is expressed on NK cells (Houchins, J. et al., 1991, J. Exp. Med 173(4):1017-20). The mouse (Vance, R. et al., 1997, Eur. J Immunol 27(12):3236-41; Ho, E. et al., 1998, Proc Natl Acad Sci USA 95(11):6320-5), rat (Berg, S. F. et al., 1998, Int. Immunol. 10(4):379-85), and porcine (Yim, D. et al., 2001, Immunogenetics 53(3):243-9). Homologs of NKG2D have also been identified. Interspecies amino acid (aa) sequence identities range from 52-78% for the entire protein, whereby mouse and rat are the most closely related sequences, and from 72-90% within the lectin domain of NKG2D. Its function was first described in 1999 by two separate groups investigating MICA/MICB ligands (Bauer, S. et al., 1999, supra) or signal transduction through the DAP10 adapter protein (Wu, J. et al., 1999, supra). More recently, several additional ligands have also been reported (Cerwenka, A. et al., 2000, Immunity 12(6): 721-7, Diefenbach, A., et al. 2000, supra; Cosman, D. et al., 2001, Immunity. 14(2):123-33).

NKG2D ligands are distantly related homologs of the MHC I proteins and are characterized by a striking structural diversity, different expression patterns and regulation mechanisms.

Preferred human NKG2D ligands are MHC class-I-related protein A, also referred to herein as MICA, MHC class-I-related protein B, also referred to herein as MICB, and UL16-binding proteins 1 to 6, also referred to herein as ULPB1 to 6. MICA (ENSG00000204520 according to the ENSEMBL database) and MICB (ENSG00000231372 according to the ENSEMBL database)), encoded by the genes within human MHC (Bauer, S. et al., 1999, supra; Groh, V. et al., 1996, Proc Natl Acad Sci USA 93:12445-50) are the only NKG2D ligands containing three immunoglobulin-like domains (α1, α2 and α3), but unlike MHC molecules, they do neither associate with β2 microglobulin nor do they bind antigenic peptides. All other NKG2D ligands are related to MHC I molecules but contain only α1 and α2 domains. In an embodiment of the beta-herpesvirus according to the present invention wherein the cellular ligand comprises at least one immunoglobulin-like domain, the cellular ligand comprises an α1 domain and an α2 domain. In a further embodiment of the beta-herpesvirus according to the present invention the cellular ligand comprises an α1 domain, an α2 domain and an α3 domain, wherein the cellular ligand is preferably selected from the group comprising MICA and MICB.

Although named by their ability to bind HCMV protein UL16, only the first two identified ULBP proteins ULBP1 (ENSG00000111981 according to the ENSEMBL database)), ULBP2 (ENSG00000131015 according to the ENSEMBL database)) and the subsequently described ULBP5 bind this viral protein (Cosman, D. et al., 2001, Immunity, 14:123-33; Radosavljevic, M. et al., 2002 Genomics, 79:114-23; Bacon L. et al., 2004, J Immunol, 173:1078-84). Like MIC proteins, ULBP5 and ULBP6 are trans-membrane proteins, while proteins ULBP1, ULBP2 and ULBP5 (ENSG00000131019 according to the ENSEMBL database)) are anchored to the membrane via glycosylphosphatidylinositol (GPI) (Eleme, K. et al., 2004, J Exp Med, 199:1005-10). The ULBP family is also known as the retinoic acid early transcript 1 (RAET-1) family since they show sequence homology to the mouse retinoic acid early 1 (RAE-1) proteins (Nomura, M. et al., 1994, Differentiation, 57:39-50; Cerwenka, A. et al., 2000, Immunity, 12:721-7; Diefenbach, A. et al., 2001, Nature, 413:165-71). Accordingly, in human and in case of the beta-herpesvirus according to the present invention for us in the vaccination of a human ligands for NKG2D are preferably selected from the group comprising MHC class-I-related proteins and UL16-binding proteins. MHC class-I-related proteins are preferably selected from the group comprising MICA and MICB. UL16-binding proteins are preferably selected from the group comprising ULPB1, ULPB2, ULPB3, ULPB4, ULPB5 and ULPB6. With regard to mouse NKG2D ligands there is a first family of ligands which is referred to as the RAE-1 family. Said RAE-1 family comprises RAE-1α, RAE-1β, RAE-1γ, RAE1-5 and RAE-1ε, which are highly related to each other (>85% amino acid homology) and differentially expressed in various mouse strains. A second family of mouse NKG2D ligands is the H60 family that comprises three members of the H60 family, namely H60a, H60b and H60c, of which H60a is a minor histocompatibility antigen (Malarkannan, S. et al., 1998, JI Immunol, 161:3501-9; Takada, A. et al., 2008, J Immunol, 180:1678-

85; Whang, M. I. et al., 2009, J Immunol, 182:4557-64). Finally, murine UL16 protein-like transcript 1, also referred to herein as MULT-I, is the sole member of the third family of mouse NKG2D ligands (Carayannopoulos, L. N. et al., 2002, J Immunol, 169:4079-83; Diefenbach, A. et al., 2003, Eur J Immunol, 33:381-91). Accordingly, in mice ligands for NKG2D are preferably selected from the group comprising proteins of the RAE-1 family, proteins of the H60 family and murine UL16 protein-like transcripts. Proteins of the RAE-1 family are preferably selected from the group comprising RAE-1α, RAE-1β, RAE-1γ, RAE1-δ and RAE-1ε. Proteins of the H60 family are preferably selected from the group comprising H60a, H60b and H60c. Murine UL16 protein-like transcripts are preferably selected from the group comprising MULT-1.

In an embodiment of the beta-herpesvirus according to the present invention the cellular ligand is a trans-membrane protein. In a preferred embodiment wherein the cellular ligand is a trans-membrane protein the cellular ligand is preferably selected from the group comprising MIC proteins, ULBP5 and ULBP6. In a further embodiment the cellular ligand is a MIC protein preferably selected from the group comprising MICA and MICB A trans-membrane protein as used herein preferably means a protein which is extending through the membrane of a cell. More preferably, a trans-membrane protein as used herein is an integral membrane protein which extends from one side of a membrane of a cell to the other side of the membrane. Furthermore, a trans-membrane protein as used herein preferably is a polytopic protein that spans an entire biological membrane.

In an embodiment of the beta-herpesvirus according to the present invention the cellular ligand is a protein anchored to or in the membrane via glycosylphosphatidylinositol, also referred to herein as GPI. In an embodiment the cellular ligand anchored to or in the membrane via GPI is preferably selected from the group comprising ULBP1, ULBP2 and ULBP3.

A "glycosylphosphatidylinosityl" which is also referred to herein as "GPI-anchor", is preferably a glycolipid which preferably is attached to a terminus, preferable the C-terminus, of a protein during posttranslational modification. The GPI-anchor is preferably composed of a phosphatidylinositol group linked through a carbohydrate-containing linker, i.e. glucosamine and mannose glycosidically bound to the inositol residue, and via an ethanolamine phosphate (EtNP) bridge to the terminal amino acid of a protein. Preferably, the terminal amino acid is the C-terminal amino acid. The two fatty acids within the hydrophobic phosphatidyl-inositol group anchor the protein to or in the membrane of a cell.

A protein anchored to or in the membrane via glycosylphosphatidylinositol also referred to herein as a GPI-linked protein, is preferably a protein which contains a signal peptide directing the protein into the endoplasmic reticulum (ER). The terminus of the protein, such as the C-terminus, is preferably composed of hydrophobic amino acids that stay inserted in the membrane of the ER. Such hydrophobic end is then cleaved off by an enzyme and replaced by the GPI-anchor. As the protein processes through the secretory pathway of the ER, it preferably is transferred via vesicles to the Golgi apparatus and finally to the extracellular space where it remains attached to the exterior leaflet of the cell membrane. In a preferred embodiment the GPI anchor is the sole means of attachment of such proteins to the membrane. It will be understood by a person skilled in the art that cleavage of the GPI-anchor by phospholipases will result in controlled release of the protein from the membrane.

It is the merit of the present inventor to have found that the insertion of at least one gene encoding a cellular ligand, such as NKG2D, into the genome of a beta-herpesvirus, results in expression of said cellular ligand which overrides inhibitory signals delivered by self-MHC class I proteins and thus triggers activation of an immune cell, more particularly NK cells.

The importance of signaling pathways in beta-herpesvirus control induced by receptor-ligand interaction, such as NKG2D signaling pathway, is best illustrated by the sophisticated mechanism that HCMV and MCMV have developed to avoid NKG2D-mediated immune control.

It is acknowledged by a person skilled in the art that more than half of the CMV genes encode gene products interfering with different immune mechanisms at all stages of the immune system of an organism infected with CMV. Such gene products which interfere with different immune mechanisms are referred to herein as so-called immunoevasins. The gene encoding an immunevasin is also referred to herein as immunevasive gene or immune modulatory gene.

Infection of the respective host organism with either of HCMV and MCMV up-regulates the transcription of NKG2D ligands in said host organisms, which can result in NKG2D-mediated lysis by NK cells of cells infected by HCMV and MCMV, respectively. Both viruses have developed different evasive mechanisms using immunevasins to prevent and/or at least counteract the expression of NKG2D ligands on the cell surface. Such immunevasins which downregulate the expression of NKG2D ligands on the cell surface of infected cells are also referred to herein as gene products regulating NK cell response.

More particularly, HCMV protein UL16 which is an immune modulatory gene encoding a gene product regulating NK cell response, binds NKG2D ligands MICB, ULBP1, ULBP2 and ULBP6 in the endoplasmatic reticulum (ER) and redirects these ligands to the lysosomes for sequestration (Cosman, D. et al., 2001, supra; Welte, S. A. et al., 2003, Eur J Immunol, 33:194-203; Dunn, C. et al., 2003, J Exp Med, 197:1427-39; Wu, J. et al., 2003, J Immunol, 170:4196-200; Vales-Gomez, M. et al., 2003, BMC Immunol, 4:4; Rolle, A. et al., 2003, J Immunol, 171:902-8). The ability of UL16 to bind its ligands depends critically on the presence of a glutamine (MICB) or closely related glutamate (ULBP1 and ULBP2) at position 169. An arginine residue at this position however, as found for example in MICA or ULBP3, would cause steric clashes with UL16 residues. The inability of UL16 to bind MICA and ULBP3 can therefore be attributed to single substitutions at key NKG2D ligand locations (Muller, S. et al., 2010, PLoS Pathog, 6(1):e1000723). UL16 doesn't bind ULBP3-5. The structure of UL16 revealed that this viral protein mimics a central binding motif of otherwise structurally unrelated NKG2D and thus enabling the virus to evade several diverse NKG2D ligands (Muller, S. et al., 2010, supra). The gene product of another HCMV immunomodulatory gene, namely the gene product of UL142, retains newly synthesized full-length MICA in the cis-Golgi compartment (Ashiru, O. et al., 2009, J Virol, 83:12345-54; Chalupny, N. J. et al., 2006, Biochemical and biophysical research communications, 346(1):175-81). Interestingly, the MICA*008 allele, which lacks the cytoplasmatic domain, is resistant to the action of UL142. Since MICA*008 is frequently found in humans, this suggests that HCMV exerts during co-evolution selective pressure to the host which drives diversity and polymorphism of NKG2D ligands. In addition to targeting already synthesized proteins, HCMV employs miRNAs to prevent the translation of ligands for NKG2D. HCMV encodes miRNA-UL112 that competes with endogenous miRNA for binding to the 3'-UTR (untranslated region) of the MICA transcript thus repressing the translation of this NKG2D ligand (Stern-Ginossar, N. et al., 2007, Science, 317:376-81; Stern-Ginossar, N. et al., 2008, Nat Immun, 9:1065-73; Wilkinson et al., 2008, J Clin Virol, 41(3):206-12). In an embodiment of the beta-herpesvirus of the present invention the beta-herpesvirus herpesvirus comprises the deletion of at least one miRNA. In a further embodiment the miRNA is capable of binding a transcript of the cellular ligand. In a further embodiment the miRNA is capable of repressing the translation of the gene coding for the cellular ligand. In a still further embodiment the miRNA is miRNA-UL112, also referred to herein as hcmv-miR-UL112 (MIMAT0001577 AAGUGACGGUGAGAUCCAGGCU (MirBase) (Stern-Ginossar et al., 2008, supra; Stern-Ginossar et al., 2007, supra)

In an embodiment of the beta-herpesvirus of the present invention, wherein binding of a gene product regulating NK cell response is capable of binding the cellular, the binding of the gene product regulating NK cell response and the cellular ligand results in reduction of expression of the cellular ligand. In connection therewith it will be acknowledged that a person skilled in the art will know tests for assessing wheter the expression of the cellular ligand is reduced. Such test is, for example, described in Cosman et al. (Dunn, C. et al., 2003, J Exp Med, 197(11):1427-39). More particularly, FACS analysis of surface expression of cellular ligands and assays for determining NK cell cytotoxicity can be performed.

MCMV also encodes immunoevasins that prevent the accessibility of mouse NKG2D ligands to the cell surface (Lenac, T. et al., 2008, Med Microbiol Immunol, 197:159-66). The product of the m152 gene, initially described as a negative regulator of MHC-I molecules (Ziegler, H. et al., 1997, Immunity, 6:57-66), retains the RAE-1 family of proteins in the ERGIC/cis-Golgi compartment (Krmpotic, A. et al., 2002, Nat Immunol, 3:529-35; Lodoen, M. et al., 2003, J Exp Med, 197:1245-53; Arapovic, J. et al., 2009, J Virol, 83:8198-207). Not all RAE-1 isoforms, however, are equally susceptible to MCMV regulation. RAE-1δ is more resistant to MCMV than other RAE-1 isoforms which is, at least in part, due to the absence of the PLWY motiv in the RAE-1δ cytoplasmatic domain (Arapovic, J. et al., 2009, supra). The product of the m155 gene causes the degradation of the H60 protein, although the underlying molecular mechanism is not yet entirely understood. The product of the m145 gene binds MULT-1 after it leaves the ER and makes MULT-1 more susceptible for m138-mediated degradation (Krmpotic, A. et al., 2005 J Exp Med, 201:211-20). Finally, the product of m138, also known as fcr-1, assists in diminishing the expression of MULT-1, H60 and RAE-1ε by interfering with their recycling on the cell surface and redirecting them to lysosomes for degradation (Lenac, T., 2006, J Exp Med, 203:1843-50; Wilkinson, G. W. et al., 2008, J Clin Virol, 41(3):206-12)).

As has been outlined above receptors, such as NKG2D, may serve as primary activating receptors, particularly on NK cells. In a preferred embodiment of the beta-herpesvirus of the present invention thus at least one gene encoding a cellular ligand, preferably a gene encoding at least one ligand for NKG2D, is introduced into the genome of the beta-herpesvirus. Expression of said cellular ligand is preferably mediated and occurring, respectively, upon infection of a cell with said beta-herpesvirus whereby the cell is preferably permissive for infection with the beta-herpesvirus.

In a further preferred embodiment of the beta-herpesvirus of the present invention at least one immune modulatory gene is deleted from the genome of the beta-herpesvirus. It is also within the present invention that more than one immune modulatory gene is deleted from the genome of the beta-herpesvirus. In CMV simultaneous deletion of several immune modulatory genes as well as other genes encoding gene products with unknown function or functions other than immunevasion has been described (Cicin-Sain et al., 2007, supra). In a further embodiment of the beta-herpesvirus of the present invention the additional deletion of at least one non-essential gene coding for a gene product with a function other than immunevasion or immunemodulation is also considered. The term non-essential gene as used herein preferably means a gene which encodes a gene product, wherein a beta-herpesvirus deficient in said gene product is not attenuated in vitro. An essential gene as used herein preferably means a gene which encodes a gene product, wherein a beta-herpesvirus deficient in said gene product is not capable of replicating in vitro. Additionally and alternatively, The an essential gene as used herein in connection with herpesvirus proteins, preferably means a gene, indicated to be an essential gene according to Liu et al. (Liu et al., PNAS 2003). In an embodiment of the present invention an essential gene of HCMV is preferably selected from the group comprising UL32, UL34, UL37.1, UL44, UL46, UL48, UL48, UL49, UL50, UL51, UL52, UL53, UL54, UL55, UL56, UL57, UL60, UL70, UL71, UL73, UL75, UL76, UL77, UL79, UL80, UL84, UL85, UL86, UL87, UL89.1, UL90, UL91, UL92, UL93, UL94, UL95, UL96, UL98, UL99, UL100, UL102, UL104, UL105, UL115 and UL122.

As far as the deletion of at least one immune modulatory gene is contemplated herein said at least one immune modulatory gene is preferably selected from the group comprising genes encoding gene products affecting antigen presentation, cytokine response, the complement system and humoral immunity. More preferably, the deleted at least one immune modulatory gene is preferably selected from the group comprising a gene encoding a gene product that down-regulates MHC I to avoid CTL response; a gene enconding a gene product that evades the NK cell response, such as a gene enconding gene product which prevents the accessibility of mouse NKG2D ligand to the cell surface; a gene enconding a gene product that interferes with MHC II presentation; a gene enconding a gene product that down-regulates adhesion molecules; a gene enconding a gene product that interacts with IL-1; a gene enconding a gene product that activates TGF-β.

In an embodiment of the beta-herpesvirus of the present invention where more than one immune modulatory gene is deleted from the genome of the beta-herpesvirus, only immune modulatory genes from one particular group of immune modulatory genes are deleted, e.g. only immune modulatory genes are deleted the gene product of which results in preventing the accessibility of an NKG2D ligand to the cell surface, more preferably of one particular NKG2D ligand. In a further embodiment immune modulatory genes from two, three, four, five or more of the above mentioned immune modulatory genes are deleted. In a still further embodiment each and any immune modulatory gene are deleted in combination with each and any other immune modulatory gene.

In an embodiment of the beta-herpesvirus according to the present invention a gene product encoded by an immune modulatory gene is preferably a gene product regulating NK cell response and more preferably is encoded by an immune modulatory gene preferably selected from the group comprising UL16, UL18, UL40, UL 141 (Prod'homme V et al., J Gen Virol. 2010; Tomasec P et al., Nat Immunol. 2005), UL142, m152, m155, m145 and m138. In an embodiment wherein the beta-herpesvirus is an HCMV a gene product encoded by an immune modulatory gene is a gene product regulating NK cell response and more preferably is encoded by an immune modulatory gene preferably selected from the group comprising UL16, UL18, UL40, UL142. In an embodiment wherein the beta-herpesvirus is an MCMV a gene product encoded by an immune modulatory gene is a gene product regulating NK cell response and more preferably is encoded by an immune modulatory gene preferably selected from the group comprising m152, m155, m145 and m138.

In an embodiment of the beta-herpesvirus according to the present invention wherein the gene product is regulating MHC class I presentation the immune modulatory gene preferably selected from the group comprising US6, US3, US2, UL18, US11, UL83 and UL40.

It will be acknowledged that a person skilled in the art is aware of further examples of an immune modulatory gene of each and any of the above mentioned groups of immune modulatory genes as well as of other groups of immunevasive genes regulating the immune response of the infected host to the advantage of viral replication, viral spread and/or viral infection. The deletion of each and any of these immune modulatory genes from the beta-herpesvirus according to the present invention is encompassed by the present invention and is preferably advantageous for the vaccine and/or vector properties as well as for the immune response mediated by said vaccine and/or vector of the present invention. Furthermore, it will be immediately understood that deletion of one or more than one immune modulatory gene which encodes one or more than one immunevasin(s) regulating the immune response of the infected host to the advantage of the virus preferably results in attenuation of the beta-herpesvirus of the present invention.

In a most preferred embodiment of the beta-herpesvirus according to the present invention at least one immune modulatory gene is deleted which encodes an immunevasin which regulates NK cell response and even more preferably is capable of binding the cellular ligand comprised in the beta-herpesvirus of the present invention. It is also preferred that if more than one such cellular ligand is comprised in the beta-herpesvirus of the present invention for at least one, preferably each and any of such cellular ligand at least one immune modulatory gene is deleted which encodes an immunevasin which regulates NK cell response and which is capable of binding said cellular ligand comprised in the beta-herpesvirus of the present invention. In connection therewith it has to be noted that dependent on the particular beta-herpesvirus and the particular cellular ligand which is comprised in the beta-herpesvirus of the present invention such deletion of an immunevasin which regulates NK cell response and which is capable of binding said cellular ligand comprised in the beta-herpesvirus is advantageous. It is important to understand that in some embodiments of the beta-herpesvirus of the present invention such deletion is nevertheless not necessary as overexpression of the cellular ligand may override the inhibitory capacity of the respective immunevasin which regulates NK cell response and which is capable of binding said cellular ligand comprised in the beta-herpesvirus. Nevertheless, it will be immediately understood that, although not necessary, in some embodiments it is preferred to delete the inhibitory gene which inhibits a or the particular interaction of the particular receptor ligand, e.g. NK cell receptor ligand, expressed by the beta-herpesvirus according to the present invention.

In an embodiment of the beta-herpesvirus of the present invention, wherein the beta-herpesvirus of the present invention encodes at least one additional heterologous nucleic acid and wherein the at least one additional heterologous nucleic acid is a functional nucleic acid, the functional nucleic acid is preferably selected from the group comprising antisense molecules, ribozymes and RNA interference mediating nucleic acids. It is a further embodiment that the at least one additional heterologous nucleic acid is a heterologous nucleic acid coding for a peptide, oligopeptide, polypeptide or protein wherein preferably the peptide, oligopeptide, polypeptide or protein constitutes or comprises at least one antigen. In a further preferred embodiment an immune modulatory gene such as US11 is used as insertion site for the at least one additional heterologous nucleic acid. In an embodiment the immune modulatory gene, such as US11 is deleted by insertion of the at least one additional heterologous nucleic acid, which preferably codes for a peptide, oligopeptide, polypeptide or protein wherein preferably the peptide, oligopeptide, polypeptide or protein constitutes or comprises at least one antigen. In a further preferred embodiment an immune modulatory gene is deleted by insertion of a gene into the beta-herpesvirus genome comprising the at least one additional heterologous nucleic acid at the position of the immune modulatory gene. For example US11 encodes an immunoevasin and its deletion will (i) lead to attenuation of the vaccine strain and (ii) will improve antigen presentation in the HLA class I pathway. Nevertheless it will be immediately understood that other ORFs encoding HCMV immnoevasins can be used as insertion sites. Such sites of insertion are preferably selected form the group comprising immune modulatory genes, wherein the immune modulatory gene preferably is selected from the group comprising UL14, UL18, UL141, UL142, US2 and US6. In a further preferred embodiment the at least one additional heterologous nucleic acid is inserted into the beta-herpesvirus genome into a sequence coding for an immunodominant CMV T cell epitope, for example IE1 or pp65. In a further preferred embodiment the sequence coding for an immunodominant CMV T cell epitope is replaced with a sequence of an epitope of an antigen as disclosed herein.

In connection therewith it is important to understand that certain beta-herpesvirus strains may not comprise all immune modulatory genes. For example, the BAC cloned genome of HCMV strain TB40E (Sinzger et al., 2008, supra) already lacks US2 and US6. In connection therewith it will also be understood by a person skilled in the art that the authentic and/or endogenous promoter of the immune modulatory gene is preferably used for expression of the at least one additional heterologous nucleic acid. For example, the authentic US11 promoter is preferably used for driving the expression of the influenza HA. A person skilled in the art will know other promoters, such as the cellular PGK promoter, promoter of the cellular phosphoglycerate kinase (PGK) housekeeping gene, the viral MCMV MIEP or the HCMV MIEP which are equally useful. It is important to note that in case one of the viral MCMV MIEP or the HCMV MIEP is used, a person skilled in the art will know that depending on the particular beta-herpesvirus strain used, the insertion preferably occurs in opposite direction to the already present copy of these elements, for example in the TB40E-ULBP2 genome.

In certain embodiments of the beta-herpesvirus according to the present invention the beta-herpesvirus of the present invention is deficient in one or more additional gene product(s) each encoded by an additional immune modulatory gene other than the immune modulatory gene which encodes an immunevasin which preferably regulates NK cell response and which is capable of binding said cellular ligand comprised in the beta-herpesvirus. In a further embodiment no immune modulatory gene which encodes an immunevasin which regulates NK cell response and which is capable of binding said cellular ligand comprised in the beta-herpesvirus is deleted but an immunevasive gene is deleted which is or is not regulating NK cell response and which is not capable of binding said cellular ligand comprised in the beta-herpesvirus.

Furthermore, in an embodiment of the beta-herpesvirus according to the present invention wherein the beta-herpesvirus of the present invention comprises a deletion of the coding sequence of the additional immune modulatory gene the coding sequence of more than one immune modulatory gene is preferably deleted. Accordingly, the beta-herpesvirus is deficient in one or more additional gene product(s) each encoded by an additional immune modulatory gene.

In an embodiment of the beta-herpesvirus of the present invention the beta-herpesvirus comprises the deletion of at least one miRNA, wherein said miRNA is preferably an miRNA which is capable of binding a transcript of the cellular ligand encoded by the beta-herpesvirus of the present invention. Nevertheless, it is within the present invention that further miRNAs are deleted from the genome of the beta-herpesvirus of the present invention which is advantageous for the beta-herpesvirus of the present invention. Thus in an embodiment of the beta-herpesvirus according to the present invention wherein the beta-herpesvirus comprises the deletion of at least one miRNA, the miRNA is preferably selected from the group comprising miRNAs having immune modulatord functions (Dolken L et al., J Virol. 2007).

In order to provide guidance to a person skilled in the art on how a beta-herpesvirus of the present invention is designed, and in particular a beta-herpesvirus of the present invention wherein an immunemodulatory gene is deleted from the genome of the beta-herpesvirus, and how such immune modulatory gene may be selected, the present inventor conceived a vaccine according to the present invention by inserting the NKG2D ligand RAE-1γ into the MCMV genome in place of the m152 gene, that otherwise negatively regulates this NKG2D ligand. Accordingly, said virus represents an embodiment, wherein an immune modulatory gene has been deleted the gene product of which results in preventing the accessibility of an NKG2D ligand to the cell surface.

Whitout wishing to be bound by any theory the present inventor currently assumes that:

the deletion of an immunomodulatory gene, which downregulates the cellular ligand, (a) prevents downregulation of both endogenous cellular ligand and cellular ligand encoded by the beta-herpesvirus of the present invention, in this particular example RAE-1γ and RAE-1γ encoded by the MCMV;

(b) may override the consistent expression of the cellular ligand, in this particular example RAE-1γ, on infected cells the effect of all other CMV immunoevasins encoded by immune modulatory genes, for NK cells, and (c) may also augment $CD8^+$ T cell response through co-stimulatory function of NKG2D on these cells.

Furthermore, since m152 additionally arrests the maturation of MHC class I molecules (Ziegler, H. et al., 1997, Immunity 6:57-66), the deletion of this gene may improve the presentation of viral proteins and enhance the T cell immune response. Herein the present inventor demonstrates that RAE-1γ-expressing MCMV, also referred to herein as RAE-1γMCMV, is dramatically attenuated in vivo not only in the immunocompetent host but even in immunologically immature neonata mice and in immunodeficient mice. However, despite tight immune control, RAE-1γMCMV infection elicited a potent, long-lasting cellular and antibody immune response able to protect animals against challenge infection. Moreover, maternal RAE-1γMCMV infection resulted in the production and placental transfer of antiviral antibodies that protected their offspring from MCMV infection following neonatal infection.

In an embodiment of the beta-herpesvirus according to the present invention, wherein the beta-herpesvirus is suitable for inducing an immune response, the immune response is preferably an immune response against a beta-herpesvirus. In a further preferred embodiment the immune response preferably comprises neutralizing antibodies against beta-herpesvirus and/or $CD4^+$ T-cells directed against epitopes of beta-herpesvirus and/or $CD8^+$ T-cells directed against epitopes of beta-herpesvirus. In connection therewith it is important to understand that the present invention considers that in connection with an immune response against a beta-herpesvirus, preferably comprising neutralizing antibodies directed against a beta-herpesvirus and/or $CD4^+$ T-cells directed against epitopes of beta-herpesvirus and/or $CD8^+$ T-cells directed against epitopes of beta-herpesvirus, the beta-herpesvirus is not necessarily from the same beta-herpesvirus strain and/or beta-herpesvirus species as the beta-herpesvirus suitable anc actually for inducing and eliciting, respectively, an immune response. A person skilled in the art will acknowledge that different strains of one species of beta-herpesvirus such as different HCMV strains is preferably used as the beta-herpesvirus according to the present invention is capable of and/or suitable for inducing an immune response, wherein the immune response is directed against a beta-herpesvirus of another strain, such as another HCMV strain. A person skilled in the art will also acknowledge that the infection with beta-herpesviruses is generally thought to be species-specific. In other words, HCMV is only capable of infecting humans, MCMV is only capable of infection mice. Nevertheless, it is also possible that a beta-herpesvirus species may infect more related species, such as MCMV is capable of infecting other rodents than mouse, or rhesus CMV is capable of infecting humans. It is also within the present invention that such species-barrier will be overcome, e.g. by genetic manipulation with regard to entry of the virus, receptors, glycoproteins expressed at the surface and/or prevention of apoptosis. Having said this it is an embodiment of the present invention that immune response against a beta-herpesvirus, preferably the neutralizing antibodies and/or $CD4^+$ T-cells and/or $CD8^+$ T-cells, is directed against the beta-herpesvirus capable of and/or suitable for inducing an immune response, wherein the beta-herpesvirus suitable for inducing an immune response is of the same strain and species, of the same species but different strain and/or from a different species and different strain as the beta-herpesvirus the immune response is directed against. In a more preferred embodiment the beta-herpesvirus suitable for inducing an immune response induces an immune response preferably comprising neutralizing antibodies against the beta-herpesvirus and/or $CD4^+$ T-cells directed against epitopes of the beta-herpesvirus and/or CD8⁺ T-cells directed against epitopes of the beta-herpesvirus, wherein the beta-herpesvirus preferably is suitable for inducing an immune response is HCMV.

The present specification also provides evidence that expression of a cellular ligand such as an NKG2D ligand on beta-herpesvirus infected cells dramatically attenuates the virus growth in vivo but in the same time does not lead to attenuation in vitro. It is immediately understood that a person skilled in the art will prefer a virus which is attenuated in vivo as attenuation is generally understood to be conterminous with safety (Cicin-Sain, L. et al., supra). Accordingly, in an embodiment of the beta-herpesvirus according to the present invention the beta-herpesvirus of the present invention is attenuated in vivo.

Attenuation as used herein preferably means that a virus such as a live attenuated virus, such as the beta-herpesvirus of the present invention, is replicating to lower titers compared to the respective wild type virus. Attenuation as used herein more preferably means that a virus has a virulence which is reduced compared to the respective wild type virus. Attenuation alters a virus so that it becomes more harmless and/or less virulent. These vaccines contrast to those produced by "killing" the virus (inactivated vaccine). Still more preferably, attenuation as used herein means that the titer of a virus is less compared to the titer of the respective wild type virus grown under the same conditions. So as to determine whether the beta-herpesvirus according to the invention and particularly the HCMV according to the present invention is attenuated compared to the respective wild type virus, preferably, the assay for assessing virus growth kinetics as described in Example 1 is used. It is known to a person skilled in the art that in connection with a titer of a virus the term "plaque-forming units" also referred to herein as PFU, is used.

The titer of a virus in terms of "plaque-forming units" is preferably a measure for the amount of infectious virus particles present in a sample, such as a sample from a subject or an in vitro sample. To determine virus titer a standard plaque assay as for example described in Krmpotic, A. et al. (Krmpotic, A. et al. 2005, supra) and/or described in Example 1 is used. A person skilled in the art will furthermore know how to determine the amount of a pathogen, such as the titer of a virus, in a subject or in an in vitro sample. The amount of bacteria, such as *Listeria monocytogenes*, in a sample or subject is preferably measured as "colony forming units", also referred to herein as CFU. To determine CFU a person skilled in the art will know appropriate assays. As an example an assay to determine CFU in mouse organs is preferably an assay as described in Example 1 herein.

In connection with attenuation it will be furthermore understood that a person skilled in the art will regard the attenuation of a virus as a measure for the safety of the virus if used as a vaccine or vaccine vector. Accordingly, it is advantageous with regard to safety if a virus is attenuated. Such attenuation is preferably achieved in many ways known to a person skilled in the art. For example the deletion of one or more immune modulatory genes preferably results in attenuation of a virus in vivo, as the immune response is stronger if the immune modulatory gene encoding a gene product down-modulating and/or down-regulating the immune response is deleted (Cicin-sain, L. et al., supra). It will be also understood that the strongest possible deletion is the absence of virus replication and/or virus progeny. Such most strongest attenuation will be achieved if an essential gene is deleted from the virus (Mohr, C. A. et al., 2010, supra).

Accordingly, it will be understood that the strongest conceivable degree of attenuation is the formal impossibility of a virus to finish its replication cycle and/or incits inability of generating viral progeny and/or incapable of generating infectious viral progeny. Such virus incapable of finishing its replication cycle and/or generating viral progeny and/or incapable of generating infectious viral progeny, is known in the art as spread-deficient and/or replication deficient virus as described for example in (Mohr, C. A. et al., 2010, supra; Snyder, C. M. et al., 2009, J Immunol, 182:128.29). In an embodiment of the beta-herpesvirus of the present invention the beta-herpesvirus is deficient in at least one gene product encoded by an essential gene and/or by a glycoprotein, wherein the deficiency of said essential gene and/or glycoprotein results in a virus which is incapable of replicating its viral genome, spreading its progeny from one cell to another and/or producing infectious viral progeny. Such deficiency is achieved in an embodiment of the present invention by deletion or partial deletion of the coding sequence of the respective gene, or by inhibition of the transcription, translation or function thereof. Respective genes are known to the person skilled in the art. By way of example, a virus having a deletion of a gene encoding a glycoprotein essential for infection is disclosed in Snyder et al., (Snyder, C. M. et al., 2009, supra) and a virus having a deletion of a gene encoding a protein being essential for virus spread is disclosed in Mohr et al. (Mohr, C. A. et al., 2010, supra). Such virus is preferably produced using a cell line which is capable of complementing the gene product of the deleted essential gene and/or glycoprotein. The generation and use of such cell lines is known to the person skilled in the art.

However, in spite of reduced antigenic load due to attenuation of the beta-herpesvirus of the present invention such as CMV expressing Rae-1γ, a beta-herpesvirus of the present invention is capable of inducing a strong immunity and protect immunocompetent subjects as well as immunodeficient subjects against infection with wild type beta-herpesvirus.

It is important to note that the present inventor provides conclusive evidence in the Examples shown herein that subjects immunized with the beta-herpesvirus of the present invention are able to resist challenge infection better than subjects immunized with the respective wild type beta-herpesvirus. In connection therewith it is important to understand that it is known for decades that infection with wild type beta-herpesvirus, especially with MCMV wild type, which is not useful as a vaccine for reasons of safety, confers protection against infection with wild type virus, preferably of the same strain.

Most importantly, the present inventor found that in naturally more resistant C57BL/6 mice immunized with the beta-herpesvirus of the present invention, more particularly RAE-1γMCMV, the CD8⁺ T cell response is stronger compared to individuals infected with the respective wild type virus. Newborn subjects derived from females immunized with the beta-herpesvirus of the present invention are protected against perinatal infection to the same extent as the offspring derived from females immunized with wild type virus. This latter finding confirmed that the beta-herpesvirus of the present invention induces neutralizing antibody response despite strong attenuation and therefore lower antigenic load. More particularly, protection of newborn individuals against challenge infection iss mediated through transplacentally transferred IgG.

Another important characteristic of the beta-herpesvirus of the present invention is its ability to provide long-lasting immunity Although the load of latent viral genome is significantly lower in subjects immunized with the beta-herpesvirus of the present invention this virus is able to reactivate upon immunosuppression of latently infected subjects. Notably, even though the beta-herpesvirus according to the present invention is under strong selective pressure by NK cells and CD8+ T cells, the present inventor has not observed any mutation of the inserted gene encoding the cellular ligand. More importantly, all the viruses recovered from latency showed no differences in comparison with parental virus mutant used for primary infection.

It is the merit of the present inventor having recognized that the beta-herpesvirus of the present invention which comprises at least one heterologous nucleic acid, wherein the at least one heterologous nucleic acid comprises a gene encoding a cellular ligand, is a suitable vaccine vector. This prompted the present inventor to insert immunodominant antigens of different pathogens into the beta-herpes virus in order to test its vector capacity in terms of eliciting an immune response in the recipient organism against said immunodominant antigens.

The present inventor unexpectedly found that when the beta-herpesvirus according to the present invention encodes an additional heterologous nucleic acid, wherein the additional heterologous nucleic acid codes for a peptide, oligopeptide, polypeptide and/or protein which constitutes or comprises at least one antigen and epitope, respectively, that said beta-herpesvirus was dramatically attenuated in vivo:

In connection therewith it is known to the person skilled in the art that NK cells have a major role in innate immune response to several viruses. Receptors, such as NKG2D, are among the most potent activating receptors expressed on all NK cells and all CD8+ T cells in humans, or activated CD8+ T cells in mice. Insertion of a gene encoding a cellular ligand, for example NKG2D ligand RAE-1γ, in place of its viral downregulator, i.e. an immune modulatory gene such as, for example m152, results in dramatic virus attenuation. Attenuation as such is not unexpected, since even the mutant viruses lacking viral inhibitors of the cellular ligand(s) are attenuated (Krmpotic, A. et al., 2002, supra; Krmpotic, A. et al., 1999, J Exp Med, 190(9):1285-96; Arapovic, J. et al., 2009, supra; Hasan, M. et al., 2005, J Virol, 79:2920-30; Lenac, T. et al., 2006, supra; Lodoen, M. et al., 2003, J Exp Med, 197(10):1245-53; Lodoen, M. B. et al., 2004, J Exp Med 200(8):1075-81), but in case of the beta-herpesvirus of the present invention expressing the cellular ligand, said beta-herpesvirus of the present invention, in an embodiment, is attenuated to such an extent that it even fails to reach salivary gland. A person skilled in the art will immediately acknowledge that salivary glands are otherwise a privileged site for virus persistency and horizontal spread. The results obtained in mice expressing Ly49H receptor, otherwise resistant to MCMV because of recognition of viral m157 protein, also demonstrate dramatic attenuation, confirming that this can not be only the consequence of an NK cell response. More particularly, in these mice NK cells are strongly activated through Ly49H/m157 interaction. Moreover, the beta-herpesvirus of the present invention expressing a cellular ligand is attenuated in otherwise severely immunocompromised subjects, for example mice lacking IFNAR, mice immunodepleted by sublethal gamma irradiation, and mice lacking perform. These latter findings are extremely important bearing in mind that the hallmark of beta-herpesviruses is an opportunistic infection in immuno-compromised individuals.

The present inventor furthermore found that when the beta-herpesvirus according to the present invention encodes an additional heterologous nucleic acid, wherein the at additional heterologous nucleic acid preferably codes for a peptide, oligopeptide, polypeptide and/or protein which more preferably constitutes or comprises at least one antigen and epitope, respectively, an unexpected strong CD8+ T cell response in spite of virus attenuation is detected, whereby preferably such stron CD8+ T cell response is directed to said antigen and epitope, respectively.

In connection therewith a person skilled in the art will acknowledge that it is a current dogma in the field of vaccination that a strong NK cell response after primary virus infection should result in compromised, i.e. weaker, CD8+ T cell response. This theory is supported by recent work by Andrews et al. (2010) who reported that NK cell response has negative effect on generation of virus specific CD8+ T cell response by restricting duration of exposure of T cells to infected antigen-presenting cells. These findings are supported by recent work in C57BL/6 mice infected with WT-MCMV, which expresses m157, or virus lacking m157 (Mitrovic, M. et al, under revision). Working on a tumor model, Soderquest, K. et al.) reported that NK cells kill recently activated CD8+ T cells and thus lead to a less efficient CD8+ T cell response (Soderquest, K. et al., 2011, Blood, 117(17):4511-8). Therefore, based on the above findings, one would expect that a beta-herpesvirus of the present invention would induce less potent CD8+ T cell response, particularly because of lower antigenic load. In contrast to the expectations of a person skilled in the art the present inventor has shown that mice infected with RAE-1γMCMV demonstrated equal or even more potent CD8+ T cell response against immunodominant MCMV epitopes. Subjects infected with the beta-herpesvirus of the present invention demonstrated equal or even more potent CD8+ T cell response against immunodominant beta-herpesvirus epitopes. Moreover, the above mentioned results were confirmed and extended by using the beta-herpesvirus of the present invention wherein the beta-herpesvirus comprises at least one heterologous nucleic acid, wherein the at least one heterologous nucleic acid comprises a gene encoding a cellular ligand, as a vector of foreign antigens such as, for example, HA of influenza or listeriolysin epitope of *Listeria monocytogenes*. When conducting experiments the present inventor found that CD8+ T cell response is much stronger in case of a beta-herpesvirus of the present invention expressing a cellular ligand in addition to foreign antigens such as viral, bacterial and/or parasite antigens, as compared to a beta-herpesvirus not expressing said cellular ligand.

In an embodiment of the beta-herpesvirus according to the present invention, wherein the beta-herpesvirus expressing a cellular ligand in addition to foreign antigens such as viral, bacterial and/or parasite antigen the antigen is an antigen specific for a virus, bacterium and/or parasite, respectively.

In an embodiment of the beta-herpesvirus according to the present invention the antigen is an antigen specific for *Listeria*, preferably selected from the group comprising listeriolysin O (LLO), whereby the beta-herpesvirus of the present invention then is useful for the treatment and/or prevention of listeriosis. In connection therewith the present inventor has surprisingly found that the beta-herpesvirus according to the present invention confers an unexpected strong protection against challenge infection with *Listeria monocytogenes*

Subjects infected with a wild type beta-herpesvirus expressing listeriolysin epitope, i.e. a beta-herpesvirus wherein the beta-herpesvirus does not comprise a heterologous nucleic acid, which comprises a gene encoding a cellular ligand; and subjects infected with the beta-herpesvirus of the present invention expressing listeriolysin both developed antilisteriolysin CD8⁺ T cell response, although the frequency of listeriolysin specific CD8⁺ T cells was higher after invention with the beta-herpesvirus of the present invention. However, when these subjects were challenged with sublethal and lethal doses of *Listeria monocytogenes* the protection was far better in the group of subjects vaccinated with the beta-herpesvirus of the present invention expressing listeriolysin. The enhanced protection was demonstrated not only with respect to reduction of bacterial load but also with regard to reduced tissue pathology. Since both groups of subjects were vaccinated and had listeriolysin specific CD8⁺ T cells, such dramatic differences with respect to protective capacity was absolutely unexpected.

MCMV infection caused depletion of conventional dendritic cells (Andrews et al., 2001, Nat Immunol, 2(11):1077-84). However, the present inventor has found that in subjects infected with the beta-herpesvirus of the present invention expressing a cellular ligand, the frequency of conventional DCs was preserved in comparison to wild type beta-herpesvirus infection. In connection therewith a person skilled in the art will acknowledge that the results obtained when using the beta-herpesvirus of the present invention are extremely surprising. The beta-herpesvirus of the present invention allows a potent CD8⁺ T cell response in spite of virus attenuation.

Finally, the present inventor has surprisingly found that the gene encoding a cellular ligand expressed in context of beta-herpesvirus infection was not subject of deletions or mutations, genetic changes, due to the selective pressure by strong immune response.

It is well established that in Ly49H⁺ mice the MCMV gene encoding m157 is subject to intense genetic changes, such as mutations and deletions, resulting in viruses which are no longer recognized by Ly49H and no longer sensitive to NK cells. After observing dramatic attenuation of the beta-herpesvirus of the present invention expressing a cellular ligand, the present inventor is currently of the opinion without wishing to be bound thereby that such intense genetic changes according to what has been said above will also appear in connection with the beta-herpesvirus of the present invention, i.e. that under selective pressure by NK cells via receptors, the gene encoding the cellular ligand will be the subject to mutations. Therefore the present inventor performed reactivation of latent beta-herpesvirus of the present invention by depleting subjects of T cells and NK cells. Surprisingly, although the beta-herpesvirus of the present invention was able to reactivate from latency, in 72 isolated clones of recurrent beta-herpesvirus of the present invention no mutation could be observed. Therefore, all viruses according to the present invention preserved an intact gene enconding cellular ligand. The present inventor deems this to be very important, because this seems to contribute to a more potent protective capacity long after initial priming, vaccination.

So as to determine whether the beta-herpesvirus of the present invention and particularly the HCMV of the present invention is expressing a cellular ligand, preferably, the assay as described in Example 2 is used. More precisely, the expression of a cell receptor ligand can be assessed by Western blot with an antibody specific for the cellular ligand and/or by FACS analysis using preferably a monoclonal antibody specific for the cellular ligand. In order to demonstrate that the immune response is enhanced in subjects which are infected with a beta-herpesvirus of the present invention an NK cell assay, preferably according to the NK cell assay described in the examples herein can be used to demonstrate susceptibility of the recombinant beta-herpesvirus of the present invention to NK cells. By blocking the receptor on immune cells, such as DC, or the cellular ligand on cells infected with the beta-herpesvirus according to the present invention, the essential role of signaling in enhanced NK cell response is demonstrated. T cell response to either beta-herpesvirus antigen(s) or antigens comprised in or encoded by an additional heterologous nucleic acid can be assessed by various means, preferably by determining the frequency of T cells specific for the antigen(s) and/or the epitope(s) by FACS analysis and/or by ELISPOT assay.

More specifically, the expression of the NK cell receptor ligand ULBP2 is preferably assessed by Western blot analysis using human ULBP-2 antibody (R&D Systems; cat. No. AF1298) and/or by FACS analysis with monoclonal anti-human ULBP-2-PE antibody (R&D Systems; cat. No. FAB1298P).

The assay used herein in connection with various mouse experiments in order to demonstrate enhanced immune response in mice infected with Rae-1MCMV or additional viruses comprising, in addition to Rae-1, an additional heterologous nucleic acid(s), more preferably expressing antigen(s) can be applied for respective HCMV viruses, such as HCMV expressing ULBP2:

1. NK cell assay can be used to demonstrate NK cell susceptibility of the recombinant virus. By blocking NKG2D receptor on NK cells or ULBP2 on infected cells one can demonstrate the essential role of NKG2D signaling in enhanced NK cell response.

2. T cell response to either HCMV antigens or foreign antigens in case of HCMV expressing cellular ligand, such as ULBP2, virus as a vector, can be assessed by various means, including determination of frequency of T cells specific for foreign antigen (epitope) by FACS or by ELISPOT assay.

In an embodiment of the beta-herpesvirus of the present invention the beta-herpesvirus is used as a vaccine and/or vector. In a further embodiment thereof the beta-herpesvirus encodes for a heterologous nucleic acid. Preferably such heterologous nucleic acid codes for an antigen and epitope, respectively, more preferably an antigen and epitope, respectively, of a pathogen. Because of this such vaccine and vector, respectively, is suitable for the treatment and/or prevention of a disease caused by or associated with said pathogen. Such pathogens preferably comprise viruses, parasites and bacteria. In an embodiment the antigen is an antigen specific for influenza and is preferably selected from the group comprising full-length form of HA of Influenza and headless form of HA of Influenza, neuraminidase and nucleo-protein, whereby the beta-herpesvirus of the present invention expressing such antigen is then useful for the treatment and/or prevention of influenza. In connection therewith it will be understood that the headless form of HA of Influenza as used herein preferably means the form of HA of influenza without the globular head domain in the HAI subunit of the hemaglutinin. Hemaglutinin (HA) is the major glycoprotein from Influenza A virus (strain A/Puerto Rico/8/1934 H1N1) Furthermore, HA is an integral membrane glycoprotein comprised out of two subunits: HA1 and HA2. Given the fact that HA2 subunit of the influenza virus hemagglutinin is relatively well conserved, but during natural infection or vaccination with conventional influenza vaccine masked by highly immunogenic globular head domain of HA. Is assumed that the HCMV-ULBP2 HA headless vaccine will elicit cross-reactive anti-HA2 antibodies. It is further assumed that a group of subjects vaccinated with HCMV-ULBP2 HA headless vaccine will develop serum neutralizing anti-HA2 antibodies prior than the placebo group and will develop anti-HA2 CD8⁺ T cells in the peripheral blood samples prior to the control group. Also, it is assumed that vaccination with HCMV-ULBP2 HA full-length and HCMV-ULBP2 HA headless vaccine will provide cross-protectively against seasonal influenza outbreaks. In connection therewith it is important to note that the vaccination of mice with headless HA elicits immune sera with broader reactivity than those obtained from mice immunized with a full-length HA (Steel, J. et al., 2010, mBio, 1(1):e00018-10). The Headless HA construct as used herein is preferably a HA immunogen comprising the conserved influenza HA stalk domain (HA2 subunit) and lacking the globular head. Without wishing to be bound by any theory the present inventors assume further that the conserved stalk HA2 subunit is masked by the highly immunogenic globular head domain in the HAI subunit during natural infections. Construction of headless HA is described by Steel et al., 2010, supra. In brief, headless HA lacks the globular head domain flanked by conserved disulfide bond linking cysteines 52 and 277 of HAL which is replaced with a GGGG linker.

In a further embodiment the antigen is an antigen specific for *Mycobacterium tuberculosis* which is preferably selected from the group comprising Antigen 85A (Accession No. P0A4V2; A85A_MYCTU; Sander, C. R. et al., 2009, Am J Respir Crit Care Med. 2009; 179(8): 724-733), Antigen 85B (Accession No. P0C5B9), -ESAT-6 (Accession No. P0A564 (ESXA_MYCTU)) (A85B_MYCTU)(Brandt, L. et al., 2000, Infect Immun, 68(2):791-5) and Antigen 85B-TB10.4 (Accession No. P0A568 (ESXH_MYCTU))(Dietrich, J. et al., 2005, J Immunol, 174(10):6332-9), whereby the beta-herpesvirus of the present invention expressing such antigen is then useful for the treatment and/or prevention of of tuberculosis.

In a still further embodiment the antigen is an antigen specific for *Plasmodium* and is preferably selected from the group comprising circumsporozoite (CS) protein, wherein *Plasmodium* is preferably selected from the group comprising *Plasmodium falciparum, Plasmodium vivax, Plasmodium ovale, Plasmodium malariae* and *Plasmodium knowlesi*, whereby the beta-herpesvirus of the present invention expressing such antigen is then useful for the treatment and/or prevention of malaria. In a still further embodiment the antigen is an antigen specific for HIV and is preferably selected from the group comprising HIV-1 gag (NC_001802.1), whereby the beta-herpesvirus of the present invention then is useful for the treatment and/or prevention of HIV. In a still further embodiment the antigen is an antigen specific for *Listeria*, whereby the antigen is preferably selected from the group comprising listeriolysin O (LLO), whereby the beta-herpesvirus of the present invention expressing such antigen is then useful for the treatment and/or prevention of listeriosis.

In a still further embodiment the antigen is an antigen specific for Respiratory syncytial virus and is preferably selected from the group comprising glycoprotein F (JN032120.1) and glycoprotein G (JN032120.1), whereby the beta-herpesvirus of the present invention expressing such antigen is then useful for the treatment and/or prevention of Respiratory syncytial virus. Respiratory syncytial virus is also referred to herein as RSV. In connection therewith it will be understood that various forms of F and G glycoproteins as well as not known F or G epitopes can be used as antigens to be expressed by the beta-herpesvirus of the present invention. It will be also understood that epitope recognition differs among individual human HLA types. In connection therewith the present inventors assume without wishing to be bound by any theory that by introduction of different forms of F and G glycoproteins and their expression in the context of the beta-herpesvirus of the present invention, infection with such beta-herpesvirus will provide wider protectivity and thus elicit stronger immune responses against RSV strains.

In an embodiment of the beta-herpesvirus of the present invention wherein the antigen is an antigen specific for Respiratory syncytial virus, the antigen is preferably selected from the group comprising full-length glycoprotein F, soluble glycoprotein F, full-length glycoprotein G, codon-optimized full-length glycoprotein F, codon-optimized soluble glycoprotein F and codon-optimized full-length glycoprotein G, wherein the glycoproteins are preferably of the RSV A2 strain. In an embodiment of the beta-herpesvirus of the present invention wherein the antigen is an antigen specific for Respiratory syncytial virus, the antigen is preferably selected from the group comprising glycoprotein F (D53); full-length glycoprotein F (D53); soluble glycoprotein F (D53); soluble glycoprotein F (D53), wherein a self-trimerizing peptide is fused to the C-terminus; soluble glycoprotein F (D53), wherein both cleavage sites are mutated so that it is not cleaved; soluble glycoprotein F (D35), wherein both cleavage sites are mutated so that it is not cleaved and wherein a self-trimerizing peptide is fused to the C-terminus; soluble glycoprotein F (D35), wherein 10 amino acids of the fusion peptide are deleted.

In a still further embodiment of the beta-herpesvirus according to the present invention the antigen is an antigen specific for HPV and is preferably selected from the group comprising E6 29-38 (TIHDIILECV; restricted by the HLA-A0201 molecule), E6 29-37 (TIHDIILEC; restricted by B48), and E6 31-38 (HDIILECV; restricted by B4002), E6 52-61 (FAFRDLCIVY; restricted by B57), E6 and E7 (JN171845.1) (Nakagawa, M. et al., 2007, J Virol, 81(3): 1412-23), whereby the beta-herpesvirus of the present invention expressing such antigen is then useful for the treatment and/or prevention of HPV.

In a still further embodiment the antigen is an antigen specific for *Helicobacter pylori* and is preferably selected from the group comprising urease, VacA, CagA, heat shock protein, neutrophil-activating protein outer membrane lipoprotein, babA2 (Kimmel, B. et al., 2000, Infect Immun, 68(2):915-20; Yamaoka, Y. et al., 2008, World J Gastroenterol, 14(27): 4265-4272), whereby the beta-herpesvirus of the present invention expressing such antigen is then useful for the treatment and/or prevention of *Helicobacter pylori*.

In the embodiments of the present invention wherein the beta-herpesvirus of the present invention encodes at least one additional heterologous nucleic acid, wherein the at least one additional heterologous nucleic acid is a heterologous nucleic acid coding for a peptide, oligopeptide, polypeptide or protein, wherein the peptide, oligopeptide, polypeptide or protein constitutes or comprises at least one antigen and epitope, respectively, the antigen and epitope, respectively, is preferably an immunodominant antigen. In a further embodiment the expression of said antigen and epitope, respectively, is sufficient for inducing an immune response, preferably an immune response protective against natural infection with the pathogen comprising said antigen and epitope, respectively.

In a further embodiment of the beta-herpesvirus according to the present invention, an/the additional heterologous nucleic acid comprised in the beta-herpesvirus of the present invention is less than ~4 kb.

In a preferred embodiment of the beta-herpesvirus according to the present invention, the additional heterologous nucleic acid comprises a promoter, preferably a viral promoter, capable of expressing the antigen with kinetics selected from the group comprising immediate-early kinetics and early kinetics, preferably immediate-early kinetics. Such promoter is preferably selected from the group comprising an IE promoter. The present inventor assumes without wishing to be bound by any theory that expression of the antigen with immediate-early kinetics will lead to a boost of the immune response independent of the generation of infectious progeny.

A person skilled in the art will acknowledge that it is preferred that the antigen is properly processed in order to guarantee transport and presentation by MHC class I molecules. In a further embodiment of the beta-herpesvirus according to the present invention the beta-herpesvirus encodes one or more than one additional heterologous nucleic acid(s). In connection therewith it is within an embodiment of the beta-herpesvirus according to the present invention that the one or more than one additional heterologous nucleic acid(s) code(s) for a peptide, oligopeptide, polypeptide or protein. In a further embodiment the one or more than one heterologous nucleic acid(s) codes for one or more than one peptide(s), one or more than one oligopeptide(s), one or more than one polypeptide(s) and/or one or more than one protein(s). It is a further embodiment that the peptide(s), oligopeptide(s), polypeptide(s) and/or protein(s) constitute(s) or comprise(s) one or more than one antigen(s) and epitope(s), respectively. Accordingly, the beta-herpesvirus of the present invention is preferably suitable to or capable of inducing an immune response against beta-herpesvirus, and additionally is suitable to or capable of inducing an immune response against the one or more than one peptide(s), the one or more than one oligopeptide(s), the one or more than one polypeptide(s) and/or the one or more than one protein(s). In an embodiment the beta-herpesvirus of the present invention is suitable to or capable of inducing an immune response against one or more pathogen(s) having the one or more than one antigen(s).

In the embodiments of the beta-herpesviruses of the present invention where the beta-herpesvirus expresses one or more than one antigen derived from one or more than one pathogen(s) the beta-herpesvirus is suitable to or capable of inducing an immune response against the respective pathogen an antigen of which is expressed by the beta-herpesvirus according to the present invention. For example a beta-herpesvirus of the present invention is suitable to induce an immune response against beta-herpesvirus, is suitable to induce an immune response against beta-herpesvirus and influenza, is suitable to induce an immune response against beta-herpesvirus and *listeria*, or is suitable to induce an immune response against beta-herpesvirus, influenza and *listeria*. It is important to understand that each and any antigen suitable to induce an immune response against the respective pathogen is preferably combined with each and any other antigen suitable to induce an immune response against the same or different pathogen in order to generate a beta-herpesvirus of the present invention preferably being a vaccine against each and any of the above mentioned pathogens.

In a further embodiment wherein more than one antigen is encoded these antigens are preferably derived from one pathogen. Accordingly a beta-herpesvirus of the present invention is suitable to induce an immune response against beta-herpesvirus and against more than one antigen and epitope, respectively, of the respective pathogen. In connection therewith it is an embodiment to introduce different epitopes of one pathogen, preferably immunodominant epitopes of one pathogen into the genome of the beta-herpesvirus. In a further embodiment more than one epitope of different species and/or strains of the pathogen are introduced into the beta-herpesvirus genome. For example, different strains of *mycobacterium* will exhibit different epitopes, accordingly said different epitopes derived from different strains will be comprised in the genome of the beta-herpesvirus of the present invention.

A person skilled in the art will acknowledge that in connection with various embodiments antigens displaying a limited variability are preferred. More preferably, antigens having conserved domains are used. It will also be understood immediately that if a peptide is considered as an antigen, the selection of said peptide will depend on HLA restriction.

In connection with the various embodiments of the beta-herpesvirus of the present invention, the beta-herpesvirus is preferably a CMV, more preferably an HCMV.

It will be immediately understood by a person skilled in the art that more than one strain of a particular beta-herpesvirus exists. Said strains exhibit different characteristics in terms of degree of attenuation, tropism and/or genes comprised in the genome. In connection therewith it is preferred that the beta-herpesvirus of the present invention is attenuated due to genetic manipulation, and is characterized by showing expression of a cellular ligand, deletion of an immunemodulatory gene, deletion of miRNA, deletion of a non-essential gene other than immunemodulatory gene and/or deletion of an essential gene. In a further embodiment the beta-herpesvirus of the present invention has a tropism like a wild type beta-herpesvirus strain.

A wild type beta-herpesvirus strain, as preferably used herein means that the virus is a beta-herpesvirus strain which has been isolated from its native host and which preferably has maintained its ability to infect endothelial cells, epithelial cells, macrophages and DC in tissue culture. Accordingly, a wild type CMV strain as preferably used herein means that the virus is a CMV strain which has been isolated from its native host and which preferably has maintained its ability to infect endothelial cells, epithelial cells, macrophages and DC in tissue culture. With regard to CMV tropism it is also referred to the publications of Sinzger C et al. (Sinzger, C. et al., 1996, Intervirology; 39(5-6):302-19; Sinzger, C. et al., 2008, Curr Top Microbiol Immunol; 325: 63-83).

Examples for HCMV clinical isolates are, among others TB40/E, which was isolated from a patient by throat wash of a bone marrow transplant recipient and which was propagated for 5 passages in fibroblast, followed by 22 passages in endothelial cells (Sinzger, C. et al., 1999, J Gen Virol, 80(Pt 11):2867-77); the Towne strain which derived from urine of a congenitally infected newborn, which was attenuated through 125 passages in human embryonic lung fibroblast cell cultures; and AD169, which was originally recovered from adenoid tissue (Rowe, W. P. et al., 1956, Proc Soc Exp Biol Med, 92:418-424) and which has been extensively passaged in human fibroblast cell cultures and lost its natural cell tropism for endothelial cell.

In the case of laboratory-adapted HCMV-strain AD169 or attenuated Towne strain which were extensively propagated in human embryonic lung fibroblasts (HELF) both strains lost their endothelial cell tropism and leukotropism. However, inoculation of such strains in human umbilical vein endothelial cells (HUVEC) restored its endothelial tropism as confirmed by immunofluorescence using monoclonal antibodies against HCMV proteins (pp65, IE-1 and gB), or by determination of viral titer and leukotropism as confirmed by standard assays for PMNL and monocyte-tropism as reported (Gema, G. et al., 2002, J Gen Virol, 83(Pt 8):1993-2000). PMNL were isolated from healthy donors and cocultured with infected HUVEC, were subsequently placed in the upper compartment of a cell culture device separated with a transwell filter from the lower compartment with FMLP which attracts PMNLs. Infection was determined by immunofluorescence using monoclonal antibodies against HCMV proteins (pp65, IE-1 and gB), or by determination of viral titer.

In a preferred embodiment the beta-herpesvirus of the present invention is capable of infecting professional antigen presenting cells, preferably comprising dendritic cells and macrophages. In a further preferred embodiment the beta-herpesvirus of the present invention is capable of infecting endothelial cells, epithelial cells and fibroblasts. It is a further embodiment of the beta-herpesvirus of the present invention that the capability to infect certain cell types is limited. Such limitation of the capability to infect certain cell types results for example from genetic manipulation. For example if a beta-herpesvirus is deficient in at least one receptor for the infection of a certain cell type, such as a certain glycoprotein, such virus will not be able to infect the respective cell type. In a further embodiment a gene coding for a receptor for the infection of a certain cell type is introduced into the genome of the beta-herpesvirus of the present invention. In such case, expression of such receptor from the genome of the beta-herpesvirus, e.g. the receptor mediating infection of endothelial cells and/or dendritic cells, will result in a beta-herpesvirus preferentially infecting the respective cell types. In a further preferred embodiment the capability to infect certain cell types of the beta-herpesvirus is limited to certain cell types, whereby in addition a gene coding for a receptor for the infection of the certain cell type is introduced into the genome of the beta-herpesvirus of the present invention.

Such virus will preferentially infect the cell-types via the receptor for the infection of the certain cell type. In connection therewith it is important to note that beta-herpesviruses are able to infect professional antigen presenting cells. In an embodiment the beta-herpesvirus of the present invention is capable of infecting professional antigen presenting cells. In a further embodiment the beta-herpesvirus of the present invention is capable of infecting professional antigen presenting cells only or with high preference. In connection therewith it is important to note that a hallmark of HCMV infection is the targeting of monocytes. It will be acknowledged by a person skilled in the art that the HCMV genome is maintained even in the absence of a productive infection. In connection therewith, monocytes are considered to be reservoirs for viral genome involved in the viral spread and most importantly that their immunomodulation facilitates HCMV survival and avoidance of an immune response. HCMV strains that show monocyte-derived dendritic-cell (DC) tropism, like HCMV strain VHLE, is a candidate vector vaccine. The monocyte-derived dendritic-cell (DC) tropism depends on the propagation in according cell lines, more particularly the propagation on DCs following coculture with infected endothelial cells. Briefly, Peripheral blood mononuclear cells (PBMC) are isolated from peripheral blood from healthy donors and cultivated in RPMI supplemented with 10% fetal bovine serum (FBS) supplemented with 800 U human recombinant granulocyte macrophage-colony-stimulating factor $ml^{-1}$ (GM-CSF) and 500 U human recombinant IL-4 $ml^{-1}$ (R&D systems) for 5-7 days, according to a reported procedure (Sallusto, F. and Lanzavecchia, A., 1994, J Exp Med, 179(4):1109-18). Following this procedure, more than 90% adherent cells belong to the immature DC phenotype ($CD1a^+$, $HLA\text{-}DR^{low}$, $CD14^-$, $CD83^-$, $CD86^{low}$, $HLA\text{-}ABC^+$, $CD40^+$). DCs, following 24 h incubation with cell-free HCMV preparations, obtained after virus adaptation to growth in HUVEC, were co-cultured overnight with autologous PBMCs. Co-culture medium is RPMI-10% FBS supplemented with 10 μg brefeldin A $ml^{-1}$ (Sigma) to prevent release of cytokines. Cell cultures are incubated overnight at 37° C. in 5% $CO_2$ atmosphere. Ability of viral DCs infection is confirmed by FACS analysis (DC phenotype, detection of IE-1, pp65 or gB) and by determination of viral titer.

It will be also acknowledged by a person skilled in the art that cross-presentation is considered to play an important role in the immune response against beta-herpesvirus infection as well as in the immune response against various other pathogens. In an embodiment the beta-herpesvirus of the present invention is capable of infecting fibroblasts. In an embodiment the beta-herpesvirus of the present invention is capable of infecting fibroblasts only or with high preference. In an embodiment the beta-herpesvirus of the present invention is capable of infecting parenchymal cells, comprising hepatocytes and smooth muscle cells, preferably smooth muscle cells of the gastrointestinal tract (Sinzger, C. 1996, supra). In an embodiment the beta-herpesvirus of the present invention is capable of infecting parenchymal cells only or with high preference. Examples of beta-herpesviruses having a tropism limited to certain cell types which can be used as a basis for the beta-herpes virus according to the present invention were described in Revello and Gerna (Revello, M. G., Gerna, G., 2010, Rev Med Virol, 20(3):136-55). In a further embodiment of the beta-herpesvirus according to the present invention, the beta-herpesvirus persists in the subject infected with said beta-herpesvirus of the present invention. In a further embodiment of the beta-herpesvirus according to the present invention, the beta-herpesvirus does not persist in the subject infected with said beta-herpesvirus of the present invention. In an embodiment wherein the beta-herpesvirus does not persists in the subject infected with said beta-herpesvirus, the genome of the beta-herpesvirus is lost over time.

In embodiments of the beta-herpesvirus of the present invention the beta-herpesvirus preferably is a CMV, more preferably an HCMV. In an embodiment of the beta-herpesvirus of the present invention the beta-herpesvirus is an HCMV, and/or an HCMV wherein the HCMV is derived from a Bacterial Artificial Chromosome. The HCMV and/or the Bacterial Artificial Chromosome can be derived from different HCMV strains. In connection therewith it is a preferred embodiment where the HCMV of the present invention has the ability to infect a wide range of different cell types, basically all cell types that will be infected by a clinical isolate of CMV and HCMV in particular. In a further embodiment the HCMV of the present invention has a tropism like a wild type beta-herpesvirus strain. In a still preferred embodiment the HCMV of the present invention is capable of infecting antigen presenting cells, including but not limited to dendritic cells and macrophages. In a further preferred embodiment the HCMV of the present invention is capable of infecting professional antigen presenting cells only. In a further preferred embodiment the HCMV of the present invention is capable of infecting fibroblasts. In a still further preferred embodiment the HCMV of the present invention is attenuated. It will be understood by a person skilled in the art that a virus is preferably attenuated to different degree. In an embodiment of the HMCV of the present invention the attenuation of the HCMV is preferably due to expression of a cellular ligand for immune receptors, more preferably due to expression of a cellular ligand for an NK cell receptor. In a still further preferred embodiment the HCMV of the present invention is attenuated due to deficiency in at least one gene product encoded by an immune modulatory gene. In a still further preferred embodiment the HCMV of the present invention is attenuated due to the deletion of at least one essential viral gene.

In an embodiment of the beta-herpesvirus according to the present invention the attenuation of the beta-herpesvirus of the present invention is due to expression of a cellular ligand, more preferably due to expression of a cellular ligand for an NK cell receptor and/or due to deficiency in at least one gene product encoded by an immune modulatory gene and/or due to the deletion of at least one essential viral gene.

In an embodiment of the beta-herpesvirus according to the present invention the beta-herpesvirus is derived from a Bacterial Artificial Chromosome. A "bacterial artificial chromosome" also referred to herein as BAC, as used herein preferably is a DNA construct, based on a functional fertility plasmid (or F-plasmid), used for transforming and cloning in bacteria, usually *E. coli*. A person skilled in the art will be aware that various herpesviruses were cloned as a bacterial artificial chromosome as for example described in Messerle, M. et al., (Messerle M. et al., 1997, Proc Natl Acad Sci USA, 94(26):14759-63). A person skilled in the art will also be aware of various techniques which allow for mutagenesis of said herpesvirus cloned as a BAC such as for example described by Tischer et al. (Tischer, B. K. et al., 2006, Biotechniques, 40(2):191-7). Transfection of the BAC plasmid containing the beta-herpesvirus genome into respective eukaryotic cells, such as transfection of HCMV BAC into HFF, leads to a productive virus infection. As has been outlined above the HCMV of the present invention and/or the HCMV of the present invention derived from a Bacterial Artificial Chromosome can be derived from different HCMV strains.

In connection with the embodiments of the HCMV of the present invention the HCMV of the present invention and/or the HCMV of the present invention derived from a Bacterial Artificial Chromosome are preferably derived from different HCMV strains and/or Bacterial Artificial Chromosomes derived from respective HCMV strains comprising AD169 BAC (Human cytomegalovirus strain AD169, complete genome, 229,354 bp linear DNA, Accession: X17403.1, GenBank: GI: 59591), modified AD169-BAC which is modified according to the modifications described in Borst et al. (Borst, E. M. et al., 1999, J Virol, 73(10):8320-9), TB40E BA (Human herpesvirus 5 strain TB40/E clone TB40-BAC4, complete sequence, 229,050 bp linear DNA, Accession: EF999921.1, GenBank: GI:157779983), 229, 700 bp linear DNA, Accession: AC146904.1, Genebank GI: 37777313), Human Herpesvirus 5 Toledo-BAC isolate (complete sequence, 226,889 bp linear DNA, Accession: AC146905.1, Genebank GI: 37777314), Human Herpesvirus 5 TR-BAC isolate (complete sequence, 234,881 bp linear DNA, Accession:AC146906.1, Genebank GI:37777315), Human Herpesvirus FIX-BAC isolate (complete sequence, 229,209 bp linear DNA, Accession: AC146907.1, Genebank GI:37777316), Human herpesvirus 5 transgenic strain Merlin (complete genome, 243,724 bp circular DNA, Accession:GU179001.1, Genebank GI:270311373) and Towne strain. In connection therewith it has to be noted that the FIX BAC clone (Hahn, G. et al., 2002, J Virol, 76:9551-5) was prepared from the VR1814 clinical isolate (Revello, M. et al., 2001, J Gen Virol, 83:1993-2000) by substituting BAC sequences for the IRS1-US6 region using the method of Borst et al. (Borst, E. M. et al, 1999, supra). In connection therewith it will be acknowledged that RV-FIX and RV-FIX deletion mutants miss single genes outside the UL131-128 locus. More particularly, RV-FIX misses UL45, UL127 and UL132. HCMV revertants, such as AD169 rev and Towne rev, reacquire both EC-tropism and leukocyte transmissibility after loss of both properties in HELF (Gerna, G. et al., 2002, supra). Furthermore, Merlin strain has been described by Stanton et al., (Stanton, R. J. et al., 2010, J Clin Invest, 1; 120(9):3191-208), BAC cloned AD169 has been described by Borst et al. (Borst, E. M. et al., 1999, supra), Full-length AD169 has been described by Hobom et al., (Hobom, U. et al., 2000, J Virol, 74(17):7720-9), BAC Cloning Towne and Toledo strains has been described by Hahn et al., (Hahn, G. et al., 2003, Virology, 307(1):164-77), BAC cloning TB40E strain has been described by Sinzger et al., (Sinzger, C. J. et al., 2008, supra) HCMV strain TRhas been described by Murphy et al., (Murphy, E. et al., 2003, Proc Natl Acad Sci USA, 100:14976-14981), Towne BAC has been described by Marchini et al. (Marchini, A. et al., 2001, J Virol, 75(4): 1870-8), Construction of a self-excisable bacterial artificial chromosome containing the human cytomegalovirus genome and mutagenesis of the diploid TRL/IRL13 gene has been described by Yu et al., (Yu, D. et al., 2002, J Virol, 76(5):2316-28).

So as to determine whether the immune response elicited by the beta-herpesvirus of the present invention and particularly the human cytomegalovirus of the present invention comprises at least neutralizing antibody a person skilled in the art will know assays to determine the titer and/or how to determine the neutralizing capacity of said neutralizing antibodies such as the assay described by Cui et al. (Cui, X. et al., 2008, Vaccine, 26(45):5760-6).

In an embodiment of the beta-herpesvirus of the present invention the beta-herpesvirus is deficient in at least one gene product encoded by an essential gene. It will be acknowledged by a person skilled in the art that deficiency in at least one gene product encoded by an essential gene will result in a virus which is not replicating in vitro and/or in vivo and/or is not able to produce progeny in vitro and/or in vivo. Such virus can be produced by trans-complementing the deficient gene product (Mohr, C. A. et al., 2010, supra).

In an embodiment of the beta-herpesvirus of the present invention deficient in a gene product the beta-herpesvirus is preferably spread-deficient. Spread-deficient as used herein, preferably means that the virus which is spread-deficient infects a cell and no viral particle is released from the infected cell, whereby the viral DNA is replicated, the viral proteins except those which are deleted in accordance with the present invention are expressed in the infected cell, preferably all viral glycoproteins are expressed, more preferably all viral glycoproteins are expressed, that mediate entry of the virus into a cell, whereby, preferably, the cell is an endothelial and/or an epithelial cell.

As used herein, the term "deficient in at least one gene product" preferably means that the at least one gene product which is a biochemical material such as a nucleic acid, DNA, RNA or a peptide, polypeptide or protein, resulting from expression of the gene does not show at least one of the functions displayed by said gene product in the wild type strain. Preferably, all of the functions of said gene product in the wild type strain are not shown. This is preferably the result of a complete or partial deletion or mutation of the gene coding for said gene product, of a complete or partial deletion or mutation of the nucleic acid controlling the expression of the gene coding of said gene product, of a truncation of said gene product, of the inhibition of the otherwise complete gene product, or of the at least partial or complete deletion or mutation of a promoter or other elements necessary for the transcription of said gene. For example, a beta-herpesvirus of the present invention deficient in a gene product of an immune modulatory gene such as US11 will improve antigen presentation in the HLA class I pathway.

The term "foreign antigen" and the term "heterologous antigen" as used herein preferably mean an antigen which is constituted by a peptide, oligopeptide, polypeptide or protein encoded by a heterologous nucleic acid. In connection therewith a nucleic acid coding for an antigen and epitope, respectively, of a pathogen is also referred to herein as additional heterologous nucleic acid, whereby such heterologous nucleic acid is preferably one which is not part of a wild type genome of a beta-herpesvirus.

In an embodiment the use of beta-herpesvirus of the present invention for the manufacture of a medicament, the medicament is for the treatment and/or prevention of a disease or condition associated with beta-herpesvirus infection, preferably human cytomegalovirus infection. In connection therewith it will be understood that human cytomegalovirus (HCMV) is ubiquitous in human populations and establishes lifelong infection. In subjects with normal immune systems, HCMV does typically not cause serious disease. However, in immunosuppressed patients, for example AIDS and transplant patients, and immunologically immature newborns, HCMV can cause grave disease and even death. Congenital HCMV infection, i.e. HCMV infection present at birth, is the most common viral infection that is transmitted in-utero to the human fetus and occurs in about 0.4%-1.2% of live borne infants in most regions of the world. Symptomatic infections following congenital HCMV infection occur in about 10% of infected infants. Symptoms include clinical manifestations that include but are not limited to, (1) microcephaly or other neurologic symptoms attributable to HCMV associated neurologic disease (2) hepatosplenomegaly with jaundice, and (3) thrombocytopenia with petechial/purpuric rashes.

In an embodiment of the beta-herpesvirus of the present invention the beta-herpesvirus is for use in the manufacture of a vaccine, wherein the vaccine is or is suitable for the administration to a donor of a transplant and/or to a recipient of a transplant. It is within the present invention that the vaccine and/or the beta-herpesvirus of the present invention is administered to a subject which is scheduled as recipient or donor for singular transplantation, e.g. of a solid organ, cells, or bone marrow, or a subject which is scheduled as recipient or donor for transplantation, preferably repeated transplantation, of e.g., cells or bone marrow. It is also possible that the vaccine and/or the beta-herpesvirus of the present invention is administered to a subject suspected to be or willing to be a donor or is suspected to be a recipient of a transplantation in the future.

In connection therewith the beta-herpesvirus of the present invention is preferably administered to the donor or recipient prior to transplantation or planned transplantation or as a preventive measure. Accordingly, in an embodiment the donor is a potential donor and/or the recipient is a potential recipient.

In another aspect of the present invention the beta-herpesvirus of the present invention is part of a pharmaceutical composition. Preferably, such pharmaceutical composition contains, apart from the beta-herpesvirus of the present invention and/or a nucleic acid coding for the same, a pharmaceutically acceptable carrier. The ingredients of such pharmaceutical composition and their respective amount contained in such pharmaceutical composition are either known to a person skilled in the art or can be determined by routine measures. It will be further acknowledged by a person skilled in the art that such pharmaceutical composition is for or is for use in the treatment of the diseases and conditions as disclosed herein in connection with the beta-herpesvirus of the present invention and its use.

It will be acknowledged by a person skilled in the art that as far as the experimental evidence provided in the example part of the instant application is based on MCMV, such evidence can be directly and immediately transferred to HCMV, so that the claimed invention is plausible to a person skilled in the art also for this reason. The reason is that the genomes of different herpesvirus strains including HCMV and MCMV are linearly correlated and the mode of action of HCMV in a human host and the mode of action of MCMV in a murine host are essentially identical.

The various SEQ ID NOs., the chemical nature of the nucleic acid molecules and peptides according to the present invention, the actual sequence thereof and the internal reference number are summarized in the following table.

| SEQ.ID. NO: | Sequence | internal reference |
|---|---|---|
| 1 | YPHFMPTNL | IE1/m123 ($_{168}$YPHFMPTNL$_{176}$) peptide |
| 2 | AGPPRYSRI | m164 ($_{167}$AGPPRYSRI$_{175}$) peptide |
| 3 | GYKDGNEYI | List ($_{91}$GYKDGNEYI$_{99}$) peptide |
| 4 | 5'-<u>*gcaccga cgatctgacat tgtccagtgtg ccgtcgcacg aacatc*</u>cctag ttattaatagt aatc-3' | primer for amplification of the RAE-1γ expression cassette plus kanR, wherein italic and underlined letters are homologous to nt 210196 to 210242 of the genome of mouse cytomegalovirus according to Genbank accession number: U68299.1, flanking m152 |
| 5 | 5'-<u>*tgtcaccg ctccacgatca ccgtcggtacc cgatcgctagc ctgtaca*</u>cagg aacacttaacg gctga-3' | primer for amplification of the RAE-1γ expression cassette plus kanR, wherein italics italic and underlined letters are homologous to nt 211427 to 211378 (lower strand) of the genome of mouse cytomegalovirus according to Genbank accession number: U68299.1, flanking m152. |

-continued

| SEQ.ID. NO: | Sequence | internal reference |
|---|---|---|
| 6 | 5'-gactactg tcggacgtggg gcgctgacaat atattcattc catattgtaac cAGGATGACGA CGATAAGTAGG G-3' | primer List swap fw_1; wherein lower case letters represent homology region to m164 ORF in the MCMV genome, lowercase letters in bold and underlined represent the region coding for peptide $_{91}$GYKDGNEYI$_{99}$- List (SEQ. ID. NO: 3) and capital bold letters represent homology to Tischer kanamycin resistance cassette (Tischer, B.K. et al, 2006, supra.).. |
| 7 | 5'-gatcgagc cggtggtaccg gacgcggcgga gccgttcggaa aggactactgt cggacgtgggg cgctgac-3' | primer List swap fw_2; |
| 8 | 5'-ggttacaa agatggaaatg aatatattgtc agcgcccacg tccgacagtag tcCAACCAATT AACCAATTCTG ATTAG-3' | primer List swap rv_1; wherein lower case letters represent homology region to m164 ORF in the MCMV genome, lowercase letters in bold and underlined represent the region coding for peptide $_{91}$GYKDGNEYI$_{99}$- List (SEQ. ID. NO: 3) and capital bold letters represent homology to Tischer kanamycin resistance cassette (Tischer, B.K. et al, 2006, supra).. |
| 9 | 5'-atggcctg gttgttgacgg cccagaagatg cgcgagtaccg aggagggcccg cggttacaaag atggaaatgaa tatatt-3' | primer List swap rv_2 |
| 10 | SIINFEKL | SIINFEKL-peptide |
| 11 | 5'-GCCGCCAT GAAGGCAAACC TACTGG-3' | primer PR8HA fw |
| 12 | 5'-CGTAGAAT CGAGACCGAGG AGAGGGTTAGG GATAGGCTTAC CGATGCATATT CTGCACTGCAA AGATCC-3' | primer PR8 V5 rv |
| 13 | 5'-TCACAGTT TTTCAAAGTTG ATTATACTCGT AGAATCGAGAC CGAGGAGAGGG TTAGG-3' | primer PR8 SIINFEKL |
| 14 | 5'-GGAGGCAA CACGAAGTGTC AAACACC-3' | primer Headless fw |
| 15 | 5'-GCCACCAC ATAGTTTTCCG TTGTGGC-3' | primer Headless rv |
| 16 | GAPINSATAM | *Mycobacterium tuberculosis* H-2Db immunodominat epitope 309-GAPINSATAM-318 |
| 17 | 5'-cgcccgct gccacgatggc ctggttgttga cggcccagaac atggcggtggc | primer m164 GAP fw; lower case letters represent homology region to m164 ORF in MCMV genome, underlined letters in bold represent homology regions between primers, italic letters are I-SceI restriction site |

| SEQ.ID. NO: | Sequence | internal reference |
|---|---|---|
| | cgagttgatcg gggcgccgtca gcgcccaGCC AGTGTTACAAC CAATTAAC C-3') | sequence and capital letters represent homology to Tischer kanamycin resistance cassette (Tischer, B.K. et al., 2006, supra) |
| 18 | 5'-gccgttcg gaaaggactac tgtcggacgtgg tggggcgctgacg gcgccccgatc aactcggccac cgccatgTAGG GATAACAGGGT AATCGAT-3' | primer m164 GAP rv; lower case letters represent homology region to m164 ORF in MCMV genome, underlined letters in bold represent homology regions between primers, italic letters are I-SceI restriction site sequence and capital letters represent homology to Tischer kanamycin resistance cassette (Tischer, B.K. et al, 2006, supra). |
| 19 | 5'-<u>GTCGGTAC CGTCGCAGTCT TCGGTCTGACC ACCGTAGAACG CAGAGCT</u>ccac cATGGCAGCAG CCGccGCTAC C-3' | primer to amplify ULBP2 ORF; wherein the underlined letters indicate homology to nt position 182904-nt position 182857 (lower strand) of the mouse cytomegalovirus sequence according to GenBank Accession No.: U68299.1; |
| 20 | 5'-cccGGATC CctctccTCAGATGCCAGGGAG GATGAAG-3' | primer to amplify ULBP2 ORF; wherein the Stop codon (in inverse orientation) is indicated in bold and underlined. |
| 21 | 5'-GACACCGG GCTCCATGCTG ACGTAGGTACC GACTGGGGTCA AAAGCCTttaa acggtactttc ccatagc-3' | primer to amplify insert including ULBP2 ORF and including the promoter and KanR; wherein the capitalized letters are homologous to nucleotides 55134-55181 of the TB40E BAC (Genbank: EF999921.1) |
| 22 | 5'-CTTATAGC AGCGTGAACGT TGCACGTGGCC TTTGCGGTTAT CCGTTCAGgaa cacttaacggc tga-3' | primer to amplify insert including ULBP2 ORF and including the promoter and KanR; wherein the capitalized letters are homologous to nucleotides 55963-55915 (lower strand) of the TB40E BAC (Genbank: EF999921.1; Sbjct 55963 CTTATAGCAGCGTGAACGTTGCACGT GGCCTTTGCGGTTATCCGTTCAG 55915) and lower case letters are homologous to sequences on the plasmid carrying the MCMV MIEP, the ULBP2 ORF and KanR |
| 23 | 5'-GGCGATGC GGTATCGCGCA CA-3' | sequencing primer |
| 24 | 5'-GACACCTG TTCGTCCAGAA TC-3' | sequencing primer |
| 25 | 5'-TGACTTAA ACTCCCCAGGC AA-3' | Primer ie4fwd |
| 26 | 5'-TAGGTGAG GCCATAGTGGC AG-3' | Primer ie4rev |
| 27 | 5'-TGCCTGTT CTTTGCAGTCT GT-3' | Primer glra1fwd |
| 28 | 5'-AGTCGAGT GAAGGGTAACG AGC-3' | Primer glra1rev |

-continued

| SEQ. ID. NO: | Sequence | internal reference |
|---|---|---|
| 29 | RALEYKNL | 1E3 ($^{416}$RALEYKNL$^{423}$) peptide |
| 30 | TVYGFCLL | m139 ($^{419}$TVYGFCLL$^{426}$) peptide |
| 31 | HGIRNASFI | M45 ($^{985}$HGIRNASFI$^{993}$) peptide |
| 32 | SSPPMFRV | M38 ($^{316}$SSPPMFRV$^{323}$) peptide |
| 33 | GTGTATGTGGC CCGACGGGCGG | primer m152fw |
| 34 | CGCGGGCTACT CCCGAAAGAGT AACATC | primer m152rv |
| 35 | ATGGCCAAGGC AGCAGTGAC | primer RAEfw |
| 36 | TGCTCGACCTG AGGTAATTATA ACCC | primer RAErv |
| 37 | N-IYSTVASS L-C | H-2Kd-Balb/c restricted HA peptide HA533-541 (N-IYSTVASSL-C) immunodominant epitope |
| 38 | YPYDVPDYA | H2b-B6 mice restricted peptide HA114-122 (YPYDVPDYA)-this one is erased in case of headless mutatnt |
| 39 | TATATAGACTG AAGCGGAGT | 20 nt homologous to sequences immediately downstream of the 3'-end of the UL11 ORF of the CMV strain TB40E |
| 40 | CAGCTTTTGAG TCTAGACAGGG GAACAGCCTTC CCTTGTAAGAC AGAATGaaggc aaacctactgg tcc | UL11-HA-fw |
| 41 | GAGTCGTTTCC GAGCGACTCGA GATGCACTCCG CTTCAGTCTAT ATATCA | UL11-HA-rev |
| 42 | AAGUGACGGUG AGAUCCAGGCU | hcmv-miR-UL112 (MIMAT0001577(MirBase) (Stern-Ginossar et al., 2008, supra, Stern-Ginossar et al., 2007, supra) |
| 43 | TIHDIILECV | E6 29-38 (TIHDIILECV; restricted by the HLA-A0201 molecule), |
| 44 | TIHDIILEC | E6 29-37 (TIHDIILEC; restricted by B48), |
| 45 | HDIILECV | E6 31-38 (HDIILECV; restricted by B4002) |
| 46 | FAFRDLCIVY | E6 52-61 (FAFRDLCIVY; restricted by B57), |

It will be acknowledged by a person skilled in the art and it is insofar also within the scope of the present invention that each and any of the above nucleic acid sequences can be replaced by a nucleic acid sequence which, due to the degeneracy of the genetic code, code for the same or functionally homolog peptide, polypeptide and protein, respectively, as the above indicated nucleic acid sequences.

The present invention is now further illustrated by the following figures and examples from which further features, embodiments and advantages of the present invention may be taken.

More specifically,

FIG. 1A is a schematic illustration of the cloning process and genome organization of RAE-1γMCMV;

FIGS. 1B-I, II, III, IV, V, VI, VII, VIII, IX, X and XI are a series of histograms showing the result of FACS analysis of the surface expression of RAE-1γ in MCMV infected cells;

FIGS. 1C-I (lungs) and 1C-II (spleen) are diagrams indicating virus load in different organs of infected mice with and without blocking anti-NKG2D monoclonal antibody treatment;

FIG. 1D is a diagram indicating virus load in salivary glands at different time points;

FIGS. 1E-I (blood), 1E-II (liver) and 1E-III (salivary gland) are diagrams indicating copies of viral genome in different organs of infected mice at different time points;

FIGS. 2A-I (spleen), 2A-II (lungs), 2A-III (liver) and 2A-IV (salivary gland) are diagrams indicating virus load in different organs of infected neonatal mice at different time points;

FIGS. 2B-I (spleen), 2B-II (lungs), 2B-III (liver) and 2B-IV (salivary gland) are diagrams indicating copies of MCMV genome in different organs of infected neonatal mice at different time points;

FIGS. 3A-I (m164) and 3A-II (IE1/m123) are diagrams indicating the percentage of tetramer-specific CD8$^+$ T cells of mice infected with MCMV at different time points;

FIGS. 3B-I (Tem Tcm), 3B-II (Tem) and 3B-III (Tcm) are bar diagrams indicating the percentage of IE1/m123-specific CD8$^+$ T cells of mice infected with MCMV expressing various cell surface molecules;

FIG. 3C is a histogram showing the result of FACS analysis of surface expression of NKG2D on IE1/m123-specific CD8$^+$ T cells in spleen of mice infected with MCMV;

FIGS. 3D-I, 3D-II, 3D-III, 3D-IV, 3D-V, 3D-VI, 3D-VII and 3D-VIII are a series of dot plots showing the result of FACS analysis of tetramer-positive and/or IFN-γ positive splenocytes of mice infected with MCMV;

FIGS. 3E-I, 3E-II, 3E-III, 3E-IV, 3E-V, 3E-VI, 3E-VII and 3E-VIII are a series of dot plots showing the result of FACS analysis of splenocytes of infected mice stimulated in the presence of the αCD107a antibody and co-stained for IFN-γ and TNF-α production;

FIG. 4A is a diagram indicating the virus titer in spleen of BALB/c mice infected with MCMV after transfer of memory CD8$^+$ T from latently infected μMT/μMT B cell-deficient mice;

FIGS. 4B-I (spleen), 4B-II (blood) and 4B-III (liver) are diagrams indicating the percentage of IE1/m123 MHC class I tetramer per CD8$^+$ T cells in various organs of mice challenged with of salivary gland derived MCMV;

FIGS. 4C-I and 4C-II are survival curves indicating survival of different vaccinated mice as a function of time;

FIG. 5A is a diagram indicating viral load of various organs in latently infected B cell-deficient mice depleted of CD4$^+$, CD8$^+$, and NK1.1$^+$ cells.

FIGS. 5B-I, 5B-II, 5B-III, 5B-IV, 5B-V, 5B-VI and 5B-VII are a series of histograms showing the result of FACS analysis of surface RAE-1γ expression of SVEC4-10 cells infected with recurrent plaque purified RAE-1γMCMV viruses;

Figure 7A:
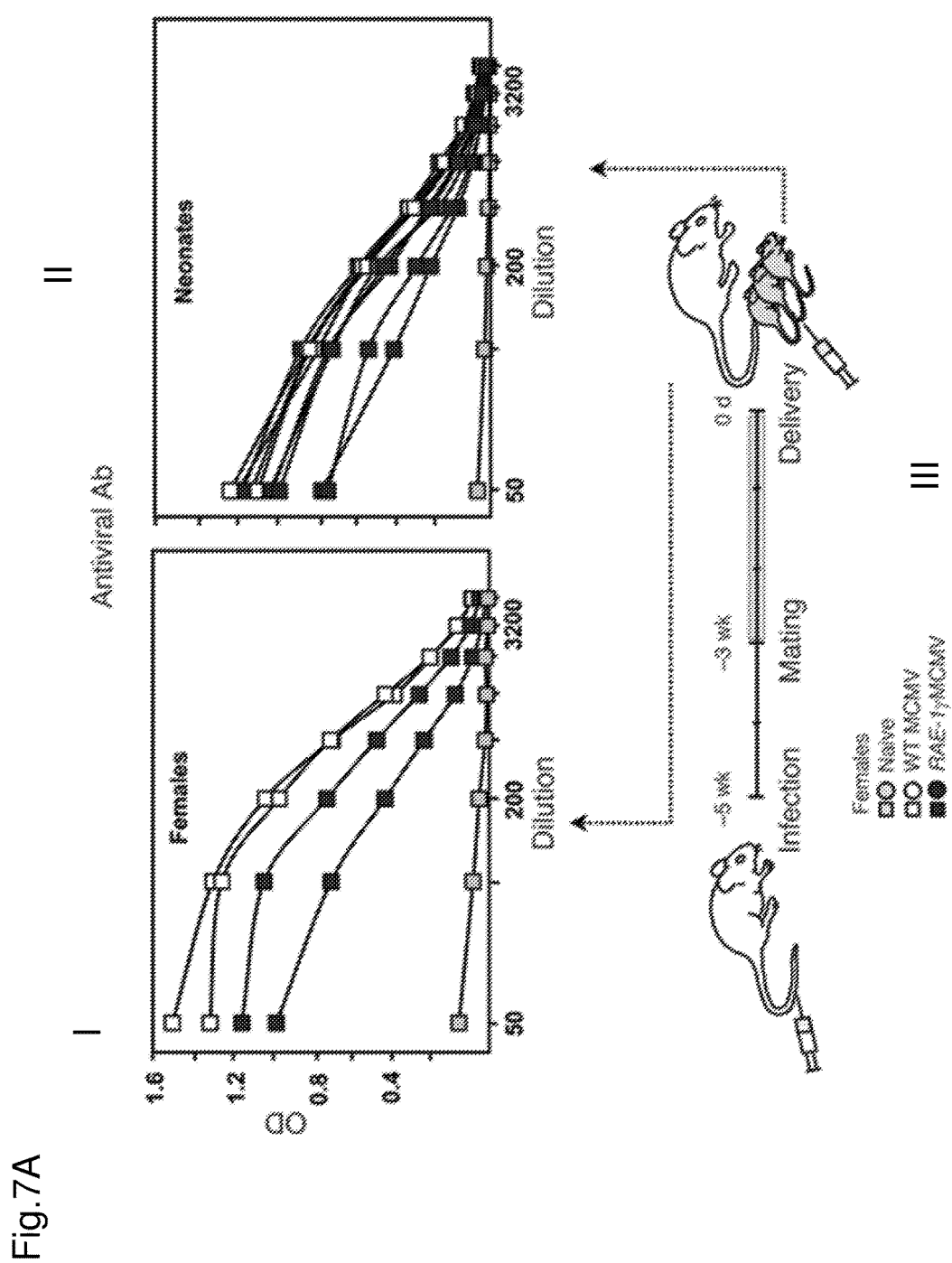
Figure 7B:
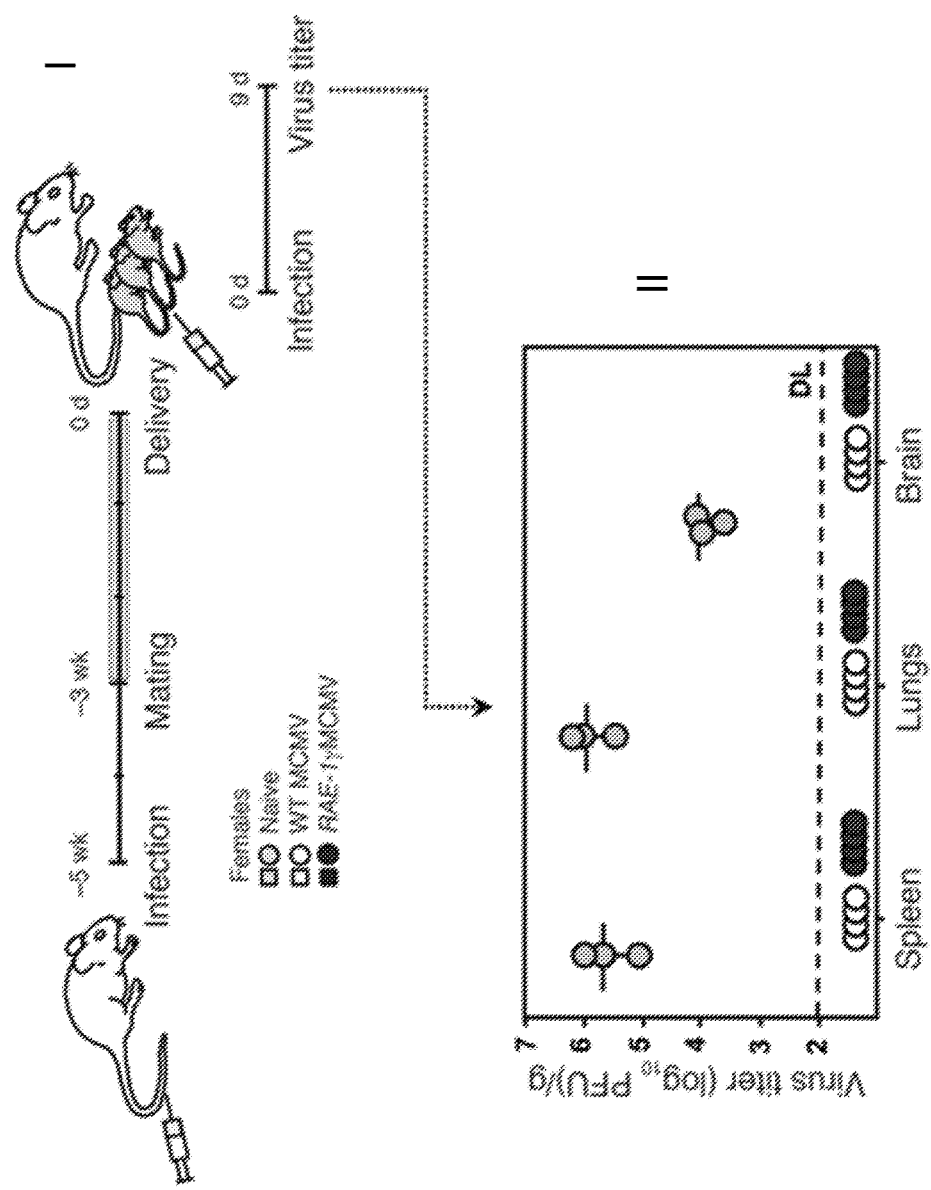
Figure 8A:
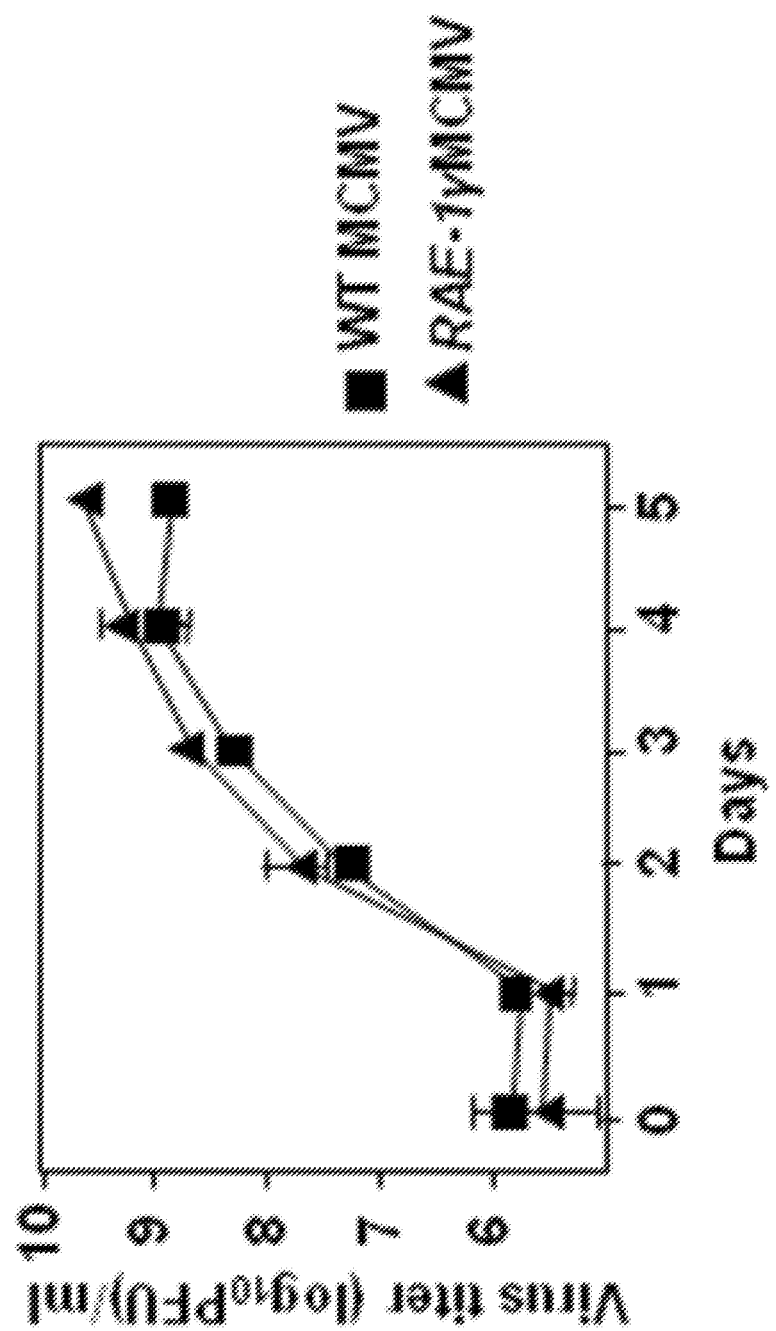
Figure 9A:
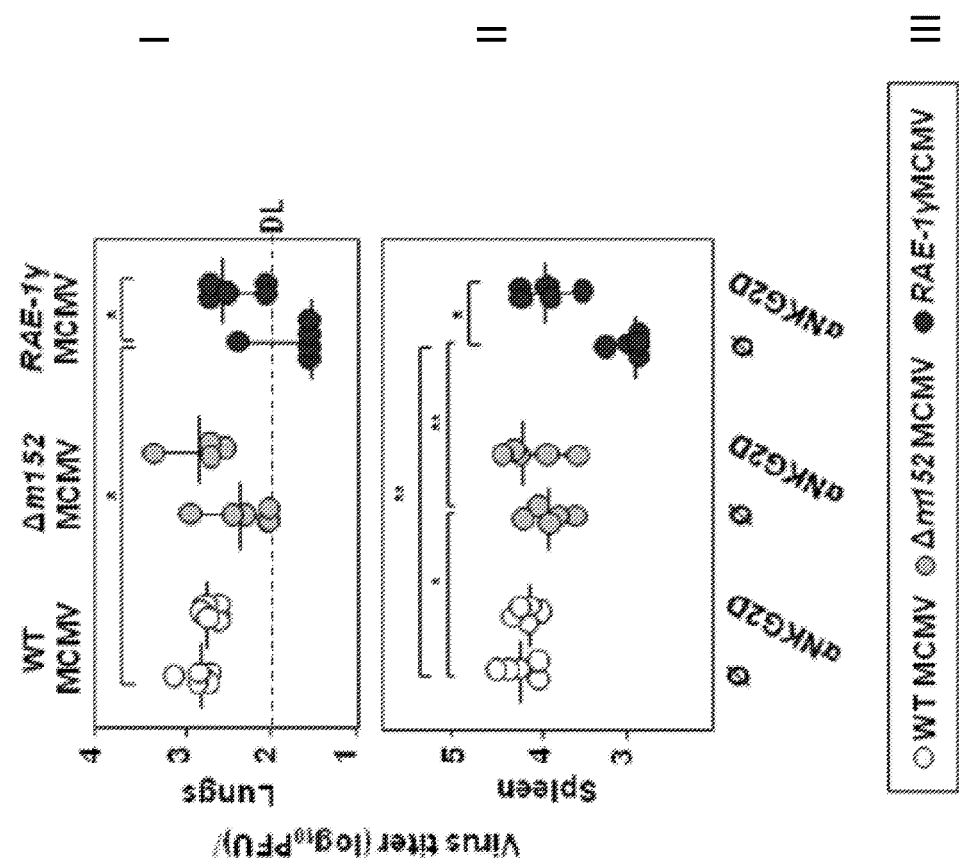
Figure 10:
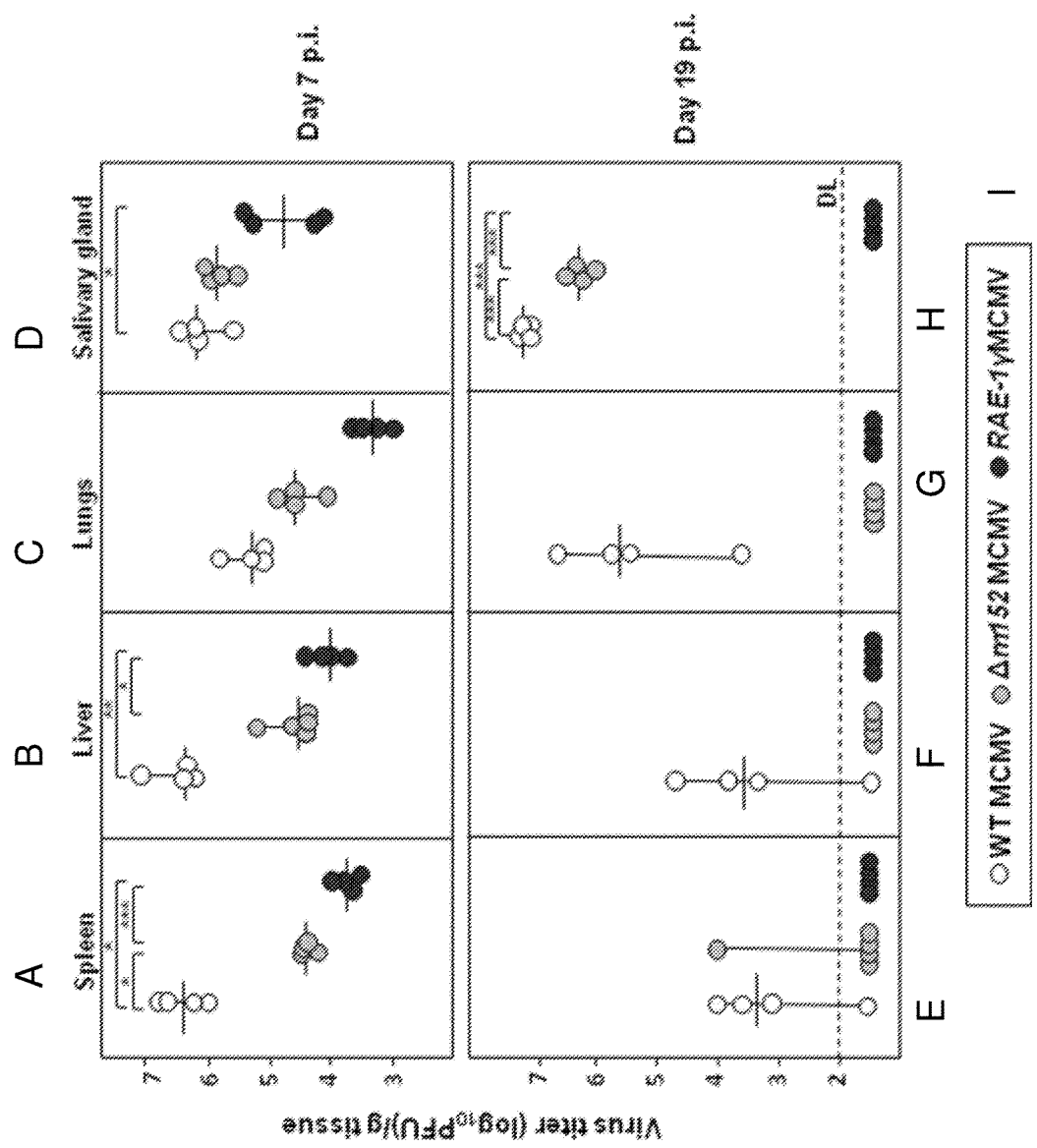
Figure 16A:
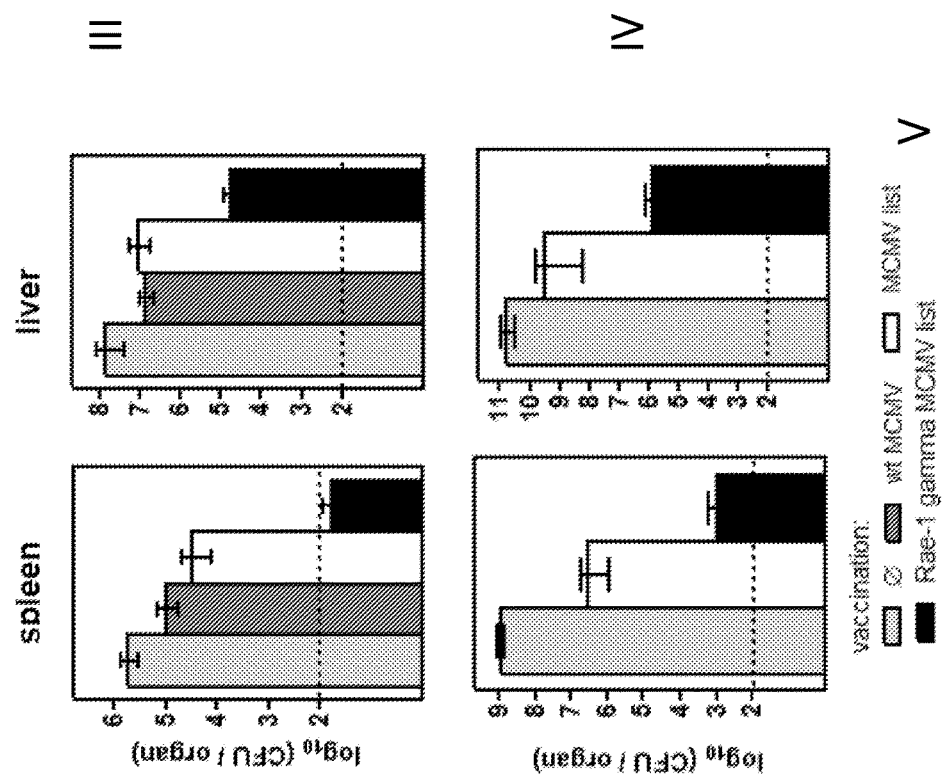
Figure 25:
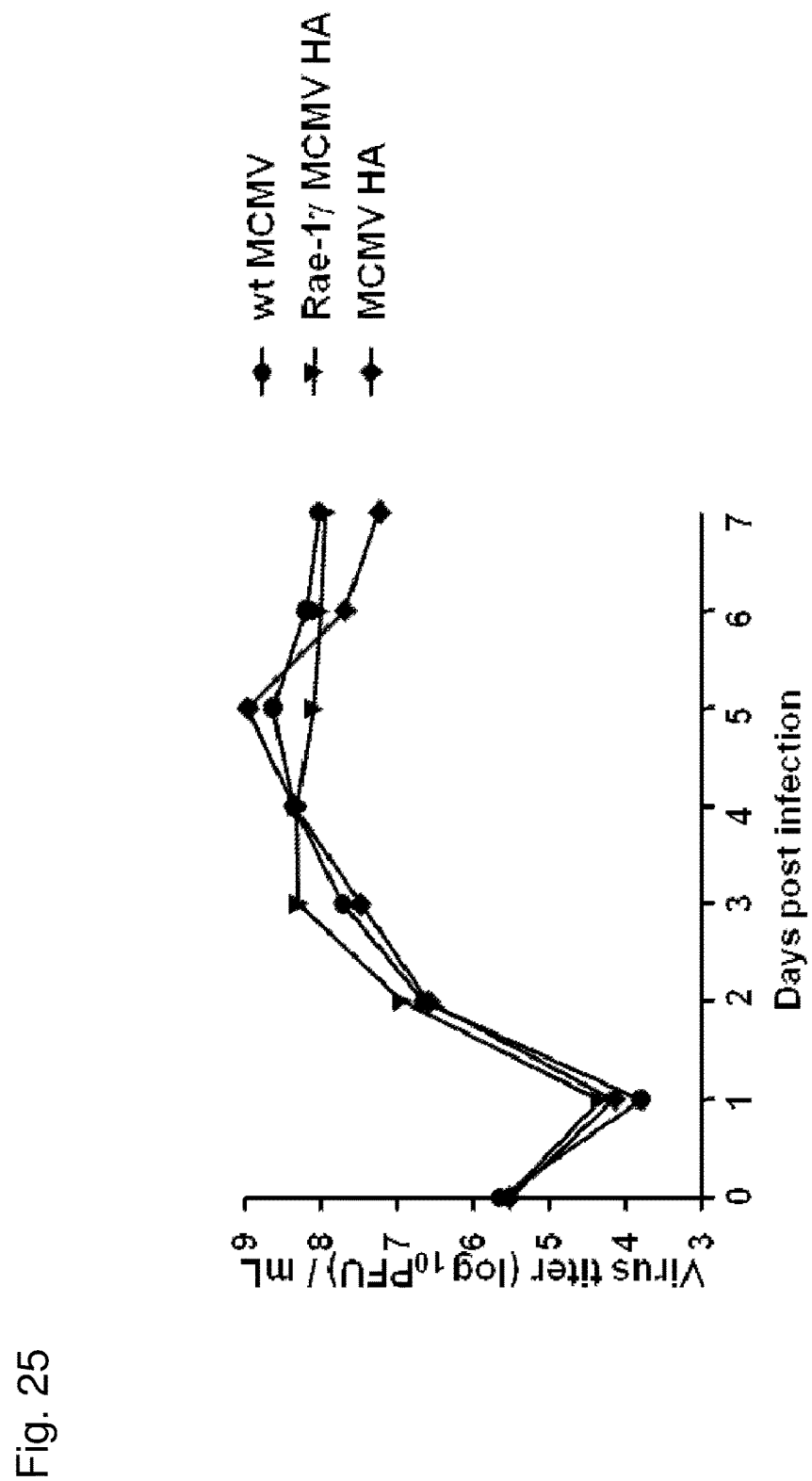
Figure 26:
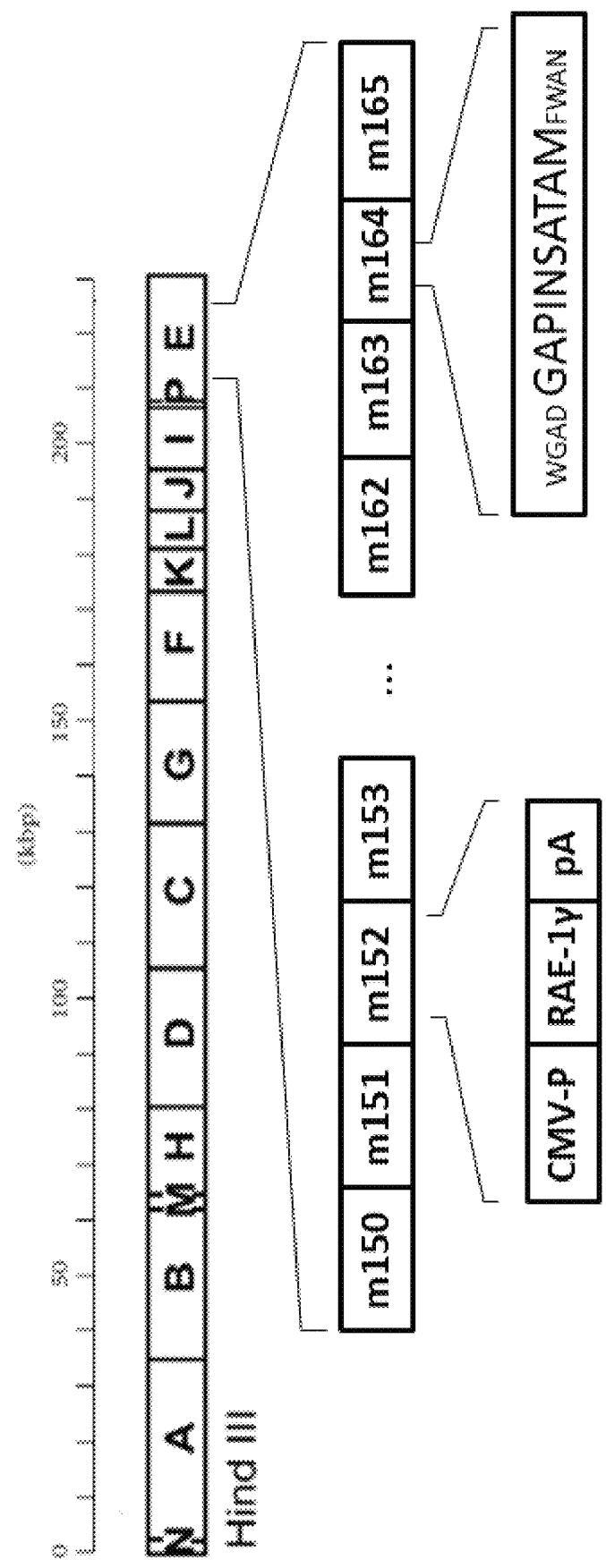
Figure 27A:
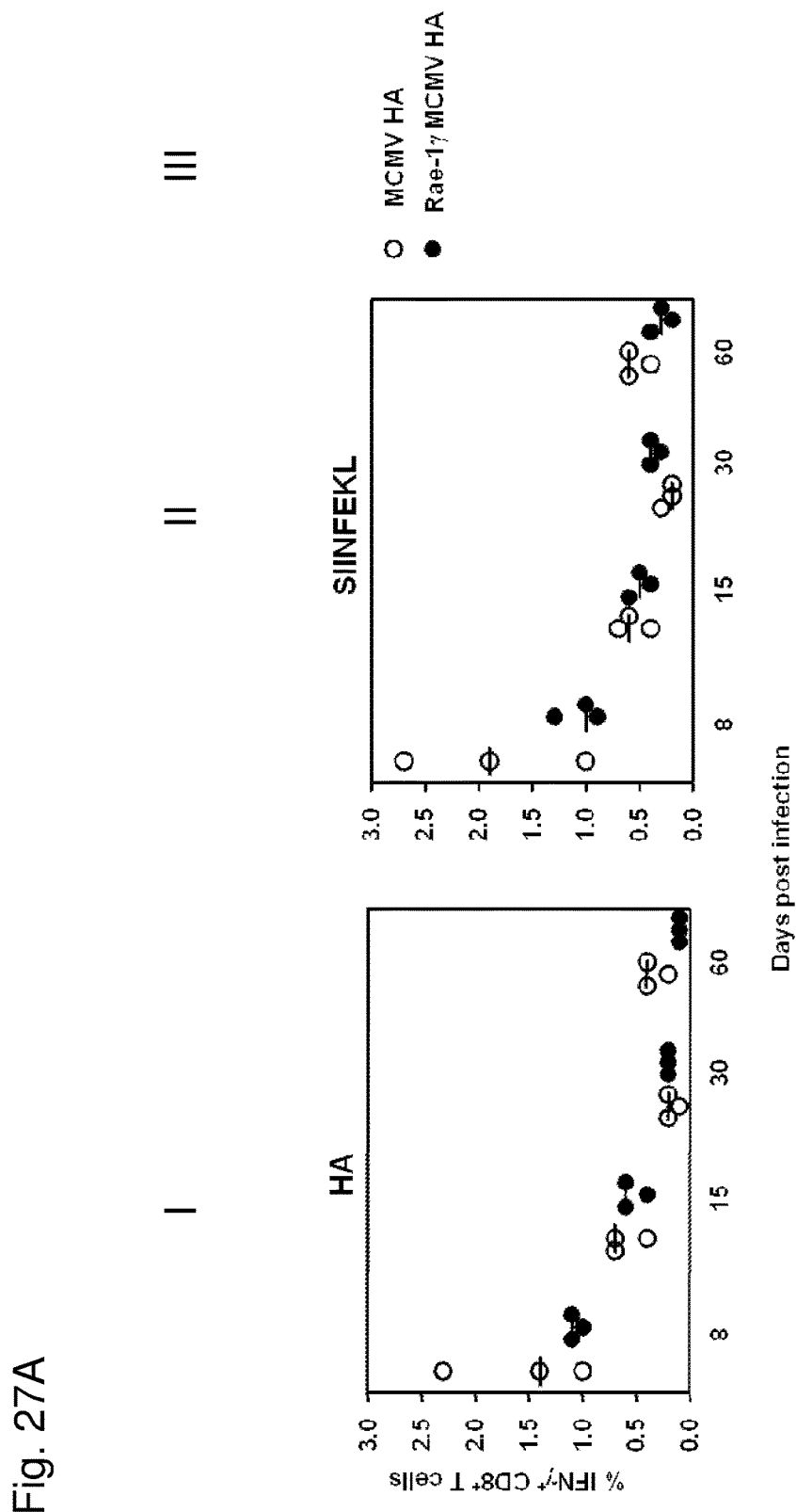
Figure 31:
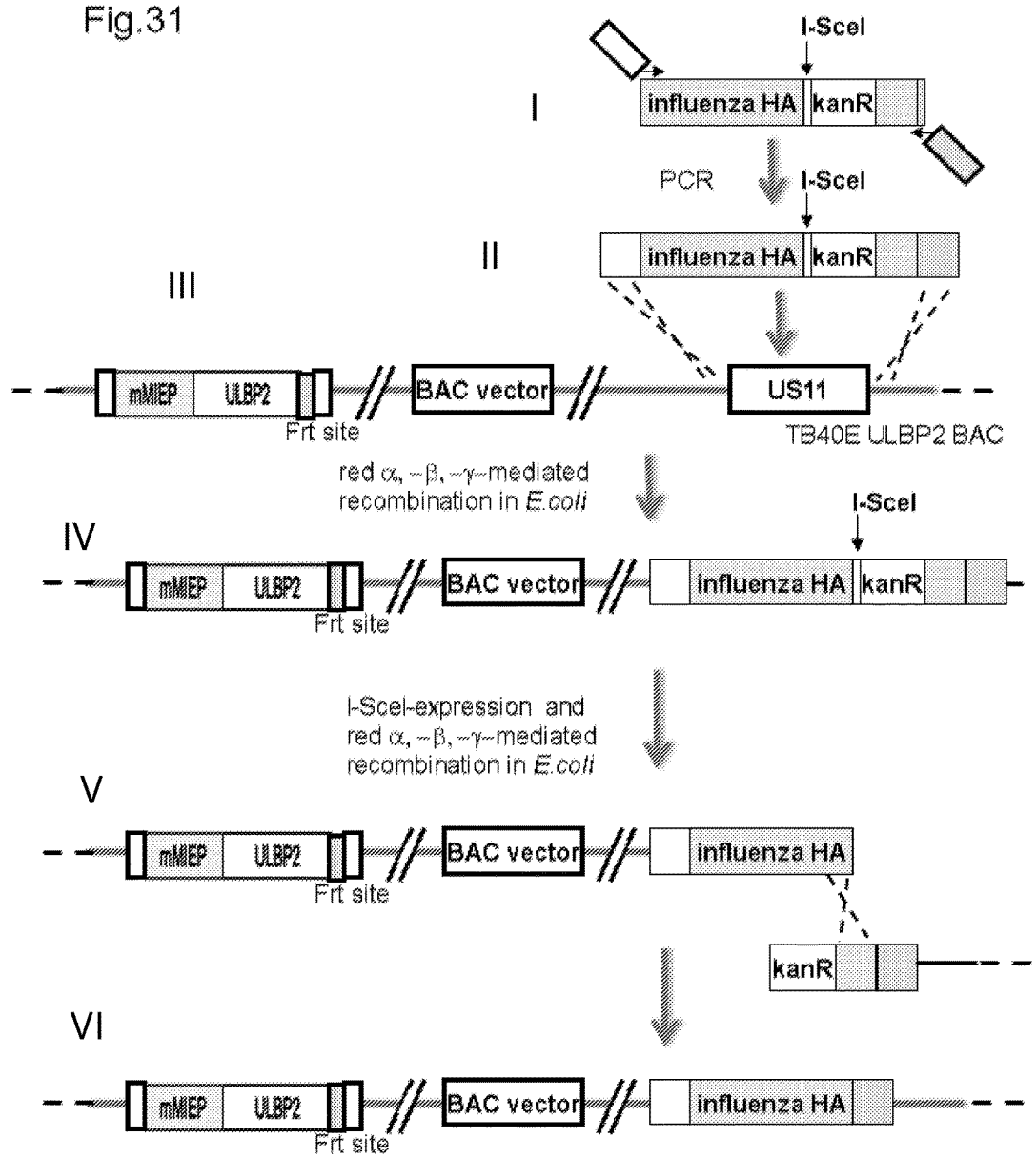
Figure 33A:
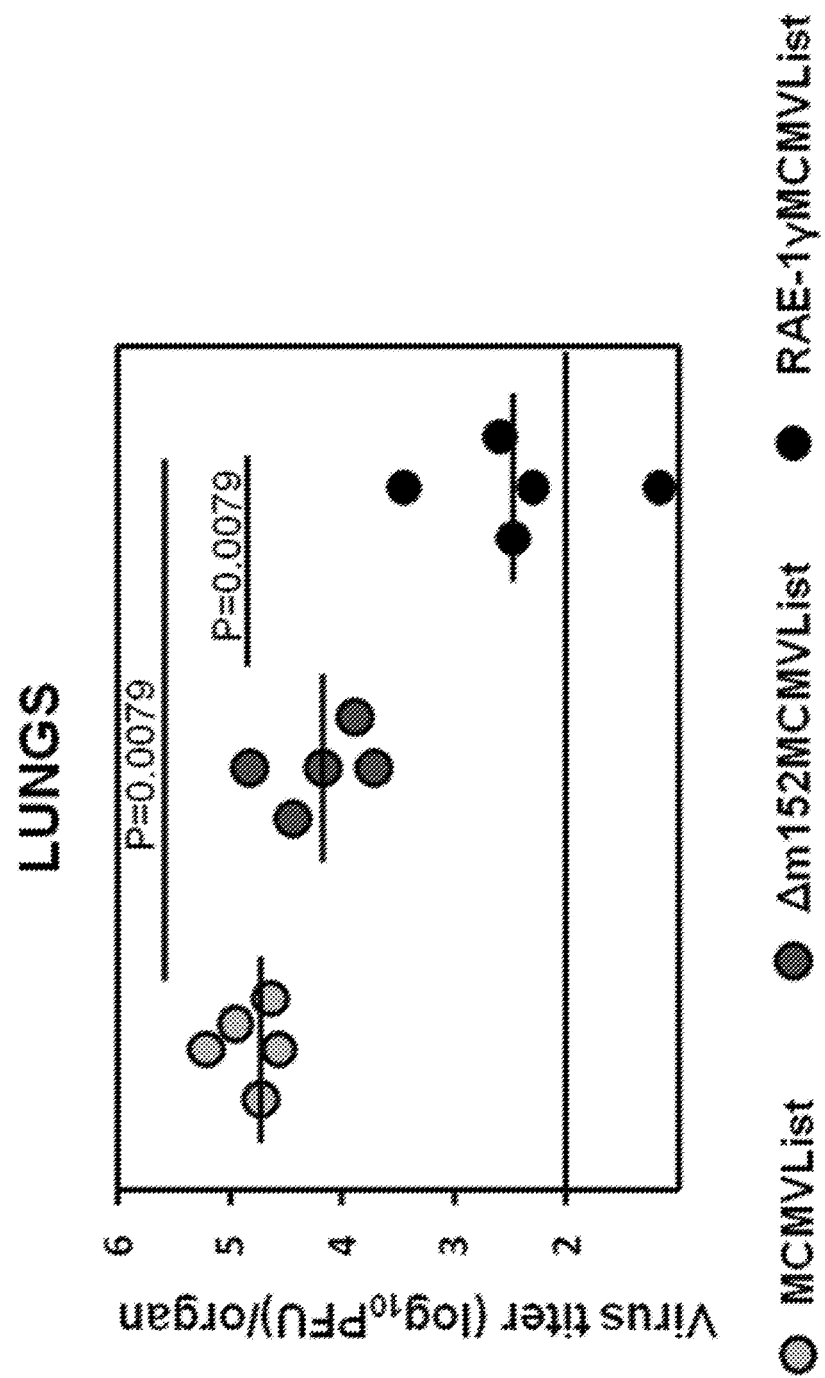
Figure 33B:
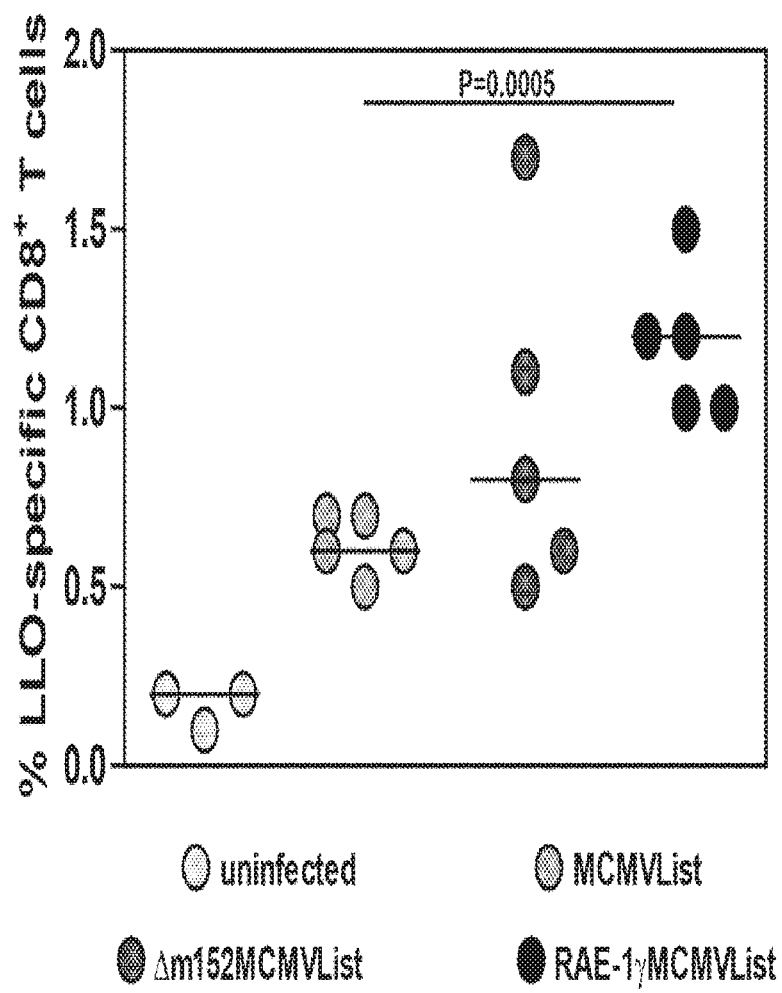
Figure 34A:
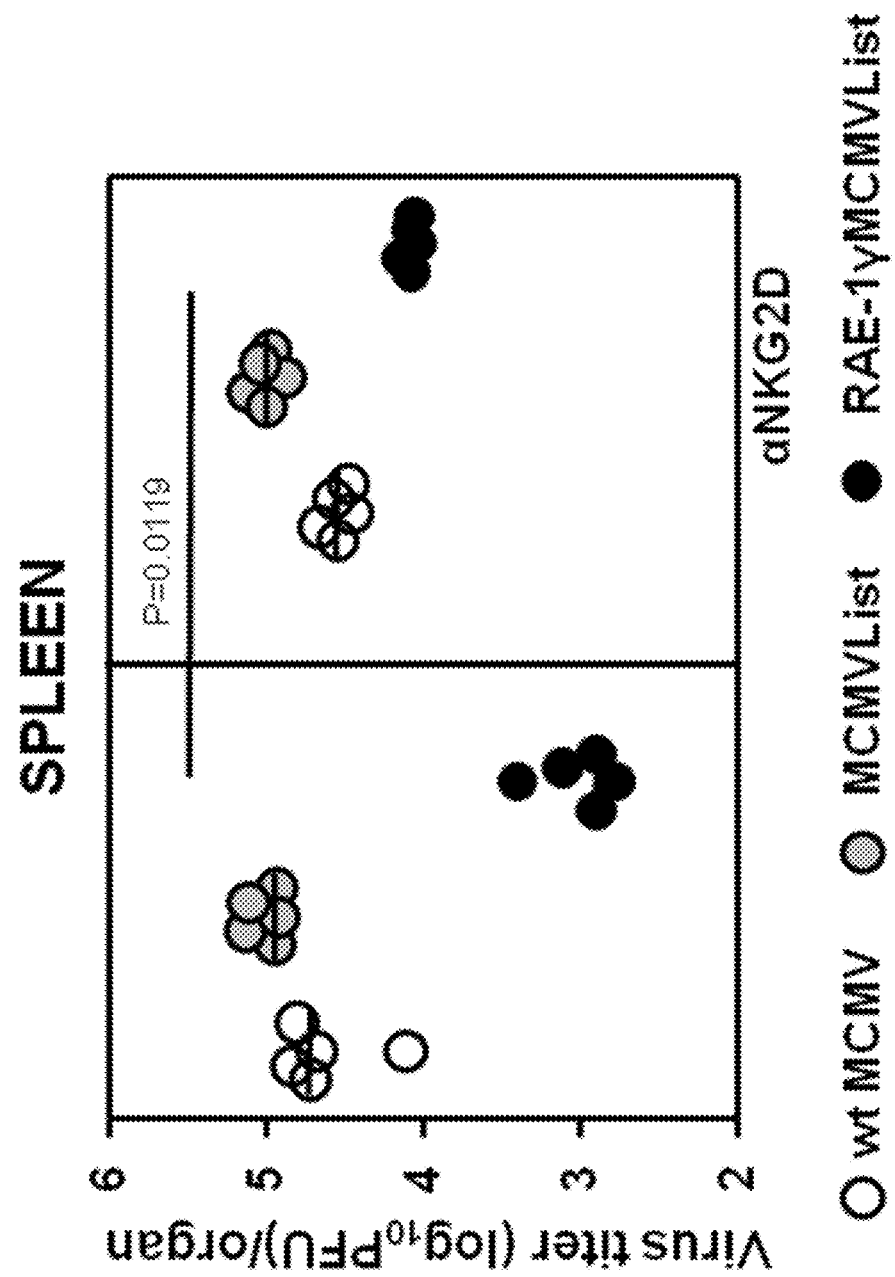
Figure 34B:
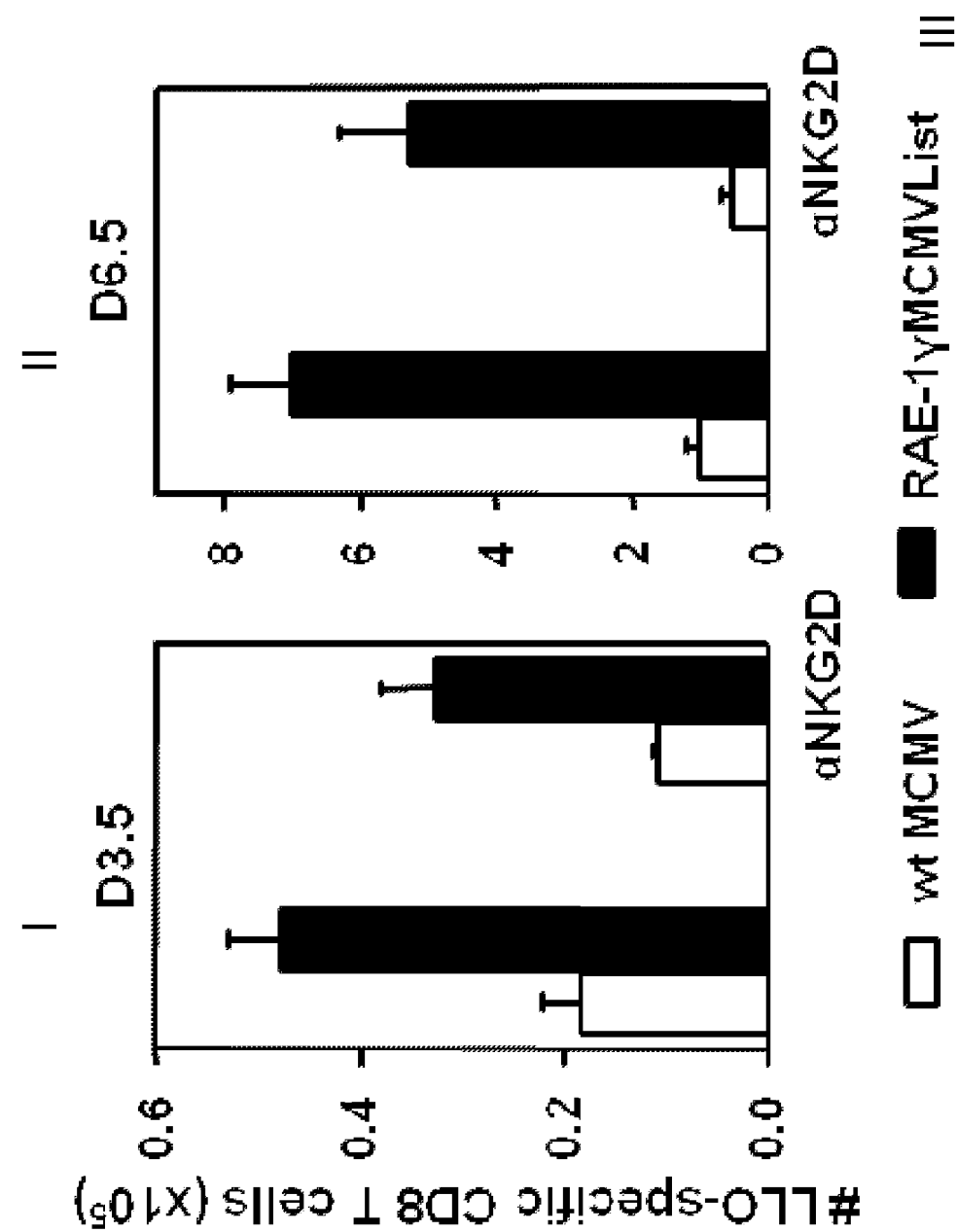
Figure 35A:
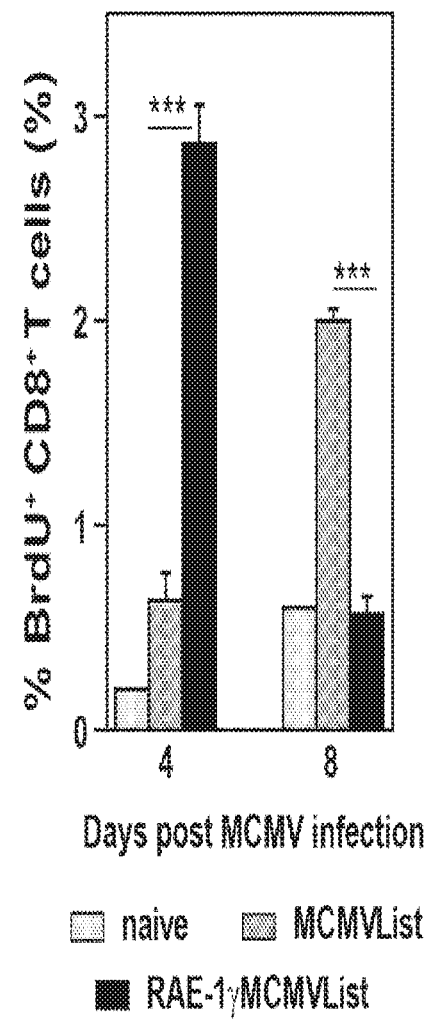
Figure 35B:
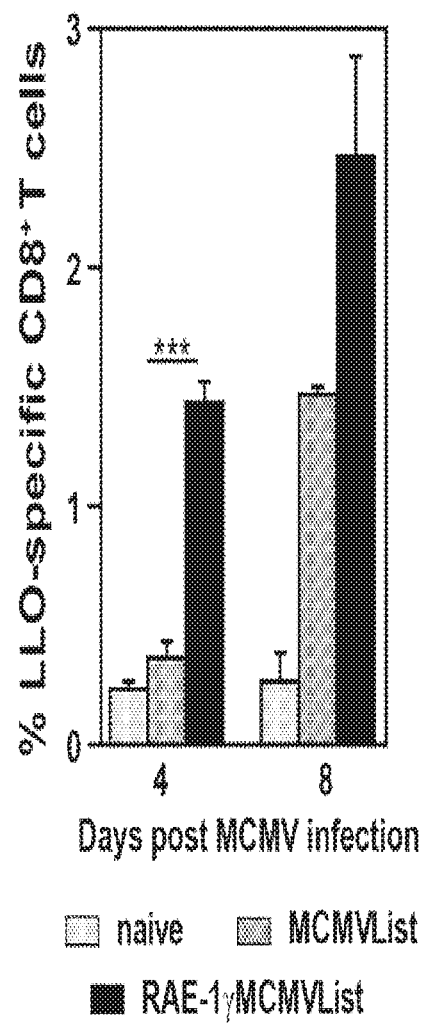
Figure 36:
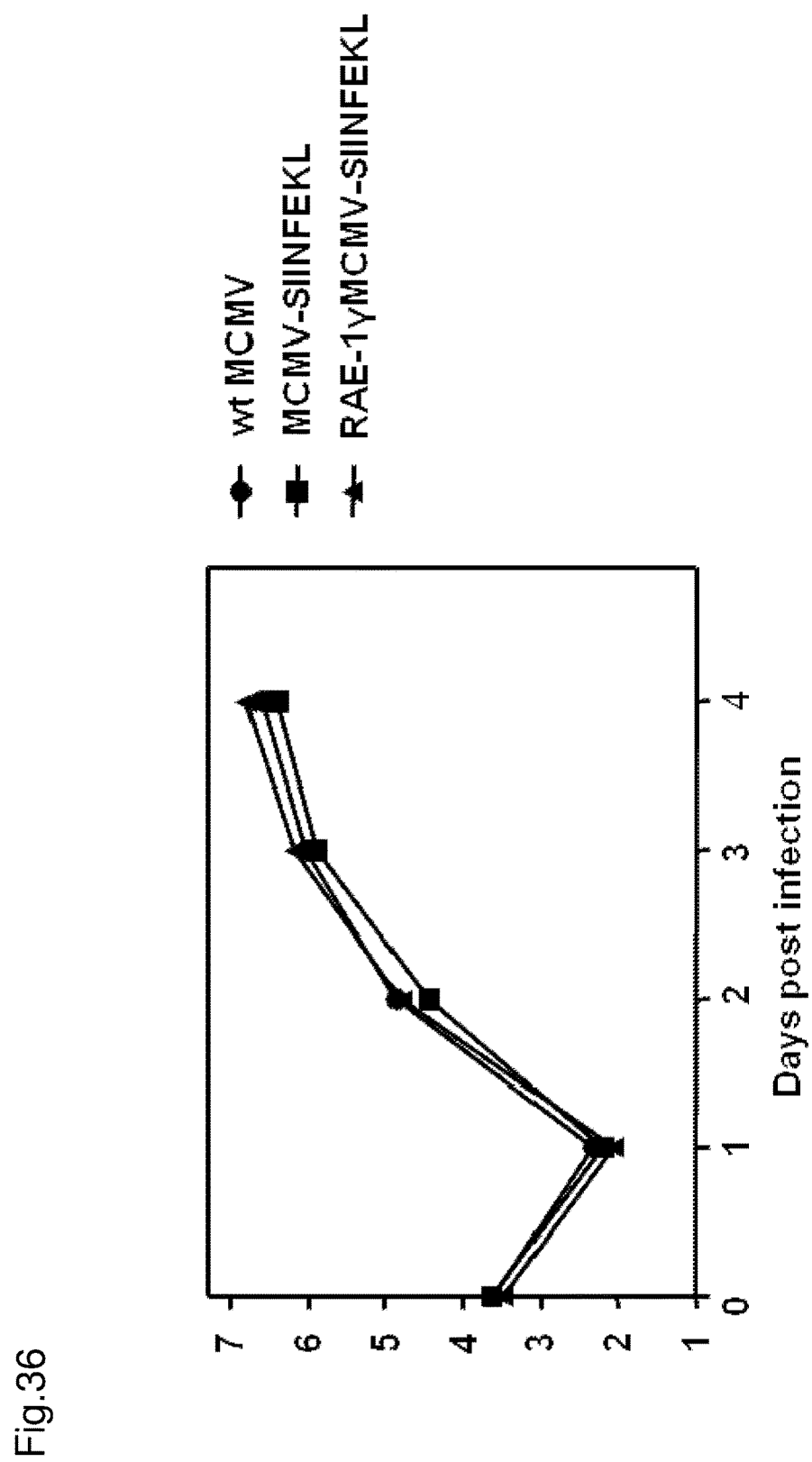
Figure 40B:
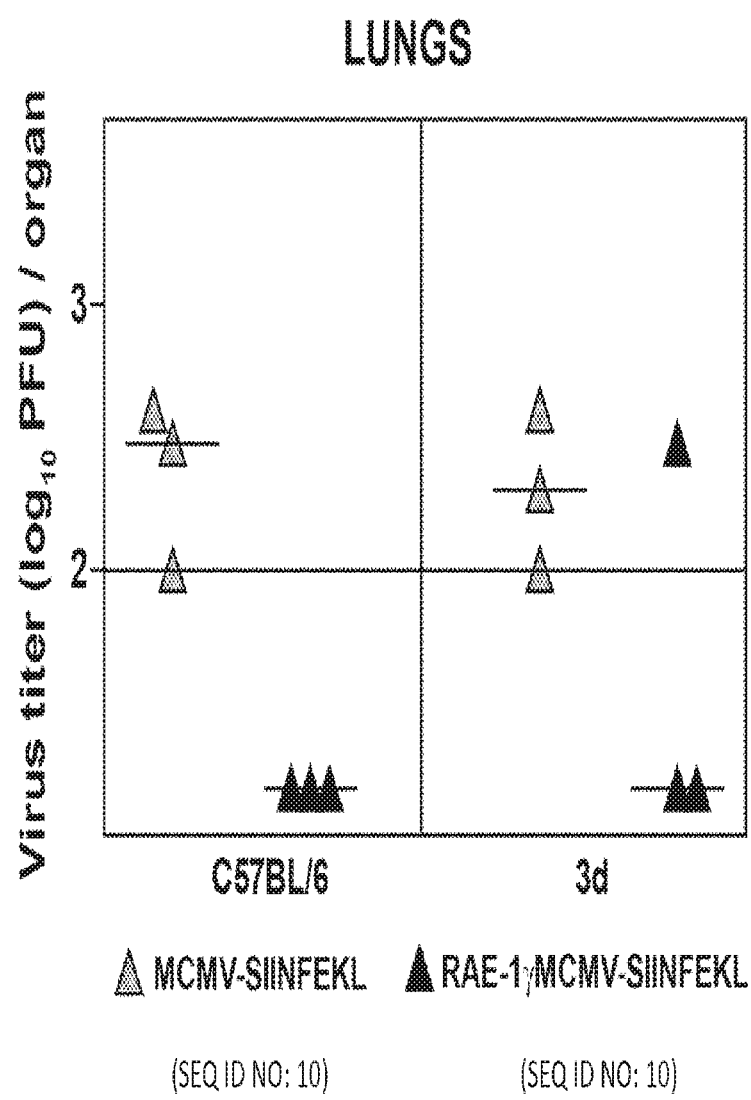
Figure 41A:
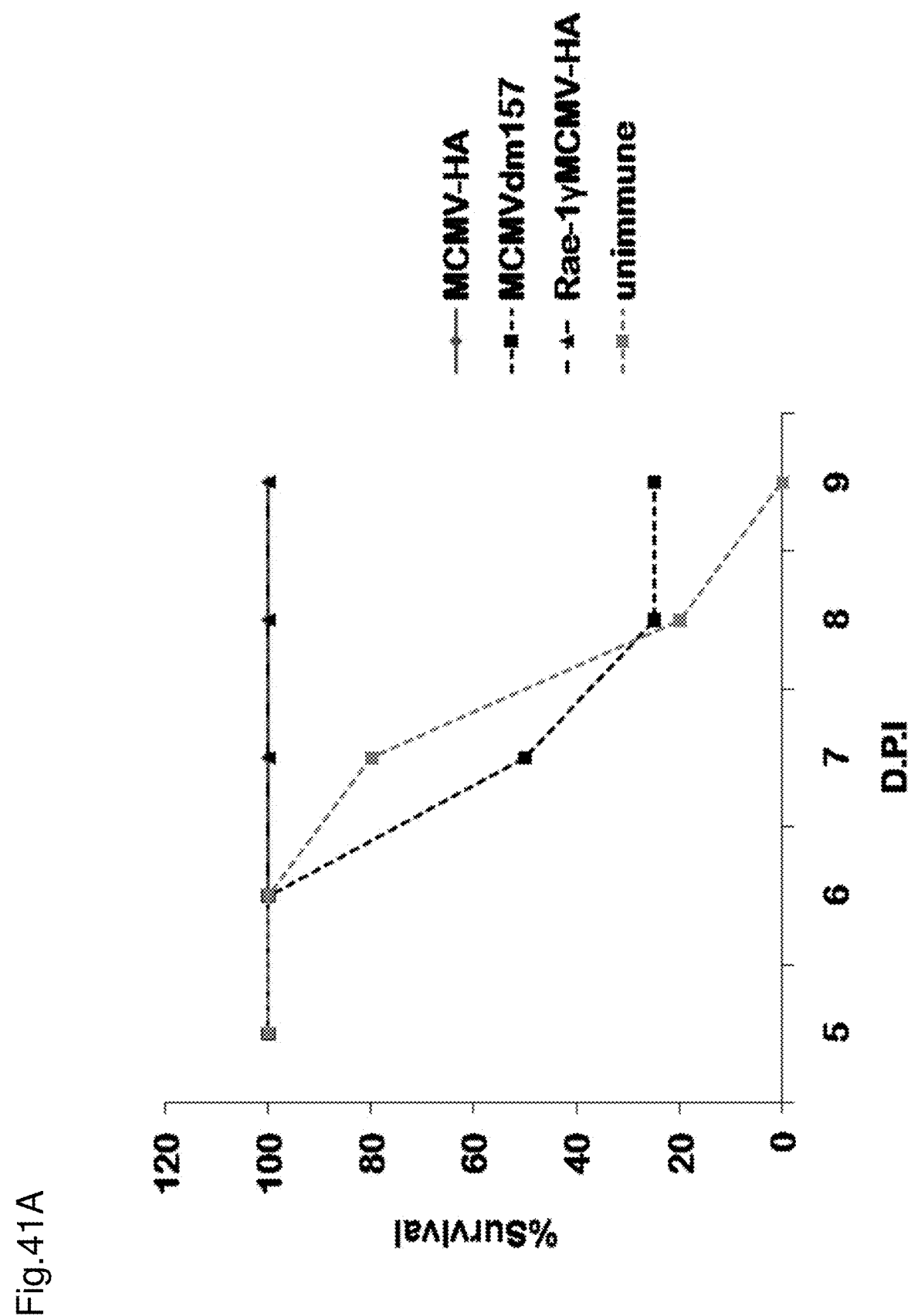
Figure 41B:
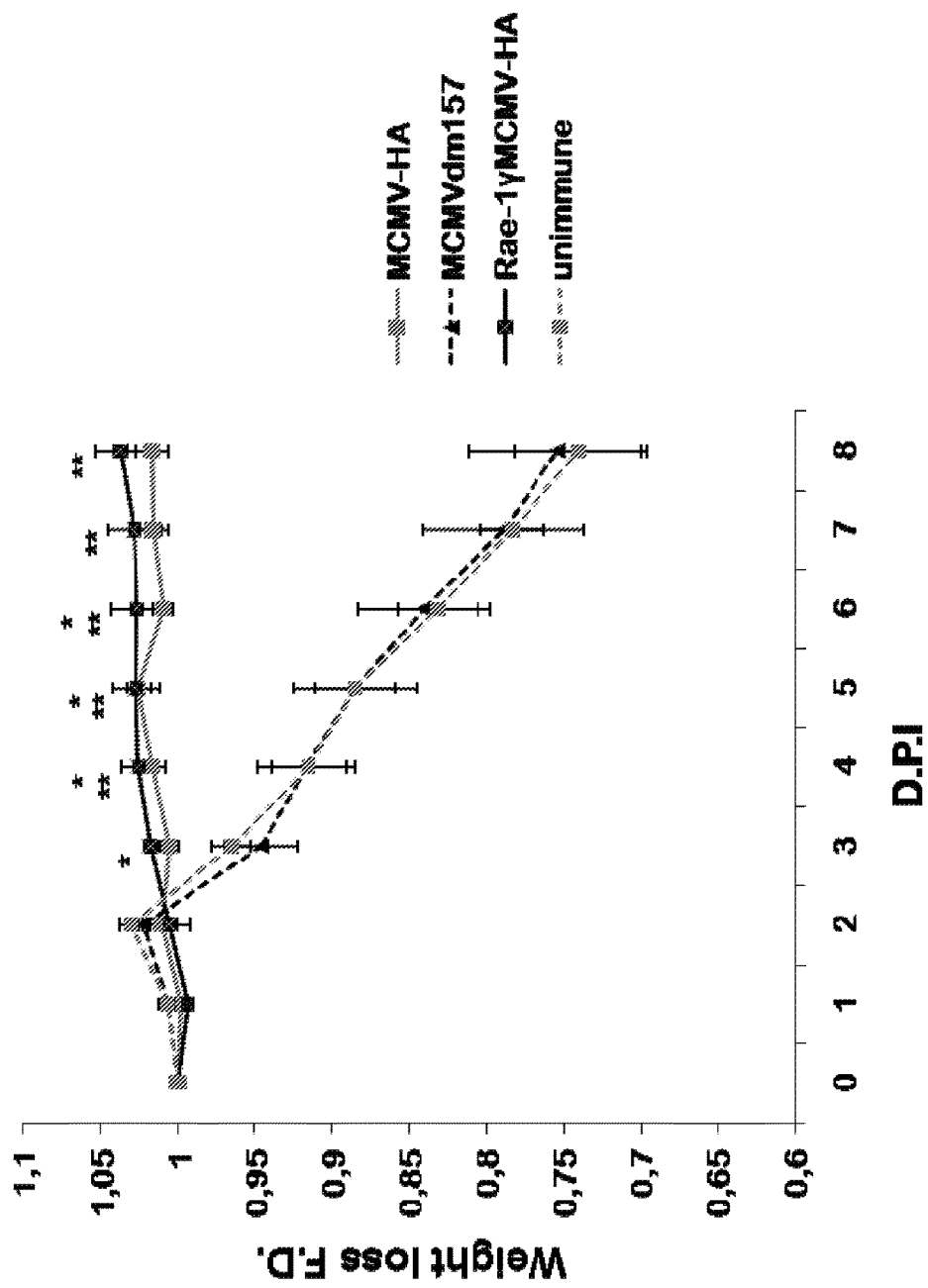
Figure 42:
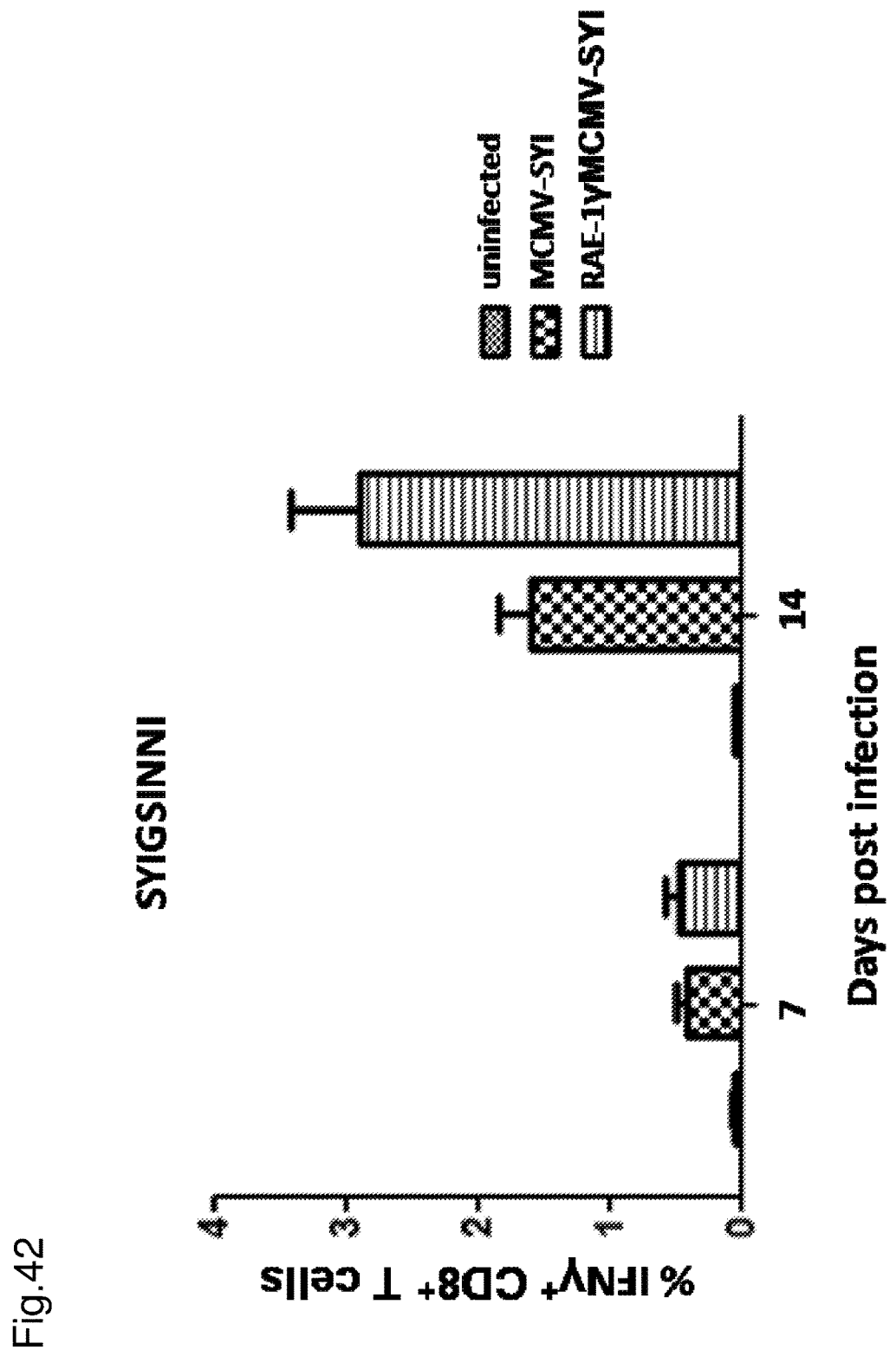

FIGS. 6B-I and 6B-II are diagrams indicating the viral load of organs of y-irradiated infected mice optionally depleted for NK cells;

FIGS. 7A-I and 7A-II are diagrams indicating antiviral antibody titers in serum of infected females and neonates, with an illustrative scheme of the experimental protocol shown in FIG. 7A-III;

FIG. 7B-I is a diagram indicating viral load in various organs of infected neonates, while an illustrative scheme of the experimental protocol is shown in FIG. 7B-II;

FIG. 8A is a diagram indicating virus titer of MCMV in vitro as a function over time;

FIGS. 8B-I to 8B-XII are a series of histograms showing the result of FACS analysis of the surface expression of NKG2D ligands on infected cells;

FIGS. 9A-I and 9A-II are diagrams indicating the virus load in organs of infected mice treated with or without with blocking anti-NKG2D antibody, while FIG. 9A-III shows the key to the diagrams;

FIGS. 9B-I, 9B-II, 9B-III and 9B-IV are diagrams indicating the percentage of IFN$^+$CD8$^+$ T cells of peptide-stimulated splenocytes from mice infected with MCMV;

FIG. 10-A to 10H are diagrams indicating the viral load in organs of MCMV infected neonatal BALB/c mice while FIG. 10I shows the key;

FIG. 11A to 11C show a series of dot plots showing the results of FACS analysis of the percentage of CD11b cDCs and CD8α cDCs in infected mice;

FIG. 12A-I to 12A-VII together are schematic illustrations of the cloning process and genome organization of RAE-1γMCMV and RAE-1γMCMVList;

FIG. 12B-I to 12B-III together show an illustrative scheme of the experimental protocol for experiments applying *Listeria monocytogenes* challenge;

FIG. 13A is a diagram indicating virus titer in vitro as a function over time, while FIG. 13B shows the key;

FIGS. 14A and 14B are diagrams indicating virus titer in salivary glands of infected mice;

FIGS. 15A to 15D are diagrams indicating percentage of IFN-r CD8$^+$ T cells of peptide-stimulated splenocytes from infected mice;

FIGS. 16A-I, 16A-II, 16A-III and 16A-IV depict diagrams indicating CFU of *Listeria monocytogenes* after challenge of virus infected mice, while FIG. 16A-V shows the key;

FIGS. 16B-I, 16B-II, 16B-III, 16B-IV and 16B-V are a series of micrographs illustrating the effect of vaccination by Rae-1γ MCMVList in limiting depletion of T cells from PALS in spleen;

FIGS. 17A and 17B depict diagrams indicating the percentage of IFNγ$^+$ CD8$^+$ T cells of splenocytes from vaccinated mice after challenge with *Listeria monocytogenes*, while FIG. 17C shows the key;

FIGS. 18A and 18B depict diagrams indicating CFU of *Listeria monocytogenes* of vaccinated mice challenged with *Listeria monocytogenes* after depletion for CD8$^+$ T cells, while FIG. 18C shows the key;

FIGS. 19A-F show a series of micrographs indicating liver pathology after *Listeria monocytogenes* challenge in vaccinated mice;

FIGS. 20A and 20B depict diagrams indicating the percentage of IFNγ$^+$ NK cells and percentage of total NK cells of splenocytes of vaccinated mice after challenge with *Listeria monocytogenes*, while FIG. 20C shows the key;

FIGS. 21A and 21B depict diagrams indicating the frequency of CD8α$^+$ DCs (CD11c$^{hi}$ CD8α$^+$) and CD11b+ DCs (CD11c$^{hi}$ CD8α$^-$) of infected mice, while FIG. 21C shows the key;

FIGS. 22A and 22B depict diagrams indicating the frequency of pDC and the concentration of serum IFNα of infected mice, while FIG. 22C shows the key;

FIGS. 23A-C depict diagrams indicating the total number of CD8$^+$ T cells, effector memory CD8$^+$ T cells and virus specific CD8$^+$ T cells infected mice, while FIG. 23D shows the key;

FIGS. 24A, 24B, 24C-I to 24C-IV, 24D-I to 24D-IV, and 24E-I and 24E-II are schematic illustrations of the genome organization and cloning process of Rae-1γMCMV or WT MCMV expressing HA and HA-headless expressed;

FIG. 25 is a diagram indicating virus titer in vitro as a function over time;

FIG. 26 is a schematic illustration of the genome organization and cloning process of GAPINSATAM expressing MCMV;

FIGS. 27A-I and 27A-II and 27B-I to 27B-IV depict diagrams indicating the percentage of IFNγ$^+$ CD8$^+$ T cells as a result of peptide-stimulation of splenocytes from infected mice, while FIG. 27A-III shows the key;

FIGS. 28A-F are diagrams indicating viral load of various organs of infected mice;

FIGS. 29A-I, 29A-II, 29B-I, 29B-II, 29C-I and 29C-II are diagrams indicating the percentage of IFNγ+CD8$^+$ T cells of splenocytes of infected mice, while FIG. 29D shows the key;

FIGS. 30A-I to 30A-IV and 30B are schematic illustrations of the genome organization and cloning process of ULBP2 expressing HCMV;

FIGS. 30C-I and 30C-II show a series of Western blots showing the expression of ULBP2 in infected cells;

FIG. 30 D is a histogram showing the surface expression of ULBP2 on human foreskin fibroblast infected with HCMV TB40 or HCMV TB40 expressing ULBP2;

FIG. 30 E is a diagram showing the results of NK cell cytotoxicity using uninfected human foreskin fibroblast or cells infected with either HCMV TB40 or HCMV TB40 expressing ULBP2;

FIG. 31, parts I-VI together show a schematic illustration of the cloning process of an HCMV vaccine expressing ULBP2 and influenza HA;

FIGS. 32A-I to 32A-IV are diagrams indicating the percentage of survival and body weight loss (upper panel), and CFU of *Listeria monocytogenes* (lower panel) of virus infected Balb/c mice after challenge with *L. monocytogenes*;

FIG. 32 B is a survivorship curve indicating survival of virus infected Balb/c mice after challenge with *L. monocytogenes*;

FIG. 32 C is a diagram showing the percentage of LLO-specific CD8$^+$ T cell-mediated cytotoxicity;

FIG. 33 A is a diagram indicating viral load of lungs in Balb/c mice infected with MCMV;

FIG. 33 B is a diagram showing the percentage of LLO-specific CD8$^+$ T cells in lungs of Balb/c mice infected with MCMV;

FIG. 34 A is a diagram indicating viral load of spleen in Balb/c mice infected with MCMV and treated with NKG2D blocking antibody;

FIGS. 34 B-I and 34B-II are diagrams indicating the absolute number of LLO-specific CD8$^+$ T cells in Balb/c mice infected with MCMV and treated with NKG2D blocking antibody, while FIG. 34B-III shows the key;

Figure 35C:
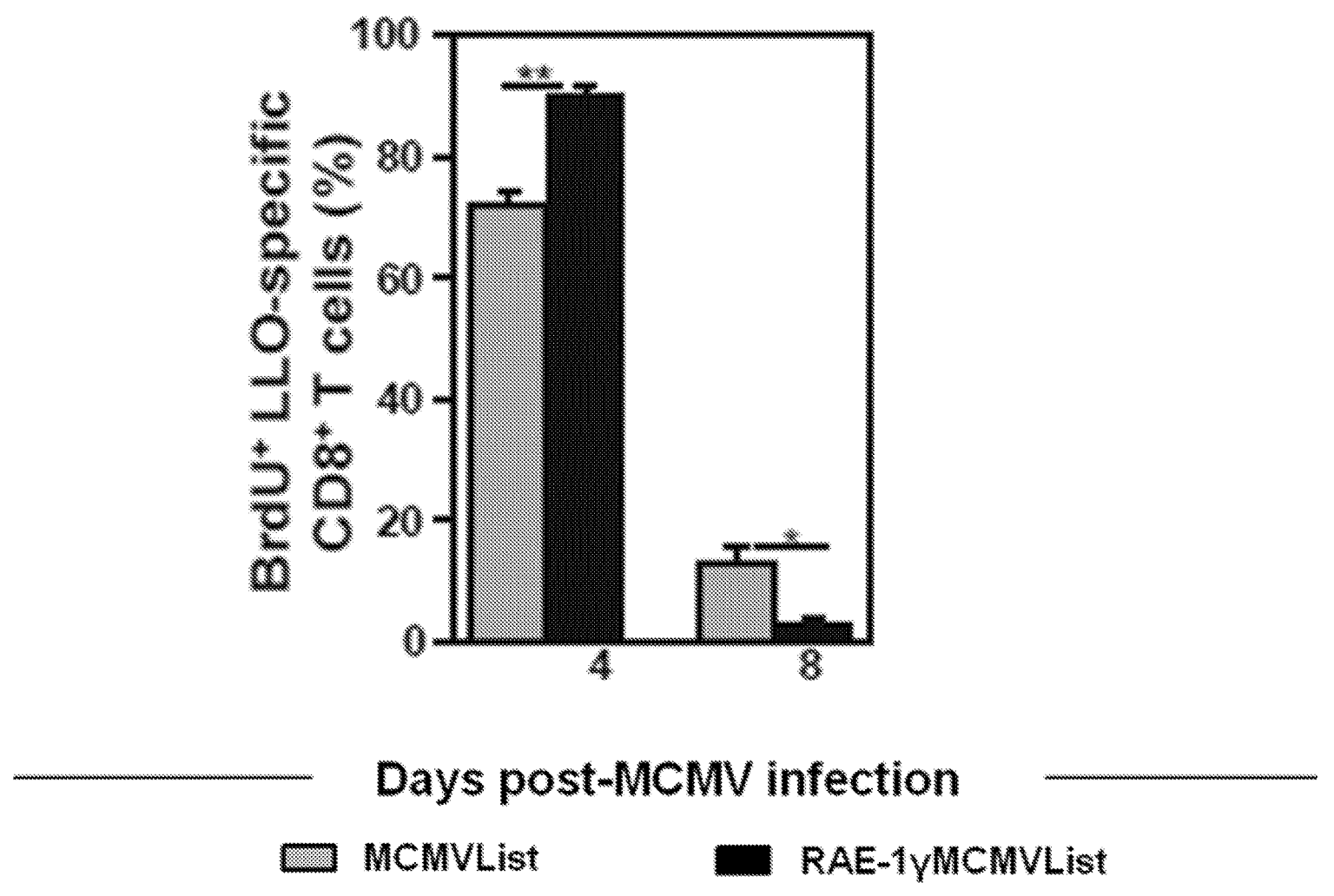

FIG. 35 A is a diagram showing the percentage of BrdU$^+$ total CD8$^+$ T cells in BALB/c mice infected with MCMV and injected with BrdU;

FIG. 35 B is a diagram showing the percentage LLO-specific CD8$^+$ T cells in Balb/c mice infected with MCMV and injected with BrdU;

FIG. 35 C is a diagram showing the percentage of BrdU LLO-specific CD8$^+$ T cells in Balb/c mice infected with MCMV and injected with BrdU;

FIG. 36 is a diagram indicating virus titer of WT-MCMV, MCMV-SIINFEKL and RAE-1γMCMV-SIINFEKL in vitro as a function over time;

FIGS. 37A-D are a series of diagrams showing the percentage of IFNγ$^+$ CD8$^+$ T cells in C57BL/6 mice infected f.p. with MCMV;

FIGS. 38A-D are a series of diagrams showing the percentage of IFNγ$^+$ CD8$^+$ T cells in C57BL/6 mice infected i.v. with MCMV;

FIGS. 39A and B are a series of diagrams indicating CFU of *Listeria monocytogenes* of vaccinated mice challenged with *Listeria monocytogenes*, while FIG. 39C shows the key;

FIGS. 40A-I and 40A-II are a series of diagrams showing the percentage of SIINFEKL- and M45-tetramer-specific CD8$^+$ T cells in MCMV infected C57BL/6 mice, while FIG. 40A-III shows the key;

FIG. 40 B is a diagram indicating the viral load in lungs of MCMV infected C57BL/6 mice;

FIG. 41 A is a survivorship curve indicating survival of C57BL/6 mice infected with MCMV and challenged with PR8 virus as a function of time;

FIG. 41 B is a weight loss curve indicating the weight loss of C57BL/6 mice infected with MCMV and challenged with PR8 virus as a function of time; and FIG. 42 is a diagram showing the percentage of IFNγ$^+$ CD8$^+$ T cells in MCMV infected BALB/c mice.

EXAMPLES

Example 1: Materials and Methods

General Laboratory Reagents and Equipment

Materials and reagents which used in the present application are listed in Table 1.

The laboratory equipment used in the present application is listed in Table 2.

TABLE 1

Materials and reagents.

| REAGENTS | DISTRUBUTOR NAME |
| --- | --- |
| αB220 clone PA3-6B2 | eBioscience |
| αCD3 clone SP7 | Abcam |
| αCD3 clone 145-2C11 | eBioscience |
| αCD8 clone 53-6.7 | eBioscience |
| αCD11c clone N418 | eBioscience |

TABLE 1-continued

Materials and reagents.

| REAGENTS | DISTRUBUTOR NAME |
|---|---|
| αCD11b clone M1/70 | eBioscience |
| αCD27clone LG.7F9 | eBioscience |
| αCD44 clone IM7 | eBioscience |
| αCD62L clone MEL-14 | eBioscience |
| αCD69 clone H1.2F3 | eBioscience |
| αCD127 clone A7R34 | eBioscience |
| αIFNg cloneXMG1.2 | eBioscience |
| αKLRGclone 1 2F1 | eBioscience |
| αMHCII clone M5/114.15.2 | eBioscience |
| αNKp46 clone 29A1.4 | eBioscience |
| αPD-1 clone J43 | eBioscience |
| αTNFa clone MP6-XT22 | eBioscience |
| Acetic acid (glacial) | BDH |
| AEC staining kit | Sigma-Aldrich Co. |
| Agarose | Carl Roth |
| Amminium chloride | Kemika |
| Ampicillin | EMD Chemicals Inc. |
| Arabinose | Carl Roth |
| Aquatex | Merck |
| 2-mercaptoethanol | Invitrogen - Gibco Cell Culture Systems |
| Bacto Agar | Carl Roth |
| Biotin blocking system | Dako |
| Brain heart infusion (BHI) broth | Difco Laboratories |
| Boric acid | Carl Roth |
| Brefeldin A | eBioscience |
| Bovine serum albumine (BSA) | Carl Roth |
| Chloramphenicol | EMD Chemicals Inc. |
| Chloroform | EMD Chemicals Inc |
| Defibrinated sheep blood | Biognost d.o.o. |
| DMEM (Dulbecco's Modified Eagle Medium) | Pan Biotech GmbH |
| DMSO | Sigma-Aldrich Co. |
| dNTPs | Hoffmann-La Roche Ltd |
| EDTA | Carl Roth |
| Eosin | Thermo Scientific |
| Ethanol | T.T.T. d.o.o. |
| Ethidium bromide | BDH |
| Foetal Bovine Serum | Pan Biotech GmbH |
| Gel loading buffer 10X Blue Juice | Invitrogen |
| Glucose | Carl Roth |
| Glycerol | EMD Chemicals Inc. |
| Hematoxillin | Thermo Scientific |
| Hydrocloric acid, 37% | Carlo Erba Reagents |
| Isoamyl alcohol | BDH |
| Isopropanol | EMD Chemicals Inc. |
| Kanamycin | EMD Chemicals Inc. |
| L-Glutamin | Invitrogen - Gibco Cell Culture Systems |
| MEM 10x | Invitrogen - Gibco Cell Culture Systems |
| Methanol | T.T.T. d.o.o. |
| Methylcellulose | Sigma-Aldrich Co. |
| mi 100 bp DNA marker GO Ladder | Metabion |
| mi 1k bp DNA marker GO Ladder | Metabion |
| Nutrient agar with NaCl | Biolife |
| Paraformaldehyde | Sigma-Aldrich Co. |
| Penicillin/Streptomycin | Pan Biotech GmbH |
| Phenol | EMD Chemicals Inc. |
| PBS-Buffer Dulbecco (Phosphate Buffered Saline) | Pan Biotech GmbH |
| Potassium acetate | Carl Roth |
| Potassium hydrogen carbonate | Kemika |
| QIAquick PCR purification kit | Qiagen Inc |
| QIAplasmid MIDI kit | Qiagen Inc |
| Restriction enzymes | New England Biolabs, Inc. |
| RPMI | Pan Biotech GmbH |
| Saponin, from *quillaja* bark | Sigma-Aldrich Co. |
| Sodium azide | Sigma-Aldrich Co. |
| Sodium chloride | Kemika |
| Sodium dihydrogen phosphate 12-hydrate | Kemika |
| Sodium dodecyl sulfate | BDH |
| Sodium hydroxide | Kemika |
| Streptavidin | eBioscience |
| Sucrose | Carl Roth |
| SuperFect Transfection Reagent | Qiagen Inc. |

TABLE 1-continued

Materials and reagents.

| REAGENTS | DISTRUBUTOR NAME |
|---|---|
| Tris base | Carl Roth |
| Trypan Blue Stain | Invitrogen |
| Trypsin-EDTA 10X | Invitrogen - Gibco Cell Culture Systems |
| Xylene | T.T.T.d.o.o. |

TABLE 2

Laboratory equipment.

| LABORATORY EQUIPMENT | DISTRIBUTOR NAME |
|---|---|
| BD Facs Aria Cell Sorter | BD Biosciences |
| Biofuge 13 microcentrifuge | Thermo Electron Corporation - Heraeus |
| Bottle Top filters | TPP Techno Plastic Products |
| Cell culture dish | Orange Scientific |
| Centrifuge C412 | Jouan |
| Centrifuge 5417R | Eppendorf |
| Centrifuge tubes | Beckman |
| CO2 Incubator 3326 | Heraeus |
| DNA engine Peltier thermal cycler | Bio-Rad Laboratories Ltd. |
| Electroporation cuvettes | Gene Pulser, BIORAD |
| Eppendorf Thermomixer | Eppendorf |
| Gene pulser II electroporator | Bio-Rad Laboratories Ltd. |
| Horizontal Gel Electrophoresis System | Owl Separation Systems |
| Incubator B6 | Heraeus |
| JA-10 rotor | Beckman Coulter Canada, Inc. |
| J2-MI highspeed centrifuge | Beckman Coulter Canada, Inc. |
| Microscope slides | Carl Roth |
| Microscope Olympus CK2 | Olympus |
| Microscope Olympus BX51 | Olympus |
| Pipettes | Gilson |
| Syringe filters | TPP Techno Plastic Products |
| Thermo Biomate 3 spectrophotometer | Thermo Electron Corporation |
| Transilluminator UV | HVD Life Sciences |
| Water bath | Kottlermann Labortechnik |

2.4G2 supernatant (Fc block), aCD8, aCD4 and aNKG2D antibodies were produced at the Center for Proteomics, Faculty of Medicine, University of Rijeka.

Peptides IE1/m123 ($_{168}$YPHFMPTNL$_{176}$; SEQ. ID. NO: 1), also known as a pp89 derived peptide, m164 ($_{167}$AGP-PRYSRI$_{175}$; SEQ. ID. NO: 2)-peptide [and $_{91}$GYKDGNEYI$_{99}$ (SEQ. ID. NO: 3) were synthesized by JPT Peptide Technologies, Germany. Tetramers were provided by NIH Tetramer Facility.

Buffers and Solutions 0.1M Citrate Buffer pH 5.5

Solution A: 21.01 g 0.1M citric acid in 1 L of distilled water.

Solution B: 35.81 g 0.1M Na2HPO4x12H20 in 1 L of distilled water.

Solutions A and were mixed in 1:1 ratio and titrated with citric acid or disodium hydrogen phosphate solution for pH adjustment.

DNA Isolation Buffers:

Buffer I: 50 mM glucose; 10 mM EDTA; 25 mM TRIS pH 8.0

Buffer II: 0.2 M NaOH; 1% SDS;

Buffer III: 3 M potassium acetate;

Buffer I was autoclaved before usage. Buffers I and III were used ice-cold. The same stock solution can be used for one month if stored at 4° C. Buffer II was always prepared fresh prior to mini preparation.

10×Lysing Solution
For 1 L:
89.9 g NH4Cl; 10 g KHCO3; 0,370 g EDTA
pH was adjusted to 7.3, solution was sterile filtered and stored at 2-8° C.
FACS Medium
1 L PBS; 0.1% NaN3; 1% BSA
4% PFA pH 7.2
For 1 L:
40.0 g paraformaldehyde; 5-10 g NaOH; PBS buffer
PBS was heated to 60° C. in water bath. Paraformaldehyde was added and solution was mixed 1-2 h on magnetic stirrer. pH was adjusted to 7.2, PBS was added up to 1 L and solution was filtered.
2% PFA pH 7.2
2% PFA pH 7.2 was prepared by 2× dilution of 4% PFA pH 7.2 in PBS.
TBS Buffer
200 mL 1M TrisHCl pH 7.5 (121.14 g Tri sin 1 L od distilled water, add concentrated HCl)
300 mL 1M NaCl (58.44 g in 1 L distilled water
add aqua up tp 2 L
Trypanblue:
4.0 g of trypanblue dye was dissolved in u 100 mL PBSa in dark bottle. After 5-7 days at +4° C. solution was filtered.
Trypsin/EDTA
Trypsin/EDTA solution diluted 1:10 with PBS was used. Final concentration: 0.5 g/l trypsin, 0.2 g/l EDTA, pH 7 0.4 to 7, 6.
Virus Suspension Buffer (VSB)/15% (w/v) Sucrose:
50 mM Tris-HCl; 12 mM KCl; 5 mM $Na_2EDTA$; 15% sucrose
Cell Culture Media
Foetal Bovine Serum (FCS)
FCS was before usage decomplemented by heating at 56° C. in water bath for 1 h.
3% DMEM (Dulbecco's Modified Eagle Medium)
500 mL DMEM; 3% (v/v) FCS; 100 U/ml Penicillin; 0.1 mg/ml Streptomycin
5% RPMI
500 mL RPMI; 3% (v/v) FCS; 500 mL 2-mercaptoethanol; 100 U/ml Penicillin; 0.1 mg/ml Streptomycin
10% RPMI
500 mL RPMI; 3% (v/v) FCS; 500 mL 2-mercaptoethanol; 100 U/ml Penicillin; 0.1 mg/ml Streptomycin
Methyl Cellulose
Methyl cellulose_was prepared according to manufacturer instructions.
In a glass bottle, 8.8 g methyl cellulose and 0.88 g NaHCO3 was added in 350 mL of distilled water, left for 10 days in the fridge to dissolve (with periodically shaking) and autoclaved afterwards at 121° C. for 20 mM 40 mL of 10× MEM, 2 mM L-glutamine, 100 U/ml penicillin, 0.1 mg/ml streptomycin, 5% (v/v) FCS was added while stirred on magnetic stirrer. It was stored at 4° C.
PBS-Buffer Dulbecco
(Phosphate Buffered Saline):
140 mM NaCl; 2.7 mM KCl; 6.5 mM Na2PO4; 1.5 mM KH2PO4, (pH 7.4)
Bacteria Culturing Media
Nutrient Agar
Nutrient agar with NaCl was prepared according to manufacturer instructions. 28 g of agar was dissolved in 1000 mL of distilled water and autoclaved for 15 min at 121° C. In cooled agar 50 mL of blood agar was added and plated in sterile Petri dish.

LB Media
10.0 g Bacto-Tryptone; 5.0 g Bacto-yeast extract; 10.0 g NaCl; ddH2O up to 1 L
LB Plates
10.0 g Bacto-Tryptone; 5.0 g Bacto-yeast extract; 10.0 g NaCl; 15.0 g Bacto-agar; ddH2O up to 1 L
LB media was autoclaved and cooled to 55° C. Appropriate antibiotics were added and media was plated in sterile bacteria culture plates.
Cells and Viruses.
Mouse embryonic fibroblasts, also referred to herein as MEFs, SVEC4-10 (ATTCC no. CRL-2181), NIH 3T3 (ATCC CRL-1658) and B12 fibroblasts (Del Val, M. et al., 1991, Cell 66(6):1145-53), were grown as described in Jonjic et al. (Jonjic, S. et al., 2008, Methods Mol Biol 415:127-149). MCMV, MW97.01, derived from a bacterial artificial chromosome, also referred to herein as BAC, has previously been shown to be biologically equivalent to the MCMV Smith strain (VR-194 [reaccessioned as VR-1399]; American Type Culture Collection) and is also referred to herein preferably as WT-MCMV. The recombinant strain Δm152-MCMV was generated as described by Wagner et al. (Wagner, M. et al., 1999, J Virol 73(8):7056-60; Wagner, M. et al., 2002, J Exp Med 196(6):805-16). Viruses were propagated on MEFs and concentrated by sucrose gradient ultracentrifugation as described by Jonic et al. (Jonjic, S. et al., 2008, supra). Salivary gland derived MCMV, also referred to herein preferably as SGV MCMV, was used as a third passage and prepared as described by Jonjic et al. (Jonjic, S. et al., 2008, supra).
Cell culture techniques were performed using a sterile cabinet, as well as sterile glass and plastic material. For the cultivation of cells $CO_2$-incubators providing the following conditions, namely 37° C., 5% $CO_2$ (v/v) and a saturated water vapor atmosphere (95% (v/v) relative humidity), were used.
For determining cell numbers, a cell suspension was mixed with trypan blue dye and transferred into a Neubauer-counting chamber. The cell number was determined according to the following formula I:

$$CN/ml = N/n \times V \times 10^4 \qquad (I),$$

wherein CN means cell number, N means number of counted cells, n means number of large squares counted, and V means dilution factor, and wherein the chamber factor is $10^4$.
Preparation of MEF
MEFs were isolated from 17 days old mouse embryos. The embryos were removed from a pregnant mouse and minced in a Petri dish using scissors. Tissue fragments were rinsed with PBS and transferred to a 500 mL Erlenmeyer flask. After addition of 30 mL trypsin solution the flask was stirred at 37° C. for 30 min Additional 30 mL of trypsin solution and 10 mL of PBS wad added and stirred at 37° C. for 30 min two more times. Cell suspension was filtered through gauze and centrifuged 10 min at 1200 rpm and room temperature. Cells were resuspended in warm 3% DMEM, plated and grown till they reached confluency, which approximately occurs within 2 to 3 days. After expansion of cells, aliquots thereof can be frozen and stored at −80° C. or used.
Production of Electrocompetent Bacterial Cells
5 mL of LB broth medium containing 17 μg/mL chloramphenicol was inoculated with the BAC containing bacteria (*E. coli* DH10B) and incubated overnight at 37° C., with minimum shaking of approximately 200 rpm. 4 mL of the resulting overnight culture were transferred into two 2 mL microcentrifuge tubes and cells were pelleted by centrifugation at 16000 g at 2° C. for 30 seconds.

To obtain highly electrocompetent cells, the procedure was performed on ice with prechilled solutions and microcentrifuge tubes. The Pellet resulting from the centrifugation step was resuspended in 1 mL of ice-cold sterile ddH2O by gentle pipetting. Cells were centrifuged at 16000 g at 2° C. for 30 seconds and the resulting pellet was resuspended in 1 mL of ice-cold sterile ddH2O. Cells were centrifuged at 16000 g at 2° C. for 30 seconds and the resulting pellet pellet was resuspended in 500 µL of ice-cold sterile 10% glycerol (v/v). Cells were pooled in one microcentrifuge tube and centrifugation was carried at 16000 g for 60 seconds at 2° C. The resulting supernatant was discarded using a pipette and the pellet containing the bacterial cells was resuspended in 100 µL of ice-cold sterile 10% glycerol (v/v). Aliquots were snap-frozen in liquid nitrogen. Cells were stored as 50 µL aliquotes at −80° C.

Electrotransformation

*E. coli* DH10B cells were electroporated with the respective MCMV BAC-plasmid to introduce the plasmid pKD46, which encodes the recombination enzymes, and to excise kanamycin cassette from the MCMV BAC-genome by the electroporation of pCP20 (Borst E M et al., Curr Protoc Immunol. 2007 May; Chapter 10:Unit 10.32).

An aliquot of electrocompetent bacteria was thawed on ice and 5 ng of plasmids and approximately 300 ng of PCR product was added. Electroporation was performed in precooled electroporation cuvettes at 2.5 kV, 200 S2 and 25 µF. Subsequent to the electroporation step, 500 µl LB-medium was added to the bacteria and the such obtained culture was incubated for 1 h at 300 rpm in a thermo-shaker at 30° C. after electroporation with pCP20, or 37° C. after electroporation with pKD46 or PCR product, respectively. After incubation, bacterial cells were plated on LB agar plates containing appropriate antibiotics, according to selection marker present in the plasmids or PCR products and incubated at 30° C. over night.

Induction of Expression of Red Genes from pKD46

After electroporation of pKD46 plasmid into bacterial cells containing the respective MCMV-BAC, a single colony was inoculated in 5 mL of LB medium containing 17 µg/mL chloramphenicol and 50 µg/mL ampicillin and such obtained culture was incubated at 30° C. and 200 rpm overnight. Such obtained overnight culture was than diluted 1:40 into 100 mL of LB medium containing 17 µg/mL chloramphenicol and 50 µg/mL ampicillin and incubated at 30° C. and 200 rpm for 3 h, or until $OD_{600\ nm}$ reached 0.5-0.6. Expression of recombination enzymes was induced by adding 1 mL of freshly prepared 10% arabinose solution (w/v) (final concentration 0.1%) and incubation for 1 h at 30° C. and 200 rpm. Cells were then made electrocompetent as described herein.

Isolation of Viral DNA from Viral Particles

To isolate DNA from MCMV particles, the supernatant of infected mouse embryonic fibroblasts was used. MEFs were grown in 3% DMEM in 10-cm cell culture dish to 90% confluence and were infected with the supernatants from transfected cells at multiplicity of infection (MOI) of 0.1. Incubation was carried at 37° C. and 5% $CO_2$ until complete cytopathic effect was observed, usually 5 to 6 days post infection. Supernatants were harvested and virions released in the supernatants were pelleted by ultracentrifugation for 1 h at 100 000 g at 4° C. Pellets were re-suspended in 500 µL of 50 mM TRIS-HCl pH 8.0/1 mM $MgCl_2$/100 µg/mL BSA, 100 U of Benzonase was added and incubated for 1 h. To inactivate Benzonase, 20 µL of 0.5 M EDTA was added. Virions were lysed by addition of 500 µL of 1% SDS. Capsid proteins were digested by 20 µL of proteinase K (500 ng/mL). Following 3 h of incubation at 56° C., the viral DNA was purified by phenol/chloroform extraction. One volume of phenol/chloroform was added to sample containing viral DNA and centrifugation for 5 minutes at 16000 g was performed. The resulting upper aqueous phase containing viral DNA was transferred to a new tube using pipettes with pipette tips with cut-off ends. To assure purity of viral DNA, 1 µL of glycogen solution (35 µg/µL) and ⅒ volume of 3 M sodium acetate pH 5.2 was added. DNA was precipitated with 0.7 volume of isopropanol. DNA was pelleted with centrifugation (30 minutes, 16000 g, 4° C.). Supernatant was discarded and pellet washed in 1 mL of 70% ethanol. Pellet was than air-dried and dissolved in 100 µL buffer for 2 h at 37° C. Viral DNA was analyzed by restriction analysis.

Long mini-Preparation of BAC::MCMV DNA 10 mL of LB medium with appropriate antibiotic was inoculated with a single bacterial colony. For verification of right clone constructs, for every mutant 10 positive clones were analyzed. Bacterial cultures were grown for 18 h at 37° C. at 200 rpm. 500 µL of overnight culture was stored at 4° C. for potential large scale preparation (midi-preparation). The rest of the culture was centrifuged at 4000 rpm at 4° C. for 10 minutes. Pellet was re-suspended in 200 µl of ice-cold buffer I. The alkaline lysis was accomplished by adding 300 µl of buffer II. After addition of buffer II sample was mixed gently by inverting the tube and then was incubated for 5 min at room temperature. After addition of 300 µl ice-cold buffer III, followed by incubation for 10 min on ice were SDS, chromosomal DNA and protein components precipitated. The precipitated components were in the lower phase after centrifugation at 13200 rpm (16,000×g) and 4° C. for 5 minutes. Supernatant containing DNA was transferred into a new tube and DNA was precipitated with 0.7 volume of isopropanol. Sample was centrifuged at 13200 rpm (16,000× g) and 4° C. for 30 minutes. Pellet was washed with 800 µL of 70% ethanol, air-dried and dissolved in the 100 µL of TE buffer that contained RNase (50 ng/ml) for 30 minutes at 37° C. at minimum shaking (300 rpm) in a thermomixer. The DNA was analyzed by restriction analysis and stored at 4° C.

Construction of Recombinant Plasmids and Recombinant Viruses.

To generate MCMV expressing RAE-1γ, i.e. RAE-1γMCMV, an ORF encoding FLAG-tagged RAE-1γ was first cloned into the plasmid pGL3 (Invitrogen) together with a kanamycin resistance gene (kanR), which was inserted further downstream. Then, the RAE-1γ expression cassette and kanR were PCR amplified using the primers 5'-gcaccgacgatctgacattgtccagtgtgccggtcgcacgaacatccctagttat-taatagtaatc-3' (SEQ. ID. NO: 4) and 5'-tgtcaccgctc-cacgtttcaccgtcggtctcccgatcgctagcctgtacacaggaacacttaacgg ctga-3' (SEQ. ID. NO: 5), which contained 50 nucleotides at their 5'-ends homologous to the intended integration site in the BAC-cloned MCMV genome. The PCR fragment was integrated into the BAC by redα, -β, -γ mediated recombination as described by. Borst et al, 2007 (Borst E M et al., Curr Protoc Immunol. 2007 May; Chapter 10:Unit 10.32), thereby in accordance with homology chosen for the intended integration site replacing the m152 ORF. The kanR cassette was subsequently excised with FLP recombinase (Borst et al., 2007, supra). The resulting MCMV BAC was characterized by restriction analysis and virus RAE-1γMCMV was reconstituted by transfection of the BAC DNA into MEF.

Construction of MCMVList and RAE-1γMCMVList

The Dd-restricted antigenic m164 peptide $_{167}$AGP-PRYSRI$_{175}$ (SEQ.ID.NO:2) of the genome of MCMV strain RAE-1γMCMV and of WT-MCMV was replaced with the Kd-restricted listeriolysin O (LLO)-derived peptide $_{91}$GYKDGNEYI$_{99}$, also referred to herein preferably as List (SEQ.ID.NO:3), by using the shuttle plasmid pST76K-m164_List as described by Lemmermann et al. (Lemmermann et al., 2010, J Virol. 84(3):1221-36).

The primers used were List swap fw_1:

(SEQ.ID.NO: 6)
5'-gactactgtcggacgtggggcgctga**aatatattcatttccat
ctttgtaacc**AGGATGACGACGATAAGTAGGG-3', List swap fw_2:
(SEQ.ID.NO: 7)
5'-gatcgagccggtggtaccggacgcggcggagccgttcggaaagg
actactgtcggacgtggggcgctgac-3', List swap rv_1:
(SEQ.ID.NO: 8)
5'-Ggttacaaagatggaaatgaatatattgtcagcgcccacgtcc
gacagtagtcCAACCAATTAACCAATTCTGATTAG-3'
and List swap rv_2:
(SEQ.ID.NO: 9)
5'-atggcctggttgttgacggcccagaagatgcgcgagtaccgagg
agggcccgcggttacaaagatggaaatgaatatatt-3', wherein lower case letters represent homology region to m164 ORF in the MCMV genome, lowercase letters in bold and underlined represent the region coding for peptide $_{91}$GYKDGNEYI$_{99}$—List (SEQ. ID. NO: 3) and capital bold letters represent homology to Tischer kanamycin resistance cassette (Tischer, B. K. et al, 2006, supra). PCR was performed with the following cycler conditions:

An initial step for 5 min at 95° C. for activation of Phusion HighFidelity DNA polymerase (New England BioLabs) was followed by 30 cycles of 45 s at 94° C., 60 s at 65° C., and 60 s at 72° C.

Construction of the RAE-1γMCMVm164SIINFEKL-Strain.

The SIINFEKL (SEQ.ID.NO:10) coding DNA sequence was inserted into ORF m164 of the genome of RAE-1γMCMV, which replaced the DNA sequences for the immunodominant intrinsic m164 peptide 167-AGP-PRYSRI-175 (SEQ.ID.NO:2), by using the shuttle plasmid pST76K-m164_SIINFEKL (SEQ.ID.NO:10)-(Lemmermann et al., 2010, supra) and a recA-mediated recombination technique (Borst E. M. et al., 2007, supra) as described in Lemmermann et al. (Lemmermann et al., 2010, supra). Correct insertion was verified by restriction analysis using ApoI and sequencing.

Construction of SIINFEKL-Peptide Expressing Recombinant Viruses.

MCMV-SIINFEKL and RAE-1γMCMVSIINFEKL were constructed by orthotopic peptide swap on the WT-MCMV or RAE-1γMCMV backbone, respectively, as described previously (Lemmermann, N. A., K. Gergely, et al. (2010) "Immune evasion proteins of murine cytomegalovirus preferentially affect cell surface display of recently generated peptide presentation complexes." J Virol 84(3): 1221-36). Lemmermann et al., 2010, supra Construction of Recombinant Plasmids Containing HA Expression Cassette Plasmids m157 pGL3 HMIEP PR8-HA full Tischer kanamycin and m157 pGL3 HMIEP PR8-HA headless Tischer kanamycin were constructed to replace the m157 ORF in the wild type MCMV-BAC and in Δm152-RAE1γMCMV-BAC, respectively. PR8-HA was obtained by PCR from pUC18 containing PR8-HA (UniProt P03452) as a template DNA, provided by Peter Stäheli, The University Medical Center Freiburg, Germany. The primers were PR8HA fw: 5'-GCCGCCATGAAGGCAAACCTACTGG-3' (SEQ.ID.NO:11), PR8 V5 rv: 5'-CGTAGAATCGAGAC-CGAGGAGAGGGTTAGGGATAGGCTTACCGATGCAT-ATTCT GCACTGCAAAGATCC-3' (SEQ.ID.NO:12), wherein the introduced V5 tag is indicated in bold and PR8 SIINFEKL: 5'-TCACAGTTTTTCAAAGTTGAT-TATACTCGTAGAATCGAGACCGAGGAGAGGGTTA GG-3' (SEQ.ID.NO:13), wherein the introduced SIINFEKL tag is indicated in bold; for the amplification of the PR8 HA full form primers Headless fw: 5'-GGAGGCAACAC-GAAGTGTCAAACACC-3' (SEQ.ID.NO:14) and Headless rv: 5'-GCCACCACATAGTTTTCCGTTGTGGC-3' (SEQ.ID.NO: 15) were used for the amplification of PR8 HA headless.

PCR was Performed with the Following Cycler Conditions:

An initial step for 2 min at 98° C. for activation of HighFidelity Phusion DNA polymerase (New England BioLabs) was followed by 30 cycles of 10 s at 98° C., 10 s at 60° C., and 60 s at 72° C. PCR amplified HA full ORF was cloned into pGL3 plasmid (Invitrogen) together with a Tischer-modified kanamycin resistance gene, also referred to herein as kan$^R$ or kanR, which was inserted further downstream (see also FIG. 24). Restriction with BglII of plasmids m157 pGL3 HMIEP PR8-HA full Tischer kanamycin and m157 pGL3 HMIEP PR8-HA headless Tischer kanamycin resulted in obtaining the 4.8 kbps long insert needed for subsequent mutagenesis, which is m157 flanked PR8-HA full or headless under control of HCMV immediate early promoter, also referred to herein as HMIEP, along with the selection marker—kanamycin cassette flanked by duplicated sequences and an adjoining I-SceI restriction site.

For the construction of recombinant PR8 hemaglutinin expressing mutants, both full and headless form, a two step markerless red recombination system as described by Tischer et al. (Tischer, B. K. et al, 2006, supra; Tischer, B. K. et al., Methods Mol Biol. 2010, 634:421-30) (see also FIG. 24) has been applied. Mutagenesis of full-length MCMV-BAC and Δm152-RAE1γ mCMV-BAC was performed in Escherichia coli strain DH10B, whereas excision of the selection marker was performed in Escherichia coli strain GS1783.

Recombinant viruses were confirmed by restriction analysis (BamHI and HindIII restriction for Δm157-PR8-HA full-MCMV-BAC and Δm157-PR8-HA-full-Δm152-RAE-1γMCMV-BAC, and NsiI restriction enzyme for Δm157-PR8-HA-headless-MCMV-BAC and Δm157-Δm157-PR8-HA headless-Δm152-RAE-1γMCMV-BAC)

In connection therewith it will be immediately acknowledged by a person skilled in the art that Δm157-PR8-HA full-MCMV is also referred to herein as MCMV-Δm157-HA and MCMV-HA.

Furthermore, Δm157-PR8-HA-full-Δm152-RAE-1γMCMV-BAC is also referred to herein as RAE-1γMCMV-HA or RAE-1γMCMV-Δm157-HA.

It will be understood that Δm157-PR8-HA-headless-MCMV is based on WT-MCMV, wherein influenza virus PR8 hemagglutinin (HA) headless form was inserted into m157.

It will also be understood that Δm157-Δm157-PR8-HA headless-Δm152-RAE-1γMCMV-BAC is based on RAE-1γMCMV, wherein influenza virus PR8 hemagglutinin (HA) headless form was inserted into m157 and is also referred to herein as Δm157-PR8-HA headless-Δm152-RAE-1γMCMV.

Generation of GAPINSATAM-Peptide Expressing Recombinant Viruses.

For the purpose of testing the vector capacity of Rae1γMCMV, a RAE-1γMCMV virus mutant has been constructed expressing *Mycobacterium tuberculosis* H-2Db immunodominat epitope GAPINSATAM (SEQ.ID.NO:16) "swapped" into the position of MCMV m164 immunodominant epitope of WT-MCMV-BAC and RAE-1γMCMV-BAC by orthotopic peptide swap as described in Lemmerman et al. (Lemmerman et al., 2010, supra). A schematic illustration of the cloning process is shown in FIG. 26.

(i) Design of Insert Containing Peptide Swap.

Primers were constructed in a way to replace the $D^d$-restricted antigenic m164 peptide 167-AGPPRYSRI-175 (SEQ.ID.NO:2) with the $D^b$-restricted Mtb32a (pepA) derived peptide 309-GAPINSATAM-318 (SEQ.ID.NO:16) (ref. UniProt O07175).

As primers m164 GAP fw:

(SEQ.ID.NO: 17)
5'-cgcccgctgccacgatggcctggttgttgacggcccagaa<u>catg</u>
<u>gcggtggccgagttgat</u>cggggcgccg*tcagcgcccca*GCCAGTGTT
ACAACCAATTAACC-3', wherein lower case letters represent homology region to m164 ORF in MCMV genome, underlined letters in bold represent homology regions between primers, italic letters are I-SceI restriction site sequence and capital letters represent homology to Tischer kanamycin cassette; and m164 GAP rv:

(SEQ.ID.NO: 18)
5'-gccgttcggaaaggactactgtcggacg*tggggcgctgac*<u>gg</u>
<u>cgcccgatcaactcggccaccgccatg</u>TAGGGATAACAGGGTAATC
GAT-3', wherein lower case letters represent homology region to m164 ORF in MCMV genome, underlined letters in bold represent homology regions between primers, italic letters are I-SceI restriction site sequence and capital letters represent homology to Tischer kanamycin cassette, were used. PCR was performed with the following cycler conditions:

An initial step for 2 min at 98° C. for activation of HighFidelity Phusion DNA polymerase (New England BioLabs) was followed by 30 cycles of 10 s at 98° C., 10 s at 60° C., and 60 s at 72° C. As DNA template plasmid pEP-SaphAI provided by K. Tischer was used.

For the construction of recombinant mutants a two step markerless red recombination system as described by Tischer et al. (Tischer, B. K. et al, 2010, supra) (see FIG. 24) has been applied. Mutagenesis of full-length MCMV-BAC and Δm152-RAE1γ mCMV-BAC was performed in *Escherichia coli* strain DH10B, whereas excision of the selection marker was performed in *Escherichia coli* strain GS1783.

Construction of the ULBP2 Expressing HCMV Recombinant

The ULBP2 ORF was amplified using primers (SEQ.ID.NO: 19)
5'-<u>GTCGGTACCGTCGCAGTCTTCGGTCTGACCACCGTAGAACGCAG
AGCT</u>ccaccATGGCAGCAGCCgccGCTACC-3'', wherein the underlined letters indicate homology to nt position 182904-nt position 182857 (lower strand) of the mouse cytomegalovirus sequence according to GenBank Accession No.: U68299.1; and 5'-cccGGATCCctctcc<u>TCAGATGCCAGGGAGGATGAAG</u>-3' (SEQ.ID.NO: 20), wherein the Stop codon is indicated in bold and underlined and wherein small and large letters comprise additional details, e.g. Koszak sequence; and an ULBP2 cDNA clone (Open Biosystems; Genbank accession number: BC034689), and was cloned via KpnI and BamHI restriction digest and ligation, between the MCMV major immediate-early promoter sequences and a Kanamycin resistance (KanR) cassette flanked by FRT sites. The whole insert comprising promoter MCMV MIE (nt 183088 to 182903 (lower strand) of Genbank accession entry: U68299.1) and KanR was amplified with primers 5'-GACACCGGGCTC-CATGCTGACGTAGGTACCGACTGGGGTCAAAAGC-CTttaaacggtact ttcccatagc-3'(SEQ.ID.NO: 21), wherein the capitalized letters are homologous to nucleotides 55134-55181 of the TB40E BAC (Genbank: EF999921.1) and 5'-CTTATAGCAGCGTGAACGTTGCACGTGGCCTTT-GCGGTTATCCGTTCAGgaacacttaac ggctga-3' (SEQ.ID.NO: 22), and inserted into the BAC-cloned genome of the HCMV strain TB40E (Genbank Accession Nr.: EF999921.1) (Sinzger C. et al., J Gen Virol. 2008 February; 89(Pt 2):359-68) by red-α, -β, -γ-mediated recombineering (Borst E. M. et al., 2007, supra) replacing the UL16 ORF. The KanR cassette was excised by FLP recombinase. Correct insertion was verified by restriction analysis and using BglII and NsiI and sequencing with primers 5'-GGCGATGCGGTATCGCGCACA-3' (SEQ.ID.NO: 23) and 5'-GACACCTGTTCGTCCAGAATC-3 (SEQ.ID.NO: 24).

Generation of a HCMV Vaccine Vector Expressing ULBP2 and the Influenza Hemagglutinin Protein The open reading frame (ORF) for influenza hemagglutinin (HA), according to Genbank accession number V01088, influenza A/PR/8 strain, is PCR amplified and cloned into plasmid vector (pUC19). Next to the HA ORF a PCR fragment is cloned carrying (i) a recognition site for the meganuclease I-SceI (ii) a sequence encoding kanamycin resistance, (iii) 50 nt homologous to the end of the HA coding sequences and (vi) 20 nt homologous to sequences immediately downstream of the 3'-end of the UL11 ORF of the CMV strain TB40E (5'-TATATAGACTGAAGCG-GAGT-3' (SEQ.ID.NO:39); indicated as light grey colored rectangle in FIG. 31).

A PCR fragment is generated that includes the influenza HA ORF, the kanR cassette with the I-SceI site, the 50 nt homologous to the end of the HA ORF, using the above described plasmid as template and primers that provide 50 nt of DNA sequences homologous to the sequences immediately upstream and downstream of the UL11 ORF in the TB40E genome, respectively. The sequence of the forward and reverse primers is:

UL11-HA-fw:
(SEQ.ID.NO: 40)
5'-CAGCTTTTGAGTCTAGACAGGGGAACAGCCTTCCCTTGTAAGAC
AGAATGaaggcaaacctactggtcc-3';
and UL11-HA-rev:
(SEQ.ID.NO: 41)
5'-GAGTCGTTTCCGAGCGACTCGAGATGCACTCCGCTTCAGTCTAT
ATATCA-3'

Recombination between the BAC TB40E-ULBP2 carrying the TB40E genome with the replacement of the UL16 ORF by a ULBP2 expression cassette (as described above) and the PCR fragment is performed in *E. coli* strain GS1783 (Tischer, B. K. et al., Methods Mol Biol. 2010, 634:421-30) expressing the red α, -β, -γ genes as described in Borst et al., (Borst E M et al., Curr Protoc Immunol., 2007 May; Chapter 10:Unit 10.32; Tischer, B. K. et al., 2010, supra). Bacterial clones carrying a BAC with a replacement of the US11 ORF with the HA-kanR cassette are selected on agar plates containing chloramphenicol (17 µg/ml) and kanamycin (30 µg/ml). Recombinant BACs are characterized by restriction analysis and sequencing as described in Borst et al. (Borst E M et al., 2007, supra). The kanR cassette is excised by en passant mutagenesis via cleavage of the BAC DNA with the I-SceI nuclease and red α, -β, -γ-mediated recombination in the E. coli strain GS1783 as described in Tischer, B. K. et al., (Tischer, B. K. et al., 2010, supra).

More particularly, FIG. 31 schematically shows the construction of recombinant HCMV expressing ULBP2 and influenza HA generated as described herein.

Infectious virus is generated by electroporation of human fibroblasts with the resulting BAC DNA as described in Borst et al. (Borst E M et al., 2007, supra).

Expression of the HA protein is tested in lysates of infected cells by immunoblotting using an HA-specific antibody.

Reconstitution of BAC-Derived Recombinant Viruses.

The reconstitution of recombinant viruses by transfection of BAC plasmid DNA, as well as the routine elimination of BAC vector sequences, was performed in C57BL/6 primary mouse embryo fibroblasts (MEF) for MCMV mutants and in human foreskin fibroblasts (HFF) for HCMV mutants and verified by PCR.

For the reconstitution of MCMV mutants, recombinant constructs were transfected using SuperFect reagent into 70% confluent MEFs prepared in six-well plate. Transfection solution was prepared according to SuperFect QIAGEN protocol. 7.5 µL of SuperFect was added to 150 µL total volume of recombinant construct mixed with DMEM. 10, 15 or 20 µl of purified BAC::DNA recombinant construct were used. Transfection solution was incubated for 10 min at room temperature to allow DNA complexes formation. During that period MEF were washed with 2 ml of PBS and overlaid with 500 µL of 3% DMEM. After 10 minutes, 500 µL of 3% DMEM was added to transfection solution, mixed well and drop-by-drop applied to cell culture. After 2-3 h of incubation at 37° C., medium was removed and 4 mL of fresh 3% DMEM was added. 5-7 days post transfection plaques appeared and supernatants were collected and used for second passage or stored at −70° C. till usage.

Verified BAC-vector-free virus clones were used to prepare high-titer stocks of sucrose gradient-purified viruses TB40_dUL16/ULBP2, MCMV-m164_List, also referred to herein as MCMVList and RAE1γ MCMV-m164_List, also referred to herein as RAE-1γMCMVList, Δm157 HMIEP PR8 HA full mCMV, Δm157 HMIEP PR8 HA full Δm152 RAE1γmCMV, Δm157 HMIEP PR8 HA headless mCMV or Δm157 HMIEP PR8 HA headless Δm152 RAE1γ mCMV.

MCMV Production

MEFs were prepared in a Petri dish and grown to 70-80% confluence. 3 mL of supernatant containing virus particles was added to cell culture. When production was done from virus stock, 0.01 PFU per cell was added in a volume of 6 mL 3% DMEM. After 3-4 h of incubation period at 37° C., 3% DMEM was added up to 30 mL. Cells were incubated at 37° C. for the time of maximum infection (about 5 days) when all the cells rounded and detached from the Petri dish, or could be removed by gently swirling the medium. After shaking off the cells, the mixture of cells and medium was transferred into 50 mL tubes. Cells were separated from the medium by centrifugation at 6400 g for 10 minutes. Supernatant was decanted into centrifuge tubes. The virus was pelleted by centrifugation at 26000 g for 90 minutes at 4° C. Supernatant was decanted, pellet resuspended in leftover medium and left at 4° C. overnight. Virus was laid over the 15% sterile sucrose/VSB cushion centrifuged 99 minutes at 4° C. and 52000 g. Supernatant was aspirated; pellet was overlaid with 300 mL of PBS and left over night at 4° C. The pellet was resuspended, aliquoted and stored at −70° C.

Virus Growth Kinetics

MEFs were grown in 24-well plates and infected with 0.1 PFU/cell of the virus. Virus was prepared in cold 3% DMEM. Media was removed from the cells and 200 mL of the virus suspension/well was added. After incubation period of 30 min at 37° C. 800 mL of warm 3% DMEM was added in each well. After 1 h at 37° C. supernatant was taken for day 0, and changed with 1 mL/well of warm 3% DMEM for all other time points. Supernatants were collected every day for seven days at the same time, centrifuged 4000 rpm/4 min to remove cells and cell debris and frozen at −20° C. till titration.

Preparation of Listeria monocytogenes Inoculum

The hemolytic EGD strain (serovar1/2a) of L. monocytogenes and the recombinant L. monocytogenes strain stably expressing chicken ovalbumin (aa134-387) (Zehn, D., et al. 2009, Nature 458(7235): 211-4), also referred to herein as OVA-Listeria, were grown in brain heart infusion (BHI) broth at 37° C. for 24 hours. The culture broth was centrifuged at 3000×g for 5 minutes, and the pelleted bacteria were resuspended in phosphate buffered saline (PBS), pH 7.4. The optical density of the bacterial suspension was estimated using a spectrophotometer at 600 nm, and the numbers of CFU of L. monocytogenes were extrapolated from a standard growth curve. The actual number of CFU in the inoculum was verified by plating on blood agar.

The actual number of CFU of OVA-Listeria in the inoculum was verified by plating on blood agar and BHI agar. Bacteria were grown in BHI broth to get enough material for inoculum. Blood agar was used for plating to count the number in inoculum in addition to estimation with sprectrophotometer.

Animals, Infection and Lymphocyte Subsets Depletion.

BALB/c (H-2$^d$), C57BL/6 (H-2$^b$), interferon (IFN) type I receptor$^{-/-}$ mice on 129 background (IFN-α/βR$^{-/-}$) and BALB/c (H-2$^d$) µMT/µMT$^{-/-}$ mice (Hasan, M. et al., 2002, Eur J Immunol 32(12):3463-71) were bred under specific-pathogen-free conditions at the Central Animal Facility of the Faculty of Medicine, University of Rijeka. Animals handling, experimental procedures and administration of anesthesia were performed in accordance with the guidelines contained in the International Guiding Principles for Biomedical Research Involving Animals. The Ethics Committee at the University of Rijeka approved all animal experiments described within this report.

Unless otherwise indicated, mice were f.p. injected with 2×10$^5$ PFU of tissue culture-derived MCMV at the age of 6 to 8 weeks. Neonatal mice were i.p injected with 500 PFU of MCMV 6 hours postpartum.

Infections were performed using WT-MCMV (Smith strain) and recombinant viruses constructed using WT-MCMV or RAE-1γMCMV backbone.

L. monocytogenes was injected when the log growth phase was achieved in a volume of 200 or 500 µL of pyrogen-free saline intravenously.

For challenge experiments, Listeria monocytogenes EGD serovar 1/2a was used.

In vivo blocking of NKG2D, depletion of CD4$^+$ T cells, CD8$^+$ T cells and NK cells was performed by i.p. injection of monoclonal antibody (rat anti-mouse) to NKG2D (R&D Systems), CD4 (YTS 191.1), CD8 (YTS 169.4) and asialo-AGM1 (Wako Chemicals), respectively.

Determination of CFU in Mouse Organs

After dissection, organs (spleens and livers) were aseptically removed and homogenized in sterile PBS. After centrifugation for 5 min at 3000×g supernatants were decanted, pellets were resuspended in 5 mL of cold distilled water and incubated on ice for 15 min to release intracellular bacteria. Bacterial counts were obtained by plating serial ten-fold dilutions of each organ suspension on blood agar plates incubated at 37° C. for 24-48 h. Titres of *L. monocytogenes* were expressed as $\log_{10}$ of CFU per organ. In some experiments, small portions of the spleens and livers were taken for histological analysis.

To determine organ OVA-*Listeria* burden, spleens and livers were removed from infected mice 4 days p.i. and homogenized separately in PBS, following incubation in distilled water. Serial ten-fold dilutions of suspensions were plated onto blood-agar and CFUs were determined after 24-48 h incubation at 37° C. In some experiments, small portions of the spleens and livers were taken for histological analysis.

Determination of Virus Titers

To determine virus titer a standard plaque assay (Krmpotic, A. et al., 2005, J Exp Med 201(2):211-20) was performed. MEFs were prepared in 48-well cell culture plates and grown to 70% confluence. Virus was titrated in triplicates in $\log_{10}$ dilutions series (starting from $10^{-3}$ down to $10^{-10}$). After 1 h of incubation at 37° C., cells were layered with 500 µl of methylcellulose. Four days post infection virus plaques were counted and the PFU per mL was calculated according to formula:

Virus titer (PFU/ml)=number of plaques×$V$

V: dilution factor

To determine virus titer in mouse organs, the organs were dissected, transferred into 3% DMEM and frozen at −20° C. After ≥24 h organs were thawed slowly on ice and passed through the mesh. The mesh was rinsed with 2 mL of 3% DMEM and organ homogenates were serially diluted in factor-10 steps for the virus plaque assay. MEFs were plated in 48 well plates and grown close to confluence. The most of the cell culture medium was removed in a way that the cell monolayer remained covered with fluid. A 100 µl of suspension of appropriate dilution was added in duplicates. Plates were incubated for 30 min at 37° C. for virus adsorption and penetration and then centrifuged for another 30 min at 760 g and 20° C. for enhanced penetration.

After 30 min at 37° C. MEFs were covered with 0.2 ml of methylcellulose medium to prevent the formation of secondary plaques. Virus plaques were counted after 4 days of cultivation.

Detection limit of the assay was extended to 1 PFU per organ homogenate as described previously (Polic, B. et al., 1998, supra).

Real-Time PCR.

Genomic DNA was extracted from 10 mg mouse tissue or 300 µl blood using Wizard Genomic DNA Purification Kit (Promega), according to the instruction manual, and dissolved in 100 µl of DNA Rehydration Solution. Viral genome was quantified by real-time PCR using the Light-Cycler system (Roche) and the LightCycler Fast Start DNA MasterPlus SYBR Green I and analyzed by LightCycler data analysis software version 3.3.40. Primers ie4fwd (5'-TGACTTAAACTCCCCAGGCAA-3'; SEQ.ID.NO: 25) and ie4rev (5'-TAGGTGAGGCCATAGTGGCAG-3'; SEQ.ID.NO: 26), nucleotide positions: 6692-6672 and 6592-6612, respectively (GenBank accession no. L06816), were chosen to amplify a segment of exon 4 of the ie1 gene. A cellular gene was detected with primers glra1fwd (5'-TGCCTGTTCTTTGCAGTCTGT-3'; SEQ.ID.NO: 27) and glra1rev (5'-AGTCGAGTGAAGGGTAACGAGC-3'; SEQ.ID.NO: 28), nucleotide positions: 312-332 and 403-382, respectively (GenBank accession no. X75832). Specificity of PCR products was determined by melting curve analysis. Serial dilutions of pGEM-T Easy Vector (Promega) expressing partial MCMV ie1 gene and of DNA extracted from MEF were used as standards to determine the MCMV genome copy numbers and the number of cells, respectively. Tissues DNA samples from uninfected mice and multiple samples without template served as negative controls. The PCR amplification efficiencies (E) for the ie1 and glra1 standard curves as well as for both genes in a titration of sample DNA were calculated according to the formula $E=10^{-1/slope}$ (technical note no. LC11/2000; Roche) and differed by $\Delta F<0.05$ in the reported experiments. Likewise, for each of the two genes tested, amplification efficacies differed by $\Delta F <0.05$ between a titration of sample DNA and the respective standard curve. To determine sensitivity of QPCR detection of MCMV, genomic DNA samples was spiked with serial dilutions of target plasmid pGEM-T Easy Vector containing ie1 genomic sequence as template in the PCR as previously described (Wheat, R. L., et al. 2003, J Virol Methods 112(1-2):107-13). Detection limit was found to be 6 copies of MCMV per $10^6$ cells.

Isolation of Splenocytes

Spleen was cut with scissors into small pieces in 5 cm Petri dish and put on the cell strainer (70 or 100 mm) above 50 mL blue-cap. It was pressed with the pestle into blue-cap while washing with 10 mL 5% RPMI. Suspension was centrifuged 5 min at 1500 rpm (centrifuge C412, Jouan). Supernatant was decanted and 5 mL of 1× lysing buffer was added. Pellet was resuspended and incubated for 5 min on ice. Lysis was stopped by addition of 10 ml 5% RPMI. Suspension was centrifuged 5 min at 1500 rpm. Supernatant was poured out and the precipitate was resuspended in 10 mL 10% RPMI. Suspension was strained through 70 or 100 mm cell strainer and splenocytes were counted. Cell suspension was adjusted to the final number of $10\times10^6$ splenocytes/mL in 10% RPMI.

Interferon-γ Test

100 µl ($1\times10^6$ cells) of splenocytes suspension was put on 96 well U-bottom and each sample was performed in duplicates. Peptides were added in concentration of 1 µg/sample and 100 µl of 10% RPMI was used as negative control. Samples were incubated at 37° C. for 1 h. Brefeldin A was added in 1:1000 ratio in volume of 10 µl per sample. Samples were incubated at 37° C. for 4 h.

Adoptive Transfer of MCMV-Specific CD8$^+$ T Cells.

Adoptive transfer experiment was performed as described previously (Holtappels, R. et al., 2008, J Infect Dis 197(4):622-9). In short, donors of CD8$^+$ T cells were naïve or latently infected µMT/µMT$^{-/-}$ (B cell-deficient) mice, MCMV infected 6 months before the adoptive transfer. Splenocytes from three donors per group were pooled and number of MCMV-specific CD8$^+$ T cells was assessed by combined staining with pp98, m164, m83, m84 and m04 MHC class I tetramers. Unfractionated splenocytes containing $10^5$ naïve CD8$^+$ T cells or graded numbers of MCMV-specific CD8$^+$ T cells were i.v. transferred to recipient BALB/c mice immunocompromised with a single dose of 6 Gy γ-irradiation 12 h prior to adoptive transfer. Recipients were f.p. injected with $10^5$ PFU of WT-MCMV 6 h after the adoptive transfer. Viral titers in the spleen were determined 12 days p.i. by plaque assay.

Flow Cytometry and Intracellular Staining.

After 4 h incubation, samples from IFNγ test were pooled to get $2\times10^6$ of cells per sample. Plates were centrifuged at 1500 rpm for 5 min. Cells were washed with 200 µl of FACS medium and centrifuged at 1500 rpm for 5 min Supernatant was decanted, Fc block was added in volume of 25 µl and incubated 15 min on ice. αCD8 antibody was added in volume of 25 µl and incubated 20 min on ice. 150 µl FACS medium as added and centrifuged 5 min at 1500 rpm. Supernatant was decanted and 150 µl of PBS was added. Plates were centrifuged 5 min at 4000 rpm. Supernatant was discarded and 100 µl of 2% PFA in PBS was added. Plates were incubated 25 min at room temperature and washed two times in 100 µl PBS afterwards. Intracellular antibody was diluted in 0.1% saponin in FACS medium and incubated for 20 min at room temperature. Cells were washed 2× in 150 µl of 0.05% saponin in PBS and resuspended in 200 µl of FACS medium.

Cells were put on 96 well and washed with 200 µl of FACS medium and centrifuged at 1500 rpm for 5 min Supernatant was decanted, Fc block was added in volume of 25 µl and incubated 15 min on ice. Primary antibody was added in volume of 25 µl and incubated 20 min on ice. 150 µl FACS medium as added and centrifuged 5 min at 1500 rpm. Supernatant was decanted and secondary antibody was added in volume of 50 µl and incubated for 20 min on ice. Cells were washed in FACS medium and centrifuged at 1500 rpm for 5 min Supernatant was discarded and cells were resuspended in 200 µl of FACS medium.

The $H2^b$-restricted SIINFEKL pentamer was purchased from Proimmune. SIINFEKL peptides were synthesized to a purity of >95% by Jerini Peptide Technologies. Custom MCMV-specific $H-2^d$ and $H-2^b$ class I restricted antigenic peptide synthesis to a purity of >80% was performed by Jerini Peptide Technologies. Tetramers were synthesized by the NIH tetramer core facility (www.niaid.nih.gov/reposit/tetramer/overview.html). Various fluorescently conjugated antibodies were used (CD8α (53-6.7), CD27 (LG.7F9), CD62L (MEL-14), CD122 (5H4), CD127 (A7R34), KLRG-1 (2F1), NKG2A/C/E (20D5), NKG2D (M1-6), CTLA-4 (UC10-4B9), PD-1 (J43), IL-2 (JES6-SH4), IFN-γ (XMG1.2), TNF-α (MP6-XT22), CD3β (H57-597), CD11c (N418), NKp46 (29A1.4), PDCA-1 (eBio927), RAE-1γ (CX1), RAE-1αβδε (199205), MULT-1 (237104), H60 (205326). An in vitro assay to detect cytokine production and degranulation was performed as previously described (Cicin-Sain, L. et al., 2007, supra). In short, splenocytes were resuspended in complete RPMI 1640 supplemented with 10% FCS and stimulated with 1 µg of peptides IE1/m123 ($_{168}$YPHFMPTNL$^{176}$; SEQ.ID.NO: 1), also known as a pp89 derived, m164 ($_{167}$AGPPRYSRI$_{175}$; SEQ.ID.NO:2), IE3 ($^{416}$RALEYKNL$^{423}$; SEQ.ID.NO:29), m139 ($^{419}$TVYGFCLL$^{426}$; SEQ.ID.NO:30), M45 ($^{985}$HGIRNASFI$^{993}$; SEQ.ID.NO:31) or M38 ($^{316}$SSPPMFRV$^{323}$; SEQ.ID.NO:32) for 6 h at 37° C. with brefeldin A (eBioscience) added for the last 4 hours of stimulation. For degranulation assay, CD107a monoclonal antibody (D4B) and monensin (eBioscience) were added to the cultured cells during peptide stimulation. For DC population analysis, splenocytes were digested by collagenase D (Roche) as described previously (Robbins, S. H. et al., 2007, supra). All samples were acquired by FACSAria (BD) and analyzed with FlowJo software (Tree Star).

In Vivo Cytotoxicity Assay.

Splenocytes were isolated from the spleens of uninfected BALB/c mice and loaded with 1 µg/mL of listeriolysin peptide $^{91}$GYKDGNEYI$^{99}$ per $6\times10^7$ cells for 1 h at 37° C. before labeling with CFSE. LLO peptide-pulsed splenocyte targets were labeled with a low concentration (0.5 µM) of CFSE (Invitrogen), whereas control targets, not pulsed with a peptide, were labeled with a high concentration (5 µM) of CFSE for 10 minutes at 37° C., followed by being washed and incubated for an additional 30 min at 37° C. Differentially CFSE-labeled cells were washed, mixed in equal ratios and a total of $1\times10^7$ cells per mouse was transferred intravenously into MCMVList or RAE1γMCMVList-infected or uninfected mice. Spleens were harvested 6 h later and the survival of the transferred splenocytes was analyzed by flow cytometry. Percentage-specific lysis of CFSE-labeled target cells was calculated as follows:

(1−[$r$ uninfected control mouse/$r$ infected test mouse])×100 where $r$=(frequency of unpulsed targets/frequency of peptide-pulsed targets).

Sequence Analysis of RAE-1γ.

Organ homogenates from µMT/µMT B cell-deficient mice with recurrent infection were serially diluted 2-fold across 96-well trays and added to MEF cultures in 96-well trays. Wells showing viral cytopathic effect derived from a single plaque were harvested for preparation of virus stocks. The RAE-1γ ORF was PCR amplified by using purified viral DNA. MEFs were infected with the recovered viruses and whole genomic DNA was extracted using a DNeasy blood and tissue kit (Qiagen). The region of interest was amplified by PCR with primers m152fw GTGTATGTGGCCCGACGGGCGG (SEQ.ID.NO: 33) and m152ry CGCGGGCTACTCCCGAAAGAGTAACATC (SEQ.ID.NO: 34). The amplificate was sequenced (3130 genetic analyzer, Applied Bioscience) using the primers m152fw GTGTATGTGGCCCGACGGGCGG (SEQ.ID.NO: 33), m152rv CGCGGGCTACTCCCGAAAGAGTAACATC (SEQ.ID.NO: 34), RAEfw ATGGCCAAGGCAGCAGTGAC (SEQ.ID.NO: 35) and RAErv TGCTCGACCTGAGGTAATTATAACCC (SEQ.ID.NO: 36). Sequences were aligned to the RAE-1γ ORF of the input virus using Vector NTI 11 (Invitrogen).

Quantification of MCMV-Specific Antibody and Serum IFN-α Level by ELISA.

Serum MCMV-specific IgG titers were determined by ELISA as previously described (Jonjic, S. et al., 1990, J Virol 64(11):5457-64). Serum levels of IFN-α were determined by ELISA KIT for IFN-α (PBL Biomedical Laboratories) according to the manufacturer's instructions.

Histological Methods

Hematoxylin-Eosin (HE) staining on paraffin sections was performed as described in the following:

Paraffin sections were deparaffined by washing slides 2×5 min in xylene, 2×3 min in 100% ethanol, 2×3 min in 95% ethanol and 2×5 min in PBS. Slides were stained with hematoxylin 1 min and washed for 5 min in distilled water. Eosin staining was performed for 30 sec and slides were washed as follows: 5 min 70% ethanol, 5 min 80% ethanol, 5 min 90% ethanol, 5 min 100% ethanol, 2×5 min xylene. Slides were mounted using Aquatex.

Anti-CD3 staining on paraffin sections was performed as described in the following:

Paraffin sections were deparaffined by washing slides 2×5 min in xylene, 2×3 min in 100% ethanol, 2×3 min in 95% ethanol and 2×5 min in PBS. Endogenous peroxidase was blocked for 30 min in hydrogen peroxide solution. Slides were washed 2×5 min in PBS. Antigen retrival was performed in citrate buffer at 800w for 4 min and at 400 W at 15 min Slides were cooled at room temperature for 20 min and then washed 2×3 min in distilled water and 2×5 min in PBS. Unspecific staining was blocked by incubation in serum for 20 min Biotin was blocked by 15 min incubation in avidin block solution following 15 min biotin block solution. Primary antibody was diluted in 1% BSA-TBS and incubated for 1 h. Slides were washed 2×5 min in PBS. Secondary antibody biotin labeled was diluted in 1% BSA-TBS and incubated for 30 min Slides were washed 2×5 min in PBS, incubated with streptavidin-peroxidase for 30 min and washed 3×5 min in PBS. AEC was incubated for 10 min, slides were washed 3×1 min in distilled water, 10 sec in hematoxylin, 10 min under tap water, 1 min in distilled water and mounted using Aquatex.

Histopathology and Immunohistochemistry.

Sections from formalin-fixed, paraffin-embedded spleens were stained with hematoxylin and eosin (both Thermo Scientific). CD3-expressing lymphocytes on paraffin sections were visualized by anti-CD3 (SP7) (Abcam), followed by biotinylated goat anti-mouse immunoglobulin G (IgG) antibody (BD Pharmingen, San Diego, Calif.) and avidin-biotin-peroxidase complex (Roche Applied Science, Manheim, Germany) staining. Counterstaining was performed with hematoxylin. Slides were analyzed on an Olympus BX40 microscope, and images were acquired by Olympus digital camera (C-3030).

Statistics.

Statistical significance was calculated by unpaired two-tailed Student's t test using Prisma 4 software and/or GraphPad Prism 5 software (GraphPad Software). The significant differences between tested groups are indicated with star symbols as follows: p<0.05 (*), p<0.01 () and p<0.001 (*). Statistical analyses of the virus titers were done by Mann-Whitney U test. Flow cytometry analysis was performed using BD FACSDiva software.

Example 2: Generation and In Vitro Characterization of a Recombinant MCMV Expressing the NKG2D Ligand RAE-1γ

To study how the expression of NKG2D ligand by MCMV influences immunobiology of this virus infection, the present inventor designed a recombinant virus, referred to herein as RAE-1γMCMV that expresses RAE-1γ. RAE-1γMCMV was constructed by replacing the m152 ORF in the (BAC-cloned) MCMV genome with a cassette comprising the RAE-1γ ORF under control of the HCMV immediate-early promoter (FIG. 1A).

Figure 1A:
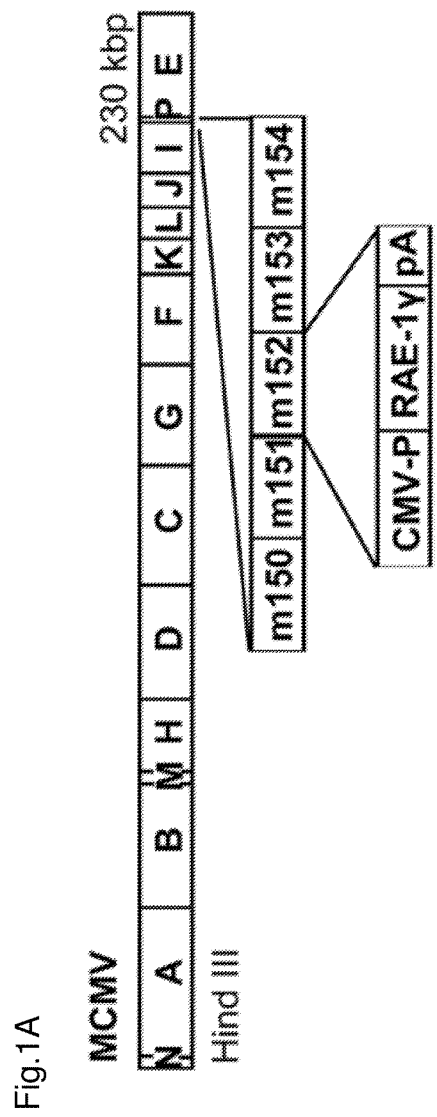

More particularly, FIG. 1A shows the HindIII cleavage map of the MCMV genome at the top with the genomic region encoding the m152 ORF below. In order to construct RAE-1γMCMV the m152 ORF was replaced by an expression cassette (bottom) comprising the HCMV major immediate early promoter (CMV-P), the RAE-1γ ORF (RAE-1γ) and the SV40 polyadenylation signal sequence (pA).

RAE-1γMCMV replication was assessed in a multistep growth kinetics assay and was compared to WT-MCMV replication. The results are shown in FIG. 8A.

More particularly, FIG. 8A shows virus titers determined in supernatants of MEF which were infected with RAE-1γMCMV (triangle) or WT-MCMV (squares) at 0.1 PFU per cell. Supernatants were harvested at time points p.i. as indicated on the x-axis and virus titers were determined by plaque assay. Means±standard errors for the representative of 3 experiments are shown. The virus titer is depicted on the y-axis as log 10 PFU per milliliter, ml.

Figure 1B:
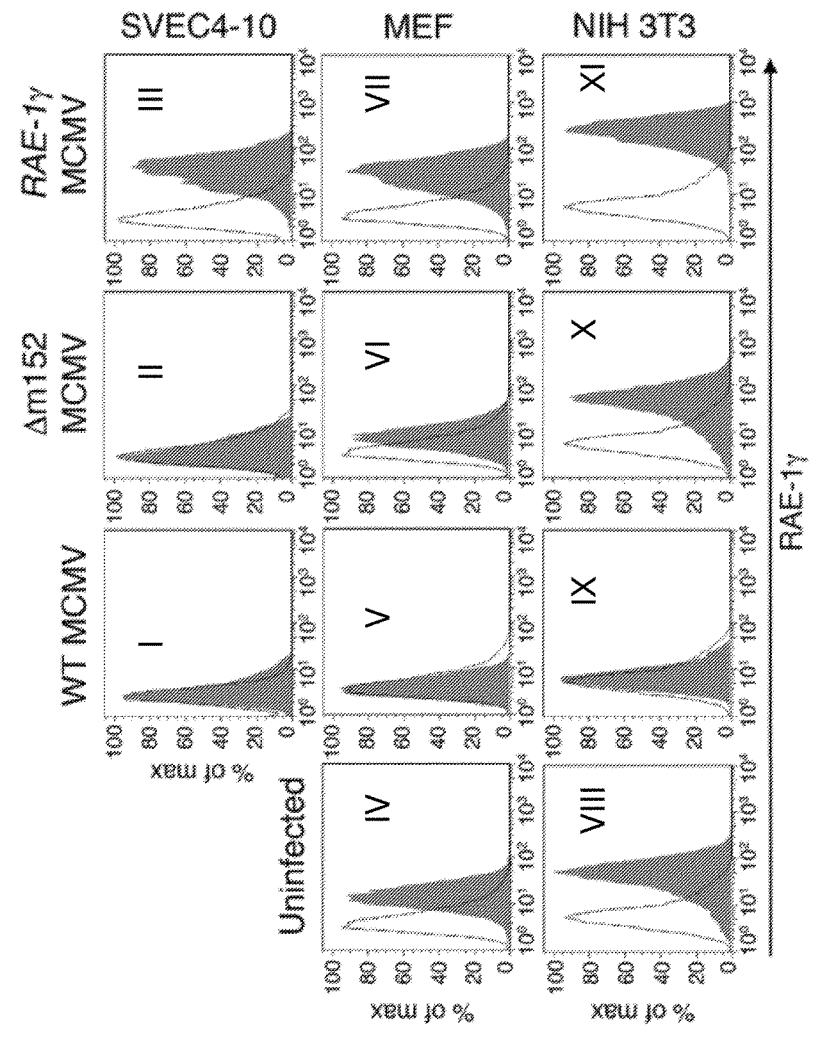

It may be taken therefrom that RAE-1γMCMV replication was comparable to replication of WT-MCMV Infection of SVEC4-10 cells, an endothelial cell line that does not express RAE-1γ, with the recombinant MCMV resulted in cell surface RAE-1γ expression, which may be taken from FIG. 1B.

More particularly, FIG. 1B shows FACS analysis of SVEC4-10 cells (upper panel), NIH 3T3 cells (lower panel) and MEF (middle panel) which were infected with indicated viruses, i.e. WT-MCMV, Δm152-MCMV or RAE-1γMCMV, or left untreated and which were analyzed 12 h later for the surface expression of RAE-1γ by staining with the anti-RAE-1γ antibody, followed by PE-conjugated goat anti-rat IgG. Cells incubated with the secondary antibody in the absence of the primary antibody were used as negative control (thin line). Each histogram represents 10,000 gated propidium iodide-negative cells. On the x-axis the relative intensity of PE (Phycoerythrin) signal is shown. The y-axis depicts the cell number as percentage of total cells. One of two similar experiments is shown.

It may also be taken from FIG. 1B that WT-MCMV infection downregulates endogenous RAE-1γ which was prevented by the deletion of m152 from the MCMV genome (Δm152 MCMV). Introduction of RAE-1γ to the Δm152-MCMV resulted in RAE-1γ over-expression on the surface of infected cells.

FIG. 8B shows the surface expression of NKG2D ligands on NIH 3T3 (left panel), SVEC 4-10 (middle panel) and B12 cells (right panel) which were infected with indicated viruses at 3 PFU per cell or left uninfected, and 12 h later analyzed for the surface expression of NKG2D ligands by staining with the biotinylated anti-H60 antibody, anti-MULT-1 antibody or anti-RAE-1αβ antibody, followed by PE-conjugated goat anti-rat IgG or PE-labeled streptavidin. Cells incubated with the secondary antibody in the absence of the primary antibody were used as negative control (thin line). Each histogram represents 10,000 gated propidium iodide-negative cells. On the x-axis the relative intensity of secondary antibody signal is shown. The y-axis depicts the cell number as percentage of total cells.

As may be taken from FIG. 8B RAE-1γMCMV infection did not change the pattern of cell surface expression of other NKG2D ligands compared to Δm152-MCMV.

Altogether, these data indicate that RAE-1γ insertion into the MCMV genome had no effect on virus replication in vitro and resulted in the expression of RAE-1γ on the surface of infected cells. Furthermore it may be taken from the above that RAE-1γMCMV is attenuated in vivo in an NKG2D-dependent manner.

Example 3: RAE-1γMCMV is Strongly Attenuated In Vivo and Fails to Establish Persistent Infection in Salivary Gland Adult BALB/c mice were injected with RAE-1γMCMV, WT-MCMV or Δm152-MCMV to study whether expression of the NKG2D ligand by the MCMV influences virus control in vivo. In agreement with previous results (Krmpotic, A. et al., 2002, Nat Immunol 3:529-535), at day 3 post infection replication of Δm152-MCMV was attenuated in an NKG2D-dependent manner as compared to WT-MCMV. Introduction of RAE-1γ to the Δm152-MCMV genome further attenuated viral replication and resulted in significantly lower viral titers in all tested organs as compared to Δm152-MCMV and WT-MCMV as may be taken from FIG. 1C.

Figure 1C:
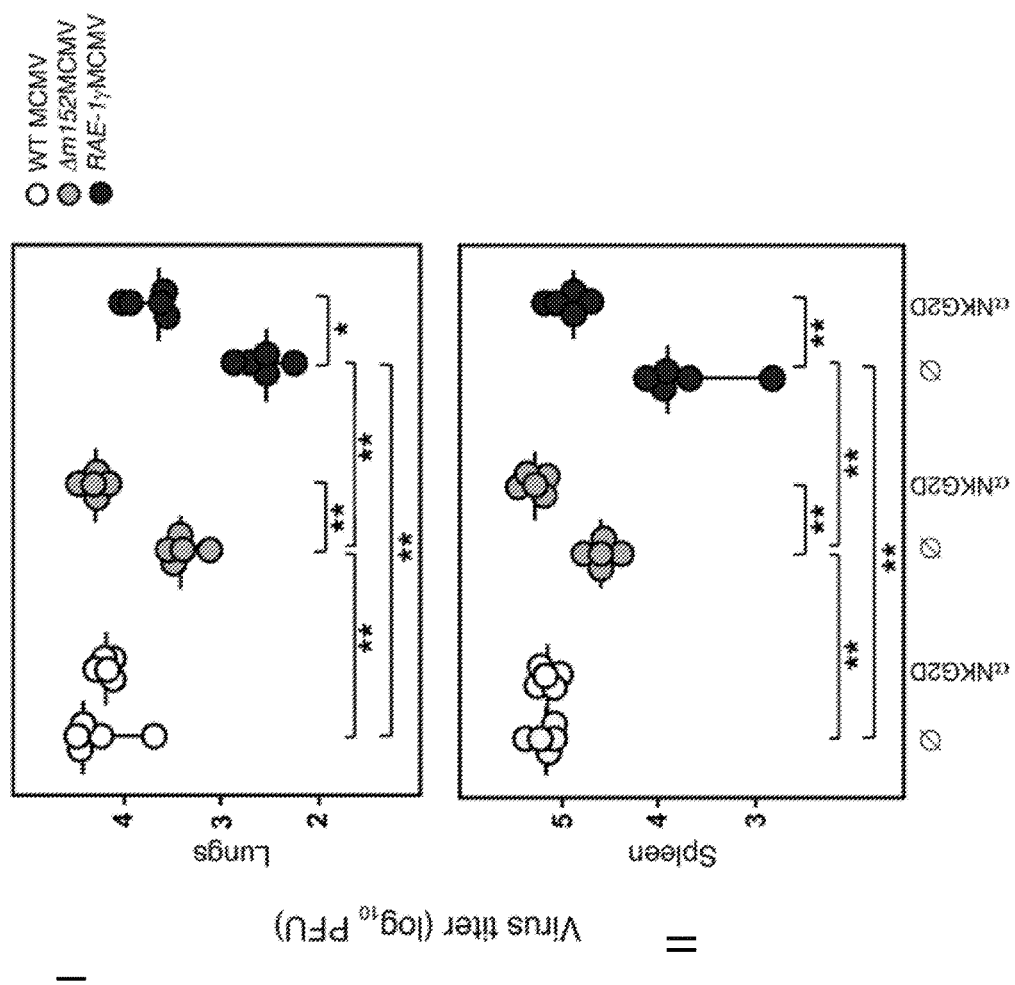

More particularly, FIG. 1C shows the virus titer in lungs (upper panel) or spleen (lower panel) of untreated BALB/c mice or BALB/c mice treated with blocking anti-NKG2D monoclonal antibody which were i.v. injected with $10^5$ PFU of the indicated viruses, i.e. WT-MCMV (white circles), Δm152-MCMV (grey circles) or RAE-1γMCMV MCMV (black circles). Viral titers were determined by plaque assay in lungs and spleen 3 days post infection, abbreviated herein preferably as d p.i. or days p.i. Virus titer in organ of individual mice (circles) and median values (horizontal bars) are shown. One of two similar experiments is shown. The virus titer is shown on the y-axis as $\log_{10}$ PFU.

The observed attenuation was NKG2D-dependent and was abolished by administration of anti-NKG2D blocking antibodies that restored RAE-1γMCMV titers almost to the WT-MCMV level.

Figure 1D:
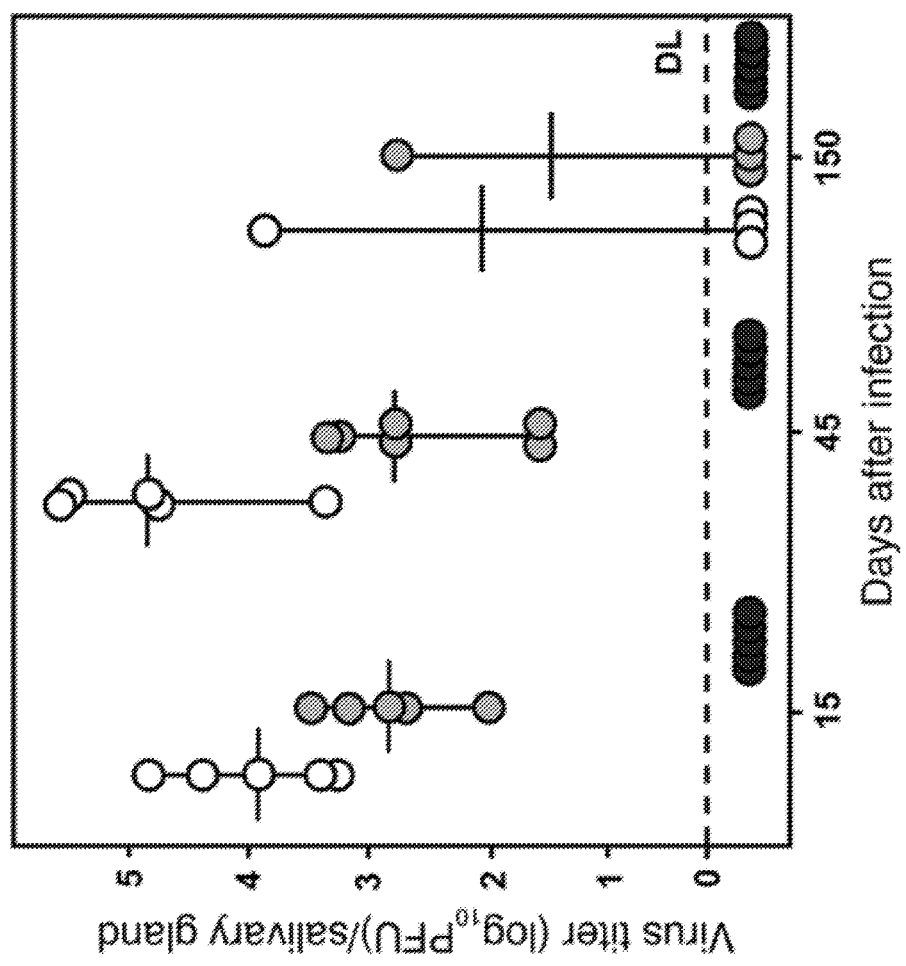

FIG. 1D shows a diagram indicating virus load in salivary glands at different time points as indicated on the x-Axis of BALB/c mice which were f.p. injected with $2\times10^5$ PFU of WT-MCMV (white), Δm152-MCMV (grey) or RAE-1γMCMV (black). Viral titers were determined by plaque assay at the indicated time points post infection. Virus titer in salivary glands of individual mice (circles) and median values (horizontal bars) are shown. Virus titer is shown on the y-axis as $\log_{10}$ PFU per salivary gland. DL means detection limit and is indicated by the dashed line. One of two similar experiments is shown.

It may be taken therefrom that the salivary glands remain persistently infected with MCMV long after productive virus replication is terminated in other tissues (Reddehase, M. J. et al., 1994, J Exp Med 179(1):185-93; Jonjic, S. et al., 1989, J Exp Med 169(4):1199-212). NK cells and $CD4^+$ T cells are essential for virus clearance in the salivary glands and prevention of horizontal virus spread (Jonjic, S. et al., 1989, supra; Campbell, A. E. et al., 2008, Med Microbiol Immunol 197(2):205-13). The present inventor therefore compared the virus titers in salivary glands 15, 60 and 150 days after RAE-1γMCMV, WT-MCMV and Δm152-MCMV infection. In contrast to a high-titer persistent virus replication in WT-MCMV infected mice, no infectious virus was detected in salivary glands following RAE-1γMCMV infection (FIG. 1D).

Although Δm152-MCMV reached slightly lower virus titers compared to WT-MCMV, replication kinetics of these two viruses in salivary glands were similar. The present inventor next determined whether marked differences between RAE-1γMCMV and WT-MCMV replication are reflected in the kinetics of viral clearance from blood and viral genome load in tissue during latency.

Figure 1E:
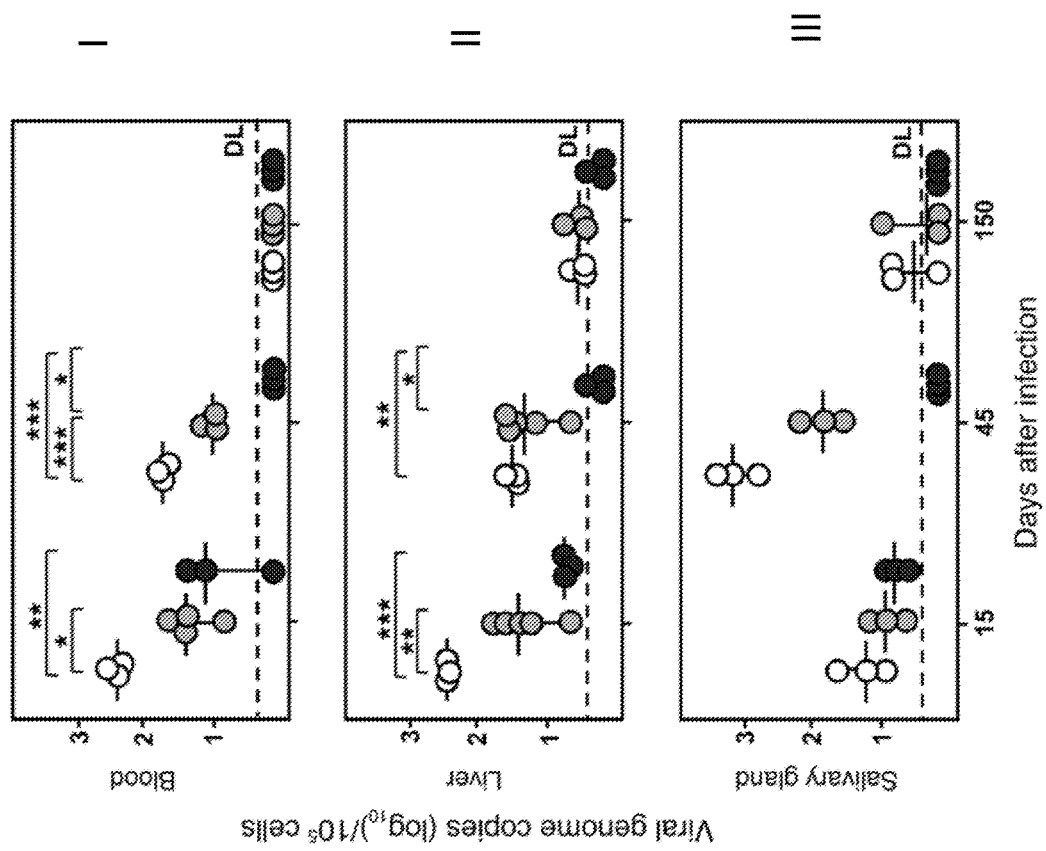

FIG. 1E shows the copies of viral genomes in blood (upper panel), liver (middle panel) and salivary gland (lower panel) of BALB/c mice which were f.p. injected with $2\times10^5$ PFU of WT-MCMV (white), Δm152-MCMV (grey) or RAE-1γMCMV (black). Viral genome load was determined by qPCR at different time points post infection as indicated on the x-axis. Viral genome load in organs of individual mice (circles) and median values (horizontal bars) are shown as $\log_{10}$ viral genome copies per $10^5$ cells. DL means detection limit and is indicated by the dashed line. One of two similar experiments is shown.

It may be taken therefrom that unlike WT-MCMV infection in which viral DNA was maintained in the blood for prolonged period of time (Balthesen, M. et al., 1993, J Virol 67(9):5360-6), viral DNA was cleared from the blood of RAE-1γ MCMV infected mice by day 45. At that time, RAE-1γMCMV DNA remained in organs, but the viral load was reduced to a barely detectable level or in some cases, to below the limit of detection. Viral DNA load in Δm152-MCMV infected mice corresponded to infectious virus titers (FIG. 1E).

To study how the expression of NKG2D ligand by the MCMV affects virus control in mice with constitutively more efficient NK cell response, the present inventor injected C57BL/6 with RAE-1γMCMV, WT-MCMV or Δm152 MCMV. MCMV resistance of C57BL/6 mice is due to the expression of Ly49H activating receptor on NK cells, which recognizes virally encoded protein m157 (Arase, H. et al., 2002, Science 296(5571):1323-6; Smith, H. R. et al., 2002, Proc Natl Acad Sci USA 99(13):8826-31).

FIG. 9A shows the virus load in lungs (upper panel) and spleen (lower panel) of untreated C57BL/6 mice or C57BL/6 mice injected with blocking anti-NKG2D antibody, as indicated on the x-axis, which were i.v. injected with $5\times10^5$ PFU of WT-MCMV (white circles), RAE-1γMCMV (black circles) or Δm152-MCMV (grey circles). Viral titers were determined in spleen 3 d p.i. by plaque assay and are indicated on the y-axis as $\log_{10}$ PFU/lungs or spleen, respectively.

It may be taken therefrom that, similarly to results in MCMV-sensitive BALB/c mice, RAE-1γMCMV reached significantly lower titers compared to WT-MCMV and Δm152 MCMV, hence RAE-1γMCMV is attenuated in $Ly49H^+$ C57BL/6 mice.

Thus, NKG2D-mediated control of RAE-1γMCMV was not covered by NK cell activation via Ly49H as in the case following infection with MCMV mutant lacking m152 only, which may be taken from FIG. 9 A. Taken together, expression of RAE-1γ by MCMV resulted in a dramatic attenuation of virus replication in different organs and a lower latent viral DNA load.

Example 4: RAE-1γMCMV is Attenuated Even in Neonatal Mice

Neonatal mice are highly sensitive to MCMV infection and intraperitoneal (i.p) injection even with low dose of cell culture-derived virus results in significant morbidity and mortality. Mice that survive MCMV infection establish a disseminated, high-titer virus replication and long-lasting persistent infection in salivary glands (Reddehase, M. J. et al., 1994, supra). To test RAE-1γMCMV replication in neonatal mice, newborn animals were injected i.p. with 500 PFU of RAE-1γMCMV or WT-MCMV.

Figure 2A:
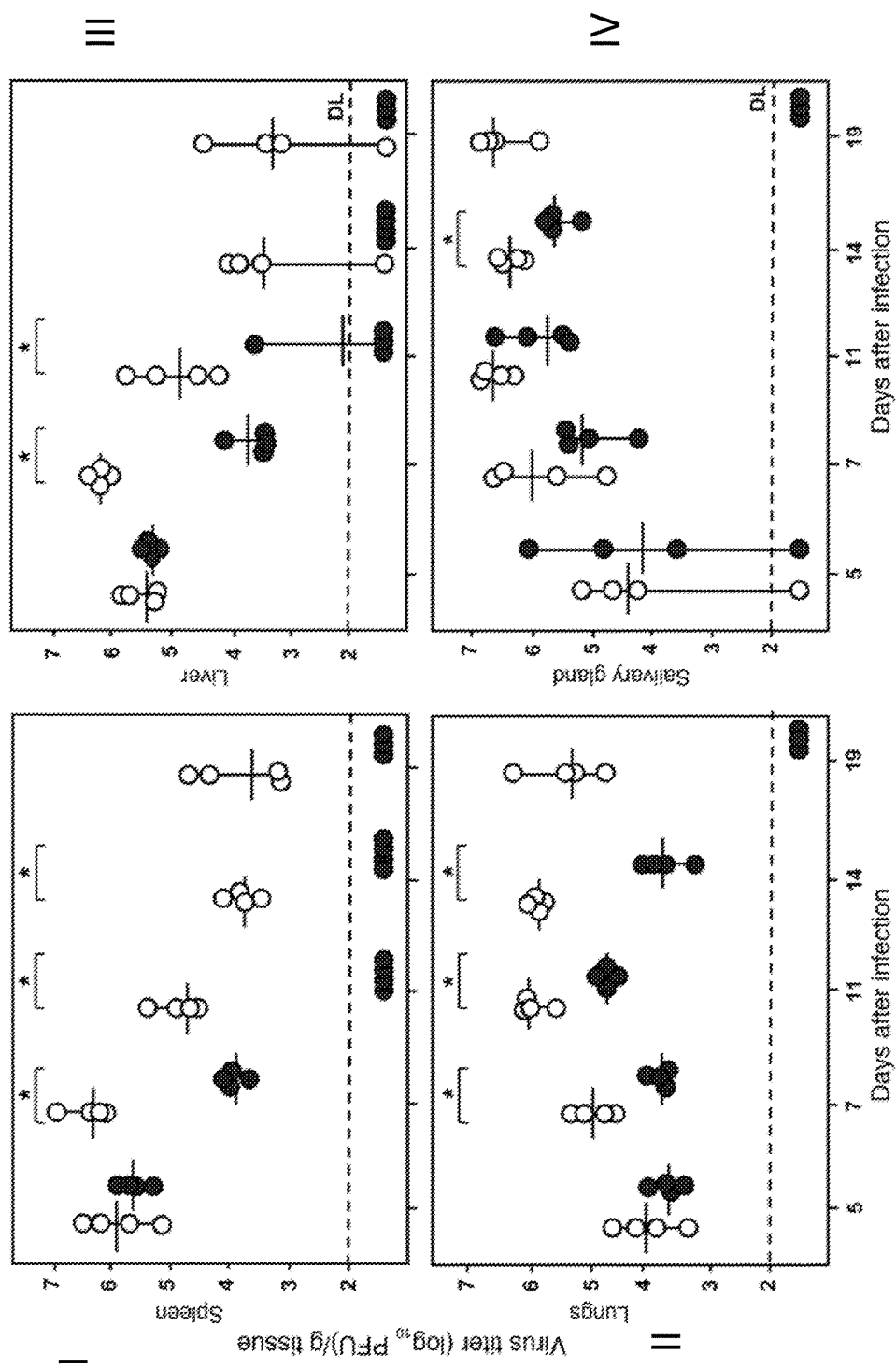

The results may be taken from FIG. 2A.

More particularly, FIG. 2A is a diagram showing virus load in spleen (upper left panel), liver (upper right panel), lungs (lower left panel) and salivary gland (lower right panel) of neonatal BALB/c mice which were i.p. injected with 500 PFU of RAE-1γMCMV (black circles) or WT-MCMV (white circles) 6 hours post partum. Viral titers were determined by plaque assay at the time points post infection indicated at the x-axis. Viral titer of organs of individual mice (circles) and median values (horizontal bars) are shown as $\log_{10}$ PFU per gram (g) tissue. DL means detection limit and is indicated by the dashed line. One representative of two experiments is shown.

It may be taken therefrom that during the first 5 days of infection both viruses replicated to comparable titers, but starting from day 7 RAE-1γMCMV replication was significantly reduced in all tested organs (FIG. 2A).

Productive RAE-1γMCMV infection was cleared by day 11 in spleen and liver and by day 19 in lungs and even in salivary glands. By contrast, around that time WT-MCMV replication in salivary glands and lungs were plateau levels (FIG. 2A) and productive infection continued for several months (Reddehase, M. J. et al., 1994, supra) and data not shown).

Accordingly, RAE-1γMCMV is attenuated in neonatal mice.

Similarly to results obtained in adult mice, Δm152-MCMV replication was attenuated compared to WT-MCMV but not to the level of RAE-1γMCMV attenuation. Furthermore ca. 3 weeks after infection, Δm152-MCMV still replicated to high titers in salivary glands, which may be taken from FIG. 10.

FIG. 10 shows the viral load in spleen, liver, lungs and salivary gland, as indicated from left to right, of neonatal BALB/c mice which were i.p. injected with 500 PFU of RAE-1γMCMV (black circles), WT-MCMV (white circles) or Δm152-MCMV (grey circles) 6 h post partum. Viral titers were determined by plaque assay at day 7 p.i. (upper panel) or day 19 p.i. (lower panel). The virus titer of individual mice (circles) and median values (horizontal bars) are shown as $\log_{10}$ PFU per gram tissue on the y-Axis. DL means detection limit and is indicated by the dashed line.

It may be taken therefrom that RAE-1γMCMV is attenuated compared to MCMV lacking the m152 gene only, namely Δm152-MCMV, in new-born mice.

Figure 2B:
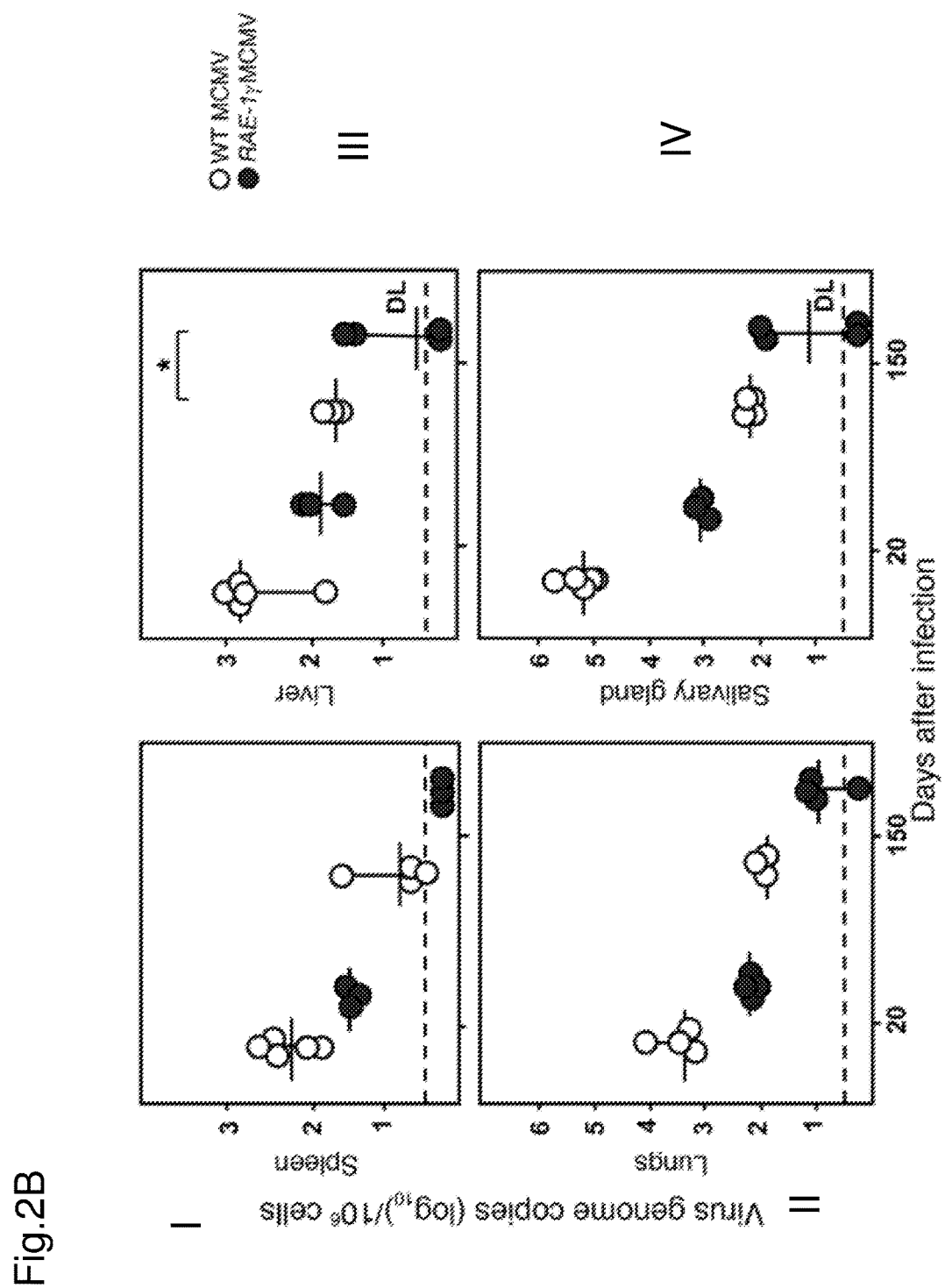

Attenuated RAE-1γMCMV replication in neonates led to a lower load of viral DNA in various organs, while prolonged, high-level WT-MCMV replication resulted in higher load of viral DNA in organs, which may be taken from FIG. 2B.

More particularly, FIG. 2B shows copies of viral genome in spleen (upper left panel), liver (upper right panel), lungs (lower left panel) and salivary gland (lower right panel) of neonatal BALB/c mice which were i.p. injected with 500 PFU of RAE-1γMCMV (black circles) or WT-MCMV (white circles) 6 hours post partum, determined by qPCR at the time points post infection, p.i., indicated on the x-axis. Virus genome copies of organs of individual mice (circles) and median values (horizontal bars) are shown on the y-axis as $\log_{10}$ virus genome copies per $10^6$ cells. DL means detection limit and is indicated by the dashed line. One representative of two experiments is shown.

As may be taken from the above, RAE-1γMCMV infection in neonates is characterized by attenuated virus replication, shorter duration of the productive infection and subsequent lower virus DNA load as compared to the WT-MCMV.

Example 5: Efficient Priming and Maintenance of Adaptive Immune Response after RAE-1γMCMV Infection To test whether the RAE-1γMCMV attenuation impacts on the adaptive antiviral immune response, adult BALB/c mice were footpad injected with $2\times10^5$ PFU of RAE-1γMCMV, WT-MCMV or Δm152 MCMV. The kinetics of the virus specific T cell response was followed by use of MHC class I tetramers loaded with MCMV peptides (Holtappels, R. et al., 2008, Med Microbiol Immunol 197(2): 125-34).

Figure 3A:
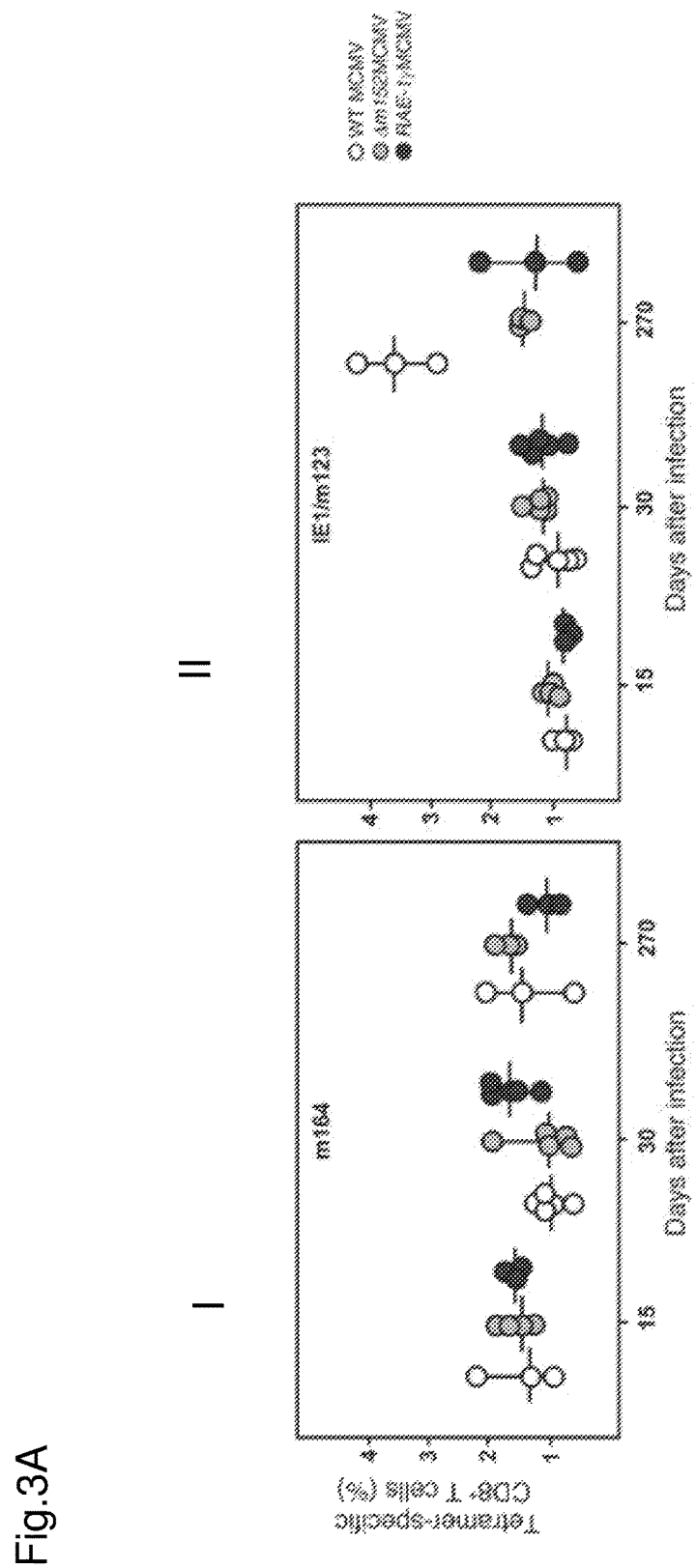

The results are shown in FIG. 3A.

More particularly, FIG. 3A shows the percentage of m164-(left panel) and IE1/m123-(rightpanel) tetramer-specific CD8+ T cells of BALB/c mice which were f.p. injected with $2\times10^5$ PFU RAE-1γMCMV (black circles), WT-MCMV (white circles) or Δm152-MCMV (grey circles). Splenocytes were isolated at different time p.i. as depicted on the x-axis. The splenocytes were stained with IE1/m123 or m164 MHC class I tetramers and anti-CD8 antibody. The percentage of tetramer-specific CD8+ T cells for individual mice (circles) and median values (horizontal bars) are shown on the y-axis.

The CD8+ T cell response was dominated by IE1/m123-specific and m164-specific cells, while the response to the 4 other studied epitopes (m04, M83, M84, M45) was low or below the level of detection (FIG. 3A and data not shown).

Following infection with either of three viruses the m164-specific CD8+ T cells displayed comparable stable memory kinetics. By contrast, immunoinflation of IE1/m123-specific T cells in spleen at 9 months p.i. was less prominent following RAE-1γMCMV and Δm152-MCMV than after WT-MCMV infection (Holtappels, R. et al., 2000, J Virol 74(24):11495-503). The kinetics of the antiviral CD8+ T cell response in the blood closely reflected that in spleen (data not shown). The phenotypic and functional properties of virus-specific CD8+ T cells were similar following RAE-1γMCMV, WT-MCMV and Δm152-MCMV infection, which may be taken from FIG. 3B.

Figure 3B:
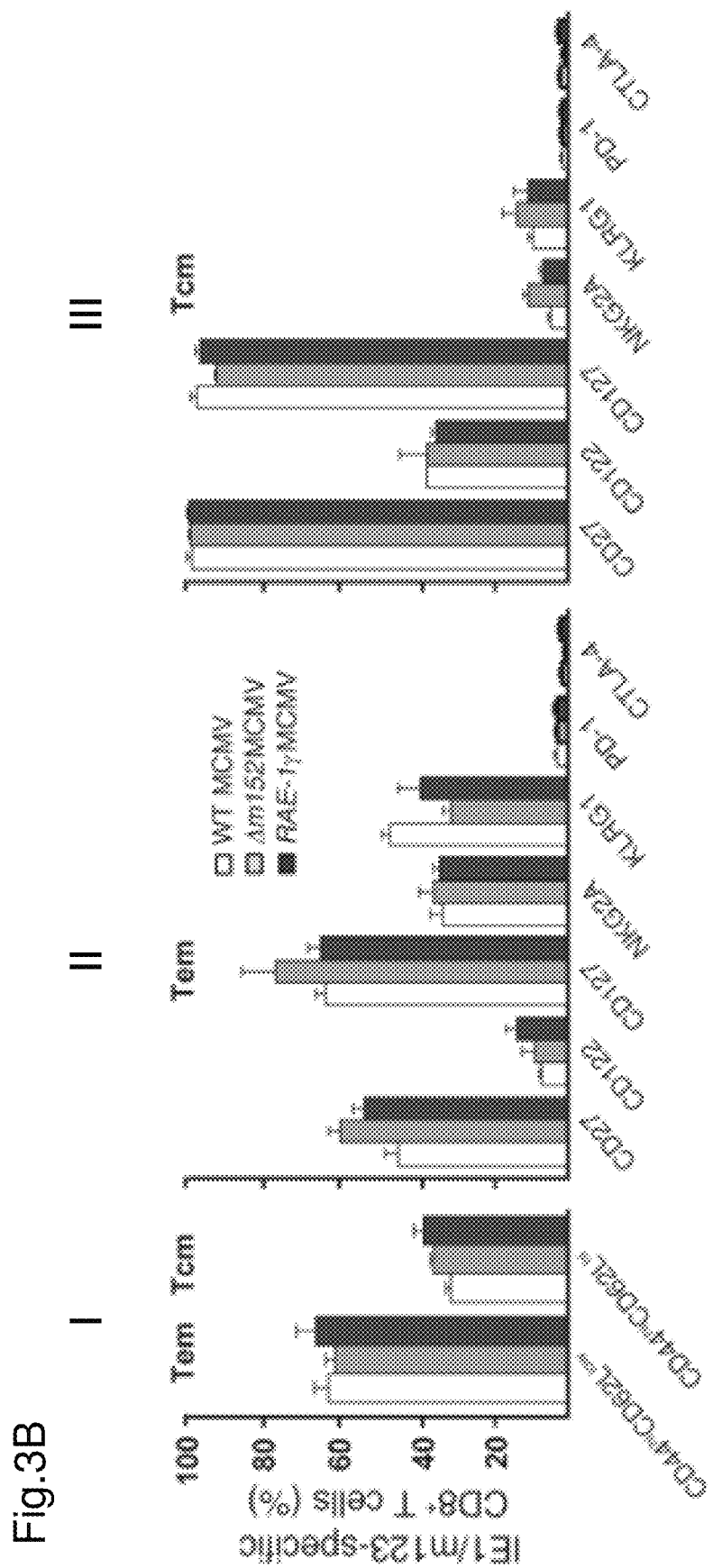

More particularly, FIG. 3B shows the percentage of IE1/m123-specific CD8+ T cells of splenocytes isolated 9 mo p.i. from BALB/c mice which were f.p. injected with $2\times10^5$ PFU RAE-1γMCMV (black bars), WT-MCMV (white bars) or Δm152-MCMV (grey bars). Splenocytes were stained with IE1/m123 MHC class I tetramer, anti-CD8 antibody and antibodies to cell surface molecules indicated on the x-axis. The percentage of IE1/m123-specific CD8+ T cells displaying Tem (TEM or effector memory) or Tcm ($T_{CM}$ or central memory) phenotype (left panel) and the percentage of Tem and Tcm expressing indicated cell surface molecules are shown (right panels). Error bars show the means±standard errors of the means.

Between 60 and 75% of IE1/m123-specific and m164-specific CD8+ T cells in spleen and blood retained effector memory phenotype (TEM) up to 9 months after the infection. It is important to note that the expression of NKG2D, a CD8+ T cell costimulatory receptor, was essentially identical following both RAE-1γMCMV and WT-MCMV infection, which may be taken from FIG. 3C.

Figure 3C:
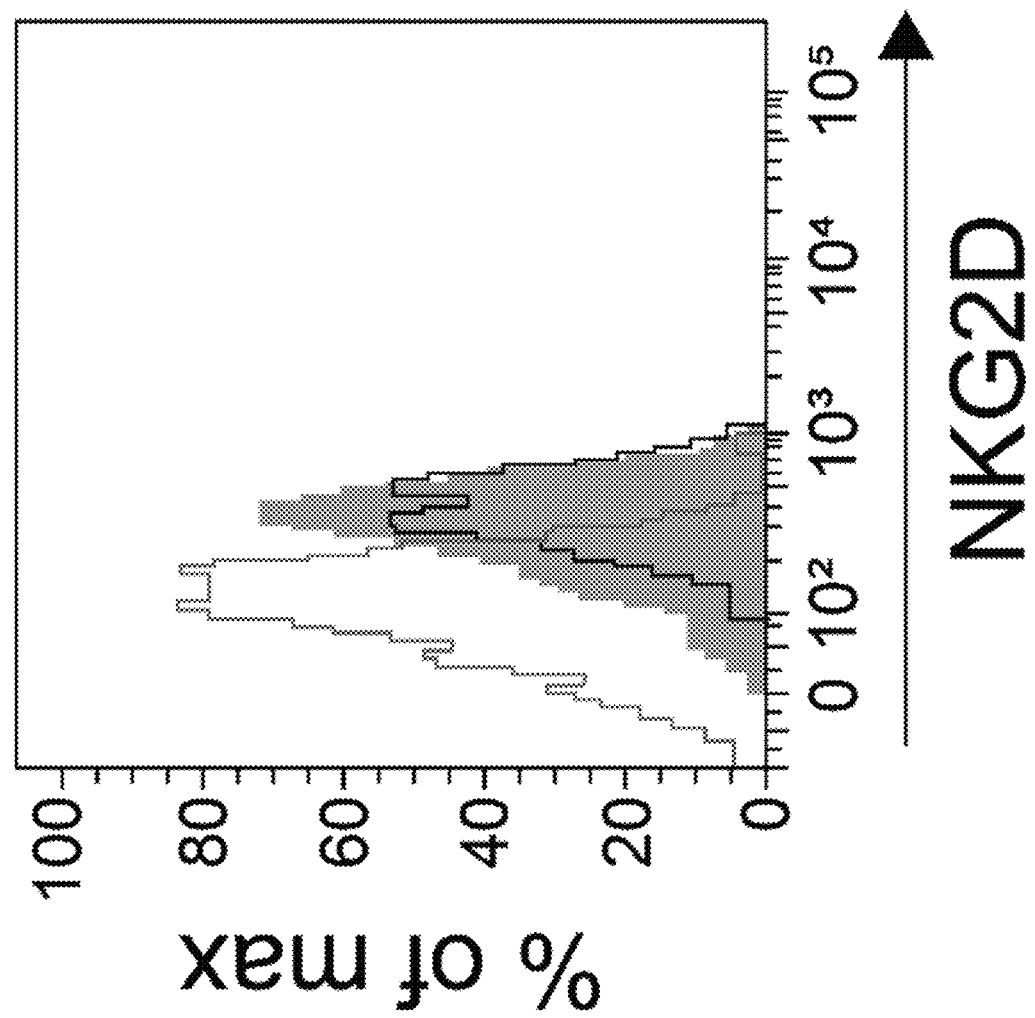

More particularly, FIG. 3C shows a representative histogram of the FACS analysis of surface expression of NKG2D on IE1/m123-specific CD8+ T cells in spleen 9 month after f.p. injection of $2\times10^5$ PFU WT-MCMV (filled histogram) or RAE-1γMCMV (dotted line). Tetramer negative CD8+ T cells are indicated as a dashed line.

Also, the inhibitory receptors PD-1 and CTLA-4, described to be associated with T cell exhaustion during persistent infections (Wherry, E. J., and Ahmed, R., 2004, J Virol 78(11):5535-45) were not upregulated on memory CD8+ T cells and the T cells remained fully functional throughout latent RAE-1γMCMV and WT-MCMV infection, which may be taken from FIG. 3D and Figure E.

Figure 3D:
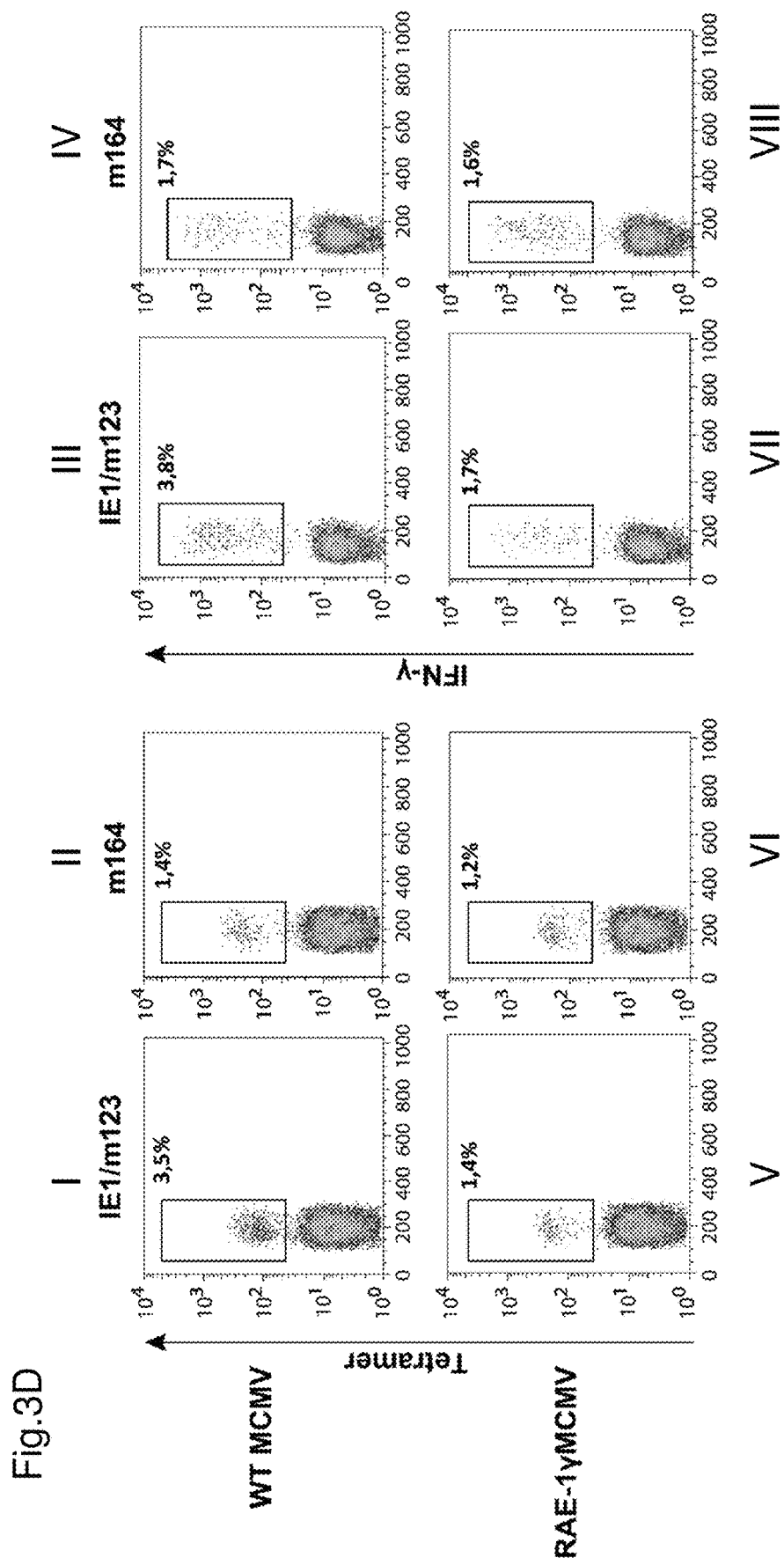

More, particularly, FIG. 3D shows a series of dot plots of FACS analysis of splenocytes from BALB/c mice which were f.p. injected with $2\times10^5$ PFU WT-MCMV (upper row) or RAE-1γMCMV (lower row), wherein the splenocytes were isolated 9 month post infection (mo p.i) and stained with the indicated tetramers, i.e. IE1/m123- or m164-tetramer, (left panel) or stimulated with the indicated peptides, i.e. IE1/m123- or m164-peptide, and stained for IFN-γ production (right panel). The representative dot plots are gated on CD8+ T cells of 3 mice per group are shown. Numbers indicate means. One of two similar experiments is shown.

FIG. 3E shows a series of dot plots showing FACS analysis of splenocytes of mice which were f.p. injected with $2 \times 10^5$ PFU WT-MCMV (upper row) or RAE-1γMCMV (lower row). The splenocytes were isolated 9 mo p.i. and stimulated with the indicated peptides, i.e. IE1/m123- or m164-peptide, in the presence of the aCD107a antibody and co-stained for IFN-γ and TNF-α production. The y-axis indicates the intensity of the staining for IFN-γ production. The x-axis indicates the intensity of the staining for TNF-α production on the left panel and the intensity of the staining for CD107a on the right panel. The representative dot plots are gated on $CD8^+$ T cells of 3 mice per group are shown. Numbers indicate means. One of two similar experiments is shown.

It may be taken therefrom that at each time point analyzed, the percentage of $CD8^+$ T cells detected by tetramer staining was similar to the percentage of $CD8^+$ T cells secreting IFN-γ upon stimulation with a viral antigenic peptide in vitro (see FIG. 3D) and most of the cells simultaneously secreted TNF-α, but not IL-2 (see FIG. 3E and data not shown) and extruded cytotoxic granules, i.e. externalized CD107a (see FIG. 3E).

It may be also taken from the above that kinetics and phenotype of MCMV-specific memory $CD8^+$ T cells in RAE-1γMCMV, WT-MCMV and Δm152-MCMV infected mice are comparable.

Interestingly, in C57BL/6 mice frequency of MCMV-specific $CD8^+$ T cells at early time point after RAE-1γMCMV infection was even higher compared to WT-MCMV, which may be taken from FIG. 9 B.

Figure 9B:
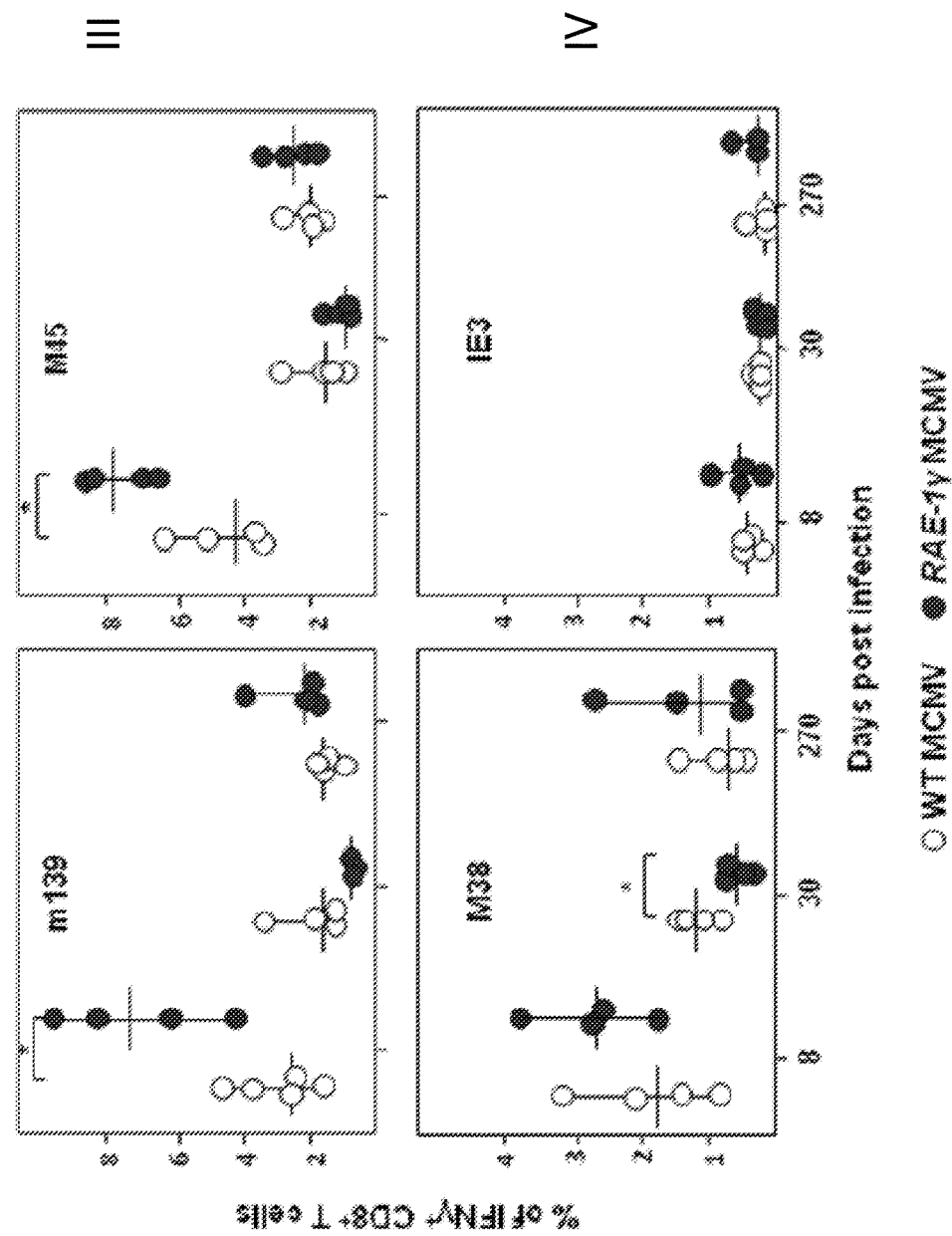

More particularly, FIG. 9B shows the percentage of $IFN^+CD8^+$ T cells of splenocytes from C57BL/6 mice which were f.p. injected with $2 \times 10^5$ PFU of RAE-1γMCMV (black circles) or WT-MCMV (white circles). Splenocytes were isolated at different time points p.i, as indicated on the x-axis, and stimulated with the indicated peptides, namely m139-peptide according to SEQ.ID.NO: 30 (upper left panel), M45-peptide according to SEQ.ID.NO: 31 (upper right panel), M38 peptide according to SEQ.ID.NO: 32 (lower left panel) or IE3-peptide according to SEQ.ID.NO: 29 (lower right panel), and stained for IFN-γ production. The percentage of $IFN^+CD8^+$ T cells for individual mice (circles) and median values (horizontal bars) are shown as percentage of $IFN^+CD8^+$ T cells on the y-axis.

Similar priming capacity and the frequency of virus specific $CD8^+$ T cells after infection with RAE-1γMCMV or WT-MCMV in spite of dramatic differences in the load of infectious virus in their tissues, prompted the present inventor to test whether this can be explained by differential effect of RAE-1γMCMV and WT-MCMV on dendritic cells (DC) in vivo. MCMV infection results in a reduction of conventional DCs (cDC) in BALB/c mice which can be prevented by efficient antiviral NK cell response in C57BL/6 strain (Robbins, S. H. et al., 2007, supra; Andrews, D. M. et al., 2010, J Exp Med 207(6):1333-43).

To test how the vaccine virus affects DCs in vivo the present inventor compared DC subsets following RAE-1γMCMV and WT-MCMV injection in BALB/c mice.

Figure 11:
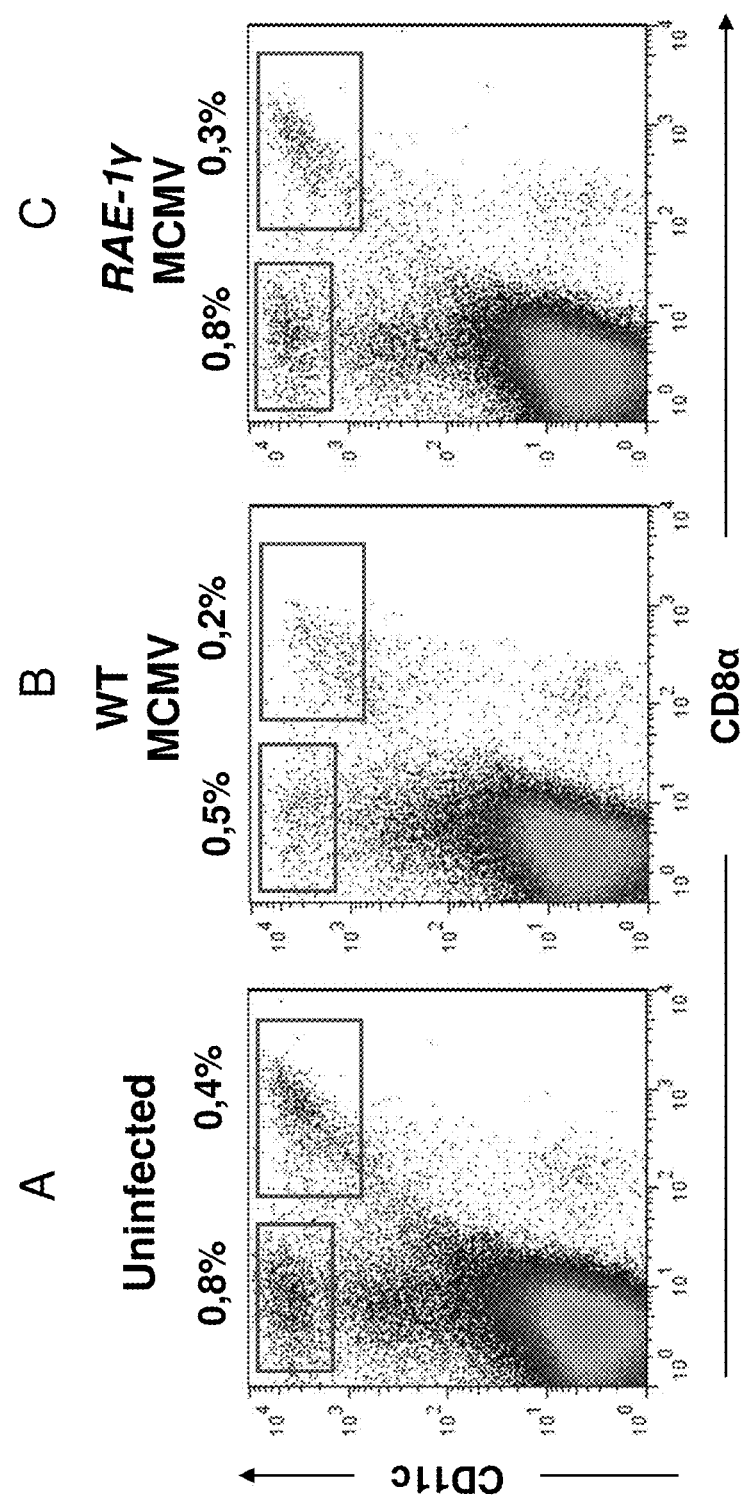

The results are shown in FIG. 11.

More particularly, FIG. 11 shows representative dot plots of FACS analysis of splenocytes which were isolated from naïve BALB/c mice (uninfected) or BALB/c mice i.v. injected with $2 \times 10^5$ PFU of RAE-1γMCMV or WT-MCMV, as indicated, 3 days p.i. and analyzed for the frequency of CD11b cDCs ($CD11c^{hi}CD8α^-$) and CD8αcDCs ($CD11c^{hi}CD8α^+$) within the $NKp46^-TCRβ^-$ population. Numbers in dot plots represent the percentage of CD11b cDCs and CD8α cDCs within the total splenocyte population for a representative animal from a group of three mice.

It may be taken therefrom that while a marked reduction of cDCs occurred at early time after WT-MCMV infection, both CD11b and CD8α subsets of cDC were preserved following RAE-1γMCMV infection (see FIG. 11).

As reported by others (Robbins, S. H. et al., 2007, supra) the frequency of cDC in spleen of infected mice inversely correlated with type I interferons levels in sera of infected mice. At day 2 post infection the average level of IFN-α in sera was significantly higher after WT-MCMV (5212±1266 pg/ml) as compared to RAE-1γMCMV infection (1459±840 pg/ml). Thus, an efficient early control of RAE-1γMCMV resulted in preservation of cDCs, possibly by preventing an overwhelming production of type I IFNs, providing optimal conditions for priming of MCMV-specific T cells.

In vivo antiviral effector activity of MCMV-specific memory $CD8^+$ T cells generated following RAE-1γMCMV and WT-MCMV infection was compared by prophylactic adoptive transfer into immunodepleted MCMV-infected recipient mice. The result is shown in FIG. 4A and FIG. 4B.

Figure 4A:
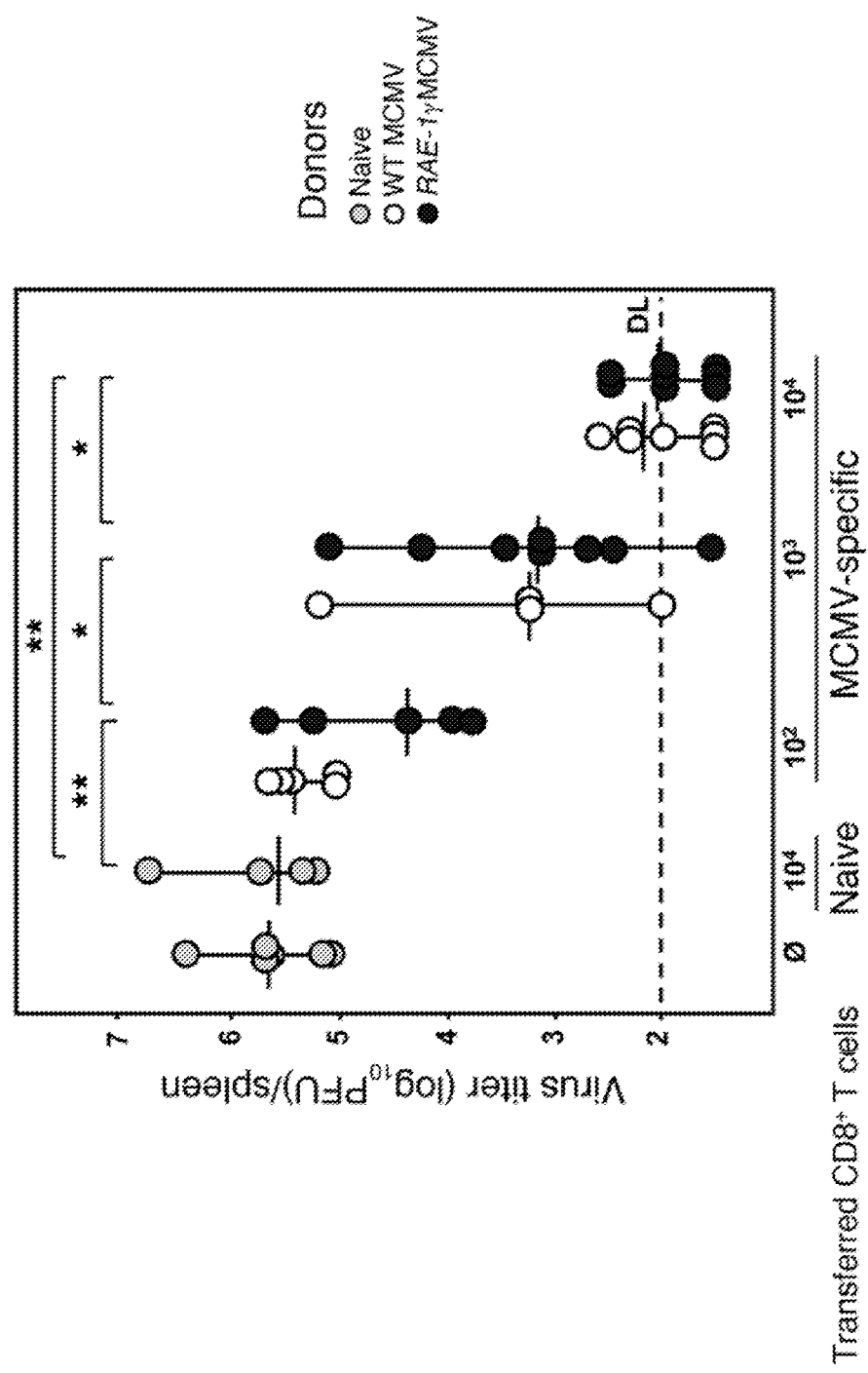

More particularly, FIG. 4A shows virus titers of BALB/c mice infected after transfer of memory $CD8^+$ T from latently infected μMT/μMT B cell-deficient mice. Donors of memory $CD8^+$ T cells were taken from μMT/μMT B cell-deficient mice either naïve (grey circles) or latently infected with RAE-1γMCMV (black circles) or WT-MCMV (white circles) at least 6 mo p.i. Splenocytes from three donors per group were pooled and the number of MCMV specific $CD8^+$ T cells was assessed by combined staining with pp98, m164, m83, m84 and m04 MHC class I tetramers. $10^4$ naïve $CD8^+$ T cells or graded numbers of MCMV-specific $CD8^+$ T cells, as indicated on the x-axis, were i.v. transferred to recipient BALB/c mice immunocompromised by 6 Gy γ-irradiation. Recipients were f.p. injected with $10^5$ PFU of WT-MCMV 6 h after the cell transfer.

Viral titers in spleen were determined 12 d p.i. by plaque assay and are shown on the y-axis as $\log_{10}$ PFU per spleen. Titers of individual mice (circles) and median values (horizontal bars) are shown. Ø means no transfer. DL means detection limit and is indicated by the dashed line.

Figure 4B:
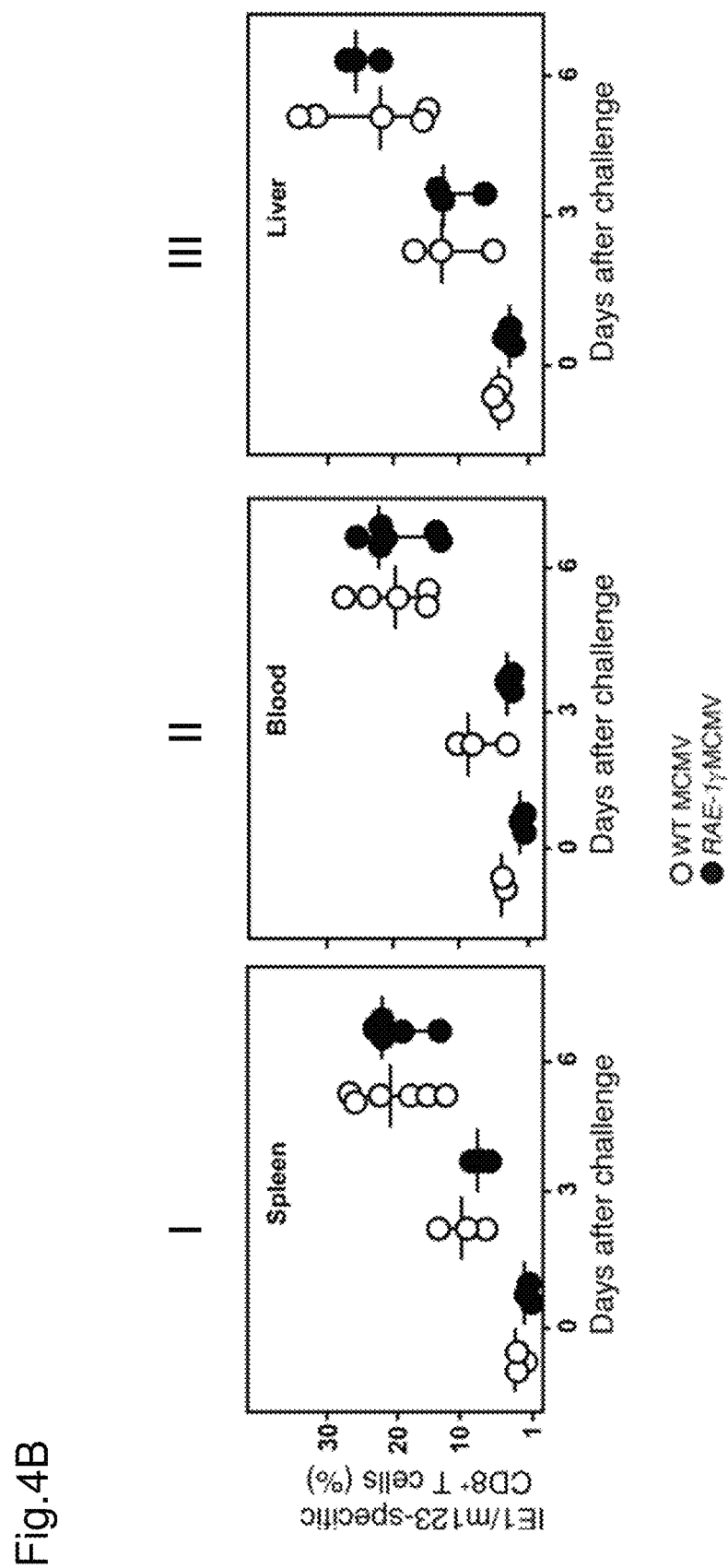

FIG. 4B shows the percentage of IE1/m123 MHC class I tetramer-positive cells per $CD8^+$ T cells of mice infected as described in FIG. 3 which were i.p. challenged with $10^5$ PFU of salivary gland derived MCMV, also referred to herein as SGV, 6 mo p.i. Lymphocytes were isolated from blood (middle panel), spleen (left panel) and liver (right panel) at different time points after the challenge as indicated on the x-axis and stained with IE1/m123 MHC class I tetramer and anti-CD8 antibody. The percentage of IE1/m123-specific $CD8^+$ T cells for individual mice (circles) and median values (horizontal bars) are shown on the y-axis.

It may be taken therefrom that adoptive transfer of only $10^3$ MCMV-specific cells markedly limited virus multiplication while $10^4$ MCMV-specific cells nearly abolished virus replication in spleen. No differences in protective capacity of $CD8^+$ T cells generated following RAE-1γMCMV and WT-MCMV infection were observed (see FIG. 4A). Recall response of memory $CD8^+$ T cells was tested 6 months after the primary infection (see FIG. 4B and data not shown). The IE1/m123-specific and m164-specific $CD8^+$ T cells in spleen, blood and tissue rapidly expanded upon challenge infection. Expansion peaked around day 6 after the challenge resulting in T cell frequencies several orders of magnitude higher than before the challenge in both RAE-1γMCMV and WT-MCMV infected mice. Thus, although initial memory T cell pool was smaller in RAE-1γMCMV than in WT-MCMV infected mice, the size of the resulting T cell pool after the challenge infection was similar in both groups of mice. Collectively, these data indicate that despite tight innate immune control, RAE-1γMCMV infection elicited a strong, enduring antiviral immune response comparable to that following WT-MCMV infection.

Example 6: RAE-1γMCMV Immunization Protects Mice from Challenge Infection

To test whether the immune response induced by the RAE-1γMCMV infection is sufficient to protect the host from challenge infection, adult BALB/c mice were footpad injected with $2\times10^5$ PFU of RAE-1γMCMV or WT-MCMV 6 months prior to lethal challenge with salivary gland derived MCMV (SGV).

Figure 4C:
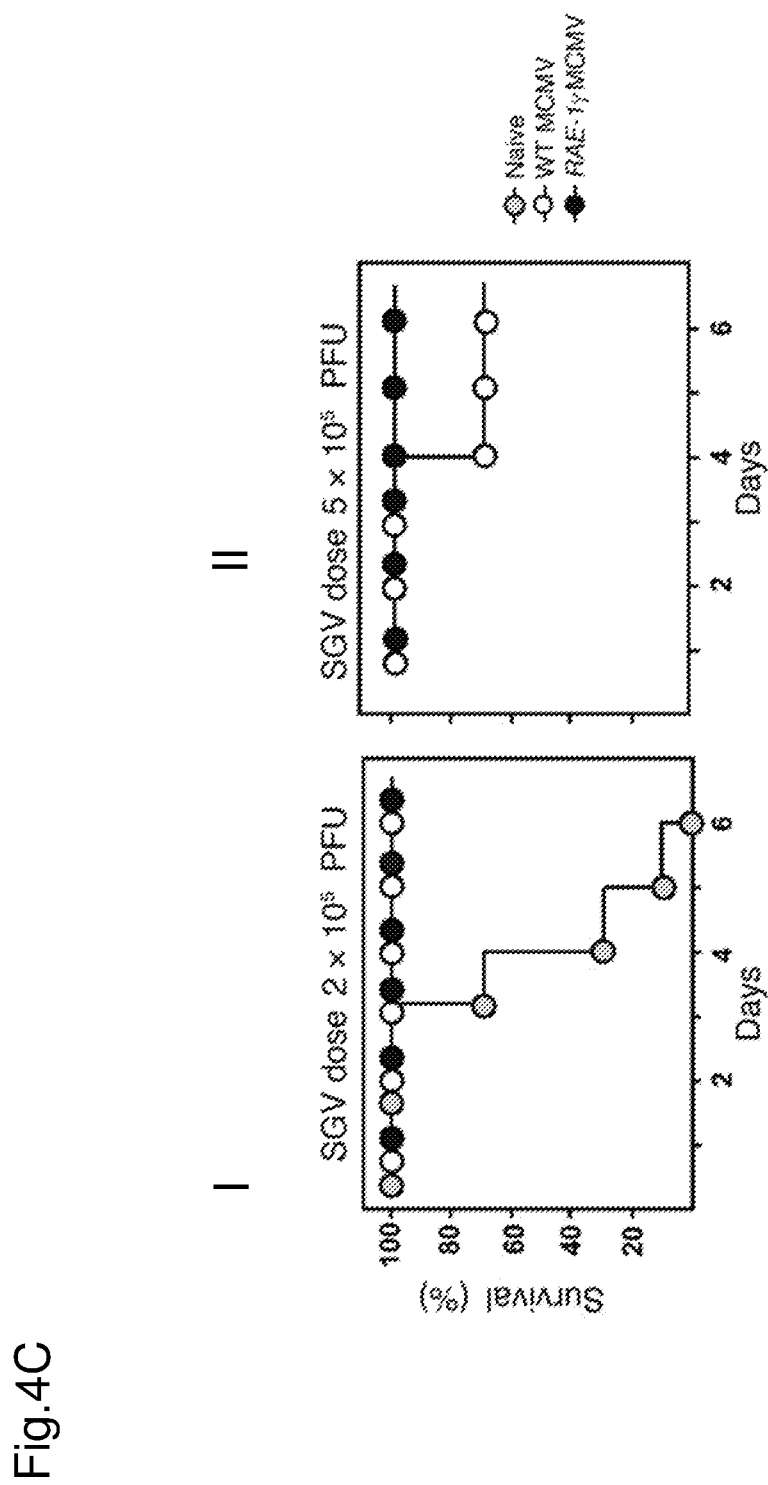

The result is shown in FIG. 4C.

More particularly, FIG. 4C shows survival of naive mice (grey circles) and mice infected as described in FIG. 3 with RAE-1γMCMV (black circles) or WT-MCMV (white circles), respectively, which were i.p. challenged with $2\times10^5$ (left panel) or $5\times10^5$ PFU (right panel) of SGV 6 mo p.i. Survival rates were monitored daily. One of two similar experiments is shown. SGV is more virulent than the cell culture-derived MCMV and injection with only $10^5$ PFU of SGV results in multi-organ damage and high mortality (Trgovcich, J. et al., 2000, Arch Virol 145(12):2601-18).

It may be taken from FIG. 4C that RAE-1γ MCMV infection induces long-term protective immunity. More particularly, while naïve mice failed to control the infection and succumbed to a dose of $2\times10^5$ SGV (2 LD50), all of the mice immunized with RAE-1γMCMV, similar to the mice previously infected with WT-MCMV, survived the challenge (see FIG. 4C). Notably, mice immunized with RAE-1γMCMV resisted challenge infection with 5 LD50 of the SGV better than WT-MCMV infected mice, suggesting that expression of NKG2D ligand provide an innate immune stimuli that enhance the effectiveness of adaptive immune response. Taken together, immunization with RAE-1γMCMV induced an immune response that conferred protection against lethal MCMV infection.

Example 7: Strong Attenuation In Vivo does not Prevent RAE-1γMCMV to Establish Latent Infection and to Reactivate Upon Immunosuppression The burden of latent viral DNA in a tissue predetermines the risk of recurrent CMV infection (Reddehase, M. J. et al., 2002, J Clin Virol 25 Suppl 2:S23-36). The barely detectable DNA load of RAE-1γMCMV during latent infection could limit viral reactivation and subsequent recurrent virus infection. However kinetics and phenotype of MCMV-specific T cells observed during latent infection were indicative of repeated antigen exposure. Therefore, the present inventor investigated the potential of RAE-1γMCMV to reactivate from latency by combined depletion of NK cells and T cell subsets in latently infected B-cell deficient μMT/μMT mice.

In this experimental system, the absence of antibodies facilitates virus multiplication and dissemination after recurrence, which increases the sensitivity of virus detection (Jonjic, S. et al., 1994, supra). Following immunosuppression, recurrent infection occurred independently in different organs in 4 out of 6 (66%) RAE-1γMCMV infected mice and in all of the WT-MCMV infected mice, which may be taken from FIG. 5A.

Figure 5A:
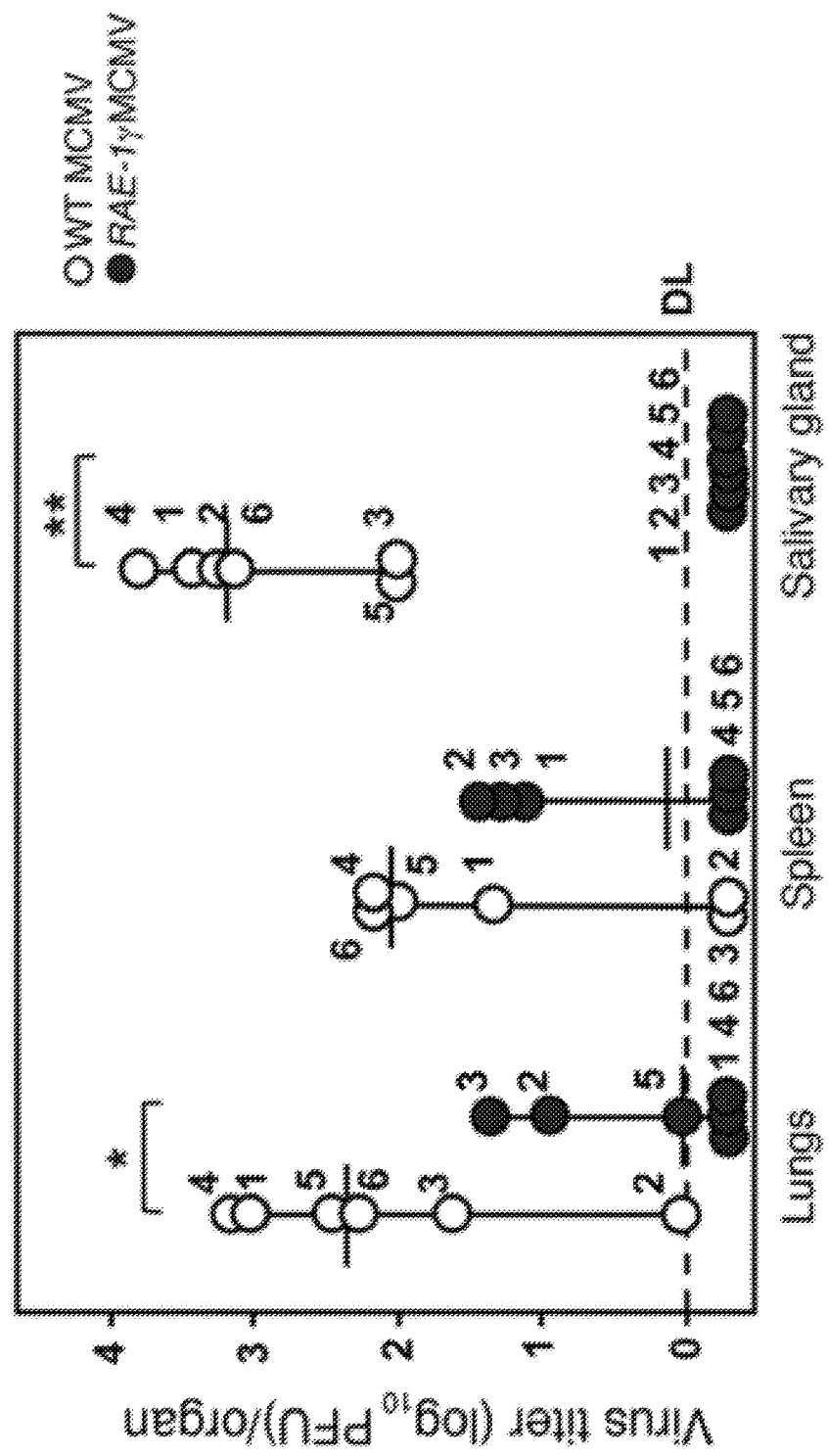
FIG. 5C is a diagram indicating the virus titer in spleen of mice infected with MCMV treated with or without blocking anti-NKG2D antibody.

More particularly, FIG. 5A shows the viral load of various organs, as depicted on the x-axis, of μMT/μMT B cell-deficient mice latently infected with RAE-1γMCMV (black circles) or WT-MCMV (white circles) which were depleted of CD4$^+$, CD8$^+$, and NK1.1$^+$ cells by use of monoclonal antibody. Viral titers were determined by plaque assay 13 d after immunodepletion. Titers of individual mice (circles) and median values (horizontal bars) are shown as $\log_{10}$ PFU per organ on the y-axis. Numbers indicate individual mice. DL means detection limit and is indicated by the dashed line.

It may be also taken therefrom that while in WT-MCMV infected mice recurrent infection first occurred in salivary glands favoring virus shedding, recurrence was not detected in salivary glands of any RAE-1γMCMV infected mice. Thus, tight immune control of the RAE-1γMCMV during primary infection did not prevent viral recurrence after immunosuppressive treatment altogether but altered incidence and sites of recurrence.

Example 8: RAE-1γ Remains Intact During Latent RAE-1γMCMV Infection

Selective pressure from the immune system can result in emergence of virus mutants that escape from the immune control, even in herpes viruses with highly accurate mechanisms of genome replication (French, A. R. et al., 2004, Immunity 20(6):747-56; Voigt, V. et al., 2003, Proc Natl Acad Sci USA 100(23):13483-8). To address whether a strong immune response can drive emergence of RAE-1γMCMV mutants that escape from NKG2D-mediated immunesurveillance the present inventor prepared plaque-purified viruses from spleen and lung homogenates of B-cell deficient μMT/μMT mice with recurrent RAE-1γMCMV infection (see above).

Figure 5B:
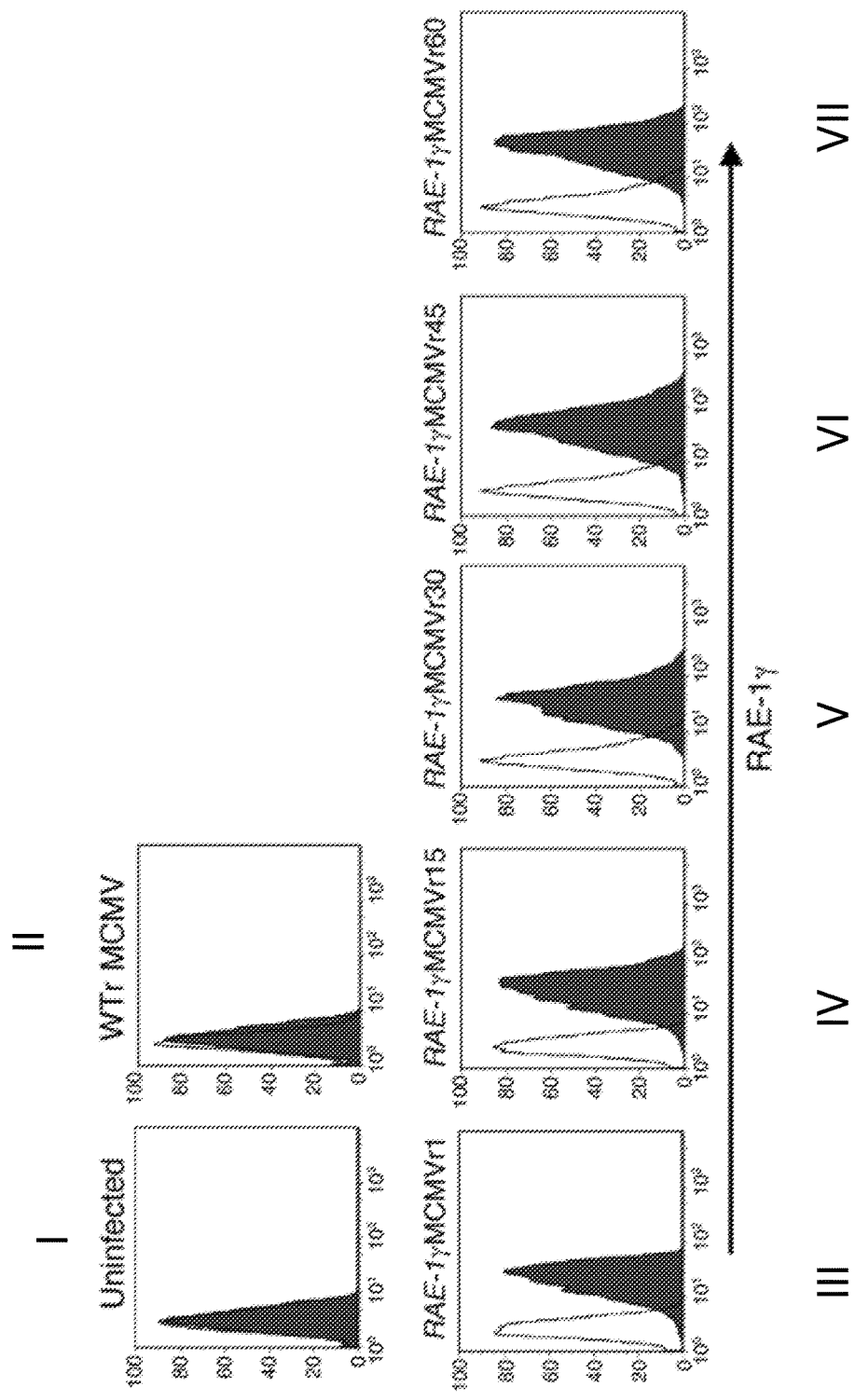
Figure 5C:
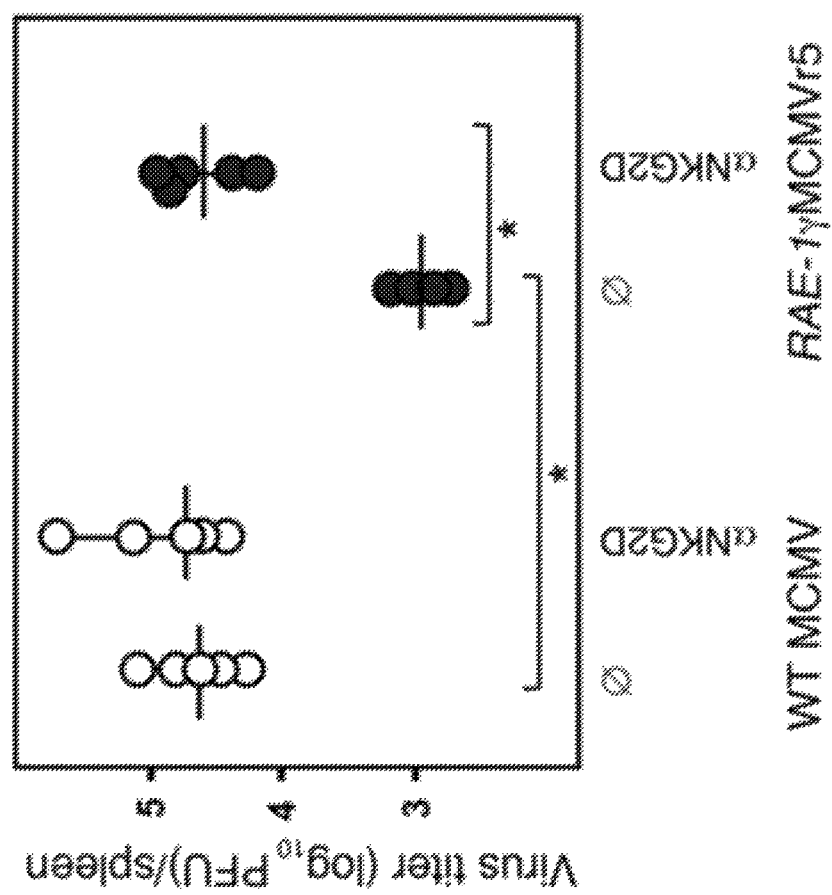

The result is shown in FIG. 5B and FIG. 5C.

More particularly, FIG. 5B shows histograms of indicating the surface RAE-1γ expression of SVEC4-10 cells which were infected with the indicated recurrent plaque purified RAE-1γMCMV viruses and analyzed for the surface RAE-1γ expression by FACS as described in FIG. 1B.

A total of 73 recurrent, plaque purified virus isolates (termed RAE-1γMCMVr1 to RAE-1γMCMVr73) were isolated from organ homogenates of B-cell deficient μMT/μMT mice with recurrent RAE-1γMCMV infection. In connection therewith it will be understood that WTr as used herein is a WT-MCMV which was isolated as recurrent, plaque purified virus. The white histogram indicates the surface expression of RAE-1γ after WTr-MCMV infection.

FIG. 5C shows virus titer in spleen of untreated BALB/c mice (ø) or BALB/c mice treated with blocking anti-NKG2D antibody (aNKG2D) which were i.v. injected with $10^5$ PFU of WT-MCMV (white circles) or recurrent plaque purified RAE-1γMCMV (clone RAE-1γMCMVr5) (black circles) as indicated on the x-Axis. Viral titers were determined in spleen 3 d p.i. by plaque assay. Titers of individual mice (circles) and median values (horizontal bars) of a representative experiment are shown as $\log_{10}$ PFU per spleen on the y-axis.

The 73 plaque purified isolates (termed RAE-1γMCMVr1 to RAE-1γMCMVr73) were tested for the expression of RAE-1γ and some of them were tested for sensitivity to the NKG2D-mediated immune control in vivo. Infection of SVEC4-10 cells with plaque purified isolates resulted in cell surface expression of RAE-1γ detected by FACS analysis as may be taken from FIG. 5B, and infection of BALB/c mice with a RAE-1γMCMVr isolate (RAE-1γMCMVr5) resulted in NKG2D-dependent attenuation of virus replication similar to the attenuation of parental RAE-1γMCMV as may be taken from FIG. 5C. Finally, PCR amplification of RAE-1γ was performed and sequence analysis of PCR products did not reveal sequence variation in any of 30 RAE-1γMCMVr isolates tested (data not shown). These data indicate that despite strong selective pressure imposed by NKG2D-dependent immune control mechanisms the RAE-1γ transgene encoded by RAE-1γMCMV remained intact.

Example 9: Control of RAE-1γMCMV in Mice Lacking the Receptor for Type I Interferons and after Haemoablative Irradiation Type I interferons, also referred to herein as IFNs, play an important role in limiting MCMV replication during the early stage of infection. Consequently, mice lacking the receptor for type I IFNs, also referred to herein as IFNα/βR$^{-/-}$, are 1,000-fold more susceptible to MCMV infection than the parental mouse strain (Presti, R. M. et al., 1998, J Exp Med 188(3):577-88). To test whether RAE-1γMCMV is efficiently controlled even in the severely immunodeficient host, IFNα/βR$^{-/-}$ mice were i.p. injected with RAE-1γMCMV, WT-MCMV or Δm152 MCMV.

Figure 6A:
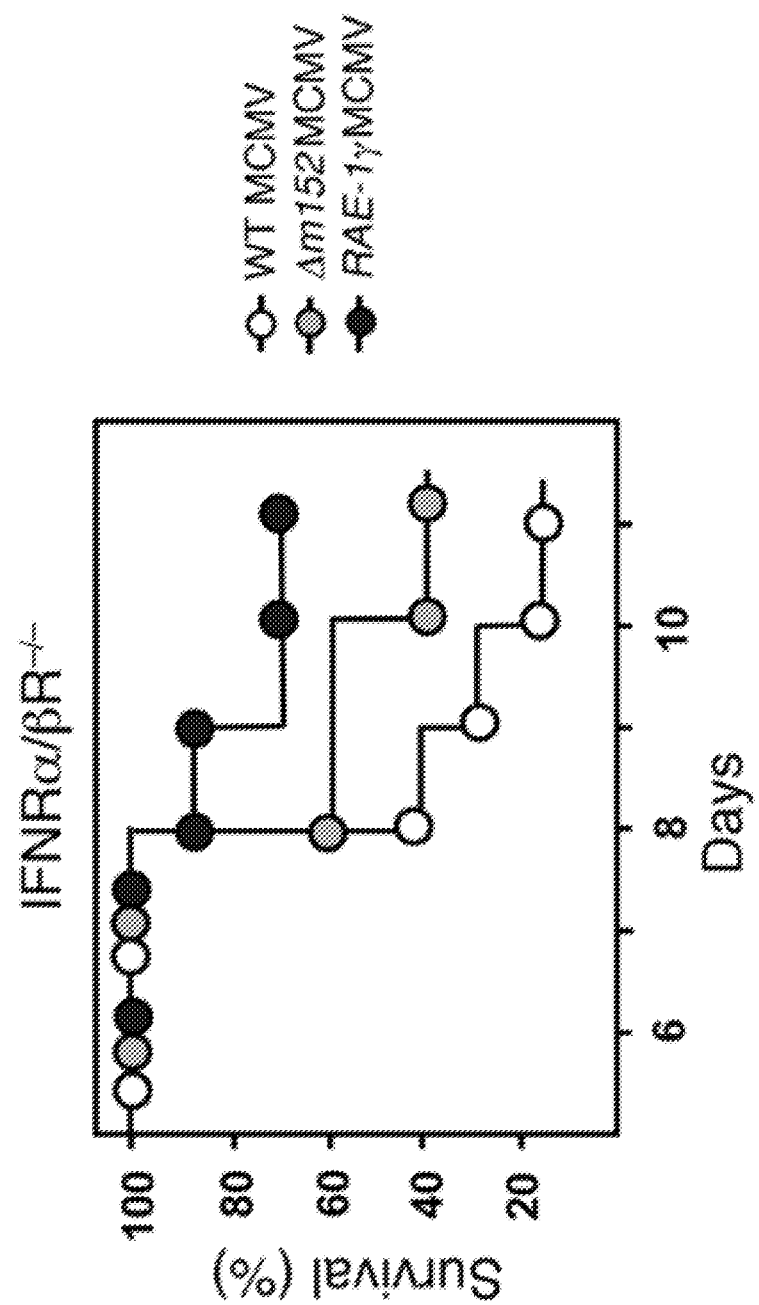
FIG. 6A is a survivorship curve indicating survival of IFNa/bR ko mice infected with MCMV as a function of time.

The result is shown in FIG. 6A.

More particularly, FIG. 6A shows the survival of IFNα/βR$^{-/-}$ mice, also referred to herein as IFNa/bR ko mice, which were i.p. injected with 2×10$^5$ PFU of RAE-1γMCMV (black circles), WT-MCMV (white circle) or Δm152-MCMV (grey circles) and survival rates of which were monitored daily. Combined results of two similar experiments are shown.

It may be taken therefrom that while most of the WT-MCMV and Δm152-MCMV infected mice succumbed to the infection, i.e. 85% and 60%, respectively, the mortality rate of the RAE-1γMCMV infected animals was significantly lower (30%) (see FIG. 6A). NK cells are more resistant to irradiation than other lymphoid cells (Ogasawara, K. et al., 2005, Nat Immunol 6(9):938-45; Erlach, K. C. et al., 2008, Med Microbiol Immunol 197(2):167-78) and RAE-1γMCMV is extremely sensitive to the NK cell control. The present inventor assessed whether residual NK cells, after hematoablative treatment, are sufficient to control RAE-1γMCMV infection. BALB/c mice were hematoablated using a sublethal dose (6 Gy) of total body γ-irradiation 6 hours prior to footpad injection with 10$^5$ PFU of RAE-1γMCMV or WT-MCMV and viral titers were compared on day 7 after infection.

Figure 6B:
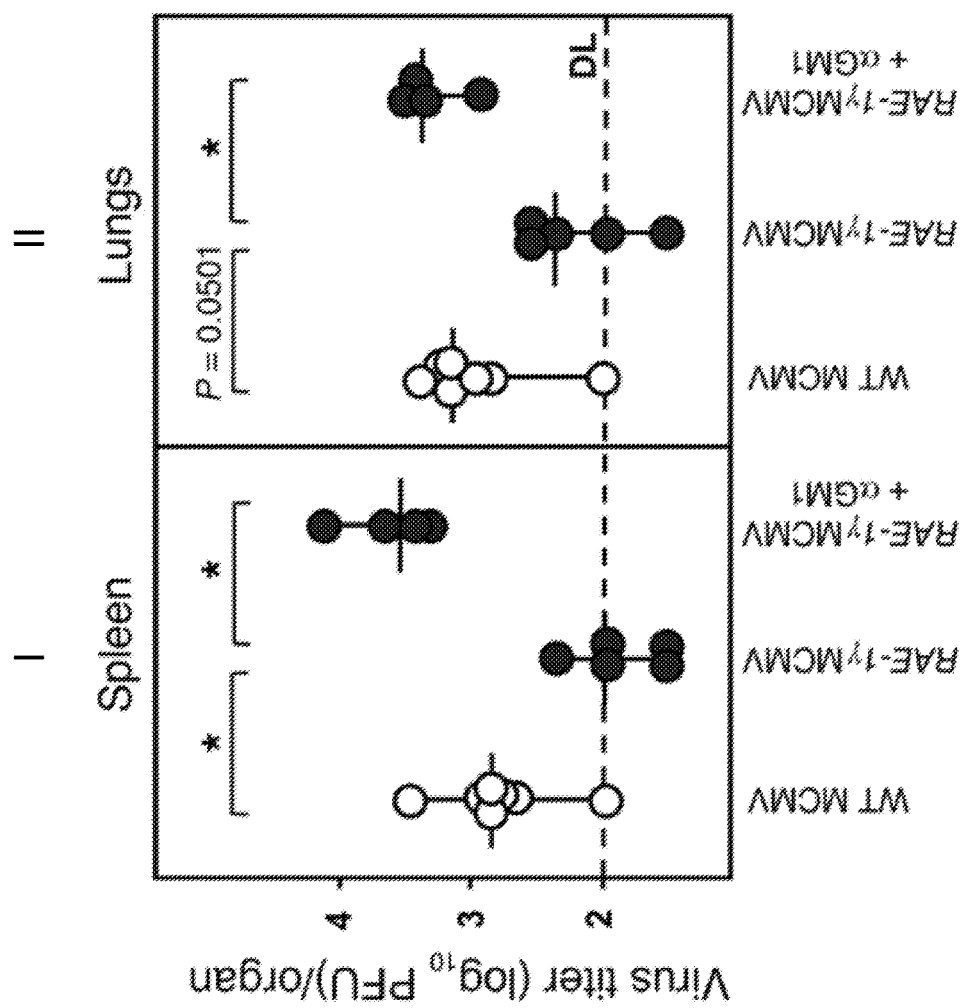

The result is shown in FIG. 6B.

More specifically, FIG. 6B shows the viral load of spleen (left panel) and lungs (right panel) of BALB/c mice which were subjected to 6 Gy total-body γ-irradiation 6 hours prior to f.p. injection with 10$^5$ PFU of RAE-1γMCMV (black circles) or WT-MCMV (white circles).

Were indicated mice were depleted for NK cells by anti-asialoGM1 antibody (αGM1). Viral titers were determined 7 d p.i. by plaque assay. Titers of individual mice (circles) and median values (horizontal bars) are shown as log$_{10}$ PFU per organ on the y-axis. DL means detection limit and is indicated by the dashed line.

It may be taken therefrom that RAE-1γMCMV infection in hematoablated mice resulted in significantly lower viral titers as compared to the WT-MCMV suggesting that residual NK cells are sufficient to restrain RAE-1γMCMV infection (see FIG. 6B).

Together these data argue that infection with the RAE-1γMCMV presents a low risk for disease, even in severely immunodeficient hosts.

Example 10: Maternal RAE-1γMCMV Immunization Protects Neonatal Mice from MCMV Infection Maternal preconception immunity to CMV provides substantial protection against congenital infection (Fowler, K. B. et al., 2003, Jama 289(8):1008-11; Boppana, S. B., and Britt, W. J., 1995, J Infect Dis 171(5):1115-21; Boppana, S. B. et al., 2001, N Engl J Med 344(18):1366-71). The presence of maternal antiviral antibodies is associated with a decreased incidence of intrauterine transmission and better neurological outcomes in the setting of congenital infection. The role of antibodies in the prevention of congenital infection has also been emphasized in the guinea-pig CMV model (Schleiss, M. R., 2008, J Clin Virol 41(3):224-30). Since the mouse hemoplacental barrier does not support MCMV transfer the present inventor established a model of i.p. neonatal MCMV infection whose pathogenesis closely resembles congenital HCMV infection (Koontz, T. et al., 2008, J Exp Med 205(2):423-35). To test whether the maternal antibody response induced by the RAE-1γMCMV immunization can protect neonatal mice from MCMV infection, female BALB/c mice were injected with RAE-1γMCMV, WT-MCMV or mock infected two weeks before mating. A number of neonates were sacrificed on the day of birth and tested for the presence of antiviral antibodies in serum, while the others were i.p. injected with 500 PFU of WT-MCMV and tested for replicating virus in the tissue.

The results are shown in FIG. 7A and FIG. 7B.

More specifically, FIG. 7A, upper panel, shows the antiviral antibody titer indicated as the Optical Intensity, OD, as determined by ELISA of serum of female BALB/c mice which were i.v. injected with 2×10$^5$ PFU of RAE-1γMCMV (black squares) or WT-MCMV (white squares) or mock injected (grey squares) 2 weeks before mating. Antiviral antibody titers in the serum of said females (left panel) and in the serum of the neonates of said females (right panel) were determined by ELISA 6 h post partum. On the x-axis the "-fold" factor of the dilution of the serum subjected to ELISA is indicated. The lower panel is a illustrative scheme of the experimental protocol.

FIG. 7B, upper panel shows an illustrative scheme of the experimental protocol, the lower panel shows a diagram indicating the viral load of the neonates of female BALB/c mice of FIG. 7A, wherein the females were i.v. injected with 2×10$^5$ PFU of RAE-1γMCMV (black squares) or WT-MCMV (white squares) or mock injected (grey squares) 2 weeks before mating and wherein the neonates were i.p. injected with 500 PFU of WT-MCMV 6 h post partum. Viral titers were determined in different organs 9 days post i.p. infection of neonates by plaque assay. Titers of individual mice (circles) and median values (horizontal bars) are shown as log$_{10}$ PFU per gram neonate. DL means detection limit and is indicated by the dashed line.

It may be take therefrom that no antiviral antibodies were detected in the serum of neonates of naive females. By contrast, antiviral antibodies were detected in serum of RAE-1γMCMV and WT-MCMV immunized females and in serum of their neonates confirming passive placental transfer of antiviral antibodies (see FIG. 7A).

Whereas, MCMV infection in infected neonates of naive females resulted in disseminated virus replication, no replicating virus was detected in various tissues at day 9 after the infection in neonates of RAE-1γMCMV immunized females or in neonates of WT-MCMV immunized females (see FIG. 7B).

Thus, immunization with recombinant RAE-1γMCMV induced a maternal antibody response that, upon placental transfer, limited virus dissemination and protected neonatal mice from MCMV infection.

Example 11: Generation and Characterization of Recombinant MCMV Expressing NKG2D Ligand RAE-1γ and Immunodominant CD8+ T Cell Epitope of *Listeria monocytogenes*

*Listeria monocytogenes* is a Gram-positive facultative intracellular pathogen which replicates in the cytoplasm and can spread from cell to cell without being exposed to extracellular environment Immune response to *Listeria monocytogenes* includes a complex network of cytokines and cells of innate and adaptive immunity (Unanue, E R, 1997, Immunol Rev. 158:11-25). For the clearance of *Listeria monocytogenes*, interferon γ, also referred to herein as IFNγ, secreton during early days of infection is required. IFNγ is provided by NK cells as well as by CD8+ T, therewith contributing to innate immune system in response to *Listeria monocytogenes*.

RAE-1γMCMV expressing immunodominant CD8+ T cell epitope of *Listeria monocytogenes*, also referred to herein as RAE-1γMCMVList, was constructed using orthotopic peptide swap method as described by Lemmermann et al. (Lemmermann et al., 2010, supra) on RAE-1γMCMV backbone where Dd-restricted antigenic m164 peptide $_{167}$AGPPRYSRI$_{175}$ (SEQ.ID.NO:2) was swapped with the Kd-restricted listeriolysin O (LLO)-derived peptide $_{91}$GYKDGNEYI$_{99}$ (SEQ. ID. NO: 3) (see FIG. 12A).

Figure 12A:
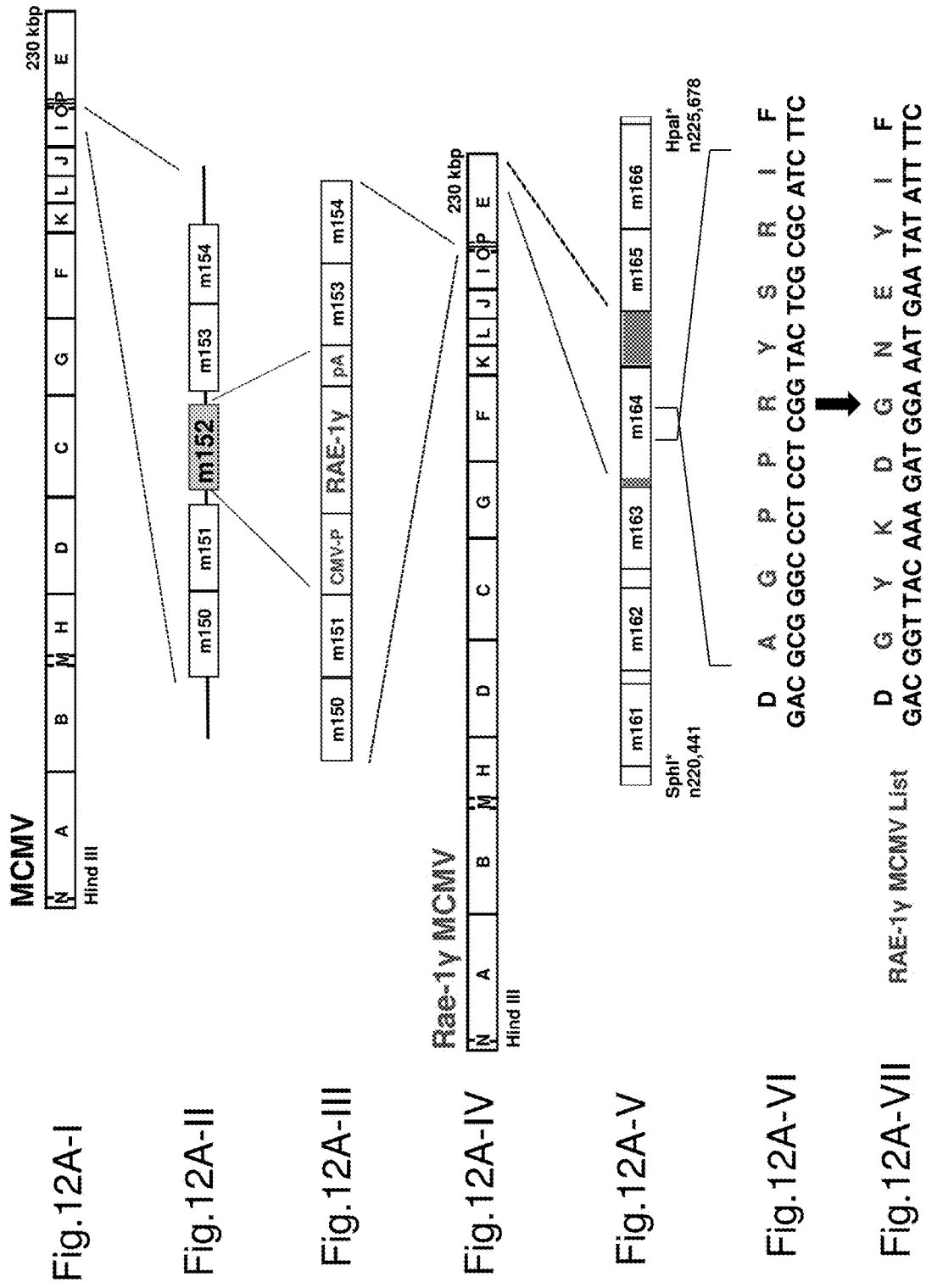

FIG. 12A shows a schematic illustration of the cloning process and genome organization of RAE-1γMCMV and RAE-1γMCMVList. The HindIII cleavage map of the MCMV genome is shown (MCMV) with the genomic region encoding the m152 ORF below. In order to construct RAE-1γMCMV the m152 ORF was replaced by an expression cassette comprising the HCMV major immediate early promoter (CMV-P), the RAE-1γ ORF (RAE-1γ) and the SV40 polyadenylation signal sequence (pA).

The HindIII cleavage map of the RAE-1γMCMV genome is shown (RAE-1γMCMV) with the genomic region encoding the m164 ORF below. In RAE-1γMCMVList the immunodominant m164 epitope ($_{167}$AGPPRYSRI$_{175}$; SEQ. ID. NO: 2) was swapped with listeriolysin epitope (GYKDGNEYI; SEQ. ID. NO: 3).

RAE-1γMCMV backbone was constructed as described herein. In addition, MCMVList virus was constructed where where Dd-restricted antigenic m164 peptide $_{167}$AGPPRYSRI$_{175}$ (SEQ.ID.NO:2) was swapped with the Kd-restricted listeriolysin O (LLO)-derived peptide $_{91}$GYKDGNEYI$_{99}$ (SEQ. ID. NO: 3) in BAC-derived MCMV as a backbone.

Figure 13:
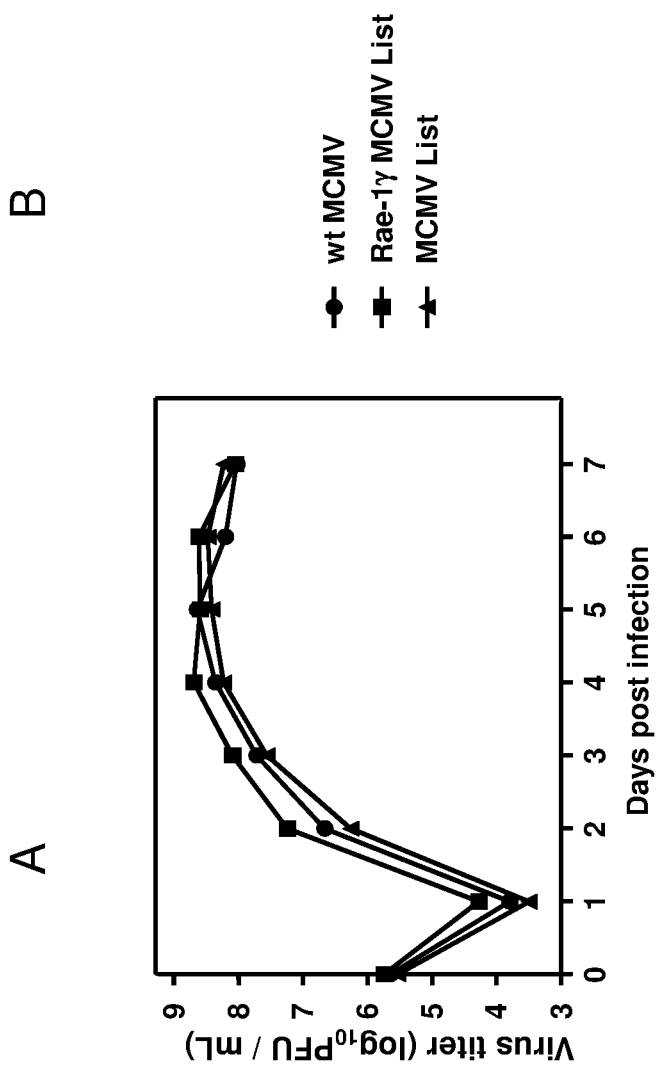

FIG. 13 shows virus titers determined in supernatants of MEF which were infected with 0.1 PFU/cell of WT-MCMV (circles), MCMVList (squares) or RAE-1γMCMVList (triangles). Supernatants were harvested at time points p.i. as indicated on the x-axis and virus titers were determined by plaque assay. The virus titer is depicted on the y-axis as log$_{10}$ PFU per milliliter, ml.

It may be taken therefrom that listeriolysin epitope expression did not interfere with growth of neither the WT-MCMV nor RAE-1γMCMV and both MCMVList and RAE-1γMCMVList had replication kinetics comparable with the one of the WT-MCMV.

Figure 12B:
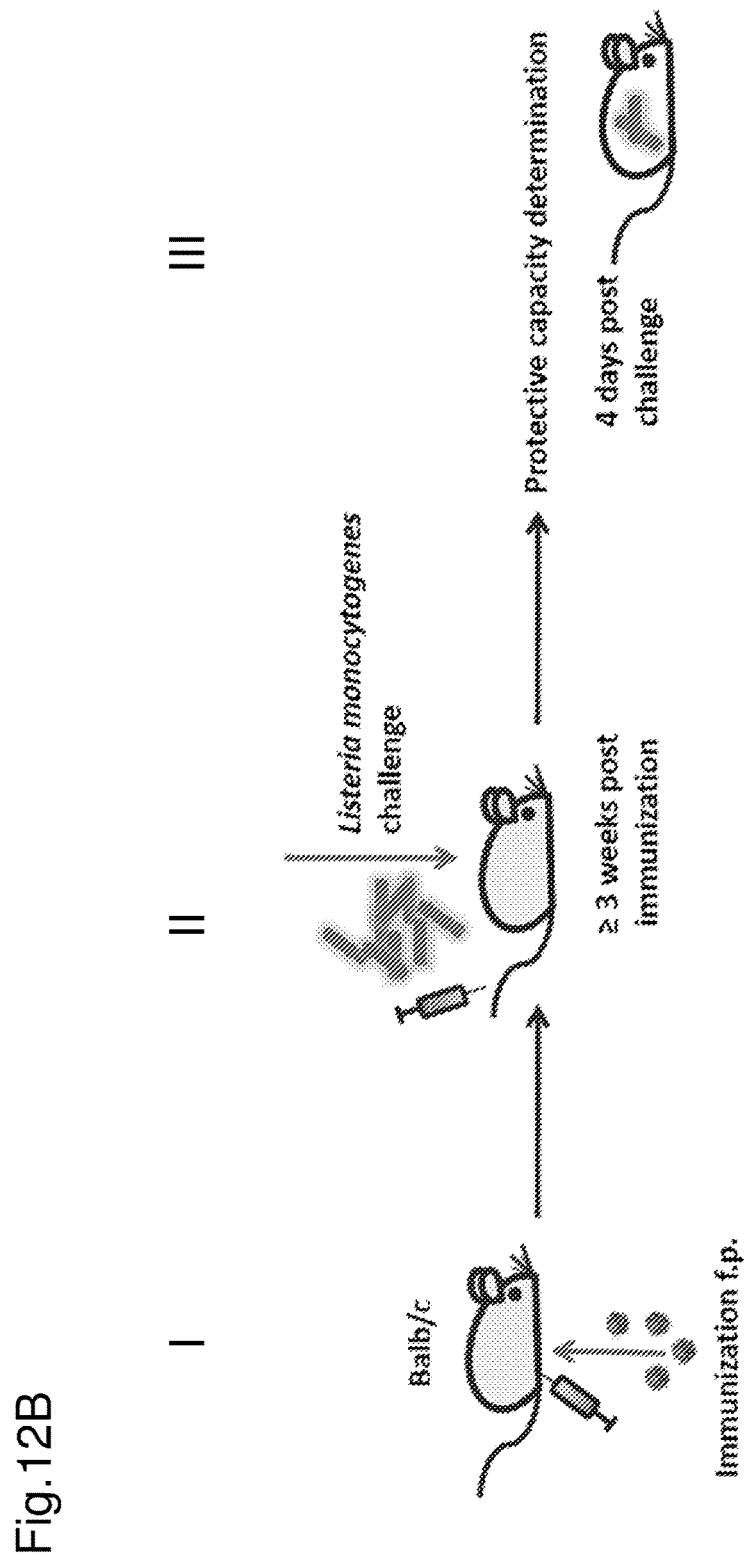

FIG. 12B shows an illustrative scheme of the experimental protocol of experiments applying *Listeria monocytogenes* challenge. Balb/c mice were vaccinated f.p. with 10$^5$ PFU of WT-MCMV, MCMVList or RAE-1γMCMVList, respectively, at least three weeks prior to *Listeria monocytogenes* challenge. Four days after challenge CFU in spleen and liver was determined. Listeriolysin-specific CD8+ T cell response was measured on isolated splenocytes by stimulation with listeriolysin peptide and intracellular staining for IFNγ.

Example 12: Expression of NKG2D Ligand Enhances CD8+ T Cell Response Against Immunodominant Epitope Derived from *Listeria monocytogenes*

To test the effect of NKG2D ligand expression in response to listeriolysin epitope, BALB/c mice were injected footpad (f.p) with 2×10$^5$ PFU of RAE-1γMCMV expressing listeriolysin epitope, also referred to herein as RAE-1γMCMVList, or WT-MCMV expressing listeriolysin epitope, also referred to herein as MCMVList. As already mentioned in Example 3 herein, MCMV expressing RAE-1γ was highly attenuated in vivo, which may also be taken from FIG. 14.

Figure 14:
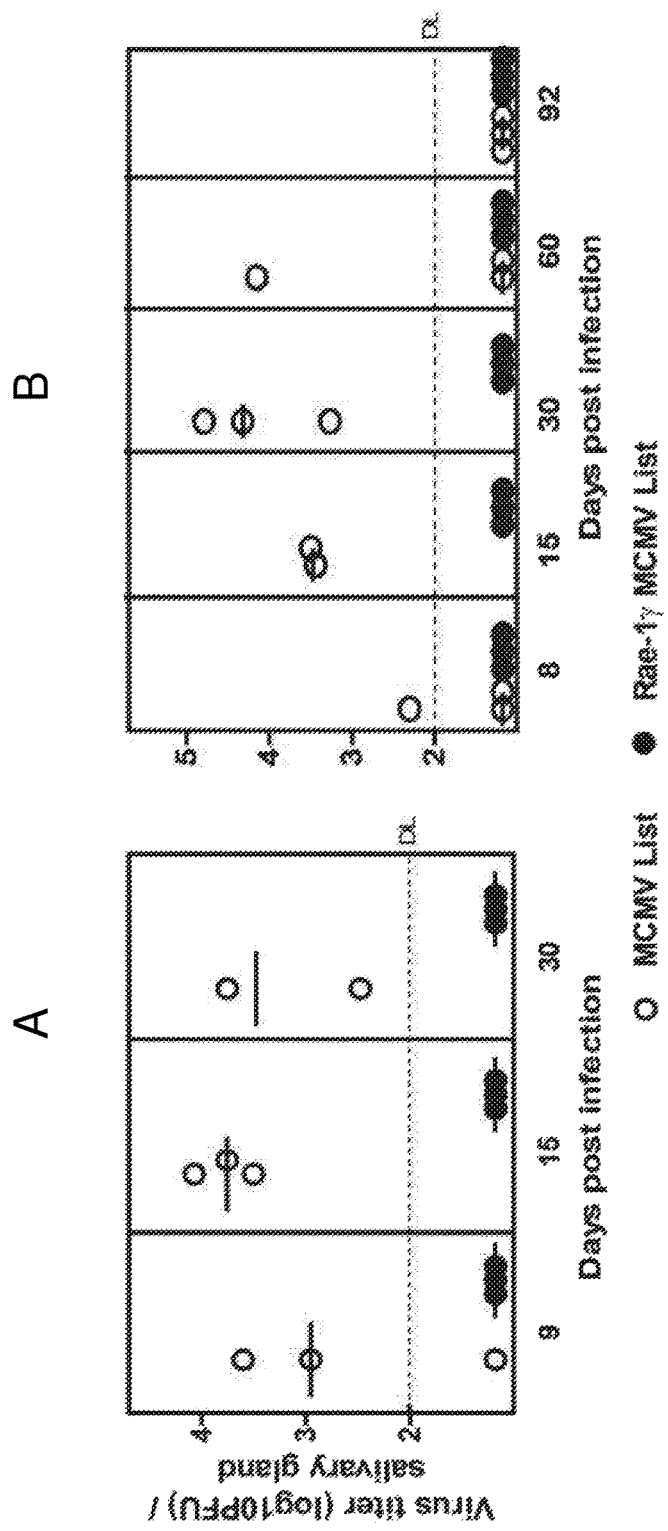

More particularly, FIG. 14 shows the results of two individual experiments (left and right panel). Balb/c mice were f.p. infected with 2×10$^5$ PFU of MCMV expressing listeriolysin epitope, i.e. MCMVList (white circles), or MCMV expressing RAE-1γ ligand and listeriolysin epitope, i.e. RAE-1γMCMVList (black circles). Virus titers in salivary glands were determined at various time points post infection by standard plaque assay. Virus titers per organ for individual animals (circles) and as median values (bars) as log$^{10}$ PFU per salivary gland on the y-axis, are shown. DL means detection limit and is indicated by the dashed line.

Figure 15:
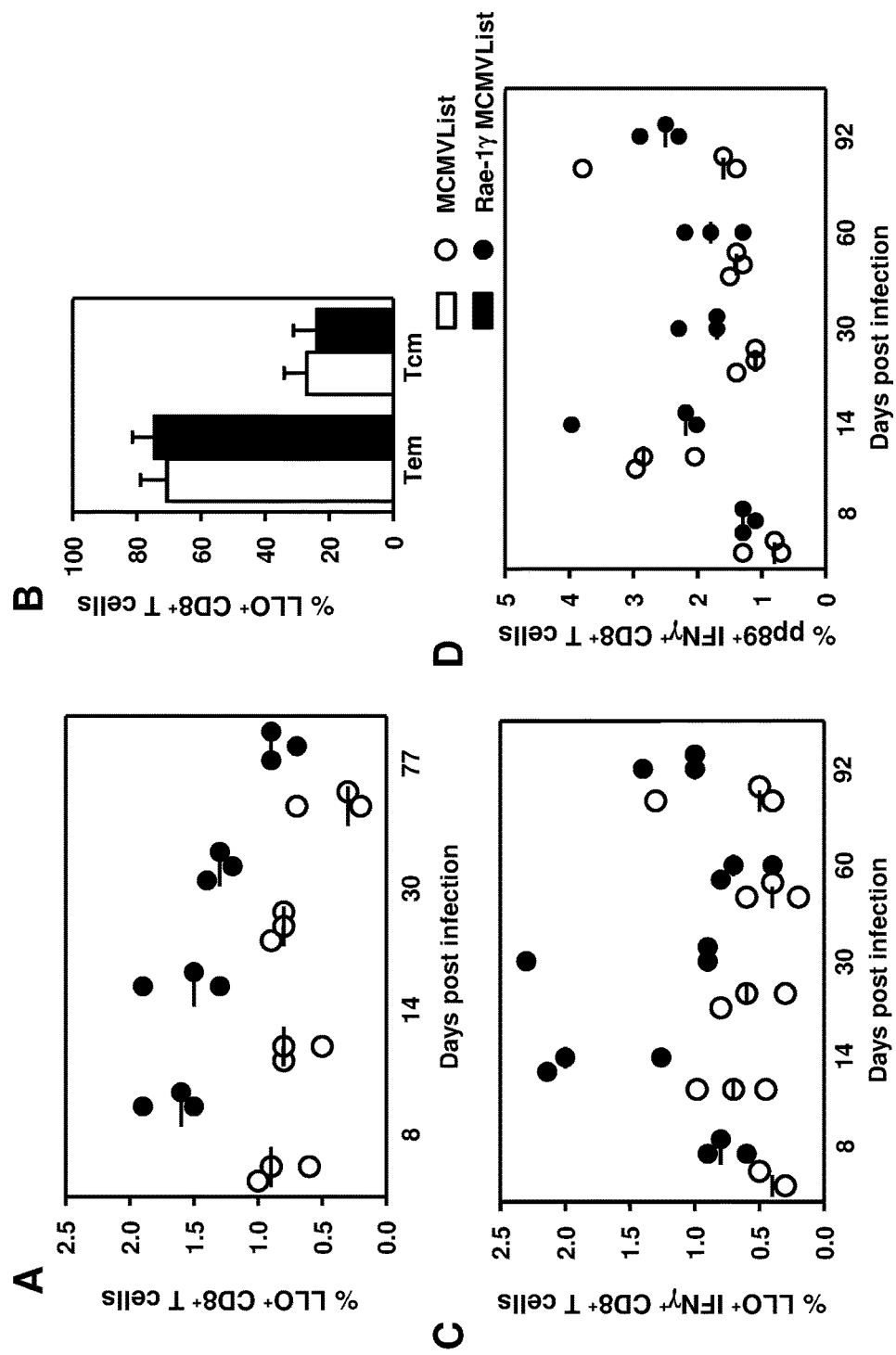

The kinetics of listeriolysin specific CD8+ T cell response was followed up to three months post infection. The results are shown in FIG. 15. BALB/c mice were infected with 10$^5$ PFU f.p. of MCMVList or RAE-1γ MCMVList. At indicated time points frequency of LLO specific CD8+ T cells was determined. The results may be taken from FIG. 15A. Effector memory (Tem, CD44+ CD62L−) and central memory (Tcm, CD44+ CD62L+) phenotype of listeriolysin specific CD8+ T cells was determined at day 77 p.i. The results may be taken from FIG. 15B. Error bars show mean±SD. BALB/c mice were infected with 2×10$^5$ PFU f.p. of MCMVList or RAE-1γ MCMVList. At indicated time points splenocytes were isolated, stimulated with listeriolysin (FIG. 15C) or pp89 peptide (FIG. 15D) and intracellulary stained for IFNγ production. Individual animals (circles) and median values are shown.

As may be taken therefrom the frequency of listeriolysin specific CD8+ T cells was higher in mice immunized with RAE-1γMCMV expressing listeriolysin compared with mice immunized with the virus expressing listeriolysin epitope only. Moreover, listeriolysin specific CD8+ T cells derived from both MCMVList and RAE-1γMCMVList infection retained effector memory phenotype. Altogether, this finding indicated that NKG2D ligand expressed in the context of MCMV enhances CD8+ T cell response to foreign epitope.

Example 13: Expression of NKG2D Ligand Dramatically Improves Protective Capacity of MCMV Vector The above results demonstrate that RAE-1γ expressed in MCMV vector considerably improves listeriolysin specific CD8⁺ T cell response. Next the present inventor tested how this correlates with protection of vaccinated mice against challenge infection with *Listeria monocytogenes*. For that reason BALB/c mice were vaccinated with 10⁵ PFU f.p. of WT-MCMV, MCMVList or RAE-1γMCMVList, or left unvaccinated. Three weeks post vaccination mice were challenged with 2×10⁵ CFU/mouse of *Listeria monocytogenes* EGD.

The result is shown in FIG. 16A.

Figure 16:
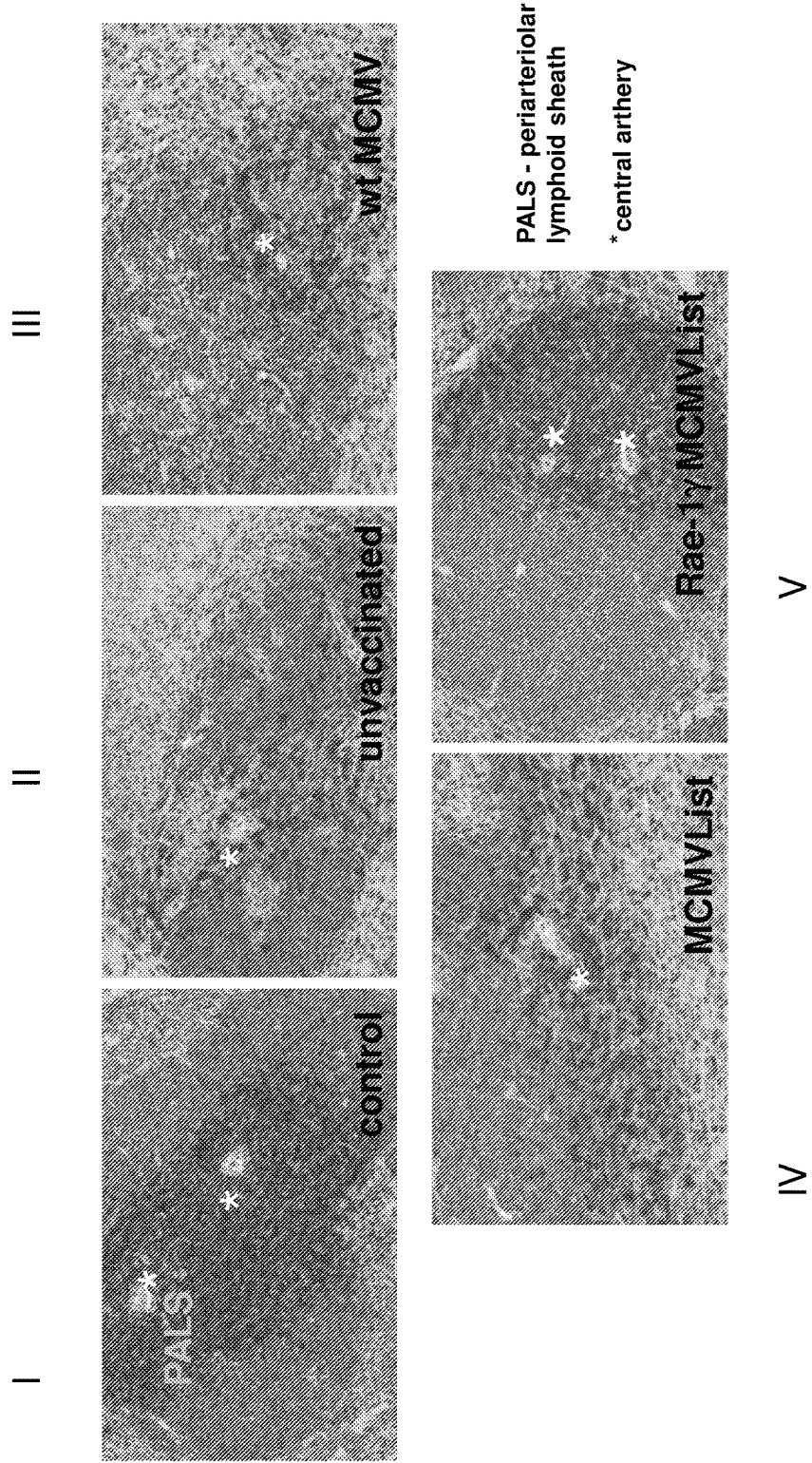

More particularly, FIG. 16 A shows colony-forming units of *Listeria monocytogenes* of Balb/c mice which were vaccinated f.p. with 10⁵ PFU of WT-MCMV (dark grey bars), MCMVList (white bars), RAE-1γMCMVList (black bars) or left uninfected (light grey bars, Ø). At ≥ three weeks post vaccination all groups were challenged i.v. with *Listeria monocytogenes*, also referred to herein as LM, EGD strain serotype 1/2a. Challenge was performed with 3000 CFU of LM (low dose, left and right upper panel) and ~2×10⁴ CFU of LM (high dose, left and right lower panel). Four days after challenge CFU was determined in spleen (upper and lower left panel) and liver (upper and lower right panel). Results are presented as mean±SEM of five mice per vaccinated group; DL means detection limit and is indicated by the dashed line.

It may be taken therefrom that injection of *Listeria monocytogenes* into naive mice resulted in high bacterial load in both spleen and liver (see FIG. 16A). Mice vaccinated with MCMV expressing listeriolysin showed significantly lower load of bacteria, both in liver and spleen in comparison to naïve mice. However, mice vaccinated with RAE-1γMCMVList almost cleared the bacteria from spleen (differences compared to naïve mice were ~6 logs). Similar differences were detected in liver (difference of ~5 logs). Therefore, NKG2D ligand expressed in context of MCMV vector dramatically enhanced protective capacity mediated by CD8⁺ T cells directed against single immunodominant epitope (see FIG. 16A). Similar results were obtained in three independent experiments. In addition, infection of mice with WT-MCMV failed to provide any protection against *Listeria monocytogenes* challenge, which may be also taken from FIG. 16A.

Additionally, four days post challenge paraffin embedded spleen sections were stained with aCD3 antibody.

The results are shown in FIG. 16B.

More particularly, FIG. 16B shows micrographs at a magnification of 40× of Paraffin-embedded spleen sections taken on day 4 post challenge and stained for CD3 expression of BALB/c mice infected with 1×10⁵ PFU/mouse [CAM: PFU?]f.p. of the indicated viruses or left uninfected. Three weeks p.i. mice were challenged with 1×10⁴ CFU/mouse of *L. monocytogenes*.

It may be taken therefrom that RAE-1γMCMVList immunization preserves a periartheriolar lymphoid sheath (PALS) in *L. monocytogenes* challenge.

In addition, the efficacy of the RAE-1γMCMVList vaccine was also illustrated by the preservation of T cells in the periarteriolar lymphoid sheath of infected spleens, which are known to be depleted after *L. monocytogenes* infection (Merrick, J. C., et al. 1997, Am J Pathol 151(3): 785-92; Carrero, J. A. et al. 2004 J Immunol 172(8): 4866-74)

Altogether, the herpesviral vector engineered to express the NKG2D ligand RAE-1γ generated a highly protective LLO-specific response that was able to efficiently cope with a *L. monocytogenes* challenge infection. In vivo protective capacity correlated well with the frequency of listeriolysin specific CD8⁺ T cells directed against listeriolysin epitope, as measured four days post challenge, which may be taken from FIG. 17. This finding is more interesting bearing in mind that the frequency of listeriolysin specific CD8⁺ T cells in mice before challenge was not so dramatically different.

Figure 17:
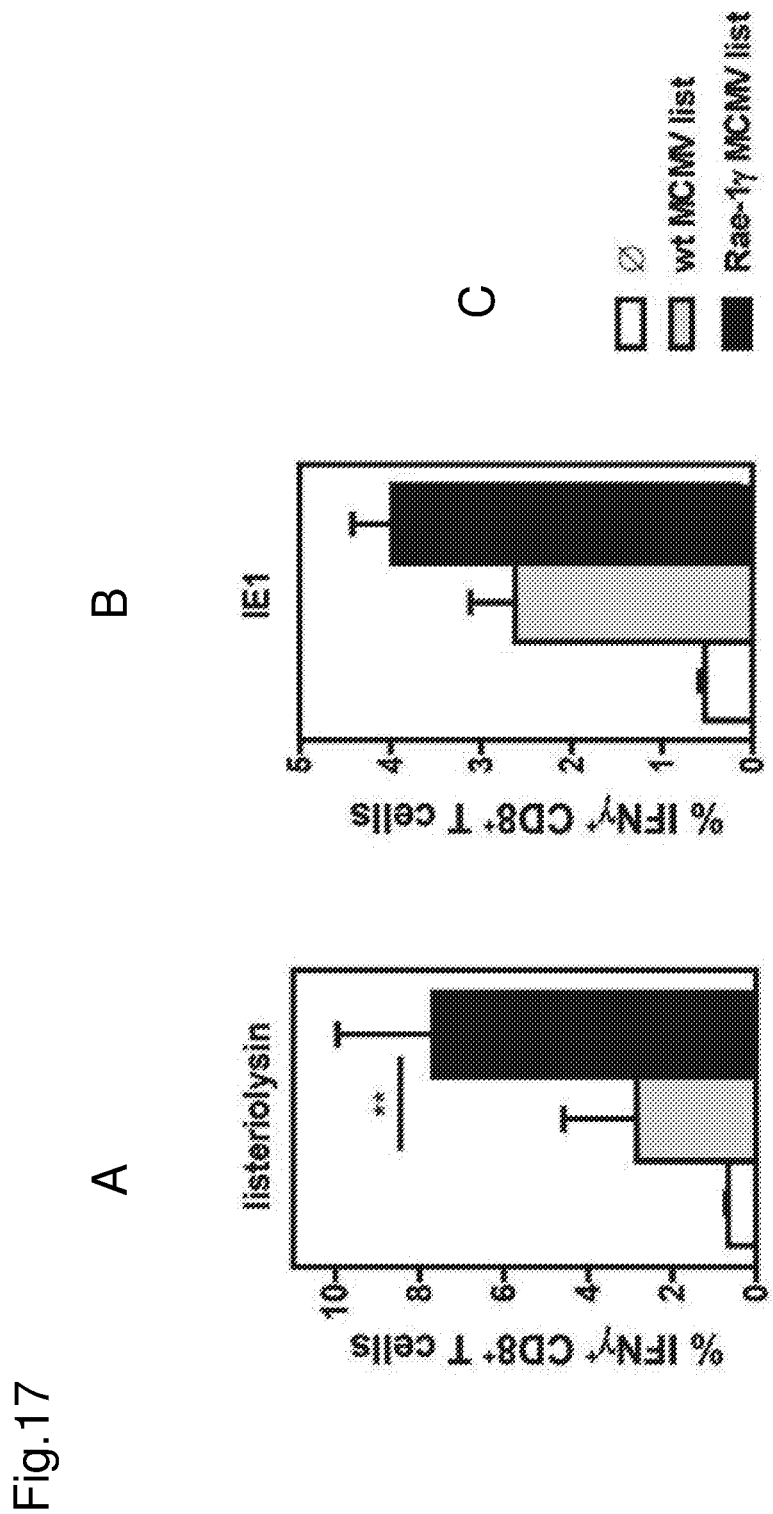

More particularly, FIG. 17 shows the percentage of IFNγ⁺ CD8⁺ T cells of splenocytes from Balb/c mice which were f.p. vaccinated with 10⁵ PFU of MCMVList (wt MCMV-List, light grey bars), RAE-1γMCMVList (black bars) or left unvaccinated (white bars, Ø). Three weeks post vaccination all groups of mice were challenged with 2×10⁴ CFU of *Listeria monocytogenes*. Four days post challenge splenocytes were isolated, stimulated with 1 listeriolysin peptide according to SEQ.ID.NO:3 (left panel) or pp89-peptide according to SEQ. ID. NO: 1 (right panel), and stained intracellularly for IFNγ production. The percentage of peptide specific IFNγ⁺ CD8⁺ T cells for five mice per group is shown. Results are shown as mean±SD and are representative of three individual experiments.

Example 14: Protective Capacity Against *Listeria monocytogenes* Challenge in RAE-1γMCMVList Immunized Mice is CD8⁺ T Cell Dependant In the light of the above described Examples, a person skilled in the art would expect that CD8⁺ T cells were responsible for protection against challenge infection with *Listeria monocytogenes*. However, mice vaccinated with either RAE-1γMCMVList or MCMVList were exposed to although immunodominant yet single epitope of this pathogen.

In connection therewith it is important to know that in the prior art it was shown so far that previous infection with herpes viruses may increase the resistance of the host against unrelated bacterial or viral pathogens (Barton E S et al. 2007, Nature; 447(7142):326-9).

Therefore, four weeks after infection with RAE-1γMCMVList, MCMVList or WT-MCMV mice were challenged with 3000 CFU of *Listeria monocytogenes* with and without depletion of CD8⁺ T cells.

Figure 18:
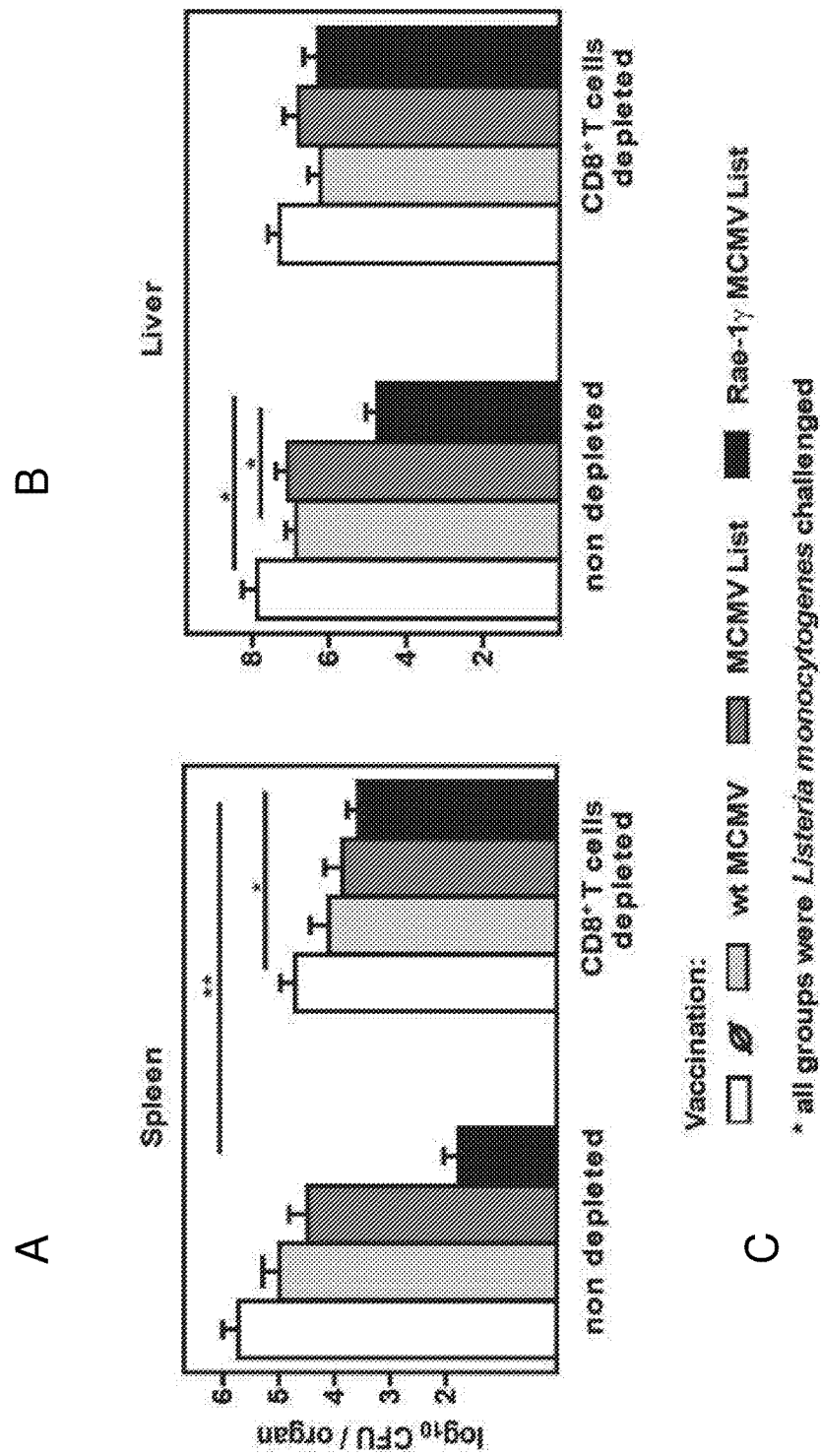

The result is shown in FIG. 18.

More particularly, FIG. 18 shows colony-forming units of *Listeria monocytogenes* of. Balb/c mice which were f.p. vaccinated with 10⁵ PFU of WT-MCMV (light grey bars), MCMVList (dark grey bars), RAE-1γMCMVList (black bars) or left unvaccinated (white bars). Four weeks post vaccination mice were challenged with 4×10³ CFU/mouse of *Listeria monocytogenes* EGD. Prior to challenge mice were depleted for CD8 T cells or left undeleted. CFU in spleen and liver was determined four days post challenge, as indicated on the x-axis. Four days post challenge CFU in liver (right panel) and spleen (left panel) was determined. Results are shown as mean±SD for five mice per group. Colony forming units are indicated as log₁₀ CFU per organ on the y-axis.

It may be taken therefrom that the protective capacity of RAE-1γMCMVList is CD8⁺ T cell dependent. More particularly, RAE-1γMCMVList immunized mice showed much lower bacterial load in spleen and liver, compared to groups of mice immunized with MCMVList, mice immunized with WT-MCMV or naïve mice. These differences were practically abolished after depletion of CD8⁺ T cells confirming that these cells present dominant protective principle.

Figure 19:
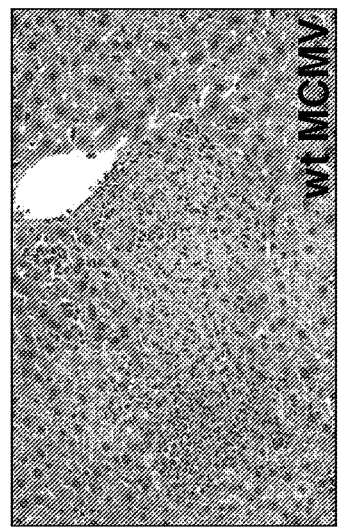
Figure 19:
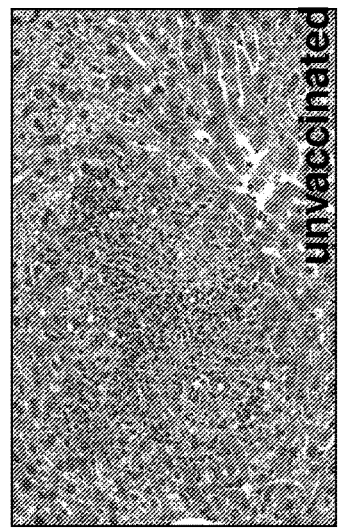
Figure 19:
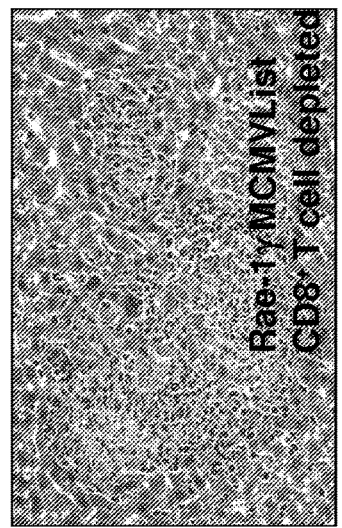
Figure 19:
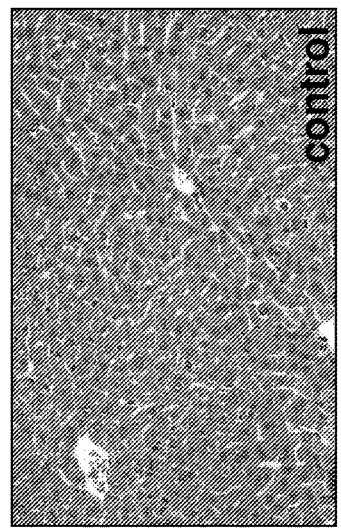
Figure 19:
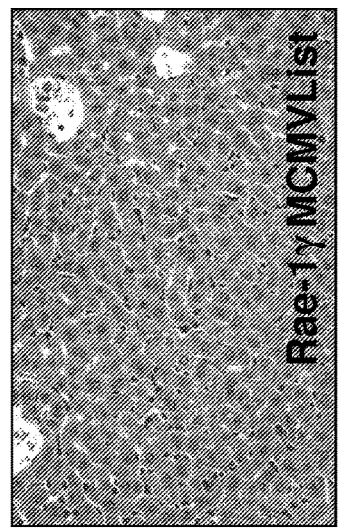
Figure 19:
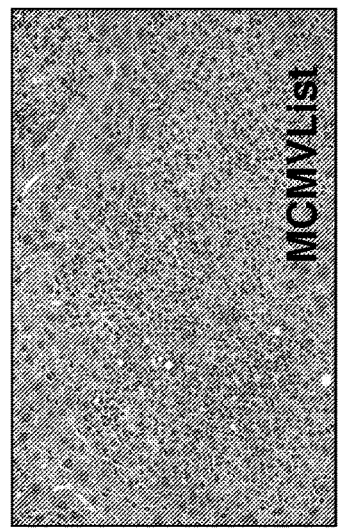

Pathohistological lesions in liver of infected mice were in accordance with these results, which may be taken from FIG. 19.

More particularly, FIG. 19 shows micrographs (Magnification 200×) of stainings of liver tissues from Balb/c mice which were left unvaccinated, or vaccinated f.p. with $10^5$ PFU of WT-MCMV, MCMVList, and RAE-1γMCMVList. Four weeks after vaccination mice were challenged with $3\times10^3$ CFU of Listeria monocytogenes. Additionally, RAE-1γMCMVList vaccinated mice were depleted for CD8+ T cells prior to challenge. Four days post challenge staining of the liver tissues was performed. Normal unvaccinated mice were used as control (HE, ×200).

It may be taken therefrom that infection of naïve mice with Listeria monocytogenes resulted in lesions throughout the liver. The lesions were characterized by multifocal inflammatory infiltrates with necrosis as well as microvesicular vacuolation of the hepatocytes. Similar pathohistological lesions were observed in mice previously infected with WT-MCMV. Interestingly, massive multifocal lesions were also observed in mice immunized with MCMVList, despite the lower bacterial load in livers and spleens as compared to nonimmunised control groups. In contrast, the liver of mice immunized with RAE-1γMCMVList was practically of normal histological appearance and only rare inflammatory foci were observed. Depletion of CD8+ T cells not only abolished protection but also resulted in multifocal inflammation and necrosis, similar to those observed in naïve Listeria monocytogenes infected mice.

Altogether, these results showed that RAE-1γMCMV is a potent vector for CD8+ T cell based vaccine approach.

In Listeria monocytogenes infection, NK cells produce IFNγ as a result of contact with infected bone marrow derived dendritic cells, also referred to herein as BMDCs, as well as in a response to different cytokines (Humann, J. and Lenz, L. L. 2010, J Immunol 184(9):5172-8).

Figure 20:
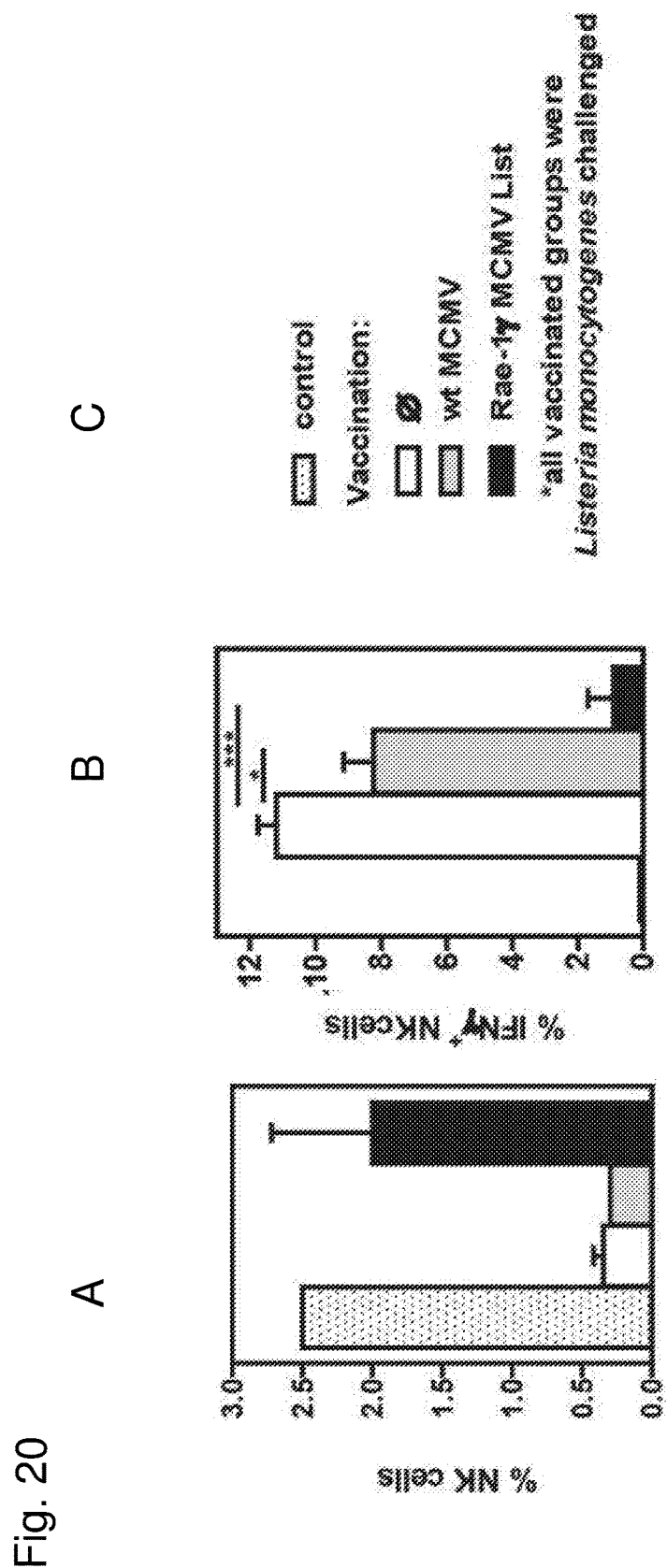

As may be taken from FIG. 20, injection of Listeria monocytogenes into naïve mice resulted in depletion of splenic NK cells.

More particularly, FIG. 20 shows the percentage of IFNγ+ NK cells and percentage of total NK cells of splenocytes of Balb/c mice which were f.p. vaccinated with $10^5$ PFU of WT-MCMV (light grey bars), RAE-1γMCMVList (black bars) or left unvaccinated (white bars, Ø). Four weeks post vaccination all groups of mice were challenged with $4\times10^3$ CFU of Listeria monocytogenes. Four days post challenge splenocytes were isolated and percentage of IFNγ producing NK cells (right panel) and percentage of total NK cells (left panel) were determined. Naïve mice non-challenged with Listeria monocytogenes were used as a control (control, dotted bar). Results are shown as mean±SD and are representative of three individual experiments.

Listeria monocytogenes challenge of naive and wt MCMV vaccinated mice resulted in dramatic reduction of splenic NK cells γ (FIG. 20, left). In contrast, frequency of NK cells in RAE1gMCMVList vaccinated mice remained similar to uninfected control. Moreover, splenic NK cells in RAE-1γMCMVList vaccinated mice remained inactive after challenge infection. However, remaining NK cells in naive and wt MCMV immunized mice after challenge infection showed activation phenotype as demonstrated by expression of CD69 (not shown) and IFNγ production (FIG. 20, right). Thus, the results indicate that efficient CD8+ T cell response in RAE-1γMCMVList not only preserved NK cell frequency but there was also no need for their activation, most likely because bacteria fail to reach splenic area and induce NK cell response Example 15: Enhanced CD8+ T Cell Response in Mice Infected with RAE-1γMCMVList Correlates with Preserved DCs It is well established that systemic MCMV infection results in depletion of splenic conventional dendritic cells (cDCs). Here the present inventor tested the impact of WT-MCMV and RAE-1γMCMVList on the frequency of cDC subsets in spleen.

Figure 21:
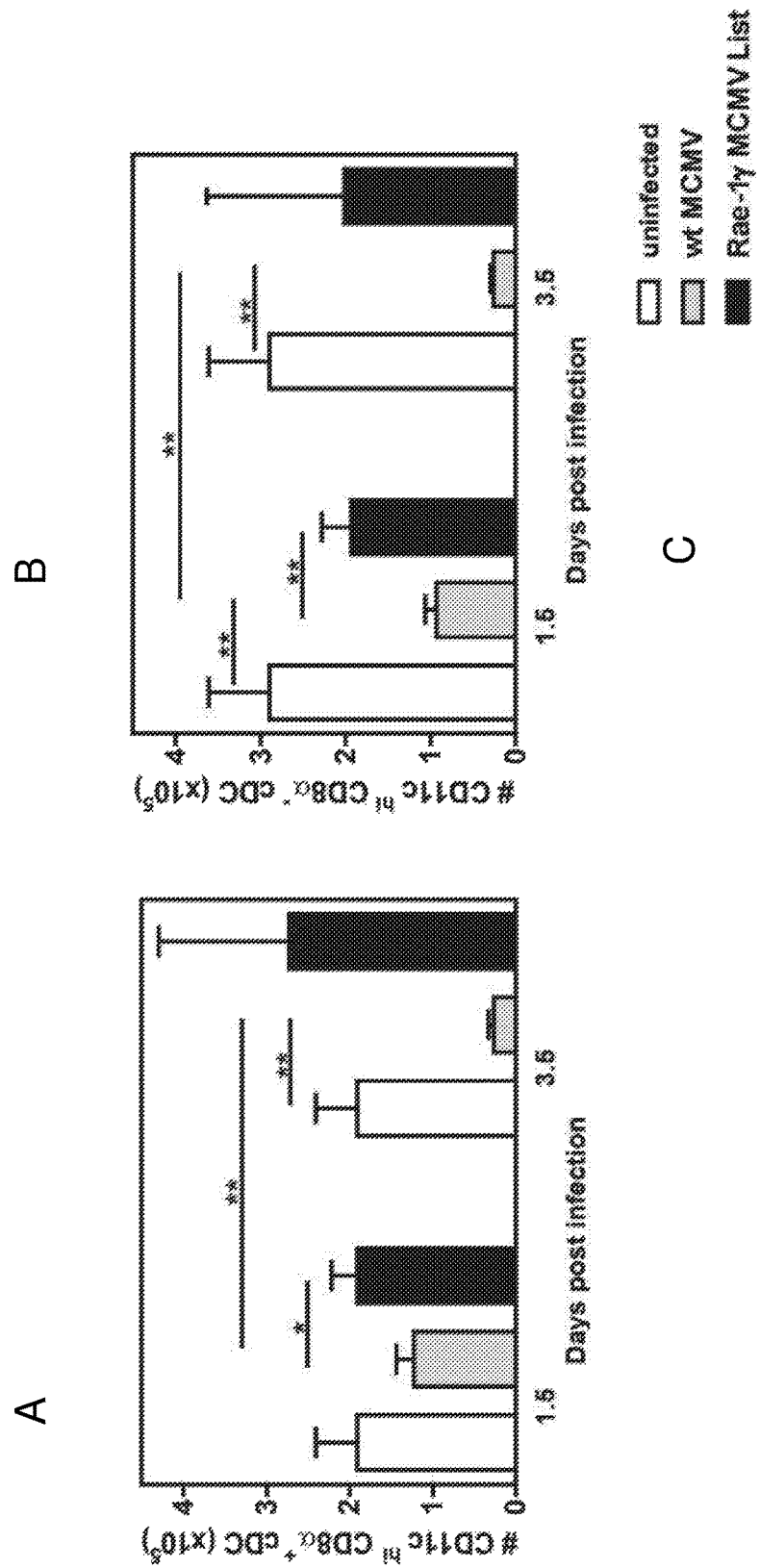

The result is shown in FIG. 21.

More particularly, FIG. 21 shows CDa+DCs (Cd11c$^{hi}$ CD8a+, left panel) and CD11bDCs (Cd11c$^{hi}$ CD8a+, right panel) of Balb/c mice which were i.v. infected with $2\times10^5$ PFU of WT-MCMV (light grey bars), RAE-1γMCMVList (black bars) or left uninfected (white bars). On indicated days post infection splenocytes were isolated and stained for the frequency of CD8a+DCs (Cd11c$^{hi}$ CD8a+, left panel) and CD11bDCs (Cd11c$^{hi}$ CD8a−, right panel) within CD3− CD19− MHCI+ population. Results are shown as mean±SD for three mice per group and are representative of two individual experiments. The number of CDa+DCs (Cd11c$^{hi}$ CD8a+, left panel) and CD11bDCs (Cd11c$^{hi}$ CD8a−, right panel) cells, respectively, is depicted as the $10^5$th part of total number (#×$10^5$) on the y-axis.

More precisely, mice were infected i.v. with indicated viruses or left uninfected and splenic cDCs were isolated using collagenase D digestion and analyzed for CD3− CD19− MHCII+ CD11c$^{hi}$ CD8α expression. It may be taken from FIG. 21 that on day 1.5 p.i. the frequency of CD8αDCs (CD11c$^{hi}$ CD8α+ DCs) in WT-MCMV infected mice was already lower than in control non infected mice (see FIG. 21, left panel). The decrease in CD8αDCs cells was even more pronounced on day 3.5 p.i. However, in mice infected with RAE-1γMCMVList the frequency of CD8αDCs was not affected, or was even slightly increased at later time point. The frequency of CD11bDCs (CD11c$^{hi}$ CD8α− DCs) was reduced after infection with WT-MCMV, but also after infection with RAE-1γMCMVList (see FIG. 21, right panel).

Yet, the loss of CD11b DC subset was less pronounced in RAE-1γMCMVList infected mice when compared to WT-MCMV infected (see FIG. 21).

Next the present inventor tested frequency of plasmacytoid dendritic cells (pDCs) and serum level of interferon alfa (IFNα). IFNα is known to promote NK cell cytotoxicity (Biron, C A. et al., 1999, Annu Rev Immunol. 17:189-220), but can also act immunosuppressive when produced in high concentrations.

Figure 22:
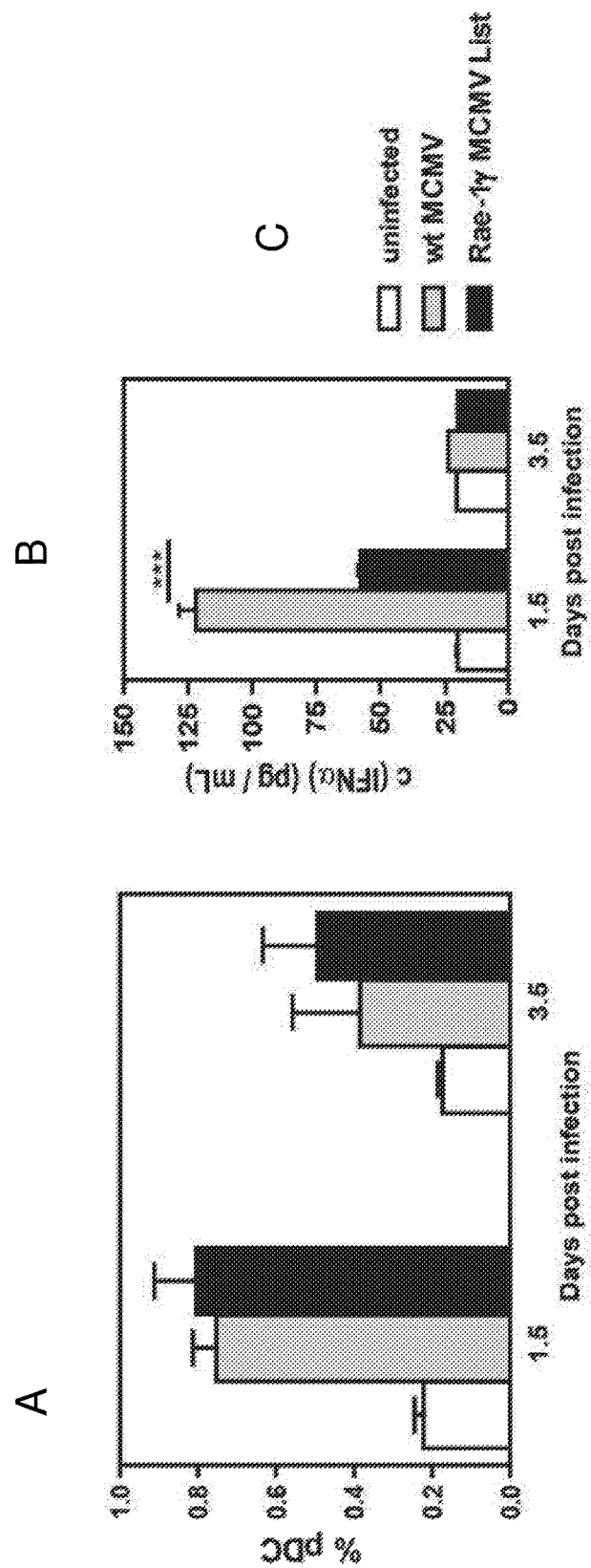

The result is shown in FIG. 22.

More particularly, FIG. 22 shows the percentage of pDC (left panel) and the concentration of IFNa of Balb/c mice which were i.v. infected with $2\times10^5$ PFU of WT-MCMV (light grey bars), RAE-1γMCMVList (black bars) or left uninfected (white bars) on time points post infection as indicated on the x-axis. Splenocytes were isolated and stained for B220+ PDCA-1+ phenotype (left panel) or the concentration of the IFNa in the sera of the infected mice was determined (right panel). Results are shown as mean±SD for three mice per group.

It may be taken therefrom that there was no significant difference in the frequency of pDCs during infection with both WT-MCMV and RAE-1γMCMVList. Interestingly, however, the serum level of IFNα at day 1.5 was significantly higher in mice infected with WT-MCMV as compared to RAE-1γMCMVList infected mice (see FIG. 22).

The above results indicate that early events after infection might be decisive for the differences observed in protective capacity of RAE-1γMCMVList. Therefore the present inventor also tested early CD8+ T cell response upon infection with either WT-MCMV, MCMVList or RAE-1γMCMVList.

Figure 23:
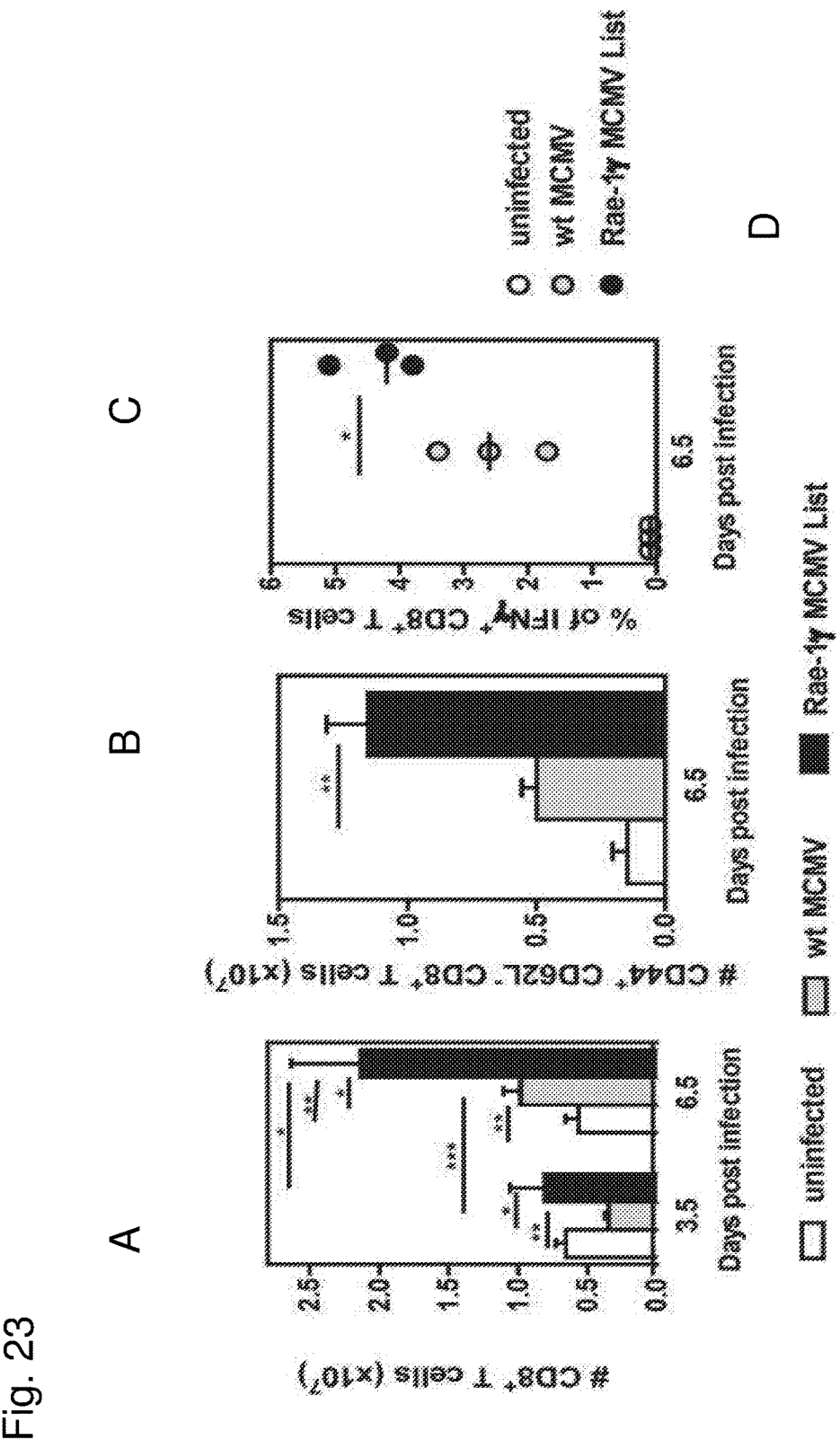
Figure 24A:
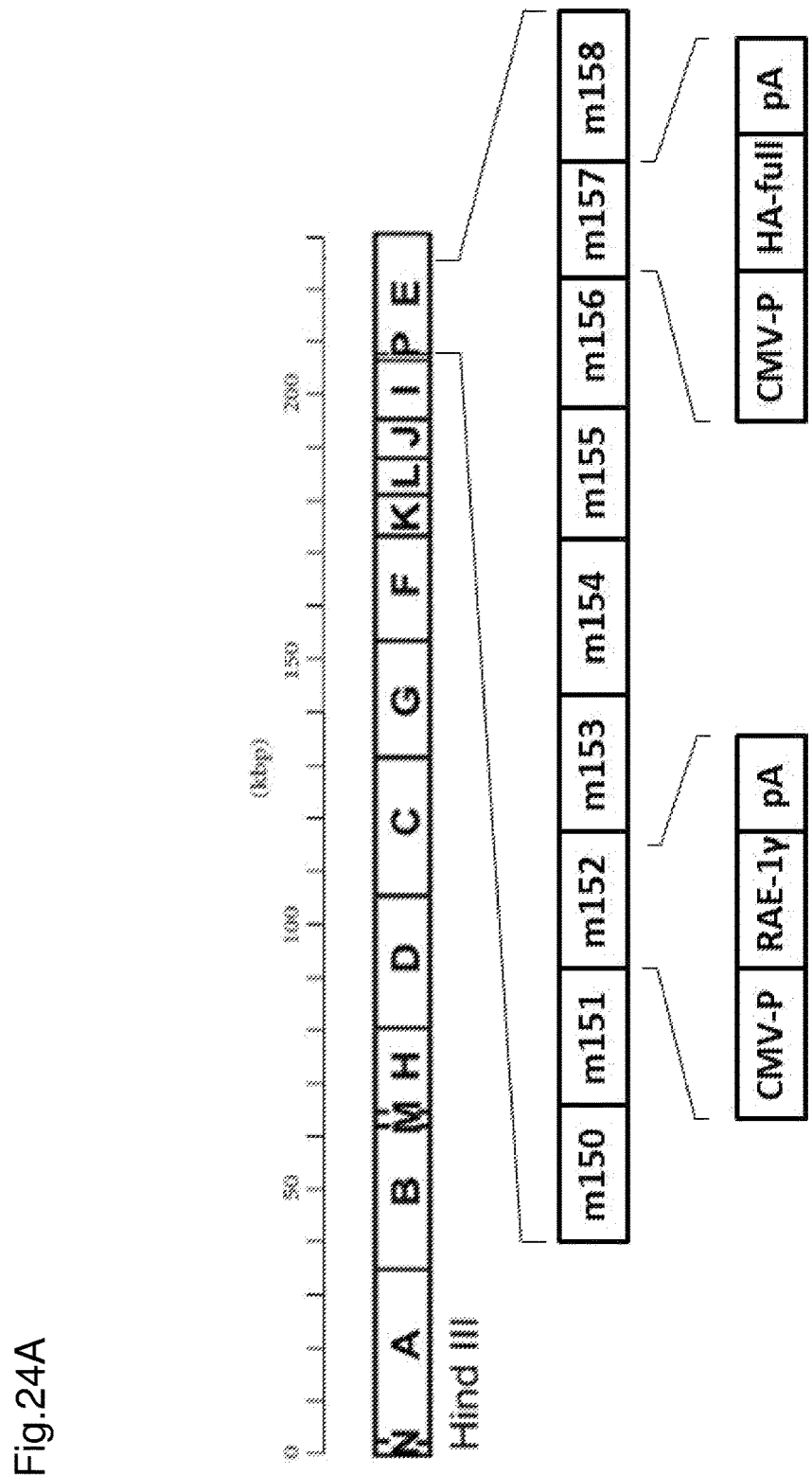
Figure 24B:
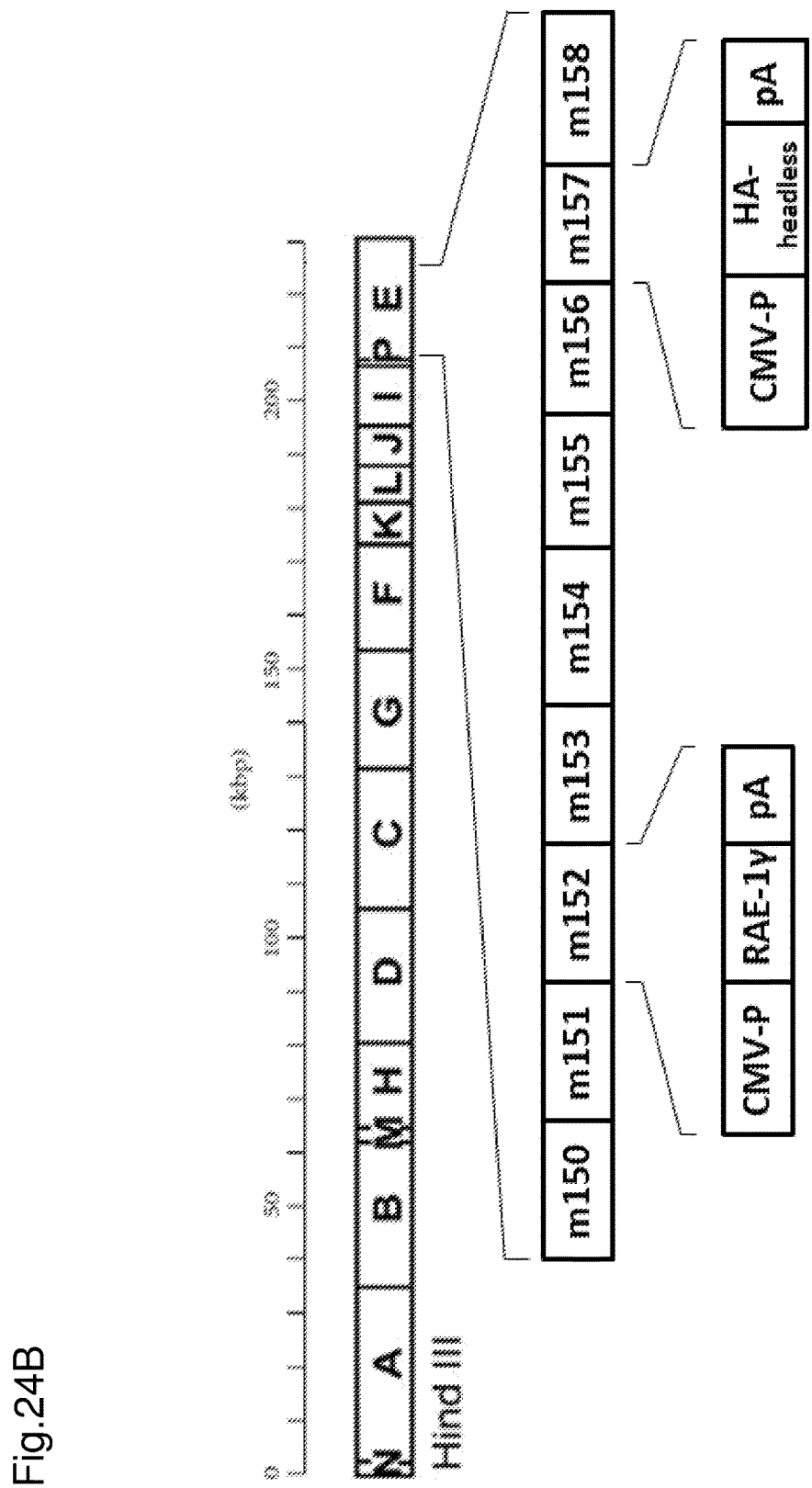
Figure 24C:
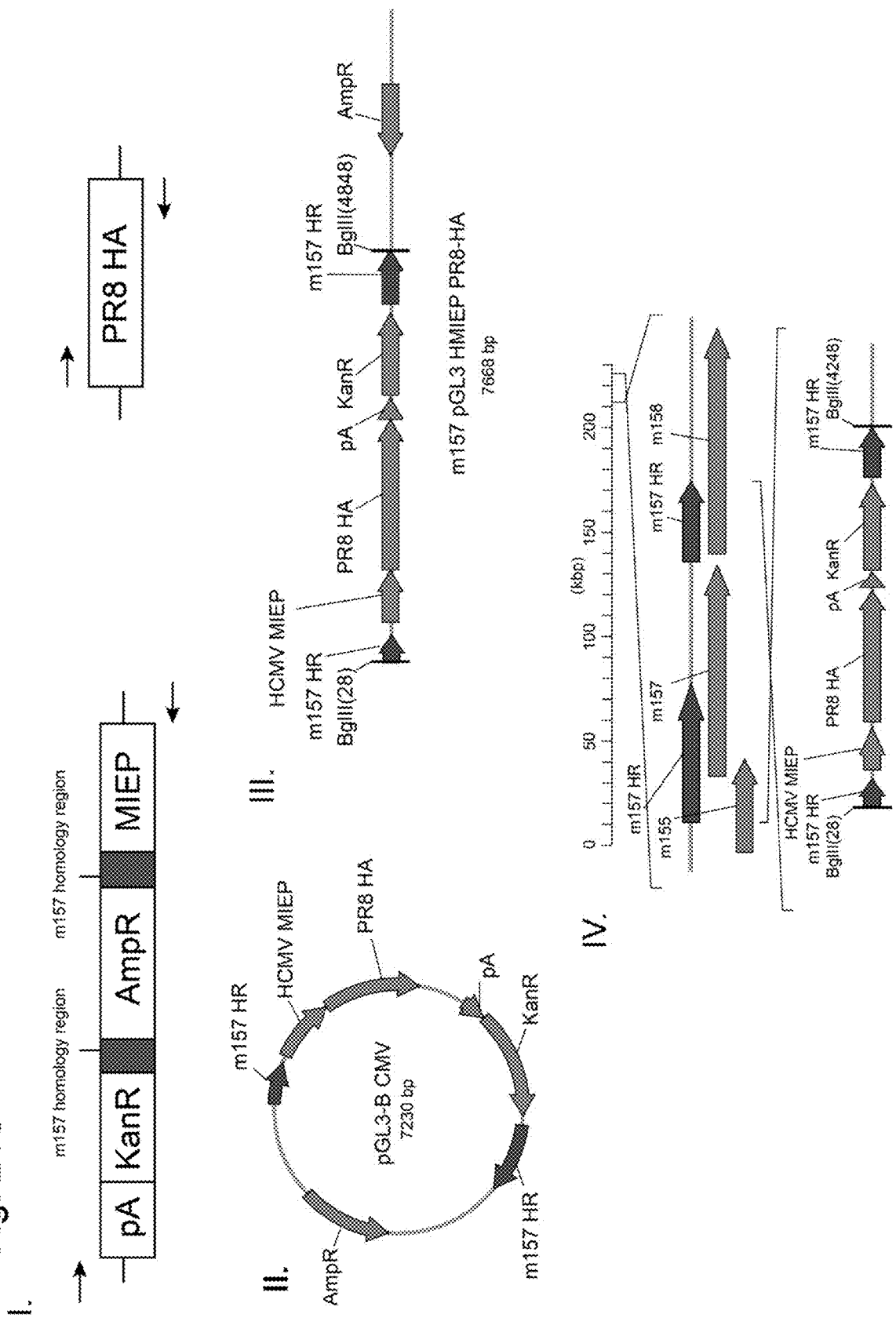
Figure 24E:
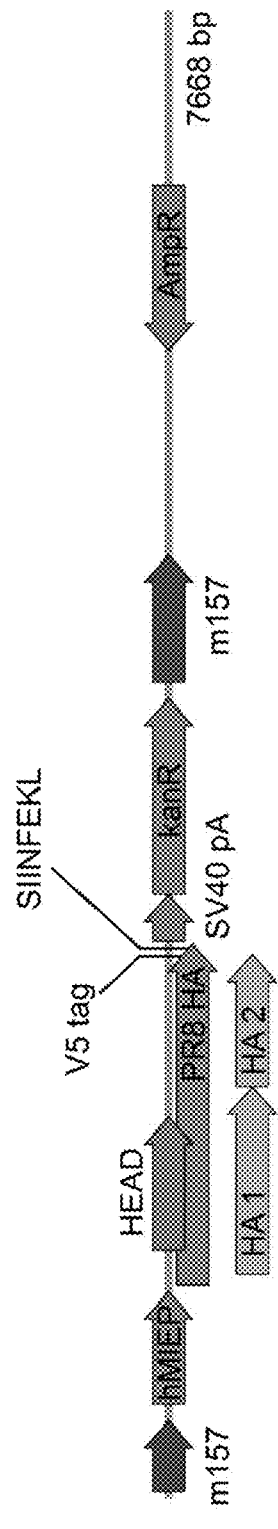
Figure 24E:
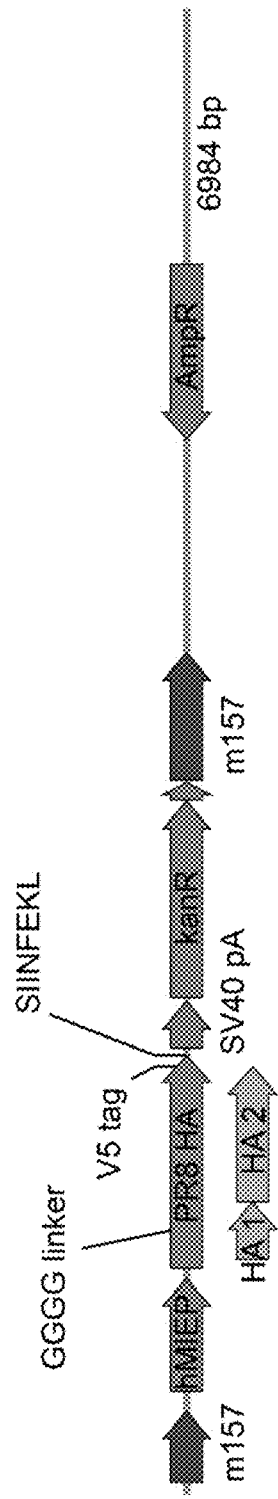

The result is shown in FIG. 23.

More particularly, FIG. 23 shows the total number of CD8+ T cells (left panel), effector memory CD8+ T cells (middle panel) and virus specific CD8+ T cells (right panel) of Balb/c mice which were i.v. infected with 2×10⁵ PFU of WT-MCMV (light grey bars; light grey circles), RAE-1γMCMVList (black bars; black circles) or left uninfected (white bars; white circles) on days post infection as indicated on the x-axis. Results are shown as mean±SD for three mice per group and are representative of two individual experiments.

It may be taken therefrom that a higher frequency of effector memory as well as virus specific CD8+ T cells is detected upon RAE-1γ infection.

Example 16: Generation of HA-Containing Recombinant Viruses

The further test vector capacity of MCMV expressing NKG2D ligand Rae1γ, the present inventor inserted influenza virus PR8 hemagglutinin, also referred to herein as HA, in WT-MCMV and RAE-1γMCMV genome, resulting in MCMV-HA and RAE-1γMCMV-HA, respectively.

The construction of recombinant plasmids comprising HA expression cassette, and recombinant HA-full (RAE-1γMCMVHA) or HA-headless (RAE-1γMCMVHAheadless) RAE-1γMCMV is schematically shown in FIG. 24A, FIG. 24B, FIG. 24C, FIG. 24D and FIG. 24E.

More particularly, FIG. 24 A to E show schematic illustrations of the genome organization and cloning process of HA-full and HA-headless RAE-1γMCMV.

FIG. 24 A shows the HindIII cleavage map of the MCMV genome at the top, with the genomic region encoding the m152 ORF and m157 ORF below. The m152 ORF was preplaced by an expression cassette (bottom) comprising the RAE-1γ ORF, the HCMV major immediate early prompter (CMV-P) and the SV40 polyadenylation signal sequence (pA). The m157 ORF was replaced by an expression cassette (bottom) comprising the HA-full ORF, the HCMV major immediate early prompter (CMV-P) and the SV40 polyadenylation signal sequence (pA).

FIG. 24 B shows the HindIII cleavage map of the MCMV genome at the top, with the genomic region encoding the m152 ORF and m157 ORF below. The m152 ORF was preplaced by an expression cassette (bottom) comprising the RAE-1γ ORF, the HCMV major immediate early prompter (CMV-P) and the SV40 polyadenylation signal sequence (pA). The m157 ORF was replaced by an expression cassette (bottom) comprising the HA-headless ORF, the HCMV major immediate early prompter (CMV-P) and the SV40 polyadenylation signal sequence (pA).

FIG. 24 C shows a schematic illustration of the construction of WT- and RAE-1γ MCMV expressing PR8 influenza hemagglutinin full form comprising the steps of I. PCR amplification of expression plasmid with HCMV MIEP and KanR; pGL3 plasmid provided by Invitrogen (left panel) and PCR amplification of PR8 HA-ORF provided by Peter Stäheli, Universitätsklinikum Freiburg, Germany;

II. Clone PR8 HA-ORF into expression plasmid (blunt-end ligation)

III. BglII restriction of plasmid with HA-expression cassette

IV. Homologous recombination with MCMV-BAC, replacing the m157 ORF, whereby the KanR cassette will subsequently be removed using Sce-I endonuclease.

FIG. 24 D shows a schematic illustration of the construction of WT- and RAE-1γ MCMV expressing PR8 influenza hemagglutinin headless form comprising the steps of I. PCR amplification of plasmid with HCMV MIEP, KanR and PR8 HA full-ORF;

II. Ligation of PCR amplified DNA fragment;

III. BglII restriction of plasmid with HA-headless-expression cassette; and

IV. Homologous recombination with MCMV-BAC, replacing the m157 ORF, whereby the KanR cassette will subsequently be removed using Sce-I endonuclease.

FIG. 24 E shows schematic illustrations of the genome organization of MCMV mutants expressing PR8-HA full form (upper panel) and PR8-HA headless form (lower panel) with GGGG linker (see also Steel J. et al., 2010, MBio. 18; 1(1)). To generate the HA full and headless MCMV mutants, an ORF encoding V5-tagged HA full was first cloned into pGL3 plasmid together with a Tischer-modified kanamycin resistance gene (kanR), which was inserted further downstream. The HA-expression cassette was linearized by restriction at BglII unique sites outside m157 homology regions. The linearized fragment was integrated into the BAC by red-α, -β, -γ-mediated recombination, thereby replacing the m157ORF. The kanR cassette was subsequently excised with Sce-I endonuclease encoded by GS1783 bacterail cells (provided by Tischer B. K.).

It will also be understood that hmIEP refers to the major immediate early promoter of HCMV; HA1 refers to the H-2Kd-Balb/c restricted peptide HA533-541; HA2 refers to the H-2Kd-Balb/c restricted peptide HA533-541; In connection therewith it will be understood that HA1 is a subunit of HA. One domain of HA1 is a globular head that is deleted in the case of headless construct; HA2 is stalk subunit of HA, which is highly conserved among different influenza strains. Accordingly, both HA1 as well as HA2 contain peptide HA533-541. SV40 pA refers to the SV40 polyadenylation signal sequence and AmpR refers to an ampicillin resistance gene.

It may be taken from the above that Hemagglutinin was inserted in a place of m157, a gene coding for protein which is directly recognized by NK cell receptor Ly49H (Arase et al., 2002, supra). The generated viruses were designated as MCMV-Δm157-HA, also referred to herein asMCMV-HA. and RAE-1γMCMV-Δm157-HA, also referred to herein as Rae1γMCMV-HA, respectively.

In connection therewith it is important to note that previous studies showed that engagement of Ly49H with m157 upon MCMV infection leads to activation of NK cells and subsequently better control of infection in Ly49H positive mice. When m157 deletion mutant MCMV is used, C57BL/6 mice lost the ability to control the virus and infection results in high virus titers in visceral organs and salivary glands (Bubic, I. et al., 2004, J Virol. 78(14):7536-44).

The major problem in designing efficient influenza vaccine is mutation of viral genes encoding immunodominant proteins. The stalk region of hemagglutinin is conserved among different strains and therefore is potentially a good candidate for generation of cross-protective immune response (Steel J. et al., 2010, supra). Therefore, in addition to recombinant MCMV expressing entire HA, the present inventor has also generated above mentioned viruses expressing headless hemagglutinin inserted in a place of m157, namely RAE-1γMCMVHA, RAE-1γMCMVHAheadless, MCMV HA, MCMV HA. Since H2b restricted immunodominant epitope $_{114}$YPYDVPDYA$_{122}$ (SEQ.ID.NO:38) is positioned in a head of hemagglutinin, the present inventor has additionally inserted ovalbumin immunodominant H2b restricted peptide $_{257}$SIINFEKL$_{264}$ (SEQ.ID.NO:10) in the stalk region of hemagglutinin to allow the present inventor following CD8$^+$ T cell response to well described foreign epitope.

It is important to understand that the H2b-B6 mouse restricted peptide HA114-122 (YPYDVPDYA)-(SEQ-.ID.NO:38) is not present in case of HA-"headless" mutant.

The H-2Kd-Balb/c restricted peptide HA533-541 (N-IYSTVASSL-C) (SEQ.ID.NO:37) is present in both headless and full length forms of HA PR8.

Recombinant plasmids were constructed according to established procedures, and enzyme reactions were performed as recommended by the manufacturers. Throughout, the fidelity of PCR-based cloning steps was verified by sequencing (GATC, Freiburg, Germany).

Growth kinetics of MCMVΔm157-HA and REA-1γMCMVΔm157-HA were compared to WT-MCMV.

The result is shown in FIG. 25.

More particularly, FIG. 25 shows virus titers determined in supernatants of MEF which were infected with 0.1 PFU per cell of WT-MCMV (circles), Rae1γMCMV Δm157-HA (triangles) MCMV Δm157-HA (diamonds). Supernatants were harvested at time points p.i. as indicated on the x-axis and virus titers were determined by plaque assay. The virus titer is depicted on the y-axis as log$_{10}$ PFU per milliliter, ml. Each sample analysis was performed in duplicates.

It can be taken therefrom that insertion of hemagglutinin into the MCMV genome had no effect on the replication kinetics of the recombinant viruses (see FIG. 25), in other words insertion of hemagglutinin does not affect virus growth in vitro.

Example 17: Efficient CD8$^+$ T Cell Response to Influenza HA after Infection with RAE-1γMCMV-HA Recombinant WT-MCMV and RAE-1γMCMV with IE1; m123/SIINFEKL or m164/SIINFEKL-peptide swap were constructed as described in Example 1 above.

FIG. 26A shows a schematic illustration of the construction of MCMV expressing SIINFEKL peptide comprising the steps of:

I. PCR amplification of KanR cassette and introduction of SIINFEKL (light grey block) and BAC homology regions, here homology to m123, (black blocks); and II. Homologous recombination with WT MCMV-BAC, replacing the respective position of the BAC according to homology regions, here m123 ORF, whereby the KanR cassette will subsequently be removed using Flp recombinase;

III. Optionally PCR amplification of RAE-1γ expression cassette, comprising major immediate early promoter of HCMV (MIEP), RAE-1γ ORF and Kanamycin Resistence gene (KanR), thereby introduction of BAC homology regions (dark grey blocks);

IV. Homologous recombination with MCMV-SIINFEKL BAC as provided by steps I. and II. according to Lemmermann et al. (Lemmermann et al., 2010, supra), thereby replacing the respective position of the BAC according to the homology regions, here the m152 ORF, whereby KanR cassette will subsequently be removed using Flp recombinase;

FIG. 26B shows the HindIII cleavage map of the MCMV genome at the top, with the genomic region spanning genes m150 through m165 expanded below to demonstrate the position of the ORFs of interest. The m152 ORF was preplaced by an expression cassette (bottom) comprising the RAE-1γ ORF, the HCMV major immediate early prompter (CMV-P) and the SV40 polyadenylation signal sequence (pA). The SIINFEKL—peptide (SEQ.ID.NO:10) was swapped in the m164 ORF as denoted in bold, resulting in RAE-1γMCMVm164SIINFEKL.

FIG. 26C shows the HindIII cleavage map of the MCMV genome at the top, with the genomic region spanning genes m121 to m124, and region from m150 to m153 expanded below to demonstrate the position of the ORFs of interest. The m152 ORF was preplaced by an expression cassette (bottom) comprising the RAE-1γ ORF, the HCMV major immediate early prompter (CMV-P) and the SV40 polyadenylation signal sequence (pA). The SIINFEKL peptide (SEQ.ID.NO:10) was swapped in the m123 ORF resulting in RAE-1γMCMVm123SIINFEKL.

To test whether hemagglutinin inserted in MCMV genome induces specific CD8$^+$ T cell response, and how the NKG2D ligand expression influences this response, the present inventor has infected C57BL6 mice with MCMV-Δm157-HA or RAE-1γMCMV-Δm157-HA.

Figure 27B:
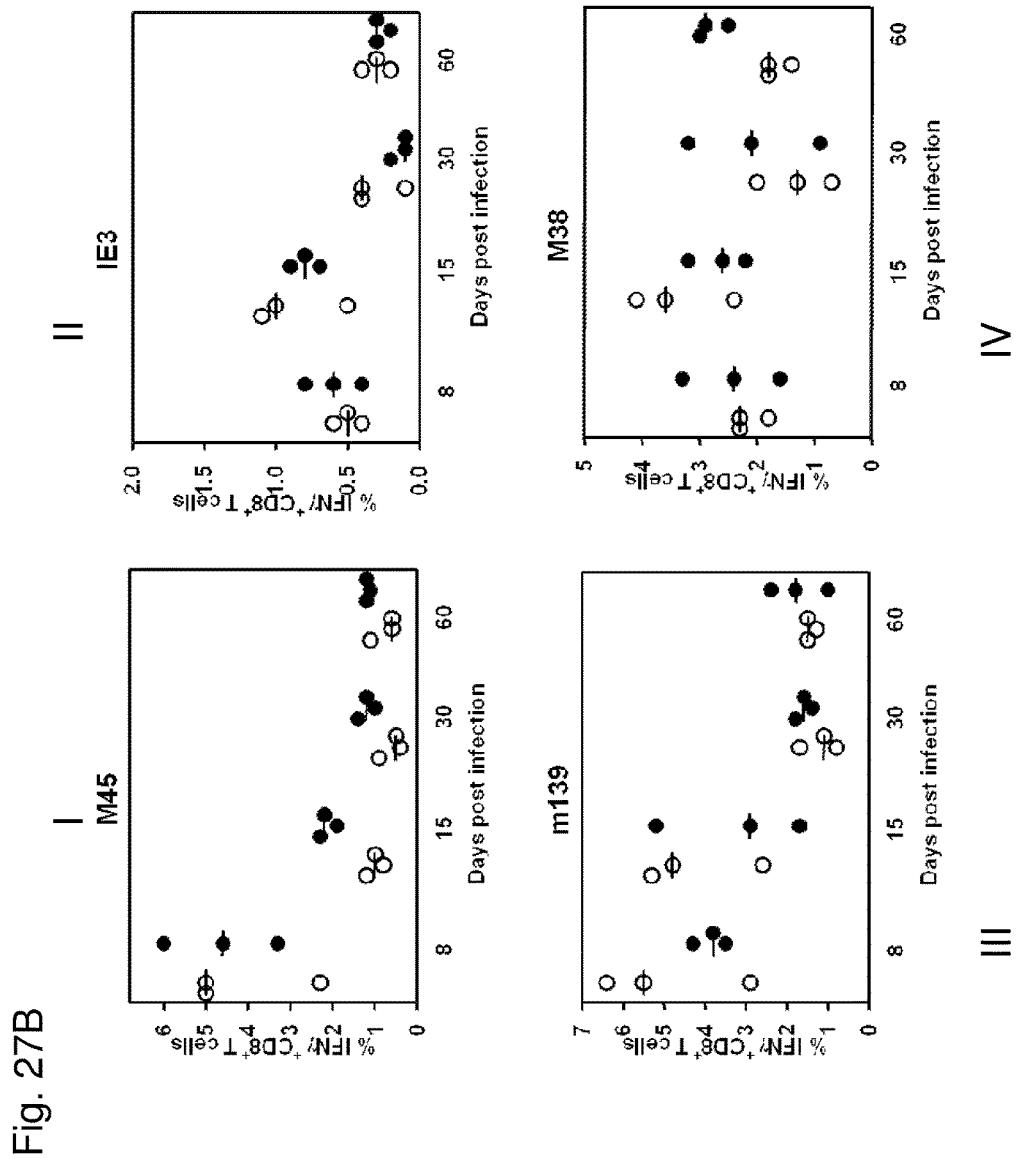

The result is shown in FIG. 27A and FIG. 27B.

More particularly, FIG. 27A shows the percentage of IFNγ+ CD8$^+$ T cells as a result of peptide-stimulation of splenocytes from C57BL/6 mice which were infected with 2×10$^5$ PFU f.p. of MCMV-HA (white circles) and RAE-1γMCMVHA (black circles). The splenocytes were stimulated with indicated peptides, i.e. Hemagglutinin (HA)-peptide HA533-541 (N-IYSTVASSL-C) (SEQ.ID.NO:37) (left panel) and Ovalbumin (SIINFEKL)-peptide (SEQ-.ID.NO:10) (right panel). Hemagglutinin (HA) and Ovalbumin (SIINFEKL)-specific CD8$^+$ T cell response was followed for 60 days. Splenocytes were isolated at time points indicated on the x-axis and stimulated with indicates peptides. IFNγ$^+$ CD8$^+$ T cell response, as a result of indicated peptides stimulation, is shown. Bars represent median values.

FIG. 27B shows the percentage of IFNγ+ CD8+ T cells as a result of peptide-stimulation of splenocytes from C57BL/6 mice which were infected with 2×10$^5$ PFU f.p. of MCMV-HA (white circles) and RAE-1γMCMVHA (black circles). The splenocytes were stimulated with indicated peptides, i.e. M45-peptide (SEQ.ID.NO:31) (upper left panel), IE3-peptide (SEQ.ID.NO:29) (upper right panel), m139-peptide (SEQ.ID.NO:30) (lower left panel) and M38-peptide (SEQ-.ID.NO:32) (lower right panel). Peptide-specific CD8+ T cell response was followed for 60 days. Splenocytes were isolated at time points indicated on the x-axis and stimulated with indicates peptides. IFNγ$^+$ CD8$^+$ T cell response, as a result of indicated peptides stimulation, is shown. Bars represent median values.

It may be taken therefrom that the hemagglutinin and SIINFEKL (SEQ.ID.NO:10)-specific CD8$^+$ T cell response was followed up to 60 days post infection (see FIG. 27A). Both, MCMV-Δm157-HA and RAE-1γMCMV-Δm157-HA infected mice generated and retained hemagglutinin and SIINFEKL (SEQ.ID.NO:10)-specific CD8$^+$ T cell response during analyzed period of time with similar frequency. There was no significant difference in the frequency of CD8$^+$ T cells following MCMV-Δm157-HA or RAE-1γMCMV-Δm157-HA. Therefore CD8$^+$T cell response to MCMV specific immunodominant epitopes obtained after RAE-1γMCMV-Δm157-HA infection was equal or even higher than after MCMV-Δm157-HA infection (see FIG. 27).

It was further assessed whether RAE-1γMCMV-Δm157-HA is attenuated in C57BL/6 mice.

Figure 28:
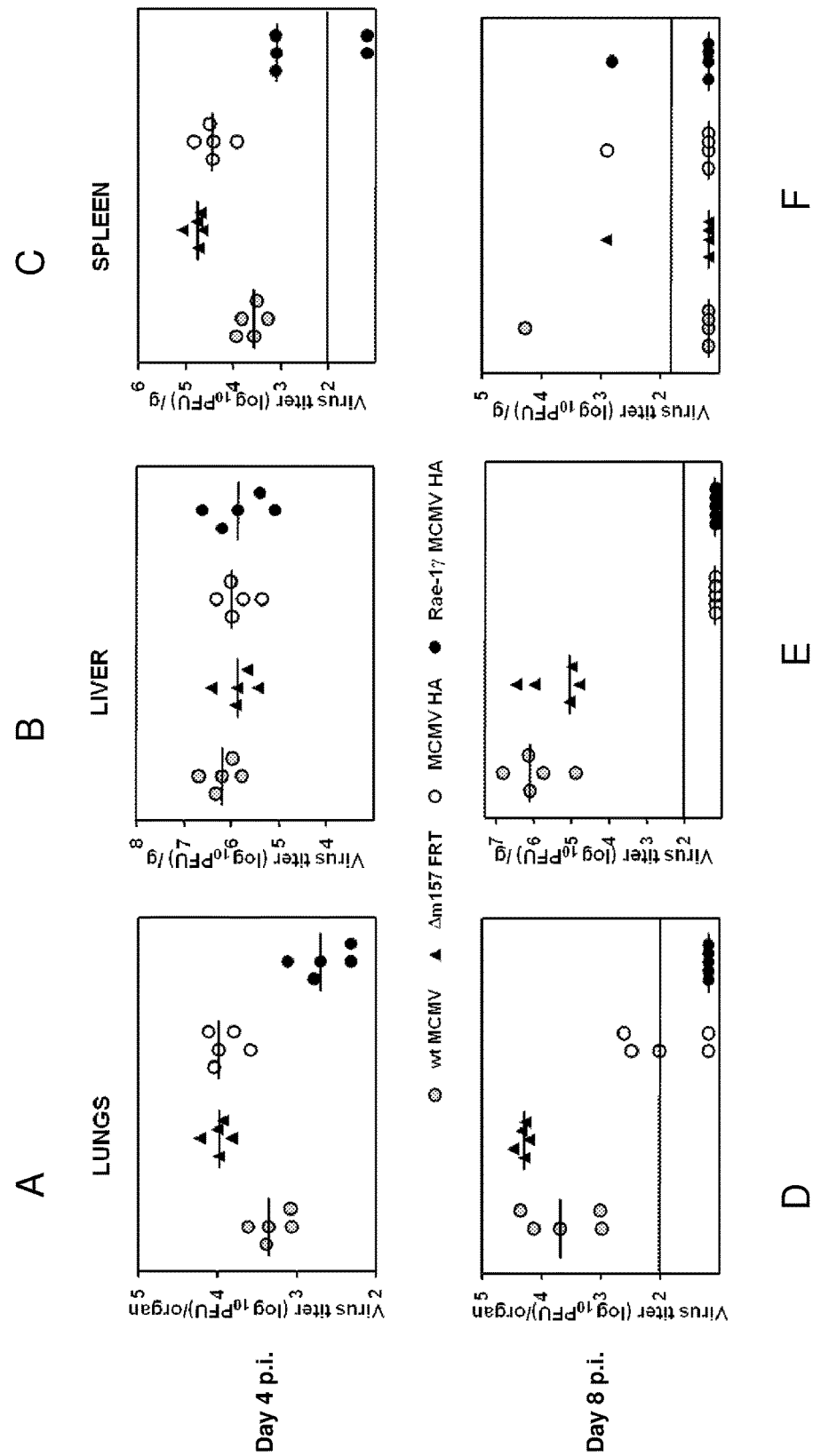

The result is shown in FIG. 28.

More particularly, FIG. 28 shows the viral load of lungs (upper and lower right panel), liver (upper and lower middle panel) and spleen (upper and lower right panel) of C57BL/6 mice which were infected with $10^5$ PFU of WT-MCMV (light grey circles), Δm157FRT (triangles) (Bubic, I. et al, 2004, supra), MCMVHA (white circles) and RAE-1γMCMVHA (black circles).

Virus titers were determined in depicted organs at 4 days post infection (upper panels), and 8 day post infection (lower panels).

Virus titers for individual animals (circles and triangles) and median values (bars) are shown as $\log_{10}$ PFU per organ on the y-axis. Detection limit is indicated by the horizontal line.

It may be taken therefrom that virus expressing NKG2D ligand are attenuated in C57BL/6 mice (see FIG. 28).

Gazit et al. (Gazit, R. et al., 2006, Nat Immunol. 7(5): 517-23) demonstrated that Ncr1 receptor expressed on NK cells is essential for elimination of influenza virus infected cells in vivo by direct recognition of viral HA protein. Therefore, the present inventor has tested whether Ncr1 would have effect on generation of hemagglutinin specific CD8$^+$ T cell response in MCMV-Δm157-HA or RAE-1γ-MCMV-Δm157-HA infection.

Figure 29:
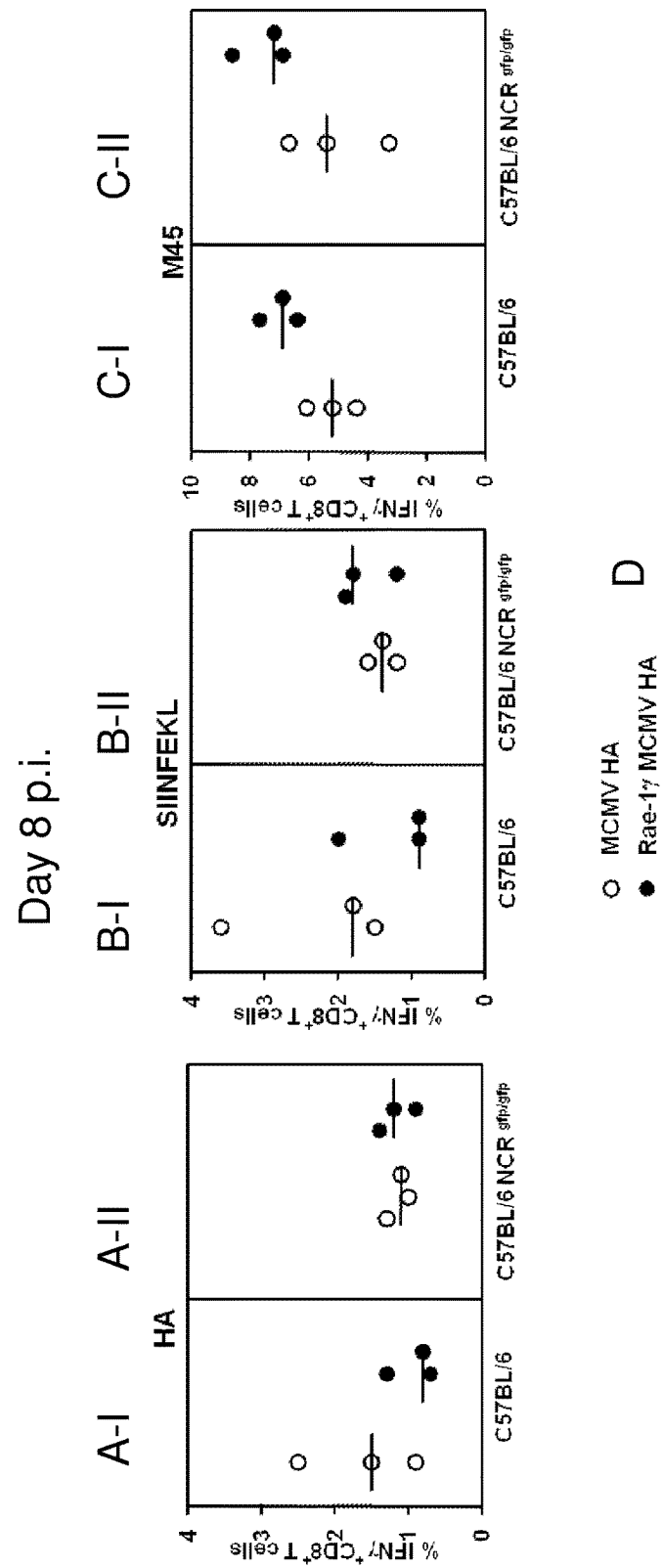

The result is shown in FIG. 29.

More particularly, FIG. 29 shows the percentage of IFNγ$^+$ CD8$^+$ T cells of splenocytes of C57BL/6 and C57BL/6 NCR $^{gfp/gfp}$ mice, respectively, as indicated on the x-axis, which were infected with $2 \times 10^5$ PFU f.p. of MCMV Δm157-HA (white circles) or Rae1γMCMV Δm157-HA (black circles). Splenocytes were isolated at 8 days p.i. (left panel), SIINFEKL-peptide (SEQ.ID.NO:10) (middle panel) and M45-peptide (SEQ.ID.NO:31) (right panel). The percentage of IFNγ$^+$ CD8$^+$ T cells of splenocytes is indicate on the y-axis. Bars represent median values.

It may be taken therefrom that RAE-1γMCMV-Δm157-HA generates efficient CD8$^+$ T cell response regardless of the role of Ncr1 in vivo. No difference in HA specific CD8$^+$ T cell response was observed at day 8 p.i. in C57BL/6 mice when compared to MCMV-Δm157-HA or RAE-1γMCMV-Δm157-HA infection in NCR$^{-/-}$ mice (see FIG. 29).

Example 18: ULBP2 Expressing HCMV Recombinant

To test NKG2D impact on virus attenuation in human MCMV model, the same principle as in RAE-1γMCMV was applied and recombinant HCMV mutants were generated expressing UL16 binding protein 2 (ULBP2, also known as RAET1 H), an NKG2D ligand, in place of UL16 gene which codes for the protein downregulating ULBP2.

Figure 30A:
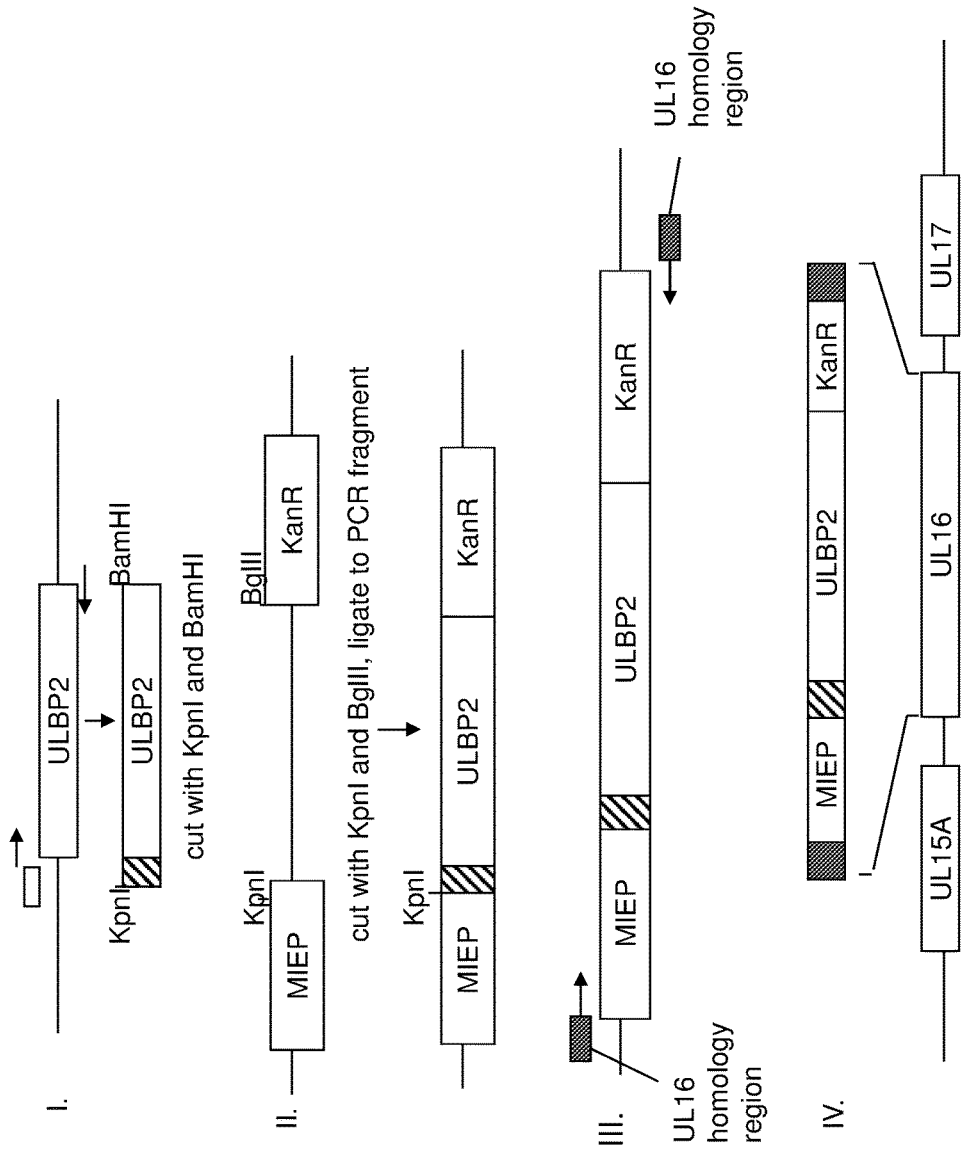

FIG. 30A and FIG. 30 B schematically show the construction of recombinant ULBP2-HCMV virus mutants.

More particularly, FIGS. 30 A and B show schematic illustrations of the genome organization and cloning process of ULBP2 expressing HCMV.

FIG. 30A shows a schematic illustration of the construction of recombinant ULBP2-HCMV virus comprising the steps of I. PCR amplification of ULBP2-ORF from ULBP2-encoding plasmid provided by Open Biosystems, subsequently subjected to enzyme restriction with KpnI and BamHI;

II. Clone into expression plasmid with MCMV MIEP and KanR applying restriction enzyme digestion and ligation;

III. Generation of PCR fragment for recombination, wherein homology regions to target site of recombination, here to UL16, is depicted as dark grey boxes; and IV. Homologous recombination with HCMV TB40E-BAC, thereby replacing the UL16 ORF, whereby KanR cassette will subsequently be removed using Flp recombinase.

Figure 30B:
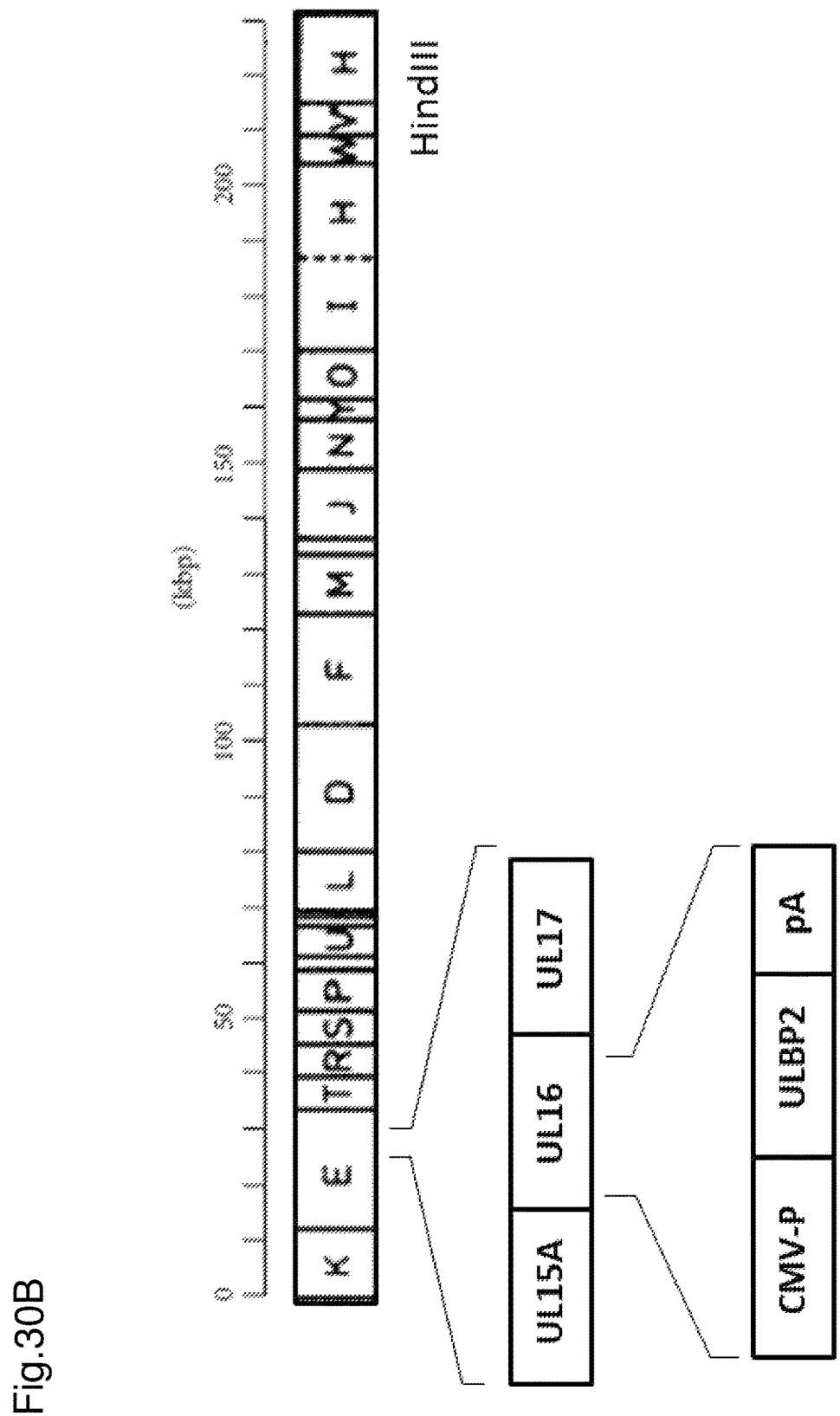

FIG. 30B shows the HindIII cleavage map of the HCMV AD169 genome at the top, with the genomic region spanning genes UL15A to UL17 expanded below to demonstrate the position of the ORF UL16. The UL16 ORF was replaced by an expression cassette (bottom) comprising the ULBP2 OR, the MCMV major immediate early promoter (CMV-P) and the SV40 polyadenyltaion signal sequence (pA).

Next ULBP2 expression was detected in TB40E-infected fibroblasts by immunoblotting.

DNA of two BAC clones (#39, #41) generated as described above were transfected into human fibroblasts as described by Borst et al. (Borst, E. M. et al., 2007, supra). For comparison DNA of the parental BAC of the TB40E strain (Sinzger, C. et al., 2008, J Gen Virol., 89 (Pt 2):359-68) was transfected. Infectious virus was reconstituted and fibroblasts were incubated until complete cytopathic effect occurred. Cells were harvested, lysed and proteins of the lysates were separated by SDS-PAGE, blotted and probed with an ULBP-2 specific antibody (R&D Cat. No. AF1298, 1:1000) followed by incubation with an HRP-anti-goat antibody (1:1000) and visualization of the signal with ECL substrate.

Figure 30C:
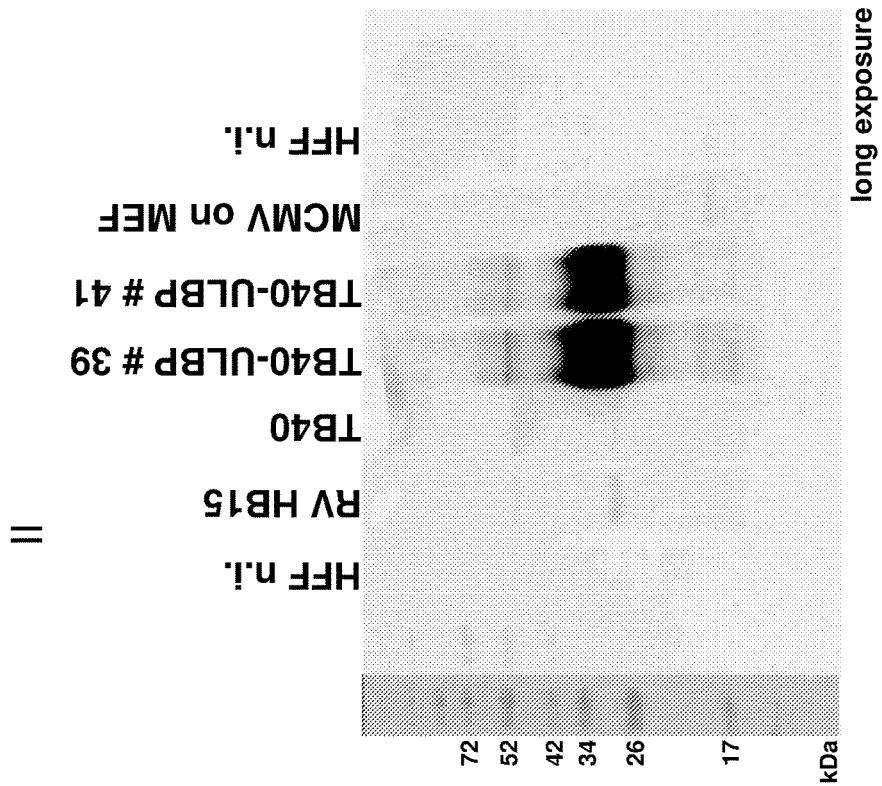
Figure 30C:

The results are shown in FIG. 30C.

More particularly, FIG. 30 C shows a Western blot analysis, wherein the immunoblot has been exposed to a film for detection of signal for a short exposure time (left panel) and for a long exposure time (right panel). As controls lysates from non-infected human fibroblast (HFF n.i), lysates from fibroblast infected with the BAC-cloned CMV strain RVHB15 (AD169-derived) {Borst et al. 1999; Hobom et al., 2000}, as mentioned above fibroblasts infected with the virus reconstituted from the parental TB40E BAC, as well as lysates from MCMV infected murine embryonic fibroblasts (MCMV on MEF) were used.

As may be taken therefrom substantial amounts of ULBP2 were detected in TB40-ULBP2 #39 and #41 infected cells, whereas basically no ULBP2 expression were detected in noninfected human fibroblasts and small amounts of ULBP2 expression were detected in RVHB15 and TB40E-infected fibroblasts.

Furthermore the Surface expression of ULBP2 after infection of HFF with HCMV-ULBP2 and control virus was assessed.

Figure 30D:
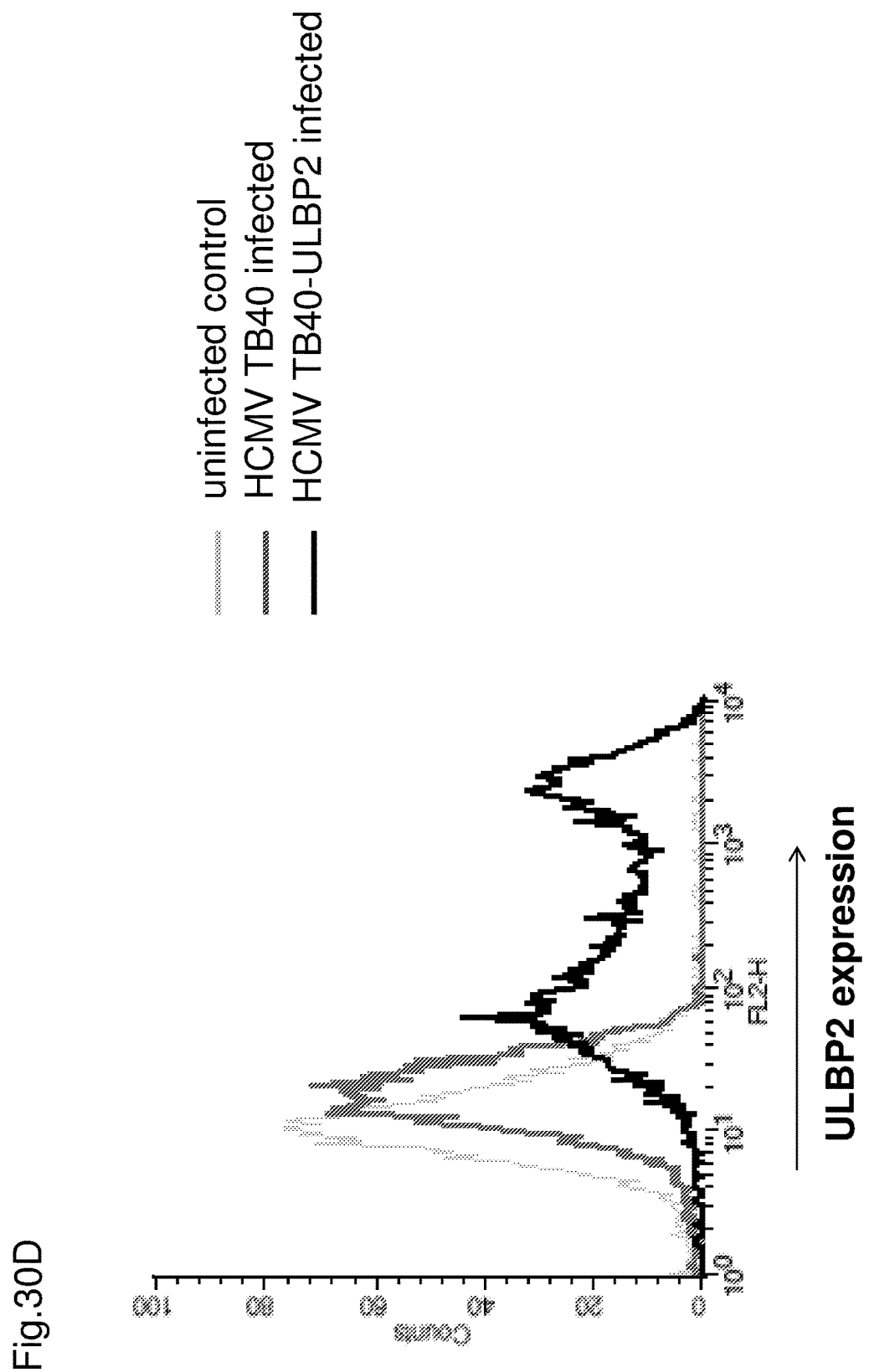
Figure 30E:
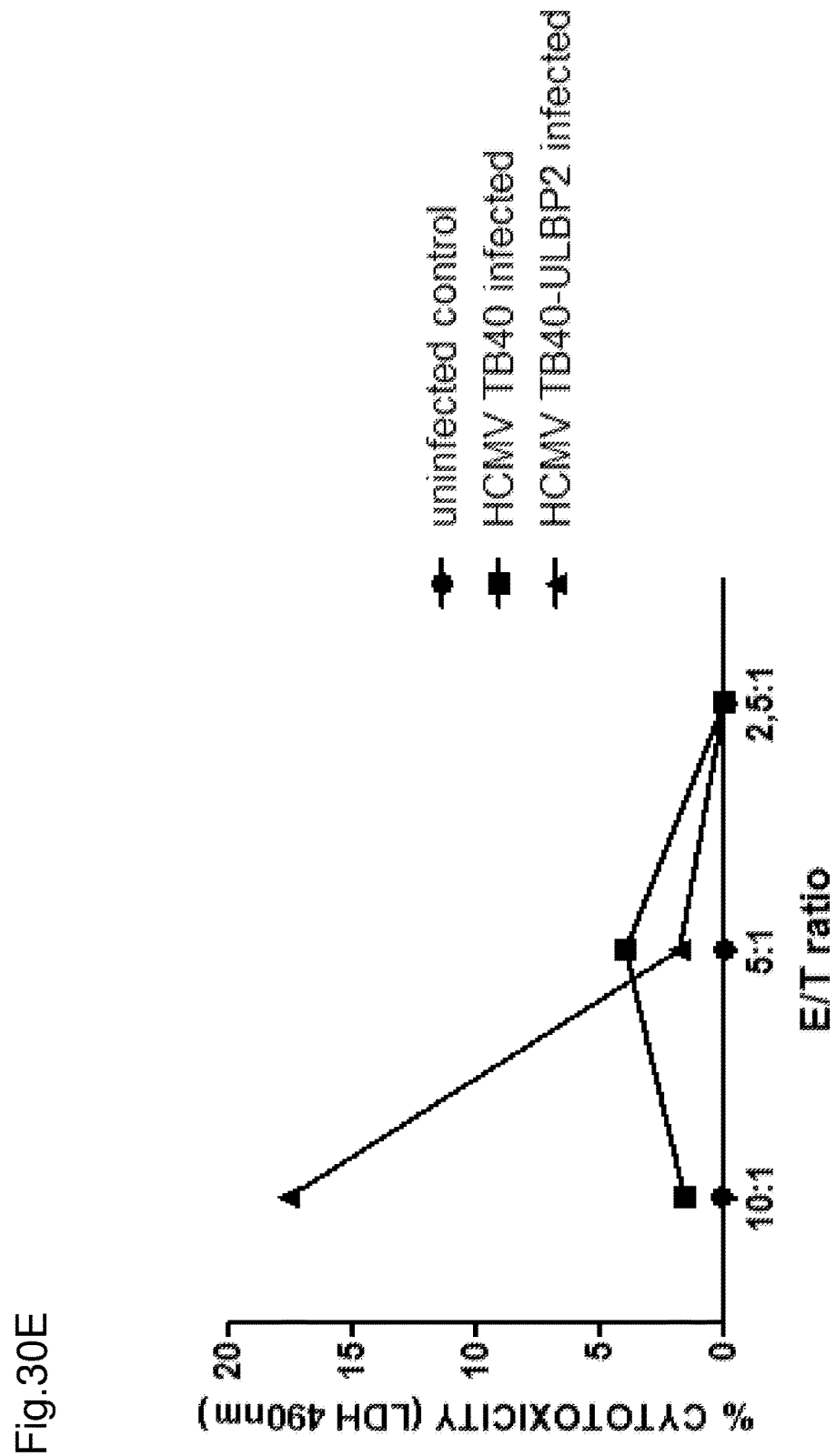

The results are shown in FIG. 30D and FIG. 30E.

More particularly, FIG. 30D shows FACS analysis of ULBP-2 expression. Human foreskin fibroblasts (HFF) were infected with 1 PFU of HCMV TB40 strain or HCMV TB40 expressing ULBP-2, or left uninfected. 24 hours post infection cells were tested for ULBP-2 expression.

Furthermore the results of NK cell assay using HFF infected with HCMV-ULBP2, HCMV TB40 and uninfected HFF as targets are shown in FIG. 30E.

FIG. 30E shows that HCMV TB40 ULBP2 expressing virus promotes cytotoxicity of NK cells. Freshly isolated human NK cells were used as effectors. Human foreskin fibroblasts as target cells were infected with 1 PFU/cell of HCMV TB40 strain or HCMV TB40 expressing ULBP-2, or left uninfected. 24 hours post infection, target cells were mixed in three different ratios 10:1, 5:1 and 2.5:1 with NK cells isolated form healthy blood donor to determine the effect of ULBP-2 on NK cell cytotoxicity using the Promega CytoTox assay. LDH release from necrotic cells was determined by assaying culture media samples. Mean and SD values are shown. Circles (uninfected HFFs), squares (HCMV strain TB40 infected HFFs), triangles (HCMV TB40 strain lacking UL16 gene expressing ULBP-2).]

Example 19: General Protocol for Vaccinating a Human Subject Using a Recombinant HCMV Expressing ULBP2

The recombinant HCMV used in accordance with this general protocol is a HCMV as described in Example 1 expressing ULBP2. The recombinant HCMV expressing ULBP2 is for use in a method of vaccinating the subject against HCMV and thus for use in a method of eliciting an immune response against HCMV.

Inclusion and Exclusion Criteria

A subject is admitted to participate in the vaccination trial if the human subject is a male or female human between 22 and 60 years of age at the time of enrollment into the trial, if the informed consent is obtained from the subject before vaccination, if the subject is healthy, as determined by a questionnaire concerning the medical history of the subject and clinical examination, and if the subject is tested to be seronegative for HCMV.

A subject is excluded from participation in the vaccination trial if the subject is tested to be seropositive for HCMV, if the subject is tested to be pregnant, if the subject is or has been undergoing drug therapy or vaccination within 30 days preceding the vaccination trial, if the subject was previously vaccinated against HCMV, if the subject has or had frequent recurrent herpes simplex infections, if the subject has or had any immunodeficiency, if the subject has or had a Hepatitis B infection or hepatitis C infection, if the subject has or had a medical history of allergic disease or reactions, if the subject has or had any major chronic illness including diabetes mellitus, if the subject has or had a medical history of any neurologic disease, if the subject is suffering from a malignancy, if the subject has an acute disease at the time of participation in the trial and/or if the subject has a medical history of administration of immunoglobulins or blood products within three months preceding the enrollment into the trial or if the subject has a history of chronic alcohol consumption or drug abuse.

Administration

HCMV expressing ULBP2 is used to inoculate the subject by a subcutaneous injection with 50 infectious units as determined by titration on permissive human fibroblast cells. Alternatively, the recombinant HCMV expressing ULBP2 is administered by oral inoculation with 250 infectious units. A placebo group is inoculated with the pharmaceutically acceptable carrier used in connection with the subcutaneous injection and oral inoculation of the HCMV expressing ULBP2.

A blood sample is taken from the patient before vaccination and a second blood sample is taken between day 28 and day 32 post vaccination.

Infection of the host is documented by comparison of the analysis of the blood sample taken before vaccination and the analysis of the blood sample taken between day 28 and day 32 post vaccination, whereby the blood samples are analyzed for (1) serological evidence of infection with HCMV,
(2) serological evidence of antibody response to HCMV, and
(3) evidence for the presence of specific CD8$^+$T cells to HCMV.

Efficacy

To determine the efficacy of the recombinant HCMV expressing ULBP2 the kinetics and magnitude of the CMV-specific immune response is assessed in the healthy HCMV-sero-negative participants compared to the placebo group.

The efficacy of the HCMV-specific immune response is assessed as follows.

a) Determination of systemic HCMV infection is determined as follows:

At day 0, as well as 1, 2, 6, 12 and 24 months post vaccination a urine sample, a blood sample and a saliva sample is taken from the participants and analyzed for HCMV using PCR.

b) Determination of antibody titers directed against HCMV.

antibody titers directed against HCMV-specific proteins determined by neutralization and enzyme-linked immunosorbent assay (ELISA) and/or by Western blot assays in samples taken at 1, 6 and 12 months following vaccination.

2 months following vaccination, a 15 ml of blood sample is taken from the subjects and peripheral blood mononuclear cells (PBMC) are recovered by standard technologies. PBMC are stimulated in standard assays for detection of the proliferation of CD8$^+$ T lymphocytes and CD4$^+$ T lymphocytes in response to (1) HCMV antigens (viral lysate).

In addition, in patients in which appropriate HLA haplotypes can be defined, CD8$^+$ T lymphocyte responses are assayed using ELISPOT and flow cytometry following ex-vivo stimulation of mononuclear cells with the heterologous antigen and CMV antigens pp65, IE-1 and gB.

Protection

The vaccination is considered successful if positive serological responses to the HCMV-specific antigens are detected. More specifically, a serological response is considered positive if a more than 4-fold rise in antibody levels is detected and/or if viral nucleic acids are detected in the urine The emphasis is on assessment of HCMV-specific CD8 T cell priming and maintenance following vaccination with HCMV ULBP2. Regarding the CD8 T cell response the vaccination is considered successful if virus-specific CD8 T cell response against HLA haplotype matched HCMV infected human foreskin fibroblasts is similar to or exceeding the one in HCMV seropositive control subjects, as assessed by proliferation capacity and frequency of HCMV-specific CD8 T cells, as well as their capacity for IFNg production.

The results of these studies are quantified and compared to identical studies carried out at 6, 12, and 24 months following vaccination.

Surrogates of vaccine efficacy include antibody levels reactive with HCMV proteins and more importantly CD8$^+$ T lymphocyte responses for HCMV antigens.

Example 20: Treatment of a Human Subject Using a Recombinant HCMV Expressing ULBP2

A 25 year old female human subject is treated in accordance with the general protocol of Example 19, whereby the recombinant HCMV expresses ULBP2. The recombinant HCMV expressing ULBP2, as described in Example 1 herein, is administered subcutaneously in a phosphate-buffered saline solution containing 50 infectious units of the recombinant HCMV.

A blood sample is taken from the subject at day 30 post vaccination and the titer of antibody against HCMV-specific protein is determined by ELISA. A significant antibody immune response against HCMV-specific protein is detected.

Furthermore, a blood sample is taken from the subject two months post vaccination and proliferation of both $CD8^+$ T lymphocytes and $CD4^+$ T lymphocytes is observed in response to (1) HCMV antigens after stimulation with lysate of HLA matched infected cells or (2) in response to virus-specific peptide epitopes, as indicated in the Example 19.

Example 21: General Protocol for Vaccinating a Human Subject Using a Recombinant HCMV Expressing a Heterologous Antigen The recombinant HCMV used in accordance with this general protocol is a HCMV as described in Example 1 expressing ULBP2 and a heterologous antigen against which an immune response is to be elicited in a human subject. Such heterologous antigen is one as described in the instant specification and includes more specifically influenza hemagglutinin protein, antigen 85A or HIV-1 gag protein. The recombinant HCMV expressing influenza hemagglutinin protein is for use in a method of vaccinating the subject against influenza and thus for use in a method of eliciting an immune response against influenza. The recombinant HCMV expressing antigen 85A of *Mycobacterium tuberculosis* is for use in a method of vaccinating the subject against *Mycobacterium tuberculosis* and thus for use in a method of eliciting an immune response against *Mycobacterium tuberculosis*. The recombinant HCMV expressing HIV-1 gag protein of HIV is for use in a method of vaccinating the subject against HIV and thus for use in a method of eliciting an immune response against HIV.

Inclusion and Exclusion Criteria

A subject is admitted to participate in the vaccination trial if the human subject is a male or female human between 22 and 60 years of age at the time of enrollment into the trial, if the informed consent is obtained from the subject before vaccination, if the subject is healthy, as determined by a questionnaire concerning the medical history of the subject and clinical examination, and if the subject is tested to be seronegative for HCMV.

A subject is excluded from participation in the vaccination trial if the subject is tested to be seropositive for HCMV, if the subject is tested to be pregnant, if the subject is or has been undergoing drug therapy or vaccination within 30 days preceding the vaccination trial, if the subject was previously vaccinated against HCMV, if the subject has or had frequent recurrent herpes simplex infections, if the subject has or had any immunodeficiency, if the subject has or had a Hepatitis B infection or hepatitis C infection, if the subject has or had a medical history of allergic disease or reactions, if the subject has or had any major chronic illness including diabetes mellitus, if the subject has or had a medical history of any neurologic disease, if the subject is suffering from a malignancy, if the subject has an acute disease at the time of participation in the trial and/or if the subject has a medical history of administration of immunoglobulins or blood products within three months preceding the enrollment into the trial or if the subject has a history of chronic alcohol consumption or drug abuse.

Administration

HCMV expressing ULBP2 and the heterologous antigen is used to inoculate the subject by a subcutaneous injection with 50 infectious units as determined by titration on permissive human fibroblast cells. Alternatively, the recombinant HCMV expressing ULBP2 and the heterologous antigen is administered by oral inoculation with 250 infectious units. A placebo group is inoculated with the pharmaceutically acceptable carrier used in connection with the subcutaneous injection and oral inoculation of the HCMV expressing ULBP2 and the heterologous antigen.

A blood sample is taken from the patient before vaccination and a second blood sample is taken between day 28 and day 32 post vaccination.

Infection of the host is documented by comparison of the analysis of the blood sample taken before vaccination and the analysis of the blood sample taken between day 28 and day 32 post vaccination, whereby the blood samples are analyzed for
(1) serological evidence of infection with HCMV,
(2) serological evidence of antibody response to the heterologous antigen, and
(3) evidence for the presence of specific $CD8^+$T cells to the heterologous antigen.

Efficacy

To determine the efficacy of the recombinant HCMV expressing ULBP2 and the heterologous antigen protein the kinetics and magnitude of the CMV-specific and antigen-specific immune response is assessed in the healthy HCMV-sero-negative participants compared to the placebo group.

The efficacy of the HCMV-specific immune response and the specific immune response against the heterologous antigen are assessed as follows.

a) Determination of systemic HCMV infection is determined as follows:
At day 0, as well as 1, 2, 6, 12 and 24 months post vaccination a urine sample, a blood sample and a saliva sample is taken from the participants and analyzed for HCMV using PCR.
b) Determination of antibody titers directed against HCMV-specific proteins and of antibody titers against the heterologous antigen.
1, 6 and 12 months following vaccination antibody titers directed against HCMV-specific proteins and against the heterologous antigen determined by neutralization and enzyme-linked immunosorbent assay (ELISA) and/or by Western blot assays in samples taken at 1, 6 and 12 months following vaccination.
2 months following vaccination, a 15 ml of blood sample is taken from the subjects and peripheral blood mononuclear cells (PBMC) are recovered by standard technologies. PBMC are stimulated in standard assays for detection of the proliferation of $CD8^+$ T lymphocytes and $CD4^+$ T lymphocytes in response to
(1) HCMV antigens (viral lysate), and
(2) the heterologous antigen.
In addition, in patients in which appropriate HLA haplotypes can be defined, $CD8^+$ T lymphocyte responses are assayed using flow cytometry following ex-vivo stimulation of mononuclear cells with the heterologous antigen and CMV antigens pp65, IE-1 and gB.

Protection

The vaccination is considered successful if positive serological responses to the heterologous antigen and optionally also the HCMV-specific antigens are detected. More specifically, a serological response is considered positive if a more than 4-fold rise in antibody levels is detected and/or if viral nucleic acids are detected in the urine.

The results of these studies are quantified and compared to identical studies carried out at 6, 12, and 24 months following vaccination.

Surrogates of vaccine efficacy include antibody levels reactive with the heterologous antigen and more importantly CD8+ T lymphocyte responses for the heterologous antigen.

Example 22: Treatment of a Human Subject Using a Recombinant HCMV Expressing Influenza Hemagglutinin Protein A 25 year old female human subject is treated in accordance with the general protocol of Example 21, whereby the recombinant HCMV expresses influenza hemagglutinin protein. The recombinant HCMV expressing influenza hemagglutinin protein, as described in Example 1 herein, is administered subcutaneously in a phosphate-buffered saline solution containing 50 infectious units of the recombinant HCMV.

A blood sample is taken from the subject at day 30 post vaccination and the titer of antibody against HCMV-specific protein and against the influenza hemagglutinin protein is determined by ELISA. A significant antibody immune response against both HCMV-specific protein and against the influenza hemagglutinin protein is detected.

Furthermore, a blood sample is taken from the subject two months post vaccination and proliferation of both CD8$^+$ T lymphocytes and CD4$^+$ T lymphocytes in response to (1) HCMV antigens (viral lysate), (2) influenza hemagglutinin protein and (3) ULBP2 is observed.

The HCMV-ULBP2 HA vaccine elicits cross-reactive anti-HA2 antibodies and anti-HA2 CD8$^+$ T cells superior than the response detected in human subjects during natural influenza infection or subjects vaccinated with conventional vaccines against seasonal influenza. Quality of T cell response is determined by ELISPOT and flow cytometry on PBMC isolated prior to vaccination and following vaccination during the outbreak of seasonal influenza epidemics or after vaccination with conventional seasonal influenza vaccine. T cell response induced by HCMV-ULBP2 expressing HA are considered successful if superior than specific T cell response in control subjects, i.e. individuals after vaccination with conventional seasonal influenza vaccine and subjects after natural influenza infection. The subjects vaccinated with HCMV-ULBP2 HA headless vaccine develop serum neutralizing anti-HA2 antibodies against the epitopes which are not induced neither by infection with HCMV-ULBP2 expressing full-length HA nor during the natural influenza infection. Such "unnatural" response to unmasked conserved HA epitope is beneficial over conventional vaccines with regard to cross-protective capacity against various influenza virus strains.

Example 23: Treatment of a Human Subject Using a Recombinant HCMV Expressing HIV-1 gag A 25 year old female human subject is treated in accordance with the general protocol of Example 21, whereby the recombinant HCMV expresses HIV-1 gag. The recombinant HCMV is administered subcutaneously in a phosphate-buffered saline solution containing 50 infectious units of the recombinant HCMV.

A blood sample is taken from the subject at day 30 post vaccination and the titer of antibody against HCMV-specific protein and against the HIV-1 gag is determined by ELISA. A significant antibody immune response against both HCMV-specific protein and against the HIV-1 gag is detected.

Furthermore, a blood sample is taken from the subject two months post vaccination and proliferation of both CD8$^+$ T lymphocytes and CD4$^+$ T lymphocytes in response to (1) HCMV antigens (viral lysate), (2) HIV-1 gag and (3) ULBP2 is observed.

For subjects vaccinated with HCMV-ULBP2 vaccine expressing HIV-1 gag antigen the successful T cell priming of gag-specific CD4+ and CD8+ T-cell responses is judged by ELISPOT and flow cytometry on PBMC isolated prior to vaccination and two months following vaccination. The obtained result is compared to the placebo group and the group of elite controllers of HIV infection. The vaccination is considered successful if the specific T cell responses are the same or exceeding the responses in the group of elite controllers of HIV infection.

Example 24: Treatment of a Human Subject Using a Recombinant HCMV Expressing Antigen 85A A 25 year old female human subject is treated in accordance with the general protocol of Example 21, whereby the recombinant HCMV expresses Antigen 85A. The recombinant HCMV is administered subcutaneously in a phosphate-buffered saline solution containing 50 infectious units of the recombinant HCMV.

A blood sample is taken from the subject at day 30 post vaccination and the titer of antibody against HCMV-specific protein and against the Antigen 85A is determined by ELISA. A significant antibody immune response against both HCMV-specific protein and against the Antigen 85A is detected.

Furthermore, a blood sample is taken from the subject two months post vaccination and proliferation of both CD8$^+$ T lymphocytes and CD4$^+$ T lymphocytes in response to (1) HCMV antigens (viral lysate), (2) Antigen 85A and (3) ULBP2 is observed.

The vaccination with HCMV-ULBP2 expressing mTB Antigen 85 (Ag85) is considered successfull in the terms of eliciting similar or better immune response against *M. tuberculosis* in the group vaccinated with HCMV-ULBP expressing Ag85 as compared to samples of patients with controlled mTB infections (i.e. patients exposed and infected but symptom free, without requirement for chemotherapy). Recall response in subjects receiving HCMV ULBP2 expressing Ag85 vaccine is considered successful if intradermal skin test response to mTB proteins is equal or better than in the unvaccinated group.

Example 25: RAE-1γMCMVList Provides Long-Term Protection Against Challenge Infection The endurance of protective immunity is a prerequisite for an efficient protection against re-infection. To assess whether the vaccination with an MCMV vector expressing RAE-1γ provides a long-lasting protection against *L. monocytogenes*, BALB/c mice were f.p. infected with 1×10$^5$ PFU of WT-MCMV, MCMVList, RAE-1γMCMVList, respectively, or left uninfected. 60 days post-vaccination groups of MCMVList or RAE-1γMCMVList infected, or uninfected BALB/c mice were challenged with 2×10$^4$ CFU/mouse of *L. monocytogenes*.

The result is shown in FIG. 32.

Figure 32A:
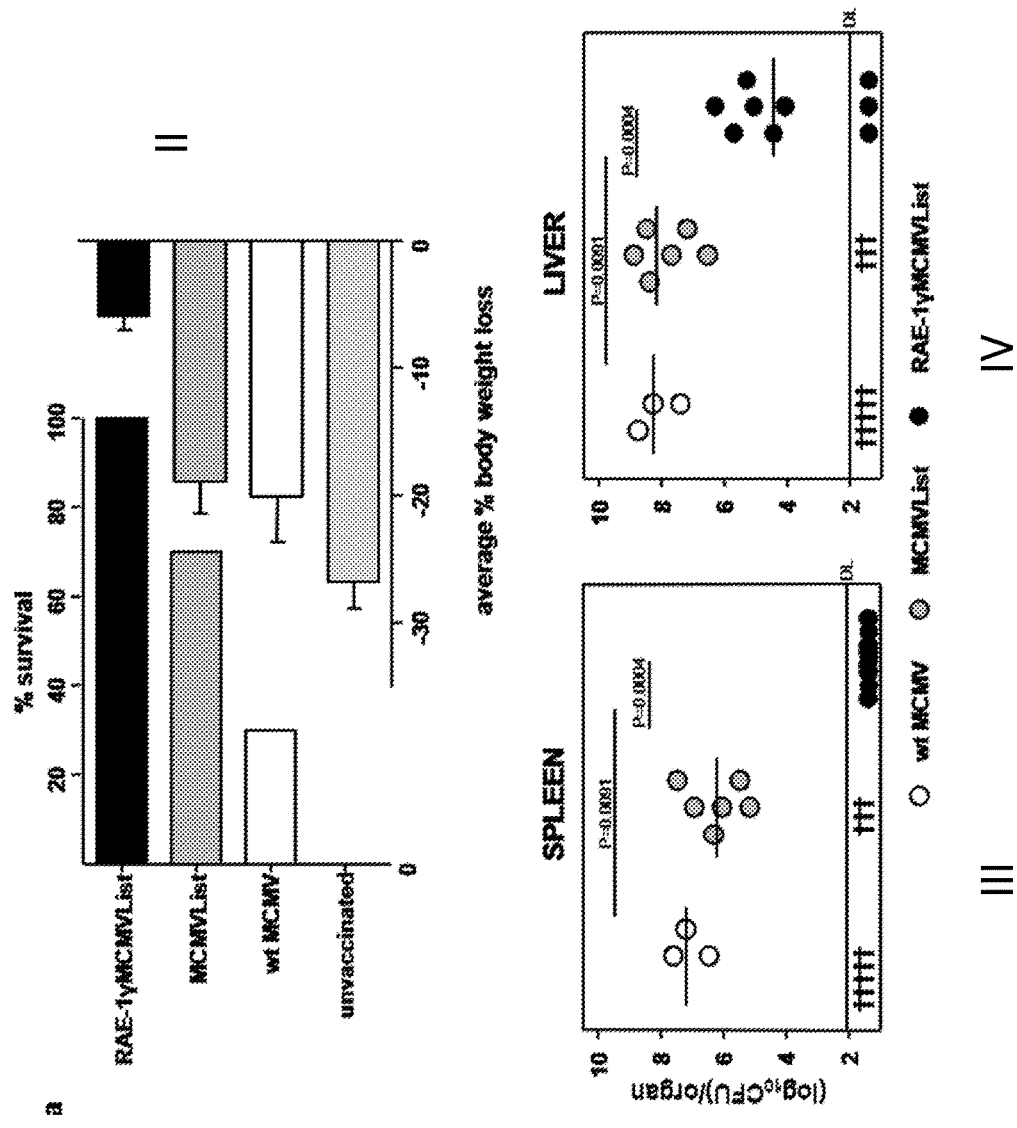
Figure 32B:
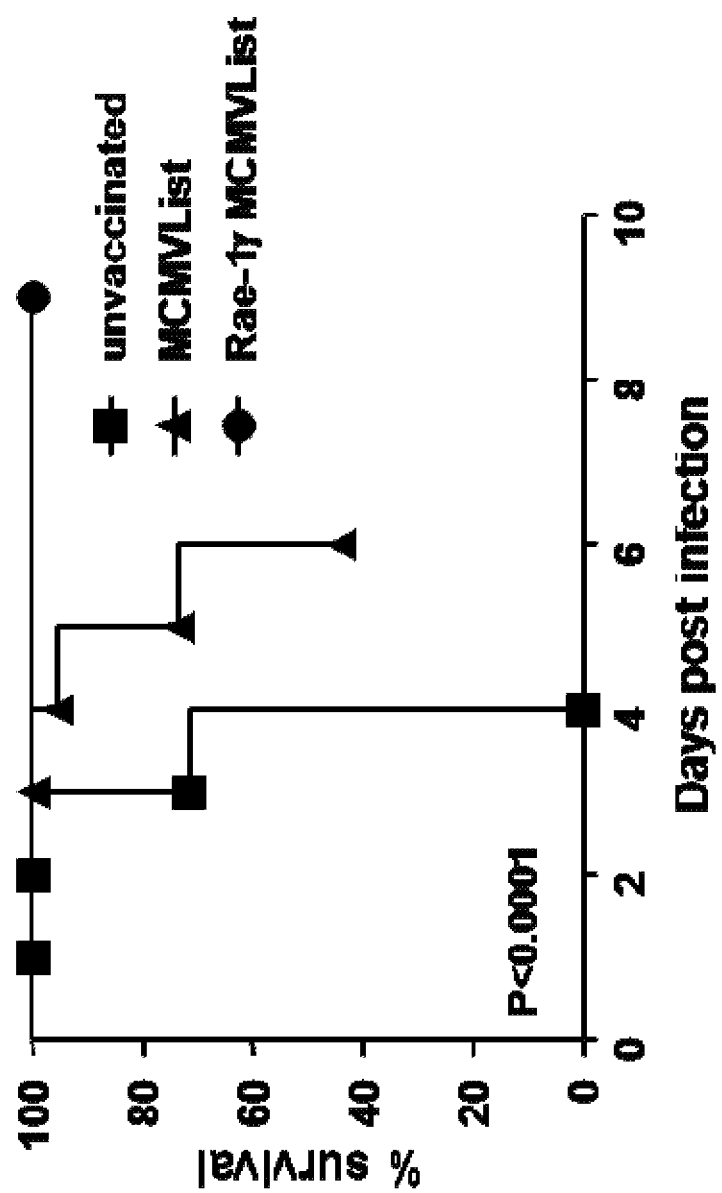
Figure 32C:
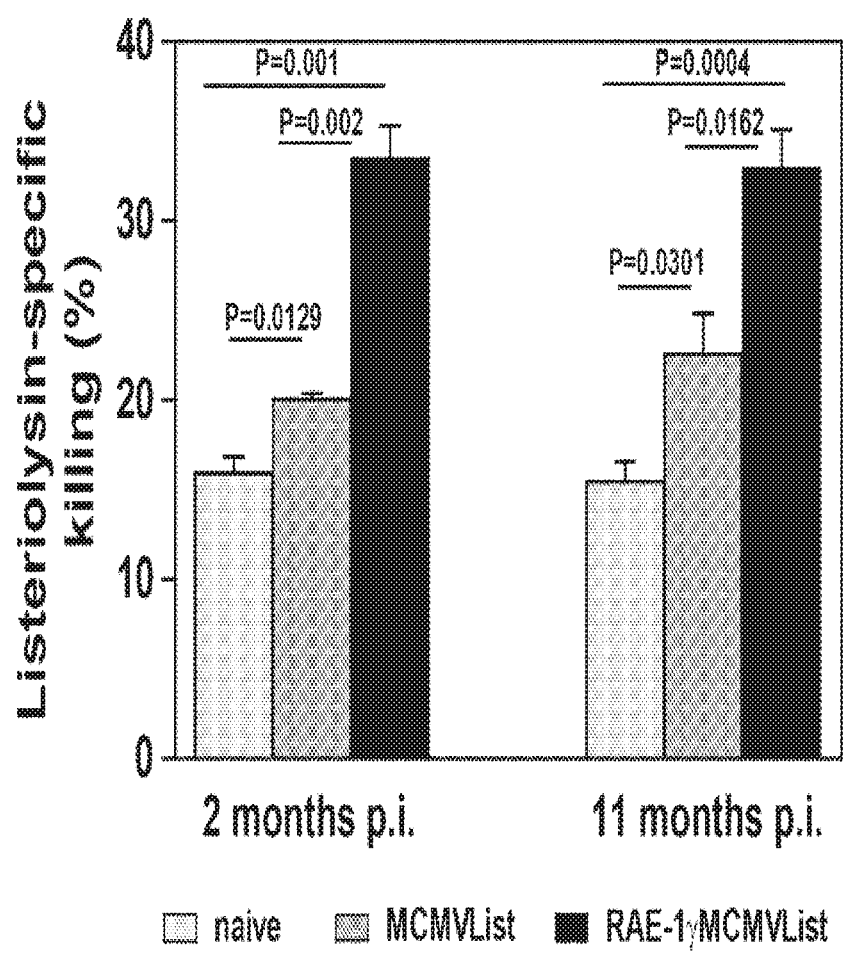

More particularly, FIG. 32A shows the percentage of survival by day 4 and body weight loss (mean±s.e.m.) on day 3 post-challenge (n=9-12 per group) (upper panel). The bacterial load in spleen and liver in individual animals (circles) and median values (horizontal bars) of survived mice on day 4 post-challenge are shown. DL means detection limit, and † indicates the death of a mouse.

It may be taken therefrom that all unvaccinated mice succumbed to infection by day four, which was accompanied by a dramatic weight loss by day three post-challenge. Similar to this was the case of mice infected with wt MCMV, although few mice survived the infection by day four, confirming that persistent MCMV infection might have a protective effect against intracellular bacteria (Barton, E. S., 2007 supra.

Vaccination with MCMVList provided a substantial protection of the immunized mice, but these mice exhibited significant weight loss. All RAE-1γMCMVList-vaccinated mice survived the infection with minimal weight loss by day four post-challenge, once again suggesting that RAE-1γMCMVList vaccination retains a long-lived and protective memory CD8$^+$ T cell response.

Mice that survived four days post challenge were sacrificed and the bacterial loads in liver and spleen were determined. Bacterial load in spleens of RAE-1γMCMVList vaccinated mice was below the limit of detection and significantly lower in livers when compared to WT-MCMV and MCMVList vaccinated mice.

In order to test whether RAE1γMCMVList-vaccinated mice could resist the challenge with higher doses of L. monocytogenes, vaccinated mice were challenged with $4 \times 10^4$ CFU/mouse and monitored for survival.

The result is shown in FIG. 32 B.

More particularly, FIG. 32 B shows the survivorship curve of mice which were vaccinated as described above and which were injected with $4 \times 10^4$ CFU/mouse of L. monocytogenes. The survival rate was followed (n=9 per group).

It may be taken therefrom that while all unvaccinated mice succumb to infection and MCMVList vaccinated mice began to die by day 4 post challenge, all RAE-1γMCMVList vaccinated mice survived the challenge.

The efficient and long-lasting protective capacity of the LLO-specific CD8$^+$ T cell response in mice vaccinated with RAE-1γMCMVList was confirmed by assessing the LLO-specific CD8+ T cell-mediated cytotoxicity in vivo.

The result is shown in FIG. 32 C.

More particularly, FIG. 32 C shows the percentage of listeriolysinpeptide-specific killing in mice which were infected f.p. with $1 \times 10^5$ PFU of MCMVList or RAE-1γMCMVList (n=3-4 per group). After 2 and 11 months p.i., mice were injected with an equal ratio of unstimulated and LLO-peptide stimulated CSFE-stained splenocytes. The Mean±s.e.m. is shown.

It may be taken therefrom that listeriolysin-specific killing was significantly higher up to 11 months post-vaccination in mice vaccinated with RAE-1γMCMVList compared to those vaccinated with MCMVList.

Example 26: RAE-1γ Expression by MCMV is Crucial for its Vaccine Vector Capacity To test the possibility that an enhanced LLO-specific CD8$^+$ T cell response in RAE-1γMCMVList-infected mice is entirely a consequence of the deletion of the m152 gene, whose protein product (m152/gp40) not only down-regulates the expression of MHC I molecules but also RAE-1, a virus expressing the LLO epitope on the backbone of the m152-deficient virus (Δm152MCMVList) was constructed.

BALB/c mice were infected with $2 \times 10^5$ PFU/mouse i.v. of the indicated viruses. On day 8 post infection viral titer in lungs was determined.

The result is shown in FIG. 33 A.

More particularly, in FIG. 33 A the viral load in lungs of individual animals is shown as circles and the median value of a group is shown as horizontal line.

It may be taken therefrom, that Δm152MCMVList showed attenuated growth in vivo, but the attenuation was much stronger with RAE-1γMCMVList.

BALB/c mice were infected with $1 \times 10^5$ f.p. of the indicated viruses. The frequency of LLO-specific CD8$^+$ T cells was determined on day 7 p.i.

The result is shown in FIG. 33 B.

More particularly, in FIG. 33 B median values are shown as horizontal lines.

It may be taken therefrom that the LLO-specific CD8$^+$ T cell response in mice infected with Δm152MCMVList was similar to that induced by MCMVList, confirming that an enhanced CD8$^+$ T cell response in RAE-1γMCMVList-infected mice was predominantly a consequence of ectopic expression of RAE-1γ rather than the deletion of immune evasion gene m152.

In connection therewith it has to be acknowledged that co-stimulation via NKG2D plays an important role in shaping the CD8$^+$ T cell response (Markiewicz, M. A., et al 2005, "J Immunol 175(5): 2825-33; Barber, A. and C. L. Sentman, 2011, Blood 117(24): 6571-81). This function may be of central importance for the success of RAE-1γMCMV as a vaccine vector, since MCMV down-regulates co-stimulatory molecules on antigen-presenting cells similarly to HCMV (Loewendorf, A., et al. 2004 J Virol 78(23): 13062-71; Mintern, J. D., et al. 2006, J Immunol 177(12): 8422-31; Arens, R., et al. 2011, J Virol 85(1): 390-6) and RAE-1-NKG2D interaction may rescue the co-stimulation signals during T cell priming.

BALB/c mice were infected with $2 \times 10^5$ i.v. of WT-MCMV; MCMVList or RAE-1γMCMVList, respectively. One day before infection and on days 2 and 4 p.i. mice were treated with NKG2D blocking antibody The result is shown in FIG. 34.

More particularly, FIG. 34 A shows the virus titer in spleen which was determined on day 3 p.i. Individual animals are shown as circles and median values are shown as horizontal lines, and FIG. 34 B shows absolute number of LLO-specific CD8$^+$ T cells which were determined on days 3.5 and 6.5 p.i. Mean±SEM is shown.

It may be taken therefrom that NKG2D stimulation by MCMV is important for the listeriolysin-specific CD8+ T cells generation.

More particularly, blocking of NKG2D by specific monoclonal antibodies significantly reduced the control of RAE-1γMCMVList at day 3 post-infection (see FIG. 34A). However, this treatment only modestly lowered the CD8+ T cell response (see FIG. 34B). An alternative explanation for the modest effect of NKG2D blocking on the CD8$^+$ response could simply be a higher antigenic viral load caused by NKG2D blocking which, on its own, may facilitate the CD8 response via cross-priming (Lemmermann, N. A., V. Bohm, et al. (2011). "In vivo impact of cytomegalovirus evasion of CD8 T-cell immunity: facts and thoughts based on murine models." Virus Res 157(2): 161-74).

BALB/c mice were infected with $2 \times 10^5$ i.v. of MCMV-List, RAE-1γMCMVList or left untreated (naïve). On days 4 and 8 post infection mice were injected with 2 mg of BrdU/mouse and sacrificed 2 h later.

The frequency of BrdU+ total CD8+ T cells, the frequency of LLO-specific CD8+ T cells and the frequency of BrdU+ LLO-specific CD8+ T cells was determined.

The result is shown in FIG. 35.

More particularly, FIG. 35 A shows the frequency of BrdU total CD8+ T cells, FIG. 35 B shows the frequency of LLO-specific CD8+ T cells and FIG. 35 C shows the BrdU LLO-specific CD8+ T cells. Mean±SEM is shown.

It may be taken therefrom that RAE-1γ expression promotes listeriolysin-specific CD8+ T cells priming. The preserved frequency of DCs during the early days of infection corresponds to the enhanced priming of CD8+ T cells in RAE-1γMCMVList-infected mice, which is illustrated by the higher frequencies and proliferation capacity of LLO-specific CD8+ T cells.

Altogether, the above data demonstrates that the expression of the NKG2D ligand RAE-1γ by CMV vectors promotes the priming of an epitope-specific CD8+ T cell response.

Example 27: RAE-1γMCMV is an Efficient Vaccine Vector in C57BL/6 Mice

To exclude the possibility that the robustness of the CD8+ T cell response after infection with RAE-1γMCMVList vector was restricted to a single MHC I haplotype, a recombinant RAE-1γMCMV and wt MCMV expressing the H-2K$^b$ restricted peptide SIINFEKL instead of m164 epitope were constructed as described in Example 1 above, referred to herein as RAE-1γMCMV-SIINFEKL and MCMV-SIINFEKL, respectively (Rotzschke, O., et al. 1991), Eur J Immunol 21(11): 2891-4).

Growth kinetics of MCMV-SIINFEKL and REA-1γMCMV-SIINFEKL were compared to WT-MCMV.

More particularly, MEF cells were infected with wt MCMV, MCMV-SIINFEKL or RAE-1γMCMV-SIINFEKL at 0.1 PFU per cell. Supernatants were harvested at indicated time p.i. and virus titers were determined by plaque assay.

The result is shown in FIG. 36.

It may be taken therefrom that the expression of SIINFEKL peptide did not impair the virus growth in vitro.

C57BL/6 (H-2$^b$) mice were infected with the viruses expressing SIINFEKL via footpad or intravenous route and kinetics of SIINNFEKL- and virus-specific CD8+ T cell response was followed up to three months post infection.

Figure 37:
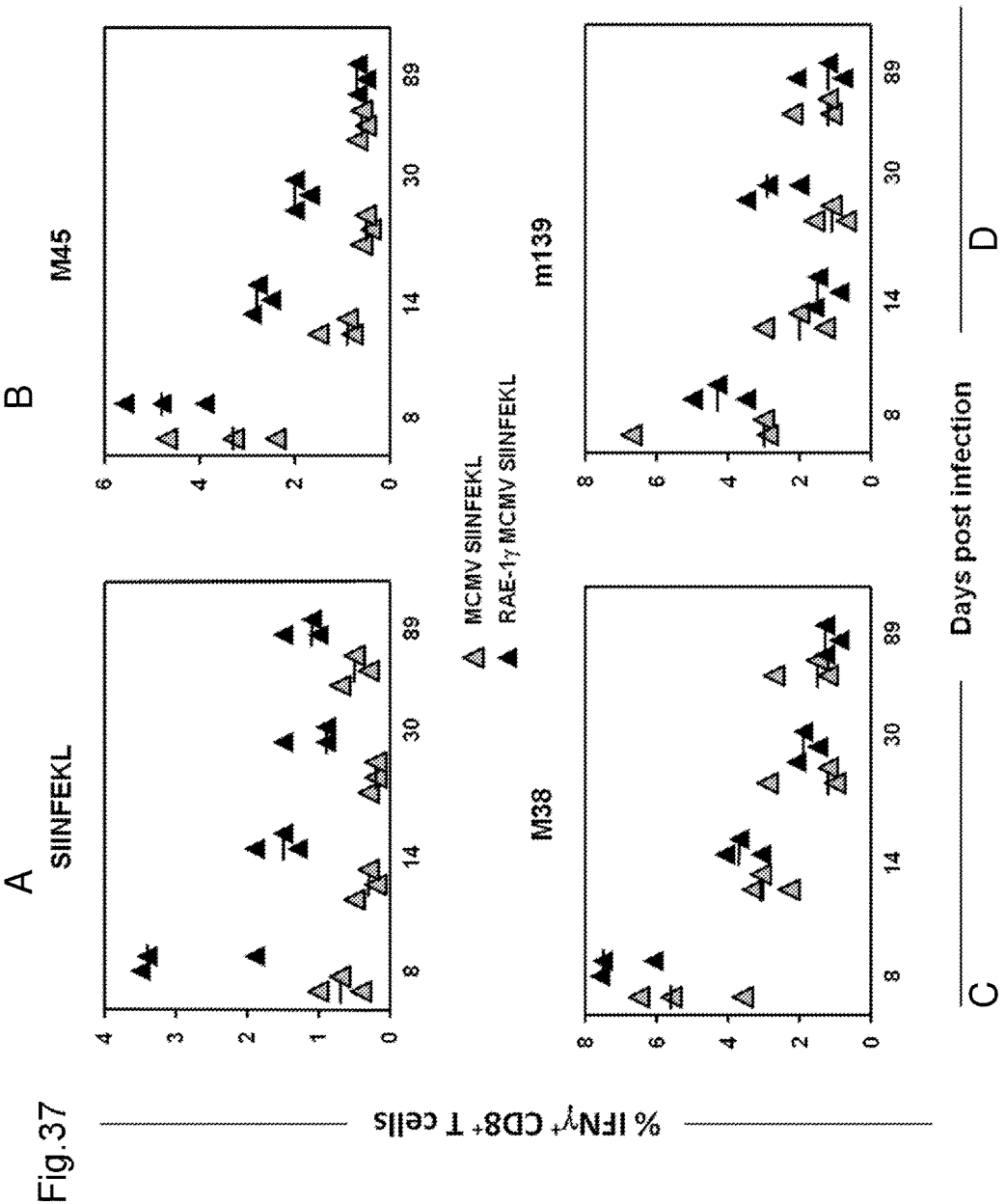
Figure 38:
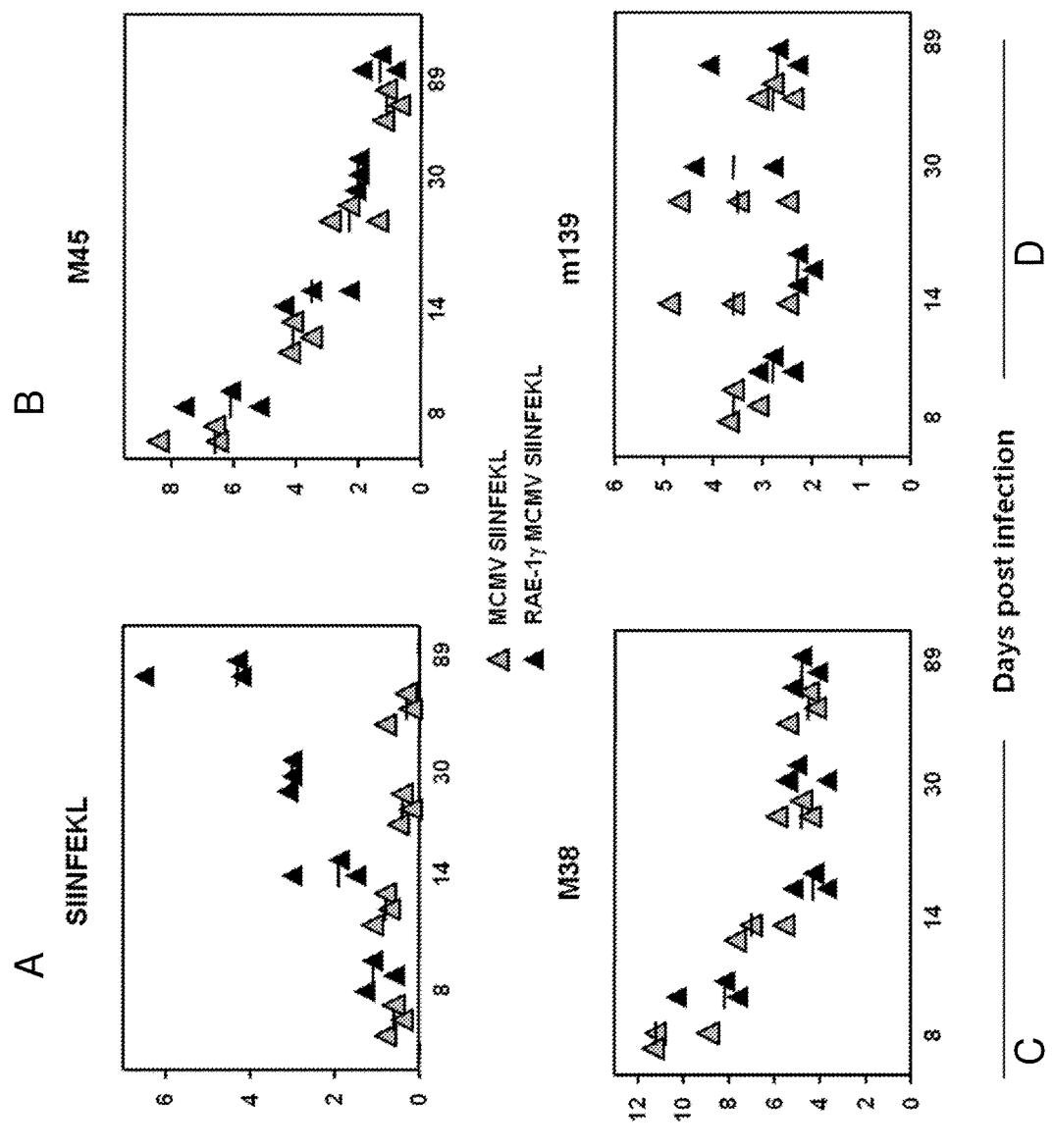

The results are shown in FIGS. 37 and 38.

More particularly, FIG. 37 shows the kinetics of SIINFEKL specific CD8+ T cell response after infection of C57BL/6 mice with 10$^5$ PFU/mouse f.p. of the indicated viruses.

SIINFEKL- and MCMV-specific CD8+ T cell response has been followed for 89 days. IFNγ+ CD8+ T cell response, as a result of indicated peptides stimulation, is shown for individual animals as triangles. Median values are shown as bars.

FIG. 38 shows the kinetics of SIINFEKL specific CD8+ T cell response after infection of C57BL/6 mice with 10$^5$ PFU/mouse i.v. of the indicated viruses SIINFEKL- and MCMV-specific CD8+ T cell response has been followed for 89 days. IFNγ+ CD8+ T cell response, as a result of indicated peptides stimulation, is shown for individual animals as triangles. Median values are shown as bars.

It may be taken therefrom that in agreement with the results obtained in BALB/c mice, the infection of C57BL/6 mice with RAE-1γMCMV-SIINFEKL resulted in a stronger CD8+ T cell response to SIINFEKL compared to the virus expressing SIINFEKL only. The CD8+ T cell response to some MCMV immunodominant epitopes was also higher in RAE-1γMCMV-SIINFEKL infection, which confirms the previously published data (Slavuljica, I., et al. 2010, J Clin Invest 120(12): 4532-45).

To assess the protective capacity of RAE-1γ expressing MCMV vector in C57BL/6 mice, mice were immunized with 10$^5$ PFU/mouse f.p. with viruses expressing SIINFEKL either with or without RAE-1γ co-expression and were challenged with low and high dose of Listeria expressing ovalbumin (OVA-Listeria) three weeks later.

Four days post challenge bacterial load in spleen and liver was determined.

Figure 39:
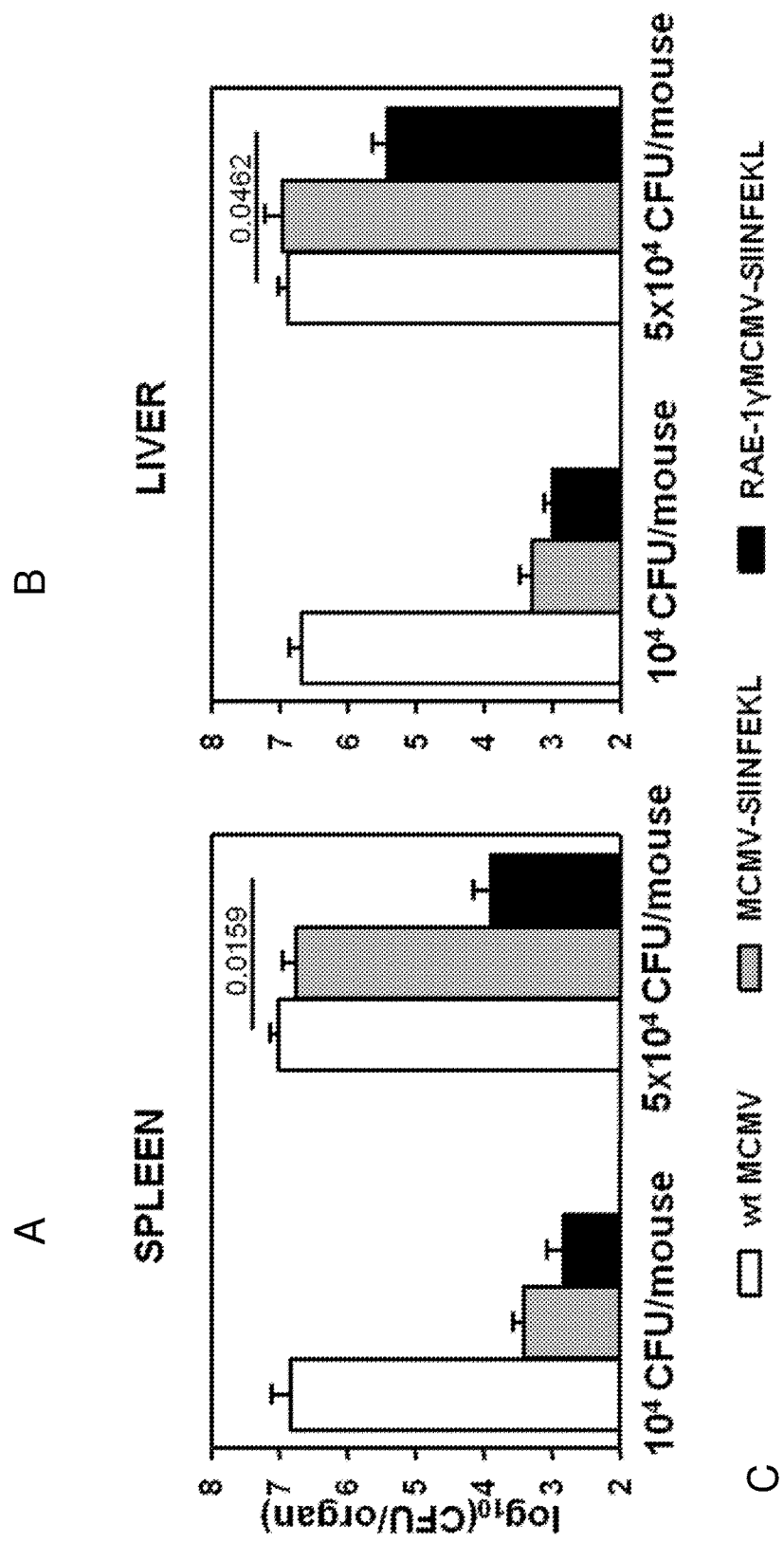

The result is shown in FIG. 39.

More particularly, FIG. 39 shows the viral lowed in spleen (left panel) and liver (right panel) of C57BL/6 mice which were infected with 10$^5$ PFU/mouse f.p of the indicated viruses, or left uninfected. Three weeks post infection mice were challenged with either 10$^4$ CFU/mouse (low dose) or 5×10$^4$ CFU/mouse (high dose). Four days post challenge bacterial load in spleen and liver was determined, shown as mean±SEM.

It may be taken therefrom that contrary to a modest protective capacity in BALB/c mice immunized with MCMVList, the protective response of C57BL/6 mice immunized with MCMV-SIINFEKL was much stronger, to the point that the beneficial effect of RAE-1γMCMV-SIINFEKL vaccination was hardly visible. However, the beneficial effect of RAE-1γ expression became evident after a challenge infection of mice with a higher dose of OVA-Listeria.

Previous studies showed that cross-presentation plays a dominant role in the priming of CD8+ T cells during MCMV infection. The present inventor proposes that MCMV expressing RAE-1γ favors direct priming due to dramatically lowered antigenic load which should reduce the cross-priming capacity of such a virus. To test the role of direct presentation in infection with the virus expressing RAE-1γ3d mice which are defective in TLR3, TLR7 and TLR9 signaling and unable to cross-present foreign antigens (Tabeta, K., et al. 2006, Nat Immunol 7(2): 156-64).

C57BL/6 and 3d mice were infected with 2×10$^5$ PFU/mouse i.p. of either MCMV-SIINFEKL or RAE-1γMCMV-SIINFEKL, or left uninfected. Seven days post infection the frequency of SIINFEKL-specific as well as MCMV-specific CD8+ T cells was determined 7 days later, and viral titer in lungs was determined.

The result is shown in FIG. 40.

More particularly, FIG. 40 A shows the frequency of SIINFEKL tetramer-specific CD8+ T cells (left panel) and M45 tetramer-specific CD8+ T cells of individual animals as triangles and median values are shown as bars.

FIG. 40 B shows the viral titer in lungs.

It may be taken therefrom that RAE-1γ expression by MCMV vector promotes direct priming of vectored antigen-specific CD8+ T cells.

Although both viruses induced an epitope-specific CD8+ T cell response, the response induced by RAE-1γMCMV-SIINFEKL was slightly better than the one in mice infected with MCMV-SIINFEKL. Thus, the absence of cross-presentation does not compromise the robust CD8+ T cell response to the viruses expressing RAE-1. In addition, RAE-1γMCMV-SIINFEKL was readily controlled in MCMV sensitive 3d mice when compared to MCMV-SIINFEKL.

Example 28: Influenza Challenge Experiments

C57BL/6 mice were immunized with 2×10$^5$ PFU/mouse f.p. of the Δm157 MCMV, MCMV-HA or RAE-1γMCMV- HA, or left non-immunized. Three weeks post immunization mice were intranasally challenged with either high or low dose (100 HU) of human influenza virus A/Puerto Rico/8/34 H1N1, also referred to herein as A/PR8. A/PR8 was generated as previously described (Achdout, H., et al. 2003 J Immunol 171(2): 915-23). For the low dose, 40 hemagglutinin units (HU) of PR8 virus were used. Mice were monitored daily for survival and weight loss.

The result is shown in FIG. 41.

More particularly, in FIG. 41 A the survival of mice immunized with Δm157 MCMV, MCMV-HA or RAE-1γMCMV-HA, or non-immunized mice is shown over time.

In FIG. 41 B the weight loss of mice immunized with Δm157 MCMV, MCMV-HA or RAE-1γMCMV-HA, or non-immunized mice is shown over time. Sigifical difference was calculated using unpaired Student's t-test, n=5 mice/group.

Example 29: Vector Capacity of RAE-1γMCMV-CD8 Epitope of RSV

BALB/c mice were infected with $10^5$ PFU/mouse f.p. of MCMV-SYI or RAE-1γ-MCMV-SYI or left uninfected and SYIGSINNI-specific CD8$^+$ T cell response has been followed.

Generation of Recombinant Viruses Expressing Respiratory Syncytial Virus (RSV) M2-Derived Peptide SYIGSINNI.

Recombinant plasmids were constructed according to established procedures, and enzyme reactions were performed as recommended by the manufacturers. Throughout, the fidelity of PCR-based cloning steps was verified by sequencing (GATC, Freiburg, Germany).

(i) Design of Insert Containing Peptide Swap.

Primers were constructed in a way to replace the Dd-restricted antigenic m164 peptide 167-AGPPRYSRI-175 with the Kd-restricted M2-derived peptide 82-SYIGSINNI-90.

The primers were m164 SYI fw (5'-cgcccgctgccacgatg-gcctggttgttgacggcccagaagatgttgttgatcgagccgatgtagctgtca-gcgccccaGCCAGT GTTACAACCAATTAACC-3') (lower case letters represent homology region to m164 ORF in MCMV genome, bold underline letters represent introduced epitope SYIGSINNI, bold italic letters homology regions between primers and capital letters represent homology to Tischer kanamycin cassette and m164 SYI ry (5'-gccgttcg-gaaaggactactgtcggacgtggggcgctgacagctacatcggctcgat-caacaacatcTAGGGATAACAG GGTAATCGAT-3') (lower case letters represent homology region to m164 ORF in MCMV genome, bold underline letters represent introduced epitope SYIGSINNI, bold italic letters homology regions between primers and capital letters represent homology to Tischer kanamycin cassette). PCR was performed with the following cycler conditions: an initial step for 2 min at 98° C. for activation of HighFidelity Phusion DNA polymerase (New England BioLabs) was followed by 30 cycles of 10 s at 98° C., 10 s at 60° C., and 60 s at 72° C. As DNA template plasmid pEP-SaphAI, a kind gift from K. Tischer was used.

(II) BAC Mutagenesis.

For the construction of recombinant mutants en passant mutagenesis; a two step markerless red recombination system was utilized, as described by Tischer, B. K. et al, 2010, supra. Mutagenesis of full-length mCMV bacterial artificial chromosome (BAC) and dm152-RAE1γ mCMV BAC was performed in *Escherichia coli* strain DH10B, whereas excision of the selection marker was performed in *Escherichia coli* strain GS1783.

The result is shown in FIG. 42.

More particularly, FIG. 42 shows the kinetics of SYIGSINNI-specific CD8$^+$ T cell response in BALB/c mice which were infected with $10^5$ PFU/mouse f.p. of the indicated viruses or left uninfected. SYIGSINNI-specific CD8 T cell response has been followed at indicated time points. Splenocytes were stimulated with SYIGSINNI peptide and frequency of IFNγ$^+$ CD8$^+$ T cells is shown as mean±SEM.

It may be taken therefrom that the frequency of SYIGSINNI-specific CD8$^+$ T cells is higher in mice infected with MCMV-SYI or RAE-1γ-MCMV-SYI compared to uninfected mice.

The frequency of SYIGSINNI-specific CD8$^+$ T cells increases from day 7 to day 14 p.i. in mice infected with MCMV-SYI or RAE-1γ-MCMV-SYI.

The frequency of SYIGSINNI-specific CD8$^+$ T cells in RAE-1γ-MCMV-SYI infected mice is higher compared to MCMV-SYI infected mice.

The features of the present invention disclosed in the specification, the claims, the sequence listing and/or the drawings may both separately and in any combination thereof be material for realizing the invention in various forms thereof.

What is claimed is:

1. An attenuated in vivo beta-herpesvirus, wherein the beta-herpesvirus comprises a first heterologous nucleic acid comprising a nucleotide sequence encoding a human UL16 Binding Protein 2 (ULBP2) that replaces a viral gene encoding the protein UL16 or a homolog thereof, wherein the beta-herpesvirus encodes a second heterologous nucleic acid, wherein the second heterologous nucleic acid is a heterologous nucleic acid coding for a peptide, oligo-peptide, polypeptide or protein, wherein the peptide, oligopeptide, polypeptide or protein constitutes or comprises at least one antigen, wherein the antigen is a tumor antigen, and wherein the antigen is suitable for being recognized by a receptor of an immune cell and triggering an immune response against said antigen.

2. The beta-herpesvirus according to claim 1, wherein the ULBP2 is capable of binding a receptor present on the surface of an immune cell is-selected from the group consisting of NK cells, γδ T cells and activated CD8+ T cells.

3. The beta-herpesvirus according to claim 1, wherein the beta-herpesvirus is human cytomegalovirus.

4. The beta-herpesvirus according to claim 1, wherein the beta-herpesvirus is deficient in at least one additional immunomodulatory gene product.

5. The beta-herpesvirus according to claim 4, wherein the at least one additional gene product is selected from the group consisting of UL18, UL40, UL142, or homologs thereof.

6. The beta-herpesvirus of claim 4, wherein the at least one additional gene product is a product that regulates MHC class I presentation selected from the group consisting of US6, US3, US2, and US11.

7. The beta-herpesvirus according to claim 1, wherein the beta-herpesvirus comprises the deletion of at least one miRNA.

8. The beta-herpesvirus according to claim 1, wherein the beta-herpesvirus is deficient in at least one glycoprotein.

9. A method for the treatment or prevention of a disease, comprising administering to a subject in need thereof an effective amount of the beta-herpesvirus of claim 1, wherein said disease is directly related to the heterologous antigen encoded by the beta-herpesvirus or wherein said disease is directly related to the beta-herpesvirus itself.

10. The method according to claim 9, wherein the disease is a disease or condition which is associated with infection from the wild-type version of said attenuated beta-herpesvirus of claim 1.

11. The method according to claim 9, wherein the disease is a malignant growth, tumor or cancer that is associated with said tumor antigen of claim 1.

12. A method for the vaccination of a subject against a disease, comprising administering to a subject in need thereof an effective amount of the beta-herpesvirus of claim 1, wherein said disease is directly related to the heterologous antigen encoded by the beta-herpesvirus or wherein said disease is directly related to the beta-herpesvirus itself.

13. A nucleic acid coding for the beta-herpesvirus of claim 1.

14. An expression vector, comprising the nucleic acid according to claim 13.

15. A pharmaceutical composition comprising the beta-herpesvirus of claim 1, and a pharmaceutically acceptable carrier.

\* \* \* \* \*